(12) United States Patent
Glazier

(10) Patent No.: US 11,744,842 B2
(45) Date of Patent: Sep. 5, 2023

(54) METHODS FOR THE EFFECTIVE TREATMENT OF METASTATIC CANCER

(71) Applicant: General Oncology, Inc., Brookline, MA (US)

(72) Inventor: Arnold Glazier, Newton, MA (US)

(73) Assignee: General Oncology, Inc., Brookline, MA (US)

( * ) Notice: Subject to any disclaimer, the term of this patent is extended or adjusted under 35 U.S.C. 154(b) by 137 days.

(21) Appl. No.: 16/215,060

(22) Filed: Dec. 10, 2018

(65) Prior Publication Data

US 2019/0240240 A1 Aug. 8, 2019

Related U.S. Application Data

(63) Continuation of application No. 15/583,108, filed on May 1, 2017, now abandoned, which is a continuation of application No. 14/437,786, filed as application No. PCT/US2013/066200 on Oct. 22, 2013, now abandoned.

(60) Provisional application No. 61/716,838, filed on Oct. 22, 2012.

(51) Int. Cl.
| | |
|---|---|
| *A61K 31/138* | (2006.01) |
| *A61P 35/00* | (2006.01) |
| *A61K 31/704* | (2006.01) |
| *A61K 31/175* | (2006.01) |
| *A61K 31/198* | (2006.01) |
| *A61K 31/5377* | (2006.01) |
| *A61K 31/69* | (2006.01) |
| *A61K 35/28* | (2015.01) |
| *A61K 38/05* | (2006.01) |
| *A61K 38/07* | (2006.01) |

(52) U.S. Cl.
CPC .......... *A61K 31/704* (2013.01); *A61K 31/138* (2013.01); *A61K 31/175* (2013.01); *A61K 31/198* (2013.01); *A61K 31/5377* (2013.01); *A61K 31/69* (2013.01); *A61K 35/28* (2013.01); *A61K 38/05* (2013.01); *A61K 38/07* (2013.01)

(58) Field of Classification Search
CPC .............................. A61K 31/138; A61P 35/00
See application file for complete search history.

(56) References Cited

U.S. PATENT DOCUMENTS

| | | | |
|---|---|---|---|
| 5,639,787 A | 6/1997 | Riordan | |
| 2009/0123447 A1 | 5/2009 | Choi | |
| 2010/0196403 A1* | 8/2010 | Hochman | .......... A61K 47/6851 424/178.1 |
| 2015/0265641 A1 | 9/2015 | Glazier | |
| 2018/0071328 A1 | 3/2018 | Glazier | |
| 2018/0338935 A1 | 11/2018 | Glazier | |

FOREIGN PATENT DOCUMENTS

| | | |
|---|---|---|
| WO | WO 1990/002746 A1 | 3/1990 |
| WO | 2004/043374 A2 | 5/2004 |
| WO | WO 2014/066400 A2 | 5/2014 |
| WO | 2017/100162 A1 | 6/2017 |

OTHER PUBLICATIONS

Cormack et al. ("Animal models of acute myelogenous leukaemia—development, application and future perspectives." Leukemia (2005) 19, 687-706.) (Year: 2005).*
Carter et al. ("Preclinical Antitumor Activity of Bizelesin in Mice." Clinical Cancer Research (Jul. 1996); 2: pp. 1143-1149) (Year: 1996).*
Yeager et al. ("Autologous bone marrow transplantation in patients with acute nonlymphocytic leukemia, using ex vivo marrow treatment with 4-hydroperoxycyclophosphamide." The New England Journal of Medicine (Jun. 30, 1986); 315(3):141-147). (Year: 1986).*
Butryn et al. (Cancer Chemotherapy and Pharmacology vol. 34, pp. 44-50(1994), ABSTRACT) (Year: 1994).*
Zsido et al. ("Resistance of CHO cells expressing P-glycoprotein to cyclopropylpyrroloindole (CPI) alkylating agents." Biochemical Pharmacology; vol. 43, Issue 8, Apr. 15, 1992, pp. 1817-1822; ABSTRACT) (Year: 1992).*
Qadir et al. ("Cyclosporin A Is a Broad-Spectrum Multidrug Resistance Modulator." Clinical Cancer Research; vol. 11, 2320-2326, Mar. 15, 2005.) (Year: 2005).*
Search results for "Tucatinib | Recruiting, Active, not recruiting Studies | cancer." NIH: U.S. National Library of Medicine—List Results—ClinicalTrials.gov. Jun. 1, 2022. https://clinicaltrials.gov/ct2/results?term=Tucatinib&cond=cancer&Search=Apply&recrs=a&recrs=d&age_v=&gndr=&type=&rslt= (Year: 2022).*
Ahmad, I. et al., "Effect of Ascorbic Acid on the Degradation of Cyanocobalamin and Hydroxocobalamin in Aqueous Solution: A Kinetic Study," AAPS PhannSciTech, vol. 15; No. 5; 1324-1333 (2014).
Akatov, V.S. et al., "Combined Vitamins B12b and C Induce the Glutathione Depletion and the Death of Epidermoid Human Larynx Carcinoma Cells HEp-2," Bioscience Reports, vol. 20; No. 5; 411-417 (2000).
Arning. J. et al., "Structure-activity relationships for the impact of selected isothiazol-3-one biocides on glutathione metabolism and glutathione reductase of the human liver cell Hep G2," Toxicoloy, vol. 246; 203-212 (2008).
Babson, J.R. and Reed, D.J., "Inactivation of Glutathione Reductase by 2-Chloroethyl Nitrosourea-Derived Isocyanates," Biochemical and Biophysical Research Communications, vol. 83; No. 2; 754-762 (1978).

(Continued)

*Primary Examiner* — Jeffrey S Lundgren
*Assistant Examiner* — Chris E Simmons
(74) *Attorney, Agent, or Firm* — Hamilton, Brook, Smith & Reynolds, P.C.

(57) ABSTRACT

The present invention relates to methods for the treatment of metastatic cancer. Methods of treating metastatic cancer by administration of a set of drugs overcome multiple mechanisms of melphalan resistance and hypersensitize cancer cells to melphalan are described. The methods involve the administration of drug(s) that induce oxidative stress in cancer cells, in conjunction with melphalan on a defined schedule.

18 Claims, 7 Drawing Sheets

(56) References Cited

OTHER PUBLICATIONS

Bailey, H.H. et al., "Phase I Clinical Trial of Intravenous $_L$-Buthionine Sulfoximine and Melphalan: An Attempt at Modulation of Glutathione," J. Clin. Oncol., vol. 12; 194-205 (1994).

Bailey, H.H. et al., "Phase I Study of Continuous-Infusion $_L$-S,R-Buthionine Sulfoximine with Intravenous Melphalan," J. Natl Cancer Inst, vol. 89; 1789-1796 (1997).

Barron, C.C. et al., "Facilitative glucose transporters: Implications for cancer detection, prognosis and treatment," Metabolism Clinical and Experimental, vol. 65; 124-139 (2016).

Berger, S.J. et al., "Sensitive Enzymatic Cycling Assay for Glutathione: Measurements of Glutathione Content and Its Modulation by Buthionine Sulfoximine in Vivo and In Vitro in Human Colon Cancer," Cancer Research, vol. 54; 4077-4083 (1994).

Berry, D.A. et al., "High-Dose Chemotherapy With Autologous Hematopoietic Stem-Cell Transplantation in Metastatic Breast Cancer: Overview of Six Randomized Trials." Journal of Clinical Oncology, vol. 29; No. 24; 3224-3231 (2011).

Bhuyan, B.K. et al., "Multidrug Resistance Is a Component of V79 Cell Resistance to the Alkylating Agent Adozelesin," Cancer Research, vol. 53; 1354-1359 (1993).

Buehring, G.C. and Jensen, H.M., "Lack of Toxicity of Methylene Blue Chloride to Supravitally Stained Human Mammary Tissues," Cancer Research, vol. 43; 6039-6044 (1983).

Butryn, R.K. et al., "V79 Chinese hamster lung cells resistant to the bis-alkylator bizelesin are multidrug-resistant," Cancer Chemother Pharmacol, vol. 34; 44-50 (1994).

Brynes, R.W., "Evidence for Involvement of Multiple Iron Species in DNA Single-Strand Scission by $H_2O_2$ in HL-60 Cells," Free Radical Biology & Medicine, vol. 20; No. 3; 399-406 (1996).

Canada, A. et al., "Glutathione depletion increases the cytotoxicity of melphalan to PC-3, an androgen-insensitive prostate cancer cell line," Cancer Chemother Pharmacol, vol. 32; 73-77 (1993).

Cao, P. et al., "The DNA Minor Groove-alkylating Cyclopropylpyrroloindole Drags Adozelesin and Bizelesin Induce Different DNA Damage Response Pathways in Human Colon Carcinoma HCT116 Cells," Molecular Cancer Therapeutics, vol. 2; 651-659 (2003).

Carter, C.A. et al., "Preclinical Antitumor Activity of Bizelesin in Mice." Clinical Cancer Research, vol. 2; 1143-1149 (1996).

Chen, Q. et al., "Ascorbate in pharmacologic concentrations selectively generates ascorbate radical and hydrogen peroxide in extracellular fluid in vivo," PNAS, vol. 104; No. 21; 8749-8754 (2007).

Chen, Q. et al., "Pharmacologic doses of ascorbate act as a prooxidant and decrease growth of aggressive tumor xenografts in mince," PNAS, vol. 105; No. 32; 11105-11109 (2008).

Chresta, C.M. et al., "Depletion of Cellular Glutathione by N,N'-Bis(trans-4-Hydroxycyclohexyl)-N'-nitrosourea as a Determinant of Sensitivity of K562 Human Leukemia Cells to 4-Hydroperoxycyclophosphamide," Cancer Research, vol. 50; 4067-4071 (1990).

Colussi, G. et al., "$H_2O_2$-induced block of glycolysis as an active ADP-ribosylation reaction protecting cells from apoptosis," FASEB J., vol. 14; 2266-2276 (2000).

Coombes, R.C. et al., "High dose chemotherapy and autologous stem cell transplantation as adjuvant therapy for primary breast cancer patients with four or more lymph nodes involved: long-term results of an international randomized trial," Annals of Oncology, vol. 16; 726-734 (2005).

Combleet. M.A. et al., "Treatment of advanced malignant melanoma with high-dose melphalan and autologous bone marrow transplantation," Br. J. Cancer, vol. 48; 329-334 (1983).

Combleet, M.A. et al., "High-Dose Alkylating Agent Therapy: A Review of Clinical Experiences," Cancer Drag Delivery, vol. 1; No. 3; 227-238 (1984).

Deponte, M. et al., "Mechanistic Studies on a Novel. Highly Potent Gold-Phosphole Inhibitor of Human Glutathione Reductase," The Journal of Biological Chemistry, vol. 280; No. 21; 20628-20637 (2005).

Du, J. et al., "Ascorbic acid: Chemistry, biology and the treatment of cancer," Biochimica et Biophysica Acta, vol. 1826; 443-457 (2012).

Duarte, T.L. and Jones. G.D.D., "Vitamin C modulation of $H_2O_2$-induced damage and iron homeostasis in human cells," Free Radical Biology & Medicine, vol. 43; 1165-1175 (2007).

Dubler, R.E. and Anderson, B.M., "Simultaneous inactivation of the catalytic activities of yeast glutathione reductase by N-alkylmaleimides," Biochimica et Biophysica Acta, vol. 659; 70-85 (1981).

Evers, B. et al., "A High-Throughout Pharmaceutical Screen Identifies Compounds with Specific Toxicity against BRCA2-Deficient Tumors," Clin Cancer Research, vol. 16; No. 1; 99-108 (2010).

Feldman, D.R. et al., "TI-CE High-Dose Chemotherapy for Patients with Previously Treated Germ Cell Tumors: Results and Prognostic Factor Analysis," Journal of Clinical Oncology, vol. 28; No. 10; 1706-1713 (2010).

Fitzgerald, G.B. et al., "2,4-dihydroxybenzylamine: A specific inhibitor of glutathione reductase," Biochemical Pharmacology, vol. 41; No. 2; 185-190 (1991).

Frei III, E. et al., "Preclinical Studies and Clinical Correlation of the Effect of Alkylating Dose," Cancer Research, vol. 48; 6417-6423 (1988).

Friedman, H.S. et al., "Phase I Trial of Carmustine Plus $O^6$-Benzylguanine for Patients with Recurrent or Progressive Malignant Glioma." J. Clin. Oncol., vol. 18; 3522-3528 (2000).

Frischer, H. and Ahmad, T., "Severe generalized glutathione reductase deficiency after antitumor chemotherapy with BCNU [1,3-bis(chloroethyl)-1-nitrosourea]," J Lab Clin Med., vol. 89; No. 5; 1080-1091 (1977).

Gosland, M.P. et al., "Reversal by Cefoperazone of Resistance of Etoposide, Doxorubicin, and Vinblastine in Multidrug Resistant Human Sarcoma Cells," Cancer Research, vol. 49; 6901-6905 (1989).

Green, J.A. et al., "Potentiation of Melphalan Cytotoxicity in Human Ovarian Cancer Cell Lines by Glutathione Depletion," Cancer Research, vol. 44; 5427-5431 (1984).

Hanrahan, E.O. et al., "Randomized Trial of High-Dose Chemotherapy and Autologous Hematopoietic Stem Cell Support for High-Risk Primary Breast Carcinoma," Cancer, vol. 106; 2327-2336 (2006).

Hoffer, L.J. et al., "Phase I clinical trial of i.v. ascorbic acid in advanced malignancy," Annals of Oncology, 6 pages (2008).

Hucl, T. et al., "A Syngeneic Variance Library for Functional Annotation of Human Variation: Application of BRCA2," Cancer Research, vol. 68; No. 13; 5023-5030 (2008).

Jevtorić-Todorović, V. and Guenthner, T.M., "Sensitization of human melanoma cells to melphalan cytotoxicity by Adriamycin and carmustine," J Cancer Res Oncol., vol. 117; 313-320 (1991).

Jevtorić-Todorović, V. and Guenthner, T.M., "Depletion of a Discrete Nuclear Glutathione Pool by Oxidative Stress, But Not by Buthionine Sulfoximine," Biochemical Pharmacology, vol. 44; No. 7; 1383-1393 (1992).

Jochheim, C.M. and Baillie, T.A., "Selective and Irreversible Inhibition of Glutathione Reductase in Vitro by Carbamate Thioester Conjugates of Methyl Isocyanate," Biochemical Pharmacology, vol. 47; No. 7; 1197-1206 (1994).

Karplus, P.A. et al., "Inhibition of human glutathione reductase by the nitrosourea drugs 1,3-bis(2-chloroethyl)-1-nitrosourea and 1-(2-chloroethyl)-3-(2-hydroxyethyl)-1-nitrosourea," Eur. J. Biochem, vol. 171; 193-198 (1988).

Kassahun, K. et al., "Effect of Carbamate Thioester Derivatives of Methyl-and 2-chloroethyl Isocyanate on Glutathione Levels and Glutathione Reductase Activity in Isolated Rat Hepatocytes," Biochemical Pharmacology, vol. 48; No. 3; 587-594 (1994).

Kelner, M. J. and Alexander, N.M., "Methylene Blue Directly Oxidizes Glutathione without the Intermediate Formation of Hydrogen Peroxide," The Journal of Biological Chemistry, vol. 260; No. 28; 15168-15171 (1985).

Keshari, K.R. et al., "Hyperpolarized $^{13}$C dehydroascorbate as an endogenous redox sensor for in vivo metabolic imaging," PNAS, vol. 108; No. 46; 18606-18611 (2011).

(56) References Cited

OTHER PUBLICATIONS

Kirkman, H.N. et al., "The Function of Catalase-bound NADPH," The Journal of Biological Chemistry, vol. 262; No. 2; 660-666 (1987).
Kirkman, H.N. et al., "Mechanisms of Protection of Catalase by NADPH," Tire Journal of Biological Chemistry, vol. 274; No. 20; 13908-13914 (1999).
Kovach, J.S. et al., "A controlled study of combined 1,3-bis(2-chloroethyl)-1-nitrosourea and 5-fluorouragil therapy for advanced gastric and pancreatic cancer," vol. 33; 563-567 (1974).
Kurz, T. et al., "Lysosomal Redox-Active Iron Is Important for Oxidative Stress-Induced DNA Damage," Ann. N.Y. Acad. Sci., vol. 1019; 285-288 (2004).
Lacagnin, L.B. et al., "Metabolic changes in alveolar type II cells after exposure to hydrogen peroxide," Am J Physiol., L57-L65 (1990).
Lakhani, S. et al., "Chemotherapy for malignant melanoma: combinations and high doses produce more responses without survival benefit," Br. J. Cancer, vol. 61; 330-334 (1990).
Lazarus, H.M. et al., "Intensive Melphalan Chemotherapy and Cryopreserved Autologous Bone Marrow Transplantation for the Treatment of Refractory Cancer," Journal of Clinical Oncology, vol. 1; No. 6; 359-367 (1983).
Liu. X. and Sturla, S., "Profiling patterns of glutathione reductase inhibition by the natural product illudin S and its acylfulvene analogues," Mol Biosyst., vol. 5; No. 9; 1013-1024 (2009).
Mav, J.M. et al., "Generation of oxidant stress in cultured endothelial cells by methylene blue: protective effects of glucose and ascorbic acid," Biochemical Pharmacology, vol. 66; 777-784 (2003).
Monti, D.A. et al., "Phase I Evaluation of Intravenous Ascorbic Acid in Combination with Gemcitabine and Erlotinib in Patients with Metastatic Pancreatic Cancer," PLOS One, vol. 7; No. 1; E29794; 7 pages (2012).
Murray, D. and Meyn, R.E., "Effect of misonidazole pretreatment on nitrogen mustard-induced DNA cross-linking in mouse tissues in vivo," Br. J. Cancer, vol. 50; 801-808 (1984).
Nakamura, J. et al., "Micromolar concentrations of hydrogen peroxide induce oxidative DNA lesions more efficiently than millimolar concentrations in mammalian cells," Nucleic Acids Research, vol. 31; No. 6; 1790-1795 (2003).
Nathan, C.F. et al., "Tumor Cell Anti-Oxidant Defenses," J. Exp. Med., vol. 153; 766-782 (1980).
Nathan, C.F. and Cohn, Z.A., "Antitumor Effects of Hydrogen Peroxide in Vivo" J. Exp. Med., vol. 154; 1539-1553 (1981).
Nazhat, N.B. et al., "Destruction of Vitamin $B_{12}$ by Reaction with Ascorbate: The Role of Hydrogen Peroxide and the Oxidation State of Cobalt," Journal of Inorganic Biochemistry, vol. 36; 75-81 (1989).
Peters, W.P. et al., "Prospective, Randomized Comparison of High-Dose Chemotherapy With Stem-Cell Support Versus Intermediate-Dose Chemotherapy After Surgery and Adjuvant Chemotherapy in Women With High-Risk Primary Breast Cancer: A Report of CALGB 9082, SWOG 9114; and NCIC MA-13," Journal of Clinical Oncology, vol. 23; No. 10; 2191-2200 (2005).
Pierson, H.F. et al., "Depletion of Extracellular Cysteine with Hydroxocobalamin and Ascorbate in Experimental Murine Cancer Chemotherapy," Cancer Research, vol. 45; 4727-4731 (1985).
Pitot, H.C. et al., "A Phase I Study of Bizelesin (NSC 615291) in Patients with Advanced Solid Tumors," Clinical Cancer Research, vol. 8; 712-717 (2002).
Porrata, L.F. and Adjei, A.A., The pharmacologic basis of high dose chemotherapy with haematopoietic stem cell support for solid tumors, British Journal of Cancer, vol. 85; No. 4; 484-489 (2001).
Rajan, A. et al., "A Phase I Combination Study of Olaparib with Cisplatin and Gemcitabine in Adults with Solid Tumors," Clinical Cancer Research, vol. 18; No. 8; 2344-2351 (2012).
Robey, R.W. et al., "Inhibition of P-glycoprotein (ABCB1)-and multidrug resistance-associated protein 1 (ABCC1)-mediated transport by the orally administered inhibitor, CBT-1®," Biochem Pharmacol., vol. 75; No. 6; 1302-1312 (2008).

Samuels, B.L. and Bitran, J.D., "High-Dose Intravenous Melphalan: A Review," J. Clin. Oncol., vol. 13; 1786-1799 (1995).
Sarosy, G. et al., "The Systemic Administration of Intravenous Melphalan." J. Clin. Oncol., vol. 6; 1768-1782 (1988).
Schwartz, G.H. et al., "A phase I study of bizelisin, a highly potent and selective DNA-interactive agent, in patients with advanced solid malignancies," Annals of Oncology, vol. 14; 775-782 (2003).
Seefeldt, T. et al., "Characterization of a Novel Dithiocarbamate Glutathione Reductase Inhibitor and Its Use as a Tool to Modulate Intracellular Glutathione," The Journal of Biological Chemistry, vol. 284; No. 5; 2729-2737 (2009).
Sirohi, B. et al., "An elective single autograft with high-dose melphalan: single-center study of 451 patients," Bone Marrow Transplantation, vol. 36; 19-24 (2005).
Smith, D.B. et al., "Phase II Evaluation of Melphalan in Adenocarcinoma of the Pancreas," Cancer Treatment Reports, vol. 69; No. 7-8; 917-918 (1985).
Solovieva, M.E. et al., "Vitamin $B_{12b}$ increases the cytotoxicity of short-time exposure to ascorbic acid, inducing oxidative burst and iron-dependent DNA damage," European Journal of Pharmacology, vol. 566; 206-214 (2007).
Spielholz, C. et al., "Increased Facilitated Transport of Dehydroascorbic Acid without Changes in Sodium-dependent Ascorbate Transport in Human Melanoma Cells," Cancer Research, vol. 57; 2529-2537 (1997).
Spitzer, G. et al., "High-Dose Chemotherapy With Autologous Bone Marrow Transplantation," Cancer, vol. 54; 1216-1225 (1984).
Stadtmauer, E.A. et al., "Conventional-Dose Chemotherapy Compared with High-Dose Chemotherapy Plus Autologous Hematopoietic Stem-Cell Transplantation for Metastatic Breast Cancer," The New England Journal of Medicine, vol. 342; No. 15; 1069-1076 (2000).
Stephenson, C.M. et al., "Phase I clinical trial to evaluate the safety, tolerability, and pharmacokinetics of high-dose intravenous ascorbic acid in patients with advanced cancer," Cancer Chemother Pharmacol., vol. 72; 139-146 (2013).
Tallman, M.S. et al., "Conventional Adjuvant Chemotherapy with or without High-Dose Chemotherapy and Autologous Stem-Cell Transplantation in High-Risk Breast Cancer," The New England Journal of Medicine, vol. 349; No. 1; 17-26 (2003).
Welsh, J.L. et al., "Pharmacological ascorbate with gemcitabine for the control of metastatic and node-positive pancreatic cancer (PACMAN): results from a phase I clinical trial," Cancer Chemother Pharmacol, vol. 71; 765-775 (2013).
Wilson, M.K. et al., "Review of high-dose intravenous vitamin C as an anticancer agent," Asia-Pacific Journal of Clinical Oncology, vol. 10; 22-37 (2014).
Yu, M. et al., "Reversal of ATP-binding cassette drug transporter activity to modulate chemoresistance: why has it failed to provide clinical benefit?," Cancer Metastasis Rev, DOI 10.1007/s10555-012-9402-8; 17 pages (2012).
Yun, J. et al., "Vitamin C selectively kills KRAS and BRAF mutant colorectal cancer cells by targeting GAPDH." Science, vol. 350; No. 6266; 1391-1396 (2015).
Zander, A.R. et al., "High-Dose Chemotherapy with Autologous Hematopoietic Stem-Cell Support Compared with Standard-Dose Chemotherapy in Breast Cancer Patients with 10 or More Positive Lymph Nodes: First Results of a Randomized Trial," Journal of Clinical Oncology, vol. 22; No. 12; 2273-2283 (2004).
Child, J.A., et al., "High-Dose Chemotherapy with Hematopoietic Stem-Cell Rescue for Multiple Myeloma," The New England Journal of Medicine, vol. 348; No. 19; 1875-1883 (2003).
Dasgupta, R. et al., "Underactive Genetic Variants of Glutathione S-Transferase P1 (GSTP1) Modulate Survival in Multiple Myeloma," Blood, vol. 98; No. 11; 161a; Abstract #680 (2001).
Denz, U. et al., "State of the art therapy in multiple myeloma and future perspectives," European Journal of Cancer, vol. 42; No. 11; 1591-1600 (2006).
Fielder, K. and Durie, B.G.M., "Primary Amyloidosis Associated with Multiple Myeloma Predictors of Successful Therapy," American Journal of Medicine, vol. 80; No. 3; 413-418 (1986).

(56) References Cited

OTHER PUBLICATIONS

Peest, D. et al., "Melphalan and Prednisone (MP) versus Vincristine, BCNU, Adriamycin, Melphalan and Dexamethasone (VBAMDex) Therapy for Multiple Myeloma," Onkologie, vol. 13; No. 4; 43-44 (1990).

Poydock, M.E and Rice, D.R.J., "Influence of Vitamins C and B12 on the Survival Rate of Mice Bearing Ascites Tumor," Experimental Cell Biology, vol. 50; No. 2; 88-91 (1982).

Poydock, M.E. et al., "Growth-inhibiting effect of hydroxocobalamin and L-ascorbic acid on two solid tumors in mice," Database Embase [online]; accession No. EMB-1984201428; 1 page; Abstract (2007).

Poydock, M.E., "Effect of combined ascorbic acid and B-12 on survival of mice with implanted Ehrlich carcinoma and L1210 leukemia," The American Journal of Clinical Nutrition, vol. 54; No. 6; 1261S-1265S (1991).

Notification Concerning Transmittal of the International Preliminary Report on Patentability for International Application No. PCT/US2013/066200, entitled: "Methods for the Effective Treatment of Metastatic Cancer," dated May 7, 2015.

Notification of Transmittal of The International Search Report and the Written Opinion of the International Searching Authority for International Application No. PCT/US2013/066200, entitled: "Methods for the Effective Treatment of Metastatic Cancer," dated Nov. 17, 2014.

Notification Concerning Transmittal of The International Preliminary Report on Patentability for International Application No. PCT/US2016/065079, entitled: "Combination For The Effective Treatment Of Metastatic Cancer In Patients," dated Jun. 21, 2018.

Notification of Transmittal of The International Search Report and the Written Opinion of the International Searching Authority for International Application No. PCT/US2016/065079, entitled: "Combination For The Effective Treatment Of Metastatic Cancer In Patients," dated Apr. 24, 2017.

Damon, L.E. et al., "High-Dose Chemotherapy and Hematopoietic Stem Cell Rescue for Breast Cancer: Experience in California," Biology of Blood and Marrow Transplantation, vol. 6; 496-505 (2000).

NHS Foundation Trust, "Patient information: High Dose Melphalan and Autologous Stem Cell Transplant," Sep. 28, 2011, retrieved from Internet URL: https://www.rbch.nhs.uk/assets/templates/rbch/documents/our_services/clinical/hematology/BMT1.pdf, [retreived on Sep. 3, 2020]; 3 pages.

Nieto, Y. et al., "High-Dose Infiisional Gemcitabine Combined with Busulfan and Melphalan with Autologous Stem-Cell Transplantation in Patients with Refractory Lymphoid Malignancies," Bio Blood Marrow Transplant, vol. 18; 1677-1686 (2012).

Volpe, D.A. et al., "Myelotoxic effects of the bifunctional alkylating agent bizelesin on human, canine and murine myeloid progenitor cells," Cancer Chemother Pharmacol, vol. 39; 143-149 (1996).

* cited by examiner

| Cell Line | µM | Metric* | Exposure Time (h) | Calculated AUC-1 (µM h) | Ref. |
|---|---|---|---|---|---|
| Bladder Cancer | | | | | |
| MGH-U1 | 16 | $IC_{90}$ | 1 | 12 | 1 |
| A1663 | 30 | $IC_{99.9}$ | 3 | 13.5 | 2 |
| J82 | 3 | $IC_{50}$ | 1 | 7 | 3 |
| J82MMC | 6 | $IC_{50}$ | 1 | 14 | 3 |
| Colon Cancer | | | | | |
| SW480 | 24 | $IC_{90}$ | 1 | 18 | 4 |
| HCT116 | 37 | $IC_{90}$ | 1 | 27 | 4 |
| CX-1 | 32 | $IC_{99.999}$ | 24 | 10 | 5 |
| HT-29 | 5 | $IC_{70}$ | 1 | 7 | 6 |
| LoVo | 9 | $IC_{70}$ | 1 | 13 | 6 |
| Gastric cancer | | | | | |
| AGS-6 | 1.3 | $D_0$ | 1 | 3 | 7 |
| Breast Cancer | | | | | |
| MCF-7 | 10 | $IC_{85}$ | 1 | 9 | 8 |
| MCF-7 | 12.6 | $IC_{90}$ | 1 | 9 | 9 |
| Prostate Cancer | | | | | |
| PC3 | 5.2 | $IC_{90}$ | 6 | 8 | 10 |
| DU145 | 30 | $IC_{90}$ | 1 | 22 | 11 |
| Renal Cell Cancer | | | | | |
| UOK130 | 50 | $IC_{50}$ | 24 | 261 | 12 |

* The melphalan concentration that corresponds to the indicated metric.

FIG. 3A

| Cell Line | µM | Metric* | Exposure Time (h) | Calculated AUC-1 (µM h) | Ref. |
|---|---|---|---|---|---|
| Small Cell Lung Cancer | | | | | |
| NCI-H69 | 6 | $IC_{90}$ | 1 | 4 | 13 |
| NCI-H69 | 0.6 | $IC_{50}$ | 24+ | 3 | 14 |
| H69/DAU4 | 0.85 | $IC_{50}$ | 24+ | 4 | |
| H69/VP | 0.4 | $IC_{50}$ | 24+ | 2 | |
| OC-NYH | 0.4 | $IC_{50}$ | 24+ | 2 | |
| NYH/VM | 0.5 | $IC_{50}$ | 24+ | 2.6 | |
| GLC4 | 1.8 | $IC_{50}$ | 1 | 4.4 | 15 |
| GLC4-CDDP | 10.5 | $IC_{50}$ | 1 | 25.6 | |
| Myeloma | | | | | |
| RPMI 8226/S | 6 | $IC_{90}$ | 1 | 4 | 16 |
| 8226 LR-5 | 20 | $IC_{90}$ | 1 | 15 | |
| 8226 Dox40 | 6 | $IC_{90}$ | 1 | 4 | |
| Melanoma | | | | | |
| M8 | 9.4 | $D_0$ | 1 | 16 | 17 |
| JUSO | 5.3 | $D_0$ | 1 | 9 | |
| GLL19 | 3.6 | $D_0$ | 1 | 6 | |
| A101D | 18.1 | $IC_{99.9}$ | 3 | 8 | 18 |
| T242 | 1.3 | $IC_{50}$ | 1 | 3 | 19 |
| T354 | 1.3 | $IC_{50}$ | 1 | 3 | |
| T508 | 3 | $IC_{50}$ | 1 | 7 | |
| T535 | 0.46 | $IC_{50}$ | 1 | 1 | |
| T355 | 0.16 | $IC_{50}$ | 1 | 0.4 | |
| MM253 | 0.8 | $D_0$ | 4 | 3 | 20 |
| MM96 | 3.6 | $D_0$ | 4 | 12 | |
| MM96 | 7.6 | $D_0$ | 4 | 25 | 21 |
| MM200 | 5 | $D_0$ | 4 | 17 | 22 |

FIG. 3B

| Cell Line | μM* | Metric | Exposure Time (h) | Calculated AUC-1 (μM h) | Ref. |
|---|---|---|---|---|---|
| MM127 | 1 | $D_0$ | 4 | 3 | 23 |
| MM214 | 2.6 | $D_0$ | 4 | 8.7 | |
| MM229 | 3.3 | $D_0$ | 4 | 11 | |
| MM253 | 1 | $D_0$ | 4 | 3 | |
| RPMI 8322 | 20 | $IC_{90}$ | 0.5 | 8 | 24 |
| HX34 | 4.2 | $IC_{99.6}$ | 1 | 1.3 | 25 |
| HX41 | 4.2 | $IC_{97}$ | 1 | 2 | |
| HX47 | 4.2 | $IC_{99.5}$ | 1 | 0.9 | |
| HX50 | 4.2 | $IC_{92}$ | 1 | 2.8 | |
| HX52 | 4.2 | $IC_{97.6}$ | 1 | 1.9 | |
| MEL-2 | 7.4 | $IC_{90}$ | 1 | 5.5 | 26 |
| MM253-c1a | 30.3 | $IC_{90}$ | 1 | 22 | |
| MM253-4cg | 11.8 | $IC_{90}$ | 1 | 8.7 | |
| G3361 | 100 | $IC_{99}$ | 1 | 37 | 27 |
| Endometrial Cancer | | | | | |
| HEC-59 | 2.7 | $IC_{50}$ | 24 | 14 | 28 |
| Normal Bone Marrow | | | | | |
| CFU-gm | 7.2 | $IC_{70}$ | 1 | 10 | 29 |
| BFU-e | 6.4 | $IC_{70}$ | 1 | 9 | |
| CFU-e | 6.5 | $IC_{70}$ | 1 | 9 | |
| Normal Human Cord Blood Progenitors | | | | | |
| CFU-gm | 2 | $IC_{70}$ | 1 | 3 | 30 |
| BFU-e | 2.8 | $IC_{70}$ | 1 | 4 | |
| CFU-e | 2 | $IC_{70}$ | 1 | 3 | |

\* The melphalan concentration that corresponds to the indicated metric.

FIG. 3C

| Pancreatic Cancer | | | | | |
|---|---|---|---|---|---|
| Cell Line | μM | Metric* | Exposure Time (h) | Calculated AUC-1 (μM h) | Ref. |
| Hx32 | 3 | $IC_{90}$ | 1 | 2.4 | 31 |
| Hx32 | 30 | $IC_{99}$ | 1 | 12 | |
| Hx58 | In vitro data unavailable, has same IC99.9 in vivo as Hx32 | | | | 32 |
| Ovarian Cancer  ( * cisplatin resistant) | | | | | |
| Hx61* | 10 | $IC_{90}$ | 1 | 7 | 33 |
| Hx62 | 13 | $IC_{90}$ | 1 | 9.5 | |
| Hx109 | 13 | $IC_{90}$ | 1 | 9.5 | |
| Hx110* | 13 | $IC_{90}$ | 1 | 9.5 | |
| A2780* | 12.4 | $IC_{50}$ | 1 | 30 | 34 |
| A2780/100* | 110 | $IC_{50}$ | 1 | 269 | |
| A2780s | 2.6 | $IC_{90}$ | 1 | 2 | 35 |
| A2780r | 16 | $IC_{90}$ | 1 | 12 | |
| IGROV1 | 0.4 | $IC_{50}$ | 1 | 1 | 36 |
| V7 | 3.2 | $IC_{90}$ | 1 | 2.4 | 37 |
| OVCAR-3* | 1 | $IC_{90}$ | 24 | 1.6 | 38 |
| OVCAR-2* | 3 | $IC_{50}$ | 2 | 11 | 39 |
| OVCAR-4* | 1.6 | $IC_{50}$ | 2 | 6 | |
| 2008 | 3.3 | $IC_{90}$ | 1 | 2.4 | 40 |
| COLO 316 | 0.7 | $IC_{90}$ | 1 | 0.5 | |
| COLO 316 | 0.2 | $IC_{50}$ | 24+ | 1 | 41 |
| COLO 316/B* | 0.9 | $IC_{50}$ | 24+ | 4.5 | |
| OAW42 | 8 | $IC_{90}$ | 2 | 9 | 42 |
| OAW42 mer | 19 | $IC_{90}$ | 2 | 22 | |
| HAC2P | 14 | $IC_{50}$ | 24+ | 22 | 43 |
| HAC2P0.1* | 44 | $IC_{50}$ | 24+ | 70 | |
| A1847 | 4 | $IC_{90}$ | 1 | 3 | 44 |
| A1847 mer | 8 | $IC_{90}$ | 1 | 6 | |

FIG. 3D

Melphan Dose mg/m²

| Cell Line | Melphalan Only | | Doxorubicin 1 µM + BCNU 1 µM + Melphalan | | |
|---|---|---|---|---|---|
| | IC$_{90}$ µM | AUC-1 (µM h) | IC$_{90}$ µM | AUC-1 (µM h) | DMF* |
| MEL-2 | 7.4 | 5.5 | 0.5 | 0.37 | 15 |
| MM253-c1a | 30 | 22 | 0.5 | 0.4 | 55 |
| MM253-4cg | 11.8 | 8.7 | 0.6 | 0.4 | 20 |

METHODS FOR THE EFFECTIVE TREATMENT OF METASTATIC CANCER

RELATED APPLICATIONS

This application is a continuation of U.S. application Ser. No. 15/583,108, filed May 1, 2017, which is a continuation of U.S. application Ser. No. 14/437,786, which is the U.S. National Stage of International Application No. PCT/US2013/066200, filed Oct. 22, 2013, which designates the U.S., published in English, and claims the benefit of U.S. Provisional Application No. 61/716,838, filed on Oct. 22, 2012. The entire teachings of the above applications are incorporated herein by reference.

BACKGROUND OF THE INVENTION

Combination chemotherapy has given high cure rates for certain types of metastatic cancer, such as childhood leukemia, lymphoma and testicular cancer. However, most common types of metastatic cancer are currently incurable.

The 5-year survival rates of some metastatic cancers are approximately as follows: cervical 16%, colorectal 12.5%, uterine 16%, esophageal 3.5%, kidney 12.3%, liver/biliary 3%, lung/bronchus 3.9%, melanoma 16.1%, ovarian 27.3%, pancreatic 2%, stomach 3.9%, bladder 5.4%, breast 24.3%. (See: Frei E 3rd.; Curative cancer chemotherapy, Cancer Res. 1985; 45:6523-37 and Howlader N, et al.; SEER Cancer Statistics Review, 1975-2010, National Cancer Institute. Bethesda, Md.).

Despite decades of research and hundreds of billions of dollars, the age-adjusted cancer mortality rates reported by the U.S. National Cancer Institute for many types of cancers showed no decline over a 35-year period, from 1975-2010. During the same period, the National Library of Medicine catalogued 2,143,002 scientific articles about cancer of which 112,429 related to the treatment of metastatic cancer and since the 1950's there have been over 22,300 medical papers and scientific reports published on clinical trials for metastatic cancer and over 152,000 scientific papers published on combination cancer therapy. Despite this truly massive scientific effort, obtaining complete response (CRs) in patients with most types of metastatic cancer has not been possible. A CR can, for example, indicate the disappearance of all detectable cancer by CT scan and other imaging technology. Generally, a 99% or 2-log reduction in cancer cell burden is needed to obtain a CR. Thus, a patient with metastatic cancer can have tens of billions of cancer cells distributed throughout his or her body. However, decreasing the tumor cell burden by 2-logs would still leave millions to billions of viable cancer cells in the patient, with time these cancer cells could multiply and cause progressive disease. For example, the rate of CRs in pancreatic cancer using FOLFIRINOX, the most effective chemotherapy is only 0.6%. In patients with metastatic melanoma treated with the state of the art therapy, Nivolumab plus ipilimumab, the complete response rate was 9.6%. The CR rate in patients with melanoma treated with the BRAF inhibitor, Vemurafenib was 1%. Similar low rates of CRs are seen with most types of metastatic cancers. Durable, long-term CRs are even rarer in patients with most types of metastatic disease. (Conroy T, et al.; N Engl J Med. May 12; 364 (19):1817-25 (2011); Wolchok J D, et al.; N Engl J Med. July 11; 369(2):122-33 (2013); and Chapman P B, et al., N Engl J Med. June 30; 364(26):2507-16 (2011)).

There have been thousands of clinical trials with a large number of different combinations of anticancer drugs, yet few drug regimens give high rates of complete responses in patients with metastatic cancer and cures for most types of metastatic cancer are very rare. Furthermore, the few types of cancers that are currently curable at a high rate with combination chemotherapy are generally characterized by properties that confer hypersensitivity to a particular chemotherapy drug(s). Given the extraordinary effort, resources and time that have been expended without success to develop such methods, over 580,000 people in the U.S. still die of metastatic cancer each year. Presently, there are no methods for the effective treatment for most types of metastatic cancer that can give high rates of complete responses and durable, long-term, complete responses in patients. Thus, a need exists to develop cancer therapy for metastatic cancer and refractory cancer that achieve high rates of complete responses, especially long-term durable complete responses.

SUMMARY OF THE INVENTION

The present invention relates to methods for the therapeutically effective treatment of refractory metastatic cancers comprising the administration of a combination of compositions to a subject, wherein the combination irreversibly inhibits the potential for cancer cell proliferation. The present invention pertains to therapeutically effective methods of treating metastatic cancers to achieve high rates of complete responses (CRs), especially long-term, durable CRs.

The methods described herein include therapeutically effective treatments of non-refractory metastatic cancer by administration of a combination of compounds that irreversibly inhibits the potential for cancer cell proliferation. The methods of the invention have less chronic side effects or require a shorter period of therapy, or provide a higher quality of life than current therapies, or provide a higher rate of CRs and durable CRs for the particular type of metastatic cancer treated.

In one aspect, the present invention relates to a method of treating metastatic cancer by administering a combination of drugs that overcome multiple mechanisms of melphalan resistance and hypersensitize cancer cells to melphalan. The method involves the administration of drug(s) that induce oxidative stress in cancer cells, in conjunction with administration of melphalan on a defined schedule. The method optionally includes administration of a proteasome inhibitor. The methods of the first aspect are also applicable not only to melphalan but also to sensitization to alkylating agents in general that crosslink DNA. Suitable DNA crosslinking agents include but are not limited to: melphalan, chlorambucil, cyclophosphamide, bendamustine, bizelesin, ifosfamide, cisplatin, carboplatin, and oxaliplatin, thiotepa, busulfan, mitomycin c, mechlorethamine, carmustine, lomustine, cisplatin, carboplatin, nedaplatin, oxaliplatin, satraplatin, picoplatin and busulfan.

Oxidative stress can profoundly sensitize cancer cells to melphalan by a number of mechanisms. For example, oxidative stress depletes intracellular glutathione levels, which impairs glutathione-mediated detoxification of melphalan; inhibits the repair of melphalan induced DNA double stranded breaks; inhibits the nucleotide excision repair of melphalan-DNA mono-adducts, which increases DNA interstrand crosslinking by melphalan; and inhibits topoisomerase 2 function, which has a role in DNA unwinding and DNA interstrand crosslinking repair among other events. The methods and aspects further include sensitizing the cancer cells for administration of one or more alkylating agent(s).

The net effect of these activities is a profound sensitization of cancer cells to cell killing and inhibition of clonogenic survival by subsequent administration of melphalan, for example, with a decrease in the melphalan AUC needed to give a 1-log reduction in clonogenic survival of about 15 to 55 fold absent such sensitization.

In a further aspect, in addition to drugs that induce oxidative stress a proteasome inhibitor can also be administered in the methods. Proteasome inhibitors impair multiple steps in the repair of DNA interstrand crosslinks and further sensitize cells to melphalan. Thus, proteasome inhibitors are further administered for continuing the inhibition of the cells for melphalan treatment.

In another aspect, melphalan is administered at intermediate to high doses in conjunction with hematopoietic stem cell support. Suitable DNA other crosslinking agents include but are not limited to: melphalan, chlorambucil, cyclophosphamide, bendamustine, bizelesin, ifosfamide, cisplatin, carboplatin, and oxaliplatin, thiotepa, busulfan, and mitomycin c, mechlorethamine, carmustine, lomustine, cisplatin, carboplatin, nedaplatin, oxaliplatin, satraplatin, picoplatin, and busulfan that can be administered at intermediate to high doses in conjunction with hematopoietic stem cell support.

In an aspect of the invention, oxidative stress is caused by the administration of an inhibitor of glutathione reductase in conjunction with an agent that undergoes redox cycling. In an embodiment, the glutathione reductase inhibitor is a carmustine (BCNU), the redox cycling agent is doxorubicin (Adriamycin) or methylene blue and the proteasome inhibitor is selected from bortezomib (Velcade) or carfilzomib (Kyprolis) or combinations thereof. In certain embodiments an inhibitor of MDR1, pgp is used in conjunction with the doxorubicin.

The methods of the present invention are also applicable not only to melphalan but also to sensitization to alkylating agents in general that crosslink DNA.

In another aspect, the set of drugs is administered multiple times (i.e., multiple course) each of which gives approximately an N-log reduction in the potential for cancer cell proliferation in the patient wherein N is in the range of approximately 2 to greater than 15.

In a first aspect, the invention pertains to a method of treating metastatic cancer or refractory metastatic cancer in a subject, by administering a combination of 1,3-bis(2-chloroethyl)-1-nitrosourea, doxorubicin and melphalan or pharmaceutically acceptable salts thereof simultaneously or within a six hour time period, an optionally administering a proteasome inhibitor within the 6 hour period or within the following 24 hours; wherein the melphalan dose is in the range of 20 to 200 mg/m$^2$.

In a second aspect, the invention pertains to a method for an effective treatment of metastatic cancer or refractory metastatic cancer in a subject, comprising administering an effective dose of a combination of 1,3-bis(2-chloroethyl)-1-nitrosourea, doxorubicin and melphalan; and optionally administering a proteasome inhibitor. In a first embodiment of the first or second aspect, 1,3-bis(2-chloroethyl)-1-nitrosourea is administered at a dose range of 50 to 300 mg/m$^2$; doxorubicin is administered at a dose of 10 to 80 mg/m$^2$; melphalan is administered at a dose of 20 to 200 mg/m$^2$; and wherein the proteasome inhibitor is carfilzomib administered at a dose of 0 or 10 to 60 mg/m$^2$; or alternatively bortezomib is administered at a dose of 0 or 1 to 1.3 mg/m$^2$. In a second embodiment of the first embodiment, 1,3-bis(2-chloroethyl)-1-nitrosourea is administered at a dose range of 100 mg/m$^2$; the doxorubicin is administered at a dose of 40 mg/m$^2$; and the carfilzomib is administered at a dose of 20 mg/m$^2$.

In a third aspect, the invention pertains to a method for obtaining a complete response in a subject with refractory metastatic cancer, comprising administering an effective amount of a combination of 1,3-bis(2-chloroethyl)-1-nitrosourea, doxorubicin and melphalan.

In a fourth aspect, the invention pertains to a method for the treatment of metastatic cancer comprising, administering to a subject, a combination of compositions that induce oxidative stress in cancer cells; administering a DNA crosslinking agent; and administering an infusion of stored hematopoietic stem cells to the subject.

In a fifth aspect, the invention pertains to a method for an effective treatment of metastatic cancer in a subject comprised of the administration of combination of one or more drugs, wherein said combination of drugs irreversibly inhibits the potential for cancer cell proliferation and wherein said method has improved patient outcome compared to current established therapies for the particular type of metastatic cancer. In a first embodiment of the fifth aspect, the invention further includes wherein the set of drugs is comprised of a DNA crosslinking agent. In a second embodiment of the first embodiment of the fifth aspect or of the fifth aspect, the invention further includes that the set of drugs includes a drug or drugs that hypersensitizes cancer cells to the crosslinking agent. In a third embodiment of the fifth aspect or of the first and second embodiment of the fifth aspect, the invention further includes that the set of drugs also comprises a drug that decreases detoxification of said crosslinking agent in cancer cells. In a fourth embodiment of the fifth aspect or of the first, second or third embodiment of the fifth aspect, the invention further includes that the set of drugs also comprises a drug that decreases nucleotide excision repair of DNA. In a fifth embodiment of the fifth aspect or of the first, second, third, or fourth embodiment of the fifth aspect, the invention further includes that the set of drugs also comprises a drug that inhibits repair of DNA interstrand crosslinks. In a sixth embodiment of the fifth aspect or of the first, second, third, fourth, or fifth embodiment of the fifth aspect, the invention further includes a drug that inhibits homologous recombination. In a seventh embodiment of the fifth aspect or of the first, second, third, fourth, fifth or sixth embodiment of the fifth aspect, the invention further includes drug(s) that induces oxidative stress or decrease intracellular GSH levels or increase the intracellular (GSSG)/(GSH)2 reduction potential, or increase levels of reactive oxygen species or inhibit the function of redox-sensitive proteins or increase glutathionylation of proteins in cancer cells. In an eighth embodiment of the fifth aspect or of the first, second, third, fourth, fifth, sixth or seventh embodiment of the fifth aspect, the set of drugs includes an electrophilic thiol-reactive drug or a drug that gives rise to an electrophilic thiol reactive species. In a ninth embodiment of the fifth aspect or of the first, second, third, fourth, fifth, sixth, seventh or eight embodiment of the fifth aspect, the set of drugs includes an inhibitor to glutathione reductase or an inhibitor to thioredoxin reductase or to one or more inhibitors to both glutathione reductase or thioredoxin reductase. In a tenth embodiment of the fifth aspect or of the first, second, third, fourth, fifth, sixth, seventh, eight or ninth embodiment of the fifth aspect, the inhibitor is 1,3-bis(2-chloroethyl)-1-nitrosourea or the inhibitor is CCNU.

In any of the aspects or embodiments of the aspects, the invention further includes a redox cycling agent.

In any of the aspects or embodiments of the aspects, when the invention further includes a redox cycling agent, the redox cycling agent is an anthracycline or other redox cycling agent selected from doxorubicin, idarubicin, epirubicin, and daunorubicin or combinations thereof.

In any of the aspects or embodiments of the aspects, wherein the crosslinking agent is melphalan.

In any of the aspects or embodiments of the invention, when the set of drugs is also comprised of a drug that inhibits repair of DNA interstrand crosslinks or inhibits homologous recombination, the drug is a proteasome inhibitor, for example, carfilzomib or bortezomib.

In any of the aspects or embodiments of the invention, the set of drugs also causes hypersensitization by one or more compounds that inhibit detoxification of the crosslinking agent, and or inhibit of nucleotide excision repair, and/or inhibit DNA double strand break repair, and/or inhibit DNA interstrand crosslink repair and or inhibit of homologous recombination.

In any of the aspects or embodiments of the invention, the crosslinking agent is melphalan.

In a sixth aspect, the invention pertains to a method for effective treatment of refractory metastatic cancer; comprising the steps of; a) administering a dose of 1,3-bis(2-chloroethyl)-1-nitrosourea, and a dose of doxorubicin; b) administering within 6 hours of step a), a dose of melphalan; and c) optionally administering a proteasome inhibitor, wherein the melphalan is administered at a dose wherein the potential for cancer cell proliferation is irreversibly inhibited and the melphalan dose is in the range of 20 to 200 mg/m$^2$.

In a seventh aspect, the invention pertains to a method for treatment of metastatic cancer in a patient with metastatic cancer or refractory metastatic cancer; comprising; a) administering 70-300 mg/m$^2$ of 1,3-bis(2-chloroethyl)-1-nitrosourea; b) administering 20-80 mg/m$^2$ of adriamycin; c) administering 30 to 200 mg/m$^2$ Melphalan and d) optionally administering one or more doses of kyprolis 20 mg/m$^2$ and repeating steps a-d if needed), wherein the potential for cancer cell proliferation is irreversibly inhibited.

In a second embodiment of the first aspect, the oxidative stress is obtained by the administration at least one agent selected from BCNU, (bis-chloroethylnitrosourea), 1-cyrlohexyl-3-(z-chloroethyl)-3-nitrosourea (CCNU) and 1,(4-trans-methylcyclohexyl)-3-(2-chlororethyl)-3-nitrosourea (MeCCNU) and at least one agent selected from doxorubicin, idarubicin, epirubicin, and daunorubicin.

In a first embodiment of the seventh aspect, step a) and step b) is omitted in a subject with a BRCA-1 or a BRCA2-associated cancer.

In any of the embodiments of any of the aspects of the invention, the glutathione reductase inhibitor is carmustine (BCNU) at an intravenous dose of approximately 50-100 mg/m2.

In a second embodiment of the second aspect of the invention, methylene blue is at an intravenous dose of approximately 1-5 mg/kg.

In any of the aspects or embodiments of the aspects, the invention further includes when the cancer is refractory to prior melphalan therapy or a type of cancer that is known to be refractory to melphalan.

In any of the aspects or embodiments of the aspects, the invention further includes when the cancer is selected from malignant melanoma, pancreatic cancer, ovarian cancer, breast cancer (stage iv), cervical cancer ureter cancer, prostate cancer.

In any of the aspects or embodiments of the aspects, the invention further includes bone marrow stem cell transplantation therapy.

In an eighth aspect, the invention further includes a pharmaceutical composition for effectively treating metastatic cancer comprising a combination of 1,3-bis(2-chloroethyl)-1-nitrosourea, doxorubicin and melphalan and pharmaceutically acceptable salts thereof.

In a ninth aspect, the invention further includes the use of a pharmaceutical composition for treating metastatic cancer or refractory metastatic cancer in a subject, comprising a therapeutically effective dose of a combination of 1,3-bis(2-chloroethyl)-1-nitrosourea, doxorubicin and melphalan and optionally a proteasome inhibitor, wherein the melphalan dose is in the range of 20 to 200 mg/m$^2$.

In a tenth aspect, the invention includes a method for the treatment of metastatic cancer comprised of the following sequential steps: a) administering an inhibitor of the MDR1 pgp efflux pump; b) administering a set of drugs that induce oxidative stress in cancer cells; c) administering a DNA crosslinking agent; d) administering a proteasome inhibitor; and e) administering an infusion of stored hematopoietic stem cells. A first embodiment of the tenth aspect, the invention further includes that the pgp inhibitor is fluoxetine, the drugs that induce oxidative stress are carmustine and doxorubicin, the DNA crosslinking agent is melphalan and the proteasome inhibitor, such as Kyprolis.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3A is a table that illustrates the calculated melphalan AUCs required to produce a 1-log reduction in clonogenic cell survival (AUC-1) for bladder, colon, gastric, breast, prostate, and renal cancer cell lines, and the data source.

FIG. 3B is a table that illustrates the calculated melphalan AUCs required to produce a 1-log reduction in clonogenic cell survival (AUC-1) for small cell lung, myeloma, and melanoma cancer cell lines and the data source.

FIG. 3C is a continuation of the table in FIG. 3B that illustrates the calculated melphalan AUCs required to produce a 1-log reduction in clonogenic cell survival (AUC-1)

melanoma cancer cell lines, in addition to endometrial cancer cell lines, normal bone marrow cancer cell lines, and normal human cord blood progenitors and the data source.

FIG. 3D is a table that illustrates the calculated melphalan AUCs required to produce a 1-log reduction in clonogenic cell survival (AUC-1) for pancreatic and ovarian cancer cell lines and the data source.

Figures 4, 5:
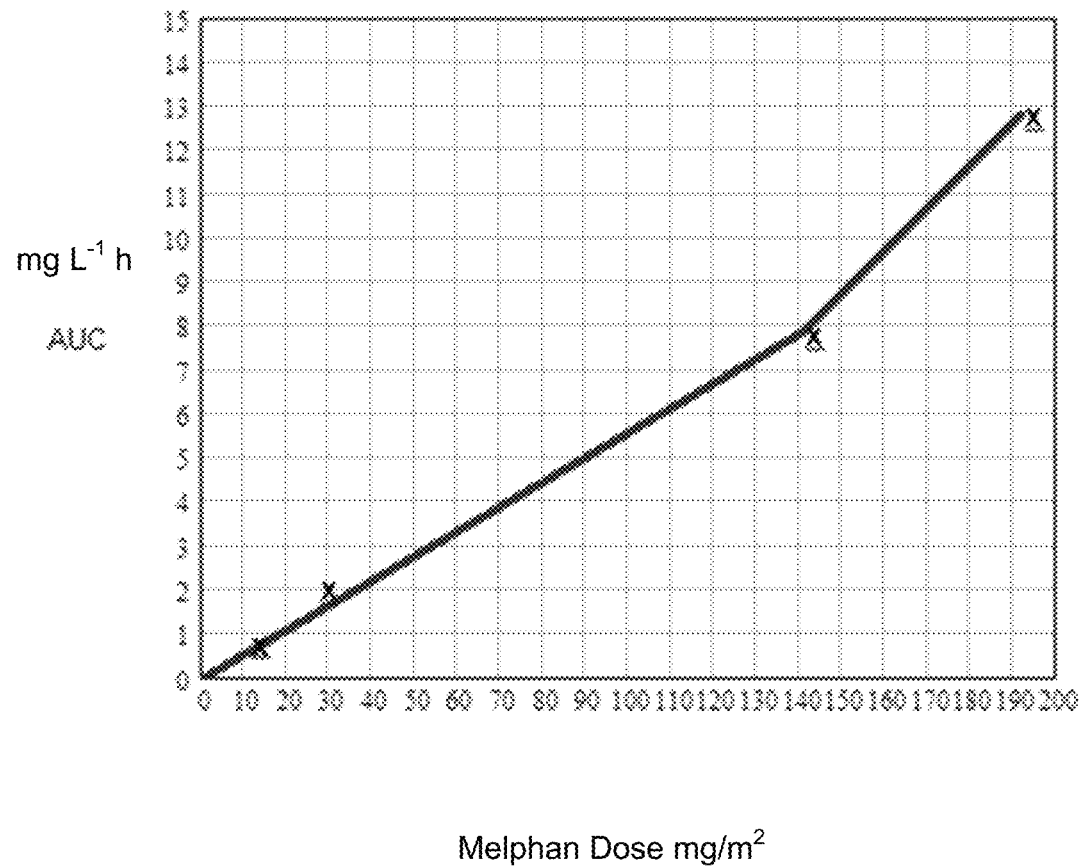

FIG. 4 is a plot that illustrates the AUC of melphalan, measured in mg/L hr versus melphalan dose measured in mg/m$^2$. AUC in µM hr may be calculated by multiplying the AUC mg/L hr value by 3.28. (See: Nath C E, et al.; Br J Clin Pharmacol. 2010 May; 69(5):484-97; Ardiet C, et al.; Cancer Chemother Pharmacol. 1986; 16(3):300-5; Smith D C, et al.; Cancer Chemother Pharmacol. 1993; 31(5):363-8; Bailey H H, et al. J Clin Oncol. 1994 January; 12(1):194-205.)

FIG. 5 is a table that illustrates the IC90, calculated AUC-1, and Dose Modification Factor (DMF) for melanoma cells treated with melphalan alone or in combination with sub-toxic concentrations (1 µM) of BCNU and doxorubicin. The incubation time was 1 hour. A colony forming assay was used to measure the inhibition of clonogenic survival. The AUC values were calculated based on a melphalan half-life of 1.1 hours in tissue culture media.

DETAILED DESCRIPTION OF THE INVENTION

The present invention relates to methods for the effective treatment of metastatic cancers including refractory metastatic cancers. An effective treatment of metastatic cancer would give high rates of one or more of the following: CRs; durable, long-term CRs; long-term progression free survival; long-term overall survival; long-term disease specific survival, long-term relative survival, long-term disease free survival and apparent cures.

In a patient with micrometastatic disease and no detectable tumor, the tumor burden N would be approximately $N \leq 10^9$ or less. For a patient with metastatic cancer and a tumor volume of 10 ml, N=about $10^{10}$. A high probability of cure of metastatic cancer requires therapy that can give at least an 11-log reduction in PCS if the tumor burden is $10^{10}$ cells and at least a 12-log reduction if the tumor burden is $10^{11}$. At least a 2-log reduction of tumor burden is needed to achieve a complete response in patients with absence of all detectable cancer cells by conventional clinical imaging technologies.

For certain types of drugs such as alkylating agents and DNA crosslinking agents there is a steep linear relationship between the log-reduction in cancer cell clonogenic survival and the drug dose or more generally the area under the drug concentration-time curve (AUC). For sensitive cancer cells this log-linear relationship can extend over many orders of magnitude. In principle, one could obtain major-log reductions in cancer cell clonogenic survival by giving high-doses of these drugs. In practice, the dose that can be safely administered to patients is limited by bone marrow toxicity and by the emergence of drug resistance. Autologous hematopoietic stem cell infusion was developed as a therapy to circumvent the problem of bone marrow suppression and allow the clinical use of high dose chemotherapy. The methods of the invention can further include hematopoietic stem cell infusion.

A description of example embodiments of the invention follows.

Definitions:

Acquired Drug Resistance refers to the ability of populations of cancer cells to escape destruction or inactivation by a drug at levels that are clinically achievable and wherein said lack of sensitivity arises or evolves in an initially drug-sensitive population.

Analog refers to a compound or moiety possessing significant structural similarity as possess substantially the same function.

Area under the curve (AUC) refers to the integral of the drug concentration-time curve for a drug in vitro or in vivo, the AUC is a measure of total drug exposure.

AUC-1 refers to the drug AUC needed to give a 1-log reduction in clonogenic cell survival.

AUC-N refers to the drug AUC needed to get an n-log reduction in clonogenic cell survival.

Allogeneic refers to refers to tissue or cells derived from another individual.

Autologous refers to tissue or cells derived from the same individual.

BCNU refers to the compound (e.g., agent or drug) carmustine or 1,3-bis(2-chloroethyl)-1-nitrosourea. It will be appreciated in the methods and compositions described herein that any suitable form of the active principle may be used, e.g., another salt form, or a prodrug or active metabolite.

Bizelesin refers to the compound 1,3-bis(2-((S)-1-(chloromethyl)-5-hydroxy-8-methyl-1,2,3,6-tetrahydropyrrolo[3,2-e]indole-3-carbonyl)-1H-indol-5-yl)urea that is an ultra-potent DNA crosslinking agent, which irreversibly inhibits the potential for cell proliferation at picomolar concentrations. It will be appreciated in the methods and compositions described herein that any suitable form of the active principle may be used, e.g. another salt form, or a prodrug or active metabolite.

Bone marrow stem cell or hematopoietic stem cell refers to a pluripotent cell that can reconstitute normal bone marrow and give rise to all normal bone marrow cell lineages; these cells are typically CD34+ cells, the cells can be isolated from bone marrow aspirates, peripheral blood, umbilical cord blood, and can be autologous or allogeneic; cells that can give rise to bone marrow stem cells for the purposes of this application are also considered to be "bone marrow stem cells."

BRCA-associated cancer refers to cancer that arises in the setting of an inherited BRCA mutation.

Buthionine sulfoximine (BSO) refers to a selective inhibitor of gamma-glutamylcysteine synthetase, the rate limiting enzyme in GSH synthesis.

Cancer is a disease defined by malignant behavior, which is cell proliferation and invasiveness in an abnormal context or setting in the body, wherein Invasiveness is the expansion of cells into new space, which can be local or distant (i.e., metastatic) with the remodeling or destruction of existing tissue architecture and the creation of infrastructure to support the metabolic needs of the cells; only malignant cells (i.e., cells that engage in malignant behavior) can sustain the clinical disease of cancer.

Clonogenic survival fraction refers to a measure of the ability of the cells to proliferate and generate new cellular colonies; the fraction of cells that are able to give rise to a colony of cells in an in vitro colony forming assay, also equal to the probability of clonogenic survival (PCS).

Combination therapy refers the administration of the therapeutic compounds (e.g., agents) in a manner, except where the timing of administration is provided, wherein each therapeutic compound is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation. The combination therapies featured in the present invention can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth. Combination therapy also refers to the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Complete Response (CR) refers to the absence of all detectable cancer, which is typically determined by CT scan, MRI or other imaging or detection technology. "New response evaluation criteria in solid tumours: revised RECIST guideline (version 1.1)," Eisenhauer E. A., et al., *Eur J Cancer,* 2009 January; 45(2): 228-47. It should be noted that the RECIST guidelines equate the presence of tumor mass with the presence of cancer and decreases in tumor mass with anticancer efficacy. While tumor mass is an accurate metric for cytotoxic anticancer drugs and therapies that kill cancer cells, it is not an accurate metric for anticancer drugs that permanently abolish the potential for cell proliferation without necessarily killing cells (for example, bizelesin acts in this manner). By definition, cell populations (i.e., tumor masses) that do not and cannot proliferate, cannot exhibit malignant behavior and are not cancerous, even though said cell populations remain viable.

Completely inhibit the potential for cancer cell proliferation in a patient refers to decrease the probability of cancer cell clonogenic survival to less than approximately $10^{-(N+1)}$, where N is the approximate number of cancer cells in the patient.

Current establish therapies refers to existing regimens that are used to treat patients.

D0 refers to the dose of drug needed to reduce clonogenic cell survival by 37% or $e^{-1}$; IC37.

Derivative refers to a compound or moiety that has been further modified or functionalized from the corresponding compound or moiety.

Detoxification refers to decreasing or abolishing the cellular toxicity of a drug by means of spontaneous or cellular metabolic processes. For example, enzymatic or spontaneous nucleophilic reaction of GSH with alkylating agents results in detoxification of the alkylating agent.

DNA interstrand crosslinking agent refers to a drug or chemical agent that binds the DNA strands of the DNA double helix together with sufficient affinity as to preclude strand separation and thereby impair DNA synthesis. In general, but not always, said binding affinity results from covalent bonds formed between the crosslinking agent and the DNS strands. Examples of DNA crosslinking agents are provided in the following: DNA Cross-Linking Agents as Antitumor Drugs.; Rajski S R, Williams R M.; Chem Rev. 1998 Dec. 17; 98(8):2723-2796.

Fanconi/BRCA pathways of DNA repair refers to the cellular machinery, proteins, and processes involved in homologous recombination and the repair of DNA interstrand crosslinks; see: Regulation of DNA cross-link repair by the Fanconi anemia/BRCA pathway; Kim H, D'Andrea A D.; Genes Dev. 2012 Jul. 1; 26(13):1393-408; How the Fanconi anemia pathway guards the genome.; Moldovan G L, D'Andrea A D.; Annu Rev Genet. 2009; 43:223-49.

DNA interstrand crosslinking agent refers to a drug or chemical agent that binds the DNA strands of the DNA double helix together with sufficient affinity as to preclude strand separation and thereby impair DNA synthesis. In general, but not always, said binding affinity results from covalent bonds formed between the crosslinking agent and the DNS strands. Examples of DNA crosslinking agents are provided in the following: "DNA Cross-Linking Agents as Antitumor Drugs," Rajski S R, Williams R M.; Chem Rev., 1998 Dec. 17; 98(8): 2723-2796.

Dose modification factor: Dose Modification Factor= [drug concentration giving a 1-log reduction in clonogenic cell survival without the second drug(s) "X]/[drug concentration giving a 1-log reduction with drug(s) "X"]. For example, the drug could be melphalan and drug "X" could be BSO.

Durable complete response (also long-term CR) refers to a long-lasting complete remission (CR), a CR lasting at least 1 year off chemotherapy; or alternatively a CR lasting for a period of time greater than 0.5 X, wherein X is the median overall survival of comparable patients with the same type and stage of cancer treated with currently established therapies that fail to have a CR. For example, if the median overall survival for a particular type and stage of cancer were 18 months with current therapies, then for a CR to be considered durable CR in this setting it would have to exceed 9 months in duration.

Effective treatment of metastatic cancer: refers to a treatment or method that in "appropriately selected patients" gives high rates or high probabilities of one or more of the following: CRs, durable long-term CRs; long-term overall survival; long-term disease specific survival, long-term relative survival, long-term disease free survival; long-term progression free survival; apparent "cure;" and which generally preserves or improves the patient's quality of life. A grant of Breakthrough Drug Designation by the Food and Drug Administration (FDA) would provide supportive evidence of effectiveness. However, a treatment that is statistically superior to placebo, prolonged overall survival or progression free survival by several months and received FDA approval would by our definition be deemed ineffective. A treatment that gave high rates (e.g., 80%) of short-term (e.g., several months duration) CRs would be deemed ineffective. The term "appropriately selected patients" refers to patients that are good candidates for the treatment and that are likely to benefit. For example, a frail, elderly patient with serious underlying medical conditions (e.g., heart disease, liver disease, renal disease, severe malnutrition) would generally not be a good candidate. A patient with such advanced metastatic disease that he or she would be unlikely to survive the treatment would not be a good candidate. A patient with extensive metastatic disease to the brain would not be a good candidate. Methods for the appropriate selection of patients are well known to one skilled in the art.

The term appropriately selected patients refers to patients that are good candidates for the treatment and that are likely to benefit. For example, a frail, elderly patient with serious underlying medical conditions (e.g., heart disease, liver disease, renal disease, severe malnutrition) would generally not be a good candidate. A patient with such advanced metastatic disease that he or she would be unlikely to survive the treatment would not be a good candidate. A patient with extensive metastatic disease to the brain would not be a good candidate. Methods for the appropriate selection of patients are well known to one skilled in the art.

Electrophilic DNA crosslinking agent: refers to a DNA crosslinking agent that reacts with nucleophilic sites on DNA; for example, the bifunctional alkylating agents melphalan is an electrophilic DNA crosslinking agents that react with the nucleophilic centers on DNA N-7 of guanine and N-3 of adenine.

Glutathione (GSH) refers to a tripeptide with a gamma peptide bond between the amine group of cysteine and the carboxyl group of the glutamate side-chain, where the cysteine is attached by peptide bond to glycine. GSH is the major intracellular thiol compound; GSH is an important antioxidant and an important agent in the intracellular detoxification of reactive electrophiles, such as alkylating agents.

Glutamylcysteine synthetase (GCS) refers to an enzyme that catalyzes the ATP-dependent condensation of the amino group of cysteine and the carboxylate group of glutamate to form the dipeptide gamma-glutamylcysteine.

GSH mediated redox cycling refers to a process in which hydrogen peroxide (or other peroxides) oxidases a compound into a positively charged radical, which is reduced by GSH back to the original compound and the GSH is converted into the negatively charged GSH radical, which in turn reacts with GSH and $O_2$ to give GSSG and $O_2^-$, superoxide can then dismutate into generated $H_2O_2$ and $O_2$ which, in turn, can regenerate the positively charged radical and repeat the entire cycle, the net results that a catalytic amount of the compound can consume a large quantity of $O_2$ and a large quantity of GSH. The compound that generates the radical that is reduced by GSH is referred to as a "GSH mediated redox cycling agent." (See: "Glutathione oxidation during peroxidase catalyzed drug metabolism," Subrahmanyam W, McGirr L G, O'Brien P J.; Chem Bioi Interact., 1987 January; 61(1):45-5).

Glutathione peroxidase refers to an enzyme that catalyzes the conversion of hydrogen peroxide into water and GSH into GSSG.

Glutathione reductase (GR) refers to an enzyme that catalyzes the reduction of GSSG into GSH, NADPH is used as the reducing agent.

Glutathione disulfide (GSSG) refers to the compound formed by linking two GSH by a disulfide bond; also referred to as "oxidized GSH."

Glutathionylation refers to the formation of mixed disulfides between glutathione and low-pKa cysteinyl residues of proteins; The following reference relates to this matter; Dalle-Donne I, Rossi R, Giustarini D, Colombo R, Milzani A.; Free Radic Biol Med. 2007 Sep. 15; 43(6):883-98.

GSH transferases (GSTs) refer to a type of enzyme that catalyzes the addition of GSH to electrophilic substrates or chemical species, GSTs can catalyze the reaction of GSH with electrophilic DNA crosslinking agents, which generally results in detoxification.

High rate (or probability) of complete responses (hCR) refers to a rate (or probability) of CR that is approximately two times or greater than the rate (or probability) obtained with current established treatments for the particular type and stage of cancer; or alternatively a rate exceeding approximately 50%; wherein the term "the particular type" of cancer can refer not only to the histological type (i.e., serous ovarian cancer) but also to other clinically relevant qualifying properties such as platinum-resistance.

Homologous recombination refers to a DNA repair process that results in the removal and repair of DNA interstrand crosslinks and the repair of DNA double stranded breaks. (See: Regulation of DNA cross-link repair by the Fanconi anemia/BRCA pathway; Kim H, D'Andrea A D.; Genes Dev. 2012 Jul. 1; 26(13):1393-408; How the Fanconi anemia pathway guards the genome.; Moldovan G L, D'Andrea A D.; Annu Rev Genet. 2009; 43:223-49).

Hypersensitize cancer cells refers to a DNA crosslinking agent: to profoundly increase the sensitivity of cancer cells to the DNA crosslinking agent, which results in a much greater inhibition of cancer clonogenic survival; to profoundly decrease the AUC of the DNA crosslinking agent needed to give a 1-log reduction in cancer cell clonogenic survival by a factor of at least 3; the degree of hypersensitization is measured by the dose modification factor (DMF) for the DNA crosslinking agent and is generally greater than approximately 3.

IC90 refers to the drug concentration that gives a 90% decrease in clonogenic cell survival.

Inhibitor of DNA interstrand crosslink repair refers to a drug or set of drugs that directly or indirectly inhibits the removal of DNA interstrand crosslinks in cells and the restoration of the DNA to a double stranded structure.

Inhibitor of glutathione reductase refers to a drug or agent that inhibits GR activity or that spontaneously or after metabolic activation generates a chemical species that inhibits or inactivates GR.

Inhibitor of homologous recombination refers to a drug or set of drugs that directly or indirectly inhibits the biochemical processes and steps involved in HR.

Inhibitor of nucleotide excision repair (NER) refers to a drug or agent that inhibits the proteins enzymes or processes involved nucleotide excision repair; the inhibition can be a direct or indirect consequence of said agent.

The intracellular GSSG/2GSH reduction potential refers to a measure of the reducing activity of GSH under the intracellular conditions, it is given by $\Delta E$ in the Nernst equation:

$$\Delta E = Eph - RT/2F \ln [GSH]^2/[GSSG]$$

Wherein Eph is E0 the reduction potential under standard state conditions, (i.e., 1 molal solution, T=298 K or 25° C. and the pH) adjusted to the intracellular pH; R is the gas constant, F is the Faraday constant, T is the temperature, [GSH] is the glutathione concentration, and [GSSG] is the glutathione disulfide concentration at the intracellular location. At pH 7.0 Eph=~−240 mV, and at 37 C, $$\Delta E = \sim -240 - 30.8 \log[GSH]^2/[GSSG] \text{ in mV}$$

"Redox environment of the cell as viewed through the redox state of the glutathione disulfide/glutathione couple," Schafer F Q, Buettner G R.; Free Radic Bioi Med., 2001 Jun. 1; 30(11): 1191-212.

Improved patient outcome (relative to established therapies) refers to a higher rate of CRs and durable long-term CRs or longer overall survival, or longer progression free survival, or a higher quality of life, or similar efficacy with fewer or less significant side effects, especially chronic irreversible side effects, compared to established cancer therapies for the particular type of cancer.

Inhibitor of DNA interstrand crosslink repair: a compound or agent that directly or indirectly inhibits the removal of DNA interstrand crosslinks and or restoration of the integrity of the normal DNA double stranded structure at the site of DNA damage from said crosslinks.

Intrinsic drug resistance refers to the ability of populations of cancer cells to escape destruction or inactivation by a drug at levels that are clinically achievable and wherein said lack of sensitivity is manifest prior to drug exposure.

Irreversibly inhibit the potential for cancer cell proliferation refers to permanently inhibit or abolish the potential for cell proliferation; this can result from killing cells or by irreversibly inactivating cellular machinery that is required for cell proliferation; for example, unrepaired DNA interstrand crosslinks can permanently inhibit the potential for cell proliferation; the net effect can be either cell death or alternatively the cell can remain viable but permanently be unable to proliferate.

Irreversible inhibitor refers to an agent that permanently inactivates an enzyme, generally this occurs by covalent modification of the enzyme at site(s) that are essential for enzyme activity.

Liquid cancer refers to a cancer derived from the bone marrow or lymphatic tissues; examples include leukemia, lymphoma, and myeloma.

Log Reduction in cell survival refers to the decrease in cell clonogenic survival, a 1-log reduction means that the treatment results in a 90% decrease in cell survival, 2-log=99%, 3-logs=99.9%, etc. . . . .

Malignant behavior refers to proliferation and invasiveness in an abnormal context or setting in the body, wherein invasiveness is the expansion of cells into new space, which can be local or distant (i.e., metastatic) with the remodeling or destruction of existing tissue architecture and the creation of infrastructure to support the metabolic needs of the cells; the mechanisms of invasiveness can be carried out by malignant cells and/or non-malignant cells in the microenvironment; malignant behavior is the defining property of cancer.

Malignant cell refers to a cancer cell that expresses or can express malignant behavior. Not all tumor cells in a patient with cancer are malignant; many tumor cells in patients with cancer are dead-end, cannot proliferate, cannot engage in malignant behavior, and are not malignant cells.

Metastatic cancer refers to cancer that has spread beyond the local tissue site of origin to distant locations in the body, non-localized cancer; micro-metastatic cancer is metastatic cancer that is not detectable with conventional imaging technology because of the small size of the metastatic lesions.

Methylene blue: 3,7-bis(dimethylamino)-phenothiazin-5-ium chloride; the reduced form of methylene blue is known as leuco-methylene blue or N,N,N',N'-Tetramethyl-10H-phenothiazine-3,7-diamine.

NADPH refers to the reduced form of Nicotinamide adenine dinucleotide phosphate (NADP).

Nitrogen mustard analog refers to a compound containing two or more chloroethylamine groups or analog thereof; a compound that can transform in vivo or vitro into one with chloroethylamine groups, a compound that can form aziridinyl groups; chloroethylamine undergo intramolecular nucleophilic reactions with elimination of CL- and form aziridinyl groups.

Neoadjuvant setting refers to the administration of a chemotherapeutic drug or therapy before surgical resection of the primary tumor.

Non-homologous end joining (NHEJ) refers to a process for the repair of DNA double stranded DNA breaks that results in error prone repair. (See: "Induction and repair of DNA double strand breaks: the increasing spectrum of non-homologous end joining pathways," Mladenov E, Iliakis G.; Mutat Res., 2011 Jun. 3; 711(1-2): 61-72).

Non-refractory metastatic cancer refers to metastatic cancer of a type that can be effectively treated with established therapies; examples include most but not all testicular cancers, childhood acute lymphocytic leukemia, Hodgkin's lymphoma, follicular thyroid cancer and other cancers that are well known to one skilled in the art.

Nucleotide excision repair (NER) refers to a DNA repair process that removes nucleotides with bulky modifications and repairs the damage. (See: Kamileri I, Karakasilioti I, Garinis G A.; Trends Genet., 2012 November; 28(11): 566-73).

Oxidative stress refers to the condition that exists when the levels of reactive oxygen species (ROS) exceed the ability of cells to maintain these reactive chemical species within normal, physiological or acceptable levels. Oxidative stress is generally associated with an increase the intracellular GSSG/2GSH reduction potential and oxidative damage to biomolecules. (See: Karihtala P, Soini Y.; APMIS, 2007 February; 115(2): 81-103). Some methods for measuring oxidative stress are reviewed in: "Measuring reactive species and oxidative damage in vivo and in cell culture: How should you do it and what do the results mean?" Halliwell B, Whiteman M.; Br J Pharmacol., 2004; May; 142(2): 231-55.

P-glycoprotein (pgp) refers to the multidrug resistance protein 1 (MDR1) or ATP-binding cassette sub-family B member 1 (ABCB1). Pgp is a protein that can pump a wide range of hydrophobic compounds out of cells.

Potential for cell proliferation refers to the ability of cells to proliferate; clonogenic survival ability as measured by the ability to form colonies of cells; the potential for cell proliferation differs from cell proliferation; all malignant cells by definition have the potential for cell proliferation all the time, but most malignant cells are not actively engaged in proliferation most of the time as the cell proliferation is episodic.

Probability of clonogenic survival: clonogenic survival fraction.

Proteasome refers to a cellular organelle that is involved in the degradation of proteins.

Proteasome inhibitor refers to an agent that inhibits proteasome function. "Covalent and non-covalent reversible proteasome inhibition," Beck P, Dubiella C, Groll M.; Biol. Chem., 2012 October; 393(10): 1101-20.

Reactive oxygen species (ROS) refers to reactive oxygen related species such as superoxide (O2-), hydrogen peroxide (H2O2), hydroxy radical (OH.), and peroxy radicals (ROO.) Nitric oxide (NO.) and peroxynitrite anion (ONOO—). (See: "Free radicals, metals and antioxidants in oxidative stress-induced cancer," Valko M, Rhodes C J, Moncol J, Izakovic M, Mazur M.; Chem Biol Interact., 2006 Mar. 10; 160(1): 1-40).

Redox cycling refers to a series of chemical reactions in which a compound is reduced and the product is then oxidized by reaction with molecular oxygen, the catalytic cycle can repeat many times and consume large quantities of the reducing agent and large quantities of oxygen; for example quinones can be reduced by a variety of cellular enzymes by one electron transfer from NADH or NADPH to give semi-quinone radicals, which can react with oxygen to regenerate the quinone and give superoxide; redox cycling causes oxidative stress in cells by generating large amounts of superoxide and other reactive oxygen species; redox cycling can be represented as repetitive cycles of equations 1 and 2:

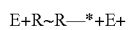  Equation 1:

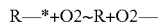  Equation 2:

where E is an electron donor, E+ is the oxidized form of E, and R—* is a free radical.

Redox cycling agent refers to a compound that engages in redox cycling; the term can refer to the reduced and/or oxidize for of the cycling chemical species that repetitively undergoes change in oxidation/reduction status; it is also used to refer to compounds that can generate by spontaneous or metabolic processes a redox cycling agent.

Refractory metastatic cancer refers to a metastatic cancer that has failed to adequately respond to therapy or metastatic cancer of a type that is known to be generally unresponsive to existing therapies and not be effectively treated by established therapies. For example, metastatic testicular cancer is highly curable and is generally not a refractory metastatic cancer, by contrast pancreatic cancer, melanoma, and platinum-resistant ovarian cancers are refractory metastatic cancers. One type of refractory is melphalan refractory cancer.

Set of drugs (e.g., agents or compositions) for use in a regimen to treat (a specified condition) refers to one or more drugs; if the set is comprised of drug #1, drug #2, drug #3 and drug #4 then term "a set of drugs for use in a regimen to treat (a specified disease) means:

drug #1 for use in a regimen to treat (a specified disease);
drug #2 for use in a regimen to treat (a specified disease);
drug #3 for use in a regimen to treat (a specified disease);
drug #4 for use in a regimen to treat (a specified disease);
wherein the regimen involves the combined use of drug #1, drug #2, drug #3 and drug #4.

Solid cancers refer to a cancer derived from a solid tissue; examples include pancreatic cancer, colon cancer, lung cancer, ovarian cancer.

Sumoylation refers to the enzymatic processes involved in the covalent attachment of small ubiquitin related modifier (SUMO) groups to proteins. (See: "The SUMO pathway: emerging mechanisms that shape specificity, conjugation and recognition," Gareau J R, Lima C D.; Nat Rev Mol Cell Biol., 2010 December; 11(12): 861-7).

As used herein, the term "subject" means a mammal in need of treatment or prevention, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of the specified treatment.

Synergy refers to a detectable effect that is greater (i.e., in a statistically significant manner relative to an appropriate control condition) in magnitude than the effect that can be detected when the compounds are used alone. The effect of the combination is greater than the expected additive effect of each component.

Thiolate refers to the negatively charged conjugate base of a thiol; a deprotonated thiol ion, in cells the protein thiolate content is largely determined by the content of cysteine-SH groups that have a pKa of approximately 7 or less.

Thiol reactive group (agent): also electrophilic-thiol-reactive group or agent or species), refers to any group or (agent) that is susceptible to nucleophilic attack by the lone-pair electrons on the sulfur atom of the thiol group or by the thiolate anion. Examples of thiol-reactive electrophilic groups include groups that have good leaving groups. For example, an alkyl group having a halide or alkoxy group attached to it or an α-halocarbonyl group are examples of thiol-reactive electrophilic groups. In another aspect, the thiol-reactive electrophilic group is an electron-deficient vinyl group. The term "an electron-deficient vinyl group" as used herein is a group having a carbon-carbon double bond and an electron-withdrawing group attached to one of the carbon atoms. An electron-deficient vinyl group is depicted in the formula Cβ=CαX, where X is the electron-withdrawing group. When the electron-withdrawing group is attached to Cα, the other carbon atom of the vinyl group (Cβ) is more susceptible to nucleophilic attack by the thiol group. This type of addition to an activated carbon-carbon double bond is referred to as a Michael addition. Examples of electron-withdrawing groups include, but are not limited to, a nitro group, a cyano group, an ester group, an aldehyde group, a keto group, a sulfone group, or an amide group. Examples of compounds possessing thiol-reactive electrphilic groups include, but are not limited to, maleimides, vinyl sulfones, acrylonitriles, α-methylene esters, quinone methides, acryloyl esters or amides, or α-halo esters or amides, isocyanates, isothiocyanates, thiocarbamates; epoxides; alpha, beta unsaturated carbonyls; gold(I) complexes auranofin, 1-chloro-2,4,dinitrochlorobenzene; disulfiram; nitric oxide, peroxynitrite.

Thioredoxin reductase (TrxR): an enzyme that utilizes NADPH to reduce thioredoxin disulfide to thioredoxin; the enzyme can also reduce a wide range of other disulfides. (See: "Reactive oxygen species, antioxidants, and the mammalian thioredoxin system." Nordberg J, Arner E S., Free Radic Biol Med., 2001 Dec. 1; 31(11): 1287-312).

Treatment refers to a therapy that provides a beneficial effect to a patient with a respect to a disease or condition. Treating refers to administering a treatment.

Ubiquitination refers to the enzymatic processes involved in the covalent attachment of ubiquitin to proteins. (See: Pickart C M, Eddins M J.; Biochim Biophys Acta., 2004 Nov. 29; 1695(1-3): 55-72).

Xeroderma pigmentosum group A protein (XP-A): an essential protein in NER recruits the ERCC1-XPF endonuclease complex to the site of DNA damage.

Disease refractory to most recent therapy-defined as less than 25% response or progression during or within 60 days after completion of therapy.

At the present time there are no effective treatment methods for most types of metastatic cancer. Currently therapies rarely give CRs. A CR corresponds to the disappearance of all detectable cancer and requires a decrease in the cancer cell burden in a patient of at least ~99% or 2-logs. Some reported rates of CRs in patients treated with state of the art therapies for metastatic cancer are as follows: pancreatic cancer—0.6%; melanoma—9.6%; platinum-resistant ovarian cancer—10.6%; platinum-resistant ovarian cancer—1.6%; Stage IV breast cancer—12%; renal cell cancer—1.1%; Androgen receptor positive, estrogen receptor negative Breast Cancer—0%; sarcoma—7%. Durable, long-term CRs are even less frequent and long-term survival rates for most types of metastatic cancer are dismal. (See: Conroy T, et al.; N Engl J Med. 2011 May 12; 364(19):1817-25; Wolchok J D, et al.; N Engl J Med. 2013 Jul. 11; 369(2): 122-33; Barber E L, et al.; J Gynecol Oncol. 2013 July; 24(3):258-64; Cadron I et al.; Gynecol Oncol. 2013 January; 128(1):34-7; Kellokumpu-Lehtinen P, et al.; Anticancer Res. 2013 June; 33(6):2623-7; Molina A M, et al.; Eur J Cancer. 2013 Sep. 16; Gucalp A, Tolaney S, Isakoff S J, Ingle J N, Liu M C, Carey L A, Blackwell K, Rugo H, Nabell L, Forero A, Stearns V, et al; on behalf of the Translational Breast Cancer Research Consortium (TBCRC 011); Clin Cancer Res. 2013 Oct. 1; 19(19):5505-5512; Lee S H, Chang M H, Baek K K, Han B, Lim T, Lee J, Park J O.; Oncology. 2011; 80(3-4):257-61).

Figure 1:
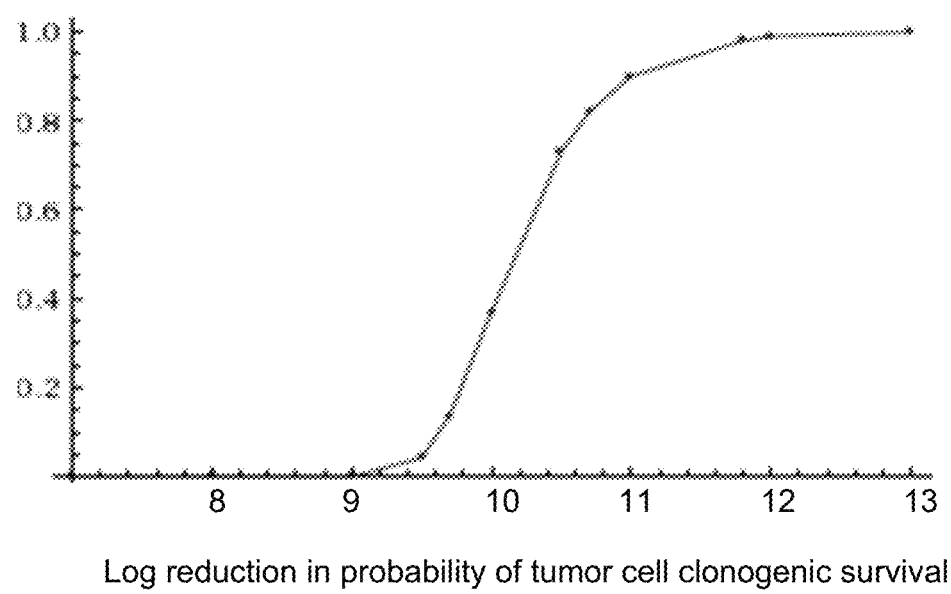
FIG. 1 is a plot that illustrates the probability of cure in a patient with a malignant cell burden of 10$^{10}$ cells versus a logarithmic reduction in the probability of clonogenic cancer cell survival after treatment. The plot demonstrates the joint probability that all cancer cells will not survive.

For obtaining a high rate of durable, long-term CRs, long-term disease free survival and cures it is necessary to kill or inactivate all malignant cells present in the patient. A single malignant cell that evades therapy can proliferate and potentially cause progressive recurrent disease. To a first approximation the probability of durable-long-term CRs or cures is given by $(1-P)^n$; where P is the probability of cancer cell clonogenic survival after the therapy and n is the number of malignant cells in the patient at the time of treatment. This formula gives the joint probability that no cancer cells will survive (See FIG. 1).

In a patient with micro-metastatic disease n is generally less than $\sim10^9$. In patients with detectable metastatic cancer n is $\sim10^9$ in early stage and be $\sim10^{12}$ in advanced metastatic disease. For a patient with a tumor cell burden of $n=10^9$, in order to obtain a high probability of long-term CR or cure, P must be less than $\sim10^{-10}$, which corresponds to a 10-log reduction in the probability of cancer cell clonogenic survival. For a patient with a tumor cell burden of $n=10^{10}$, in order to obtain a high probability of long-term CR or cure, P must be less than $10^{-11}$, (i.e., greater than an 11-log reduction in the probability of cancer cell clonogenic survival). Even greater log reductions are needed in patients with a greater tumor cell burden. Existing therapies rarely give even a 2-log reduction (e.g., a CR).

To achieve major-log reductions in the probability of cancer cell survival (e.g., a 12-log reduction), therapy must target a suitable property that is expressed by at least 99.9999999999% of malignant cells during the time period of treatment. The potential for cell proliferation is expressed by 100% of malignant cells 100% of the time, (even though most cancer cells are not actively engaged in proliferation most of the time). Most normal cells in the body are terminally differentiated and lack the potential for cell proliferation. However, cell proliferation is vital to life and health.

Figure 2A:
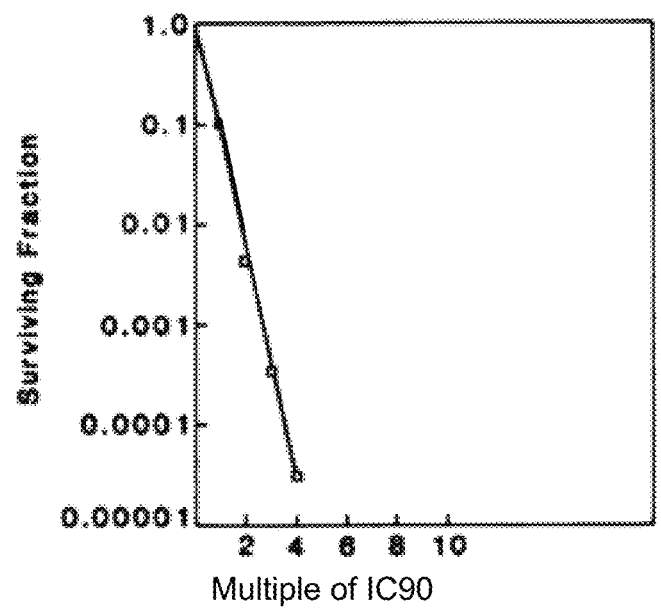
FIG. 2A is a plot that illustrates the log-linear dose response curve for the clonogenic survival fraction of MCF-7 human breast cancer cells versus melphalan concentration measured in IC90 units. The MCF-7 breast cancer cells were treated in vitro with melphalan for 1 hour. Frei E 3rd, Teicher B A, Holden S A, Cathcart K N, Wang Y Y; Cancer Res. 1988 Nov. 15; 48(22):6417-23.
Figure 2B:
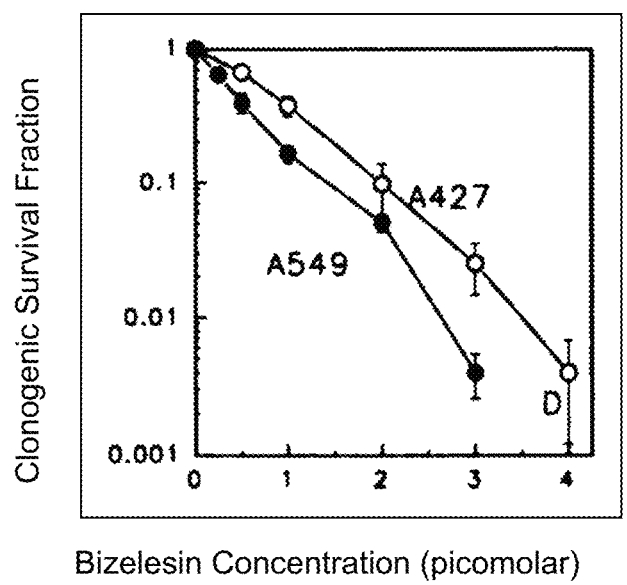
FIG. 2B is a plot that illustrates the log-linear dose response curve for the clonogenic survival fraction of A549 and A427 human lung carcinoma cells versus picomolar concentration of bizelesin. The A549 and A427 lung carcinoma cells were treated in vitro with bizelesin for 2 hours. Lee C S, Gibson N W; Cancer Res. 1991 Dec. 15; 51(24): 6586-91.

For certain types of drugs such as alkylating agents and DNA crosslinking agents there is a steep linear relationship between the log-reduction in cancer cell clonogenic survival and the drug dose or more generally the area under the drug concentration-time curve (AUC). For sensitive cancer cells this log-linear relationship can extend over many orders of magnitude. (See FIG. 2A and FIG. 2B) In principle, one could obtain major-log reductions in cancer cell clonogenic survival by giving high-doses of these drugs. In practice, the dose that can be safely administered to patients is limited by bone marrow toxicity. Normal bone marrow stem cells and most types of cancer cells have comparable sensitivity to these drugs. Accordingly, it has generally not been possible to achieve major-log reductions in the clonogenic survival of cancer cells without causing severe bone marrow toxicity in the patient.

Autologous bone marrow transplantation and hematopoietic stem cell infusion were developed four decades ago to circumvent the problem of bone marrow suppression and allow the clinical use of high dose chemotherapy. The bone marrow stem cells are infused after the chemotherapy drugs have declined to non-toxic levels in the blood. The infused stem cells then regenerate the bone marrow and restore normal bone marrow function.

High dose chemotherapy with bone marrow stem cell infusion is used for the treatment of myeloma, lymphoma, refractory leukemias, and certain rare metastatic cancers such as neuroblastoma, retinoblastoma, and progressive testicular and germ cell cancers; in these limited indications the approach has demonstrated effectiveness in prolonging survival and in some cases achieving cure. However, despite intensive efforts, and decades of research the method of high dose chemotherapy with bone marrow support has generally not been effective in the treatment of adult solid cancers. There is not a single active clinical trial involving intensive chemotherapy with bone marrow stem cell support for the treatment of common adult cancers in the U.S. listed in the National Institute of Health's clinical trial database.

See high-dose chemotherapy with autologous bone marrow transplantation; Spitzer G, Dicke K, Zander A R, Jagannath S, Vellekoop L, Freireich E J.; Cancer. 1984 Sep. 15; 54(6 Suppl):1216-25; An elective single autograft with high-dose melphalan: single-center study of 451 patients; Sirohi B, et al.; Bone Marrow Transplant. 2005 July; 36(1): 19-24; Conventional-dose chemotherapy compared with high-dose chemotherapy plus autologous hematopoietic stem-cell transplantation for metastatic breast cancer. Philadelphia Bone Marrow Transplant Group; Stadtmauer E A, et al.; N Engl J Med. 2000 Apr. 13; 342(15):1069-76; Randomized trial of high-dose chemotherapy and autologous hematopoietic stem cell support for high-risk primary breast carcinoma: follow-up at 12 years; Hanrahan E O et al., Cancer. 2006 Jun. 1; 106(11):2327-36; High dose chemotherapy and autologous stem cell transplantation as adjuvant therapy for primary breast cancer patients with four or more lymph nodes involved: long-term results of an international randomized trial.; Coombes R C et al., Ann Oncol. 2005 May; 16(5):726-34; Prospective, randomized comparison of high-dose chemotherapy with stem-cell support versus intermediate-dose chemotherapy after surgery and adjuvant chemotherapy in women with high-risk primary breast cancer: a report of CALGB 9082, SWOG 9114, and NCIC MA-13.; Peters W P, et al J Clin Oncol. 2005 Apr. 1; 23(10):2191-200; High-dose chemotherapy with autologous hematopoietic stem-cell support compared with standard-dose chemotherapy in breast cancer patients with 10 or more positive lymph nodes: first results of a randomized trial.; Zander A R, et al., J Clin Oncol. 2004 Jun. 15; 22(12):2273-83; Tallman M S, et al., N Engl J Med. 2003 Jul. 3; 349(1):17-26.; Berry D A, Ueno N T, Johnson M M, Lei X, Caputo J, Smith D A, Yancey L J, Crump M, Stadtmauer E A, Biron P, Crown J P, Schmid P, Lotz J P, Rosti G, Bregni M, Demirer T.; J Clin Oncol. 2011 Aug. 20; 29(24):3224-31.; Feldman D R, et al.; J Clin Oncol. 2010 Apr. 1; 28(10):1706-13.

Melphalan

In the methods and compositions of the invention, the compound (also referred to as agent or drug) melphalan (CAS No. 148-82-3) is administered. Melphalan is a bifunctional alkylating agent that crosslinks DNA and thereby inhibits cancer cell clonogenic survival. A number of clinical trials have evaluated the use of high dose melphalan in conjunction with bone marrow transplantation or hematopoietic stem cell infusion. It will be appreciated that in the methods and compositions described herein, any suitable form of the active principle may be used, e.g., another salt form, or a prodrug or active metabolite.

High dose melphalan has generally been ineffective in the treatment of metastatic cancer, compete remissions when they occur have typically been of short duration.

High dose melphalan (200 mg/m2) gives a melphalan AUC of approximately 40 microM h. The sensitivity of cancer cells to melphalan varies over a wide range. However, it is not unusual for a 1-log reduction in cancer cell clonogenic survival to require a melphalan AUC of ~10 microM h. This means that high dose melphalan would be expected to achieve ~4 log reduction in cancer cell survival, which is far less than the 11-12 log reduction needed for cure.

The pharmacologic basis of high dose chemotherapy with haematopoietic stem cell support for solid tumours; Porrata L F, Adjei A A.; Br J Cancer. 2001 Aug. 17; 85(4):484-9; Chemotherapy for malignant melanoma: combinations and high doses produce more responses without survival benefit; Lakhani S, Selby P, Bliss J M, Perren T J, Gore M E, McElwain T J; Br J Cancer. 1990 February; 61(2):330-4; Intensive melphalan chemotherapy and cryopreserved autologous bone marrow transplantation for the treatment of refractory cancer; Lazarus H M, Herzig R H, Graham-Pole J, Wolff S N, Phillips G L, Strandjord S, Hurd D, Forman W, Gordon E M, Coccia P, et al.; J Clin Oncol. 1983 June; 1(6):359-67; High-dose alkylating agent therapy: a review of clinical experiences.; Cornbleet M A, Leonard R C, Smyth J F.; Cancer Drug Deliv. 1984 Summer; 1(3):227-38; High-dose intravenous melphalan: a review.; Samuels B L, Bitran J D.; J Clin Oncol. 1995 July; 13(7):1786-99.

Melphalan is taken up by cancer cells by means of the LAT1 amino acid transporter and the sodium dependent ASC transport system. LAT1 is overexpressed in a wide range of metastatic cancers. Cellular pharmacokinetics of the phenylalanine mustards; Vistica D T.; Pharmacol Ther. 1983; 22(3):379-406.

In aqueous solution, melphalan undergoes intermolecular displacement of chloride with the formation of positively charged, reactive aziridinium intermediates, which react with ambient nucleophiles such as water, phosphate, thiols, and amino groups. The fate of the reactive aziridinium intermediate in cells determines the cytotoxicity of the melphalan. Reaction with DNA and the subsequent production of interstrand crosslinks leads to potentially lethal lesions. By contrast, reaction with water or intracellular thiols detoxifies the drug.

Melphalan alkylates DNA forming mono-adducts, which can further react to give interstrand crosslinks. Peak levels of melphalan-DNA mono-adducts form ~2 hours post melphalan exposure and DNA interstrand crosslinks peak after ~8 hours. DNA crosslinking interferes with cell proliferation and is the principle cytotoxic lesion of melphalan. The drug also causes double stranded DNA breaks in proliferating cells, which can be cytotoxic.

Cells can develop resistance to melphalan by a number of mechanisms including: increased efflux of drug out of the cell mediated by MDR1 or the p-glycoprotein pump; increased levels of cellular thiols, principally glutathione (GSH) and increased levels of glutathione transferase that detoxify the drug and preclude DNA crosslinking; increased levels of DNA repair enzymes that excise melphalan-DNA mono-adducts, repair melphalan-induced DNA double stranded breaks, and repair DNA interstrand crosslinks.

Depletion of intracellular GSH with buthionine sulfoximine (BSO) decreases the melphalan AUC needed to give a 1-log reduction in cancer cell survival by about a factor of 3. In other words, the dose modification factor achieved by depletion of GSH with BSO is ~3. BSO and melphalan (15 mg/m2) was evaluated in clinical trials for the treatment of a number of different types of metastatic cancer. Minimal antitumor activity was seen. Melphalan at 15 mg/m2 typically gives a drug AUC of ~3 microM h. Since the DMF for melphalan in conjunction with BSO is ~3, this would be equivalent to melphalan alone at an AUC of ~9 microM h. As discussed previously, for many cancers a melphalan AUC of ~10 microM h is needed to get a 1-log reduction in tumor cell survival. This explains in part the poor clinical responses seen in most patients treated with BSO and melphalan (15 mg/m2).

Even with high dose chemotherapy and bone marrow stem cell support, it has not been possible to achieve the 11-12 log reduction in cancer cell clonogenic survival needed to obtain high rates of long-term CRs and cures for most types of metastatic cancers. The problems are intrinsic and acquired drug resistance. This is illustrated by the clinical experience with melphalan and bone marrow transplantation. A number of clinical trials have evaluated the use of high dose melphalan in conjunction with bone marrow transplantation or hematopoietic stem cell infusion. High dose melphalan has generally been ineffective in the treatment of metastatic cancer, compete remissions when they occur have generally been of short duration.

The present invention provides a means to address the problems of intrinsic and acquired drug resistance and obtain greater than a 12-log reduction in the probability of cancer cell survival.

The methods of the present invention are also applicable to other electrophilic agents and alkylating agents that (like melphalan) cause DNA crosslinks including: for example, chlorambucil, cyclophosphamide, bendamustine, bizelesin, ifosfamide, cisplatin, carboplatin, oxaliplatin, thiotepa, busulfan, and mitomycin c. The general applicability of the method to sensitize cells to DNA crosslinking agents is due to the common mechanisms of GSH mediated detoxification of electrophiles and the common mechanisms involved in the repair of DNA interstrand crosslinks regardless of the particular crosslinking agent. (See: Rajski S R, Williams R M.; Chem Rev. 1998 Dec. 17; 98(8):2723-2796.)

Compounds (e.g., Agents or Drugs) for Oxidative Stress

The timing of GSH depletion is also determined for proper therapy. Oxidant stress and decreased GSH levels trigger the activation of a network of genes that produce proteins that act to counteract reactive oxygen species (ROS), and elevate intracellular thiol levels. Activation of NRF2 plays a key role in orchestrating this response. NRF2 activation can elevate a host of factors that could lower the cytotoxicity of melphalan. For example, NRF2 activation increases the π class of glutathione S-transferase, which can catalyze the detoxification of melphalan. NRF2 activation can also elevate metallothionein levels, which can detoxify melphalan.

Accordingly, sensitization to melphalan by GSH depletion is greatest when the GSH levels are acutely depressed simultaneously with melphalan administration. Chronic GSH depletion over many hours prior to melphalan (e.g., 24-48 hours as with BSO) will evoke compensatory responses that lessen the sensitization effect.

BCNU

BCNU, 1,3-bis(2-chloroethyl)-1-nitrosourea (CAS No. 154-93-8), inhibits glutathione reductase, which is critical to maintaining cellular GSH levels in the presence of oxidative stress. Glutathione reductase catalyzes the reduction by NADPH of GSSG to GSH. Doxorubicin undergoes redox cycling, which results in increased superoxide that is converted into hydrogen peroxide by superoxide dismutase. Glutathione peroxidase catalyzes the conversion of hydrogen peroxide and GSH into water and GSSG. The net effect of the combination of BCNU and doxorubicin is the rapid depletion of intracellular GSH and increased levels of hydrogen peroxide and other reactive oxygen species. In cancer cells this results in a period of oxidative stress, which hypersensitizes the cancer cells to melphalan and DNA crosslinking agents. The melphalan or alkylating agent needs to be given during this period of oxidative stress. (See: Jevtović-Todorović V, Guenthner T M.; J Cancer Res Clin Oncol. 1991; 117(4):313-20; Jevtović-Todorović V, Guenthner T M.; Biochem Pharmacol. 1992 Oct. 6; 44(7):1383-93.; Doroshow J H, Akman S, Chu F F, Esworthy S.; Pharmacol Ther. 1990; 47(3):359-70.; Powis G.; Pharmacol Ther. 1987; 35(1-2):57-162).

The sensitization to melphalan achieved with doxorubicin and BCNU can enable major log-reductions in cancer cell clonogenic survival at clinically achievable melphalan doses. Treatment with sub-toxic concentrations of BCNU and doxorubicin (1 microM) decreased the melphalan AUC needed to give a 1-log reduction in clonogenic survival of three separate human melanoma cell lines to ~0.5 microM h. Intermediate IV dose melphalan (70 mg/m2) would give a melphalan AUC of ~13 microM h. In the presence of doxorubicin+BCNU the AUC needed for a 1-log reduction in clonogenic survival was 26 times lower (~0.5 microM h) even in highly resistant melanoma cell lines. The log reduction in clonogenic survival is generally a linear function of melphalan AUC. Accordingly, intermediate dose melphalan (i.e., 70 mg/m2) in conjunction with sensitization with BCNU and doxorubicin would be expected to result in major, potentially curative log-reductions in cancer cell clonogenic survival.

Lomustine

Lomustine is another agent that can be used in the methods described herein. Lomustine (or CCNU; marketed under the name CeeNU in U.S.) is an alkylating nitrosourea compound used in chemotherapy. This is a highly lipid soluble drug, and thus crosses the blood-brain barrier. This property makes it ideal for treating brain tumors, and is its primary use. Lomustine has a long time to nadir (the time when white blood cells reach their lowest number). The CAS No. is 13010-47-4.

In a certain aspect the method involves the administration of a set of one or more drugs that induce oxidative stress and the administration of IV melphalan during said period of oxidative stress to a patient with metastatic cancer. In a preferred embodiment the melphalan dose is in the range of ~15 to ~200 mg/m2 and is administered over ~30 to ~60 minutes. In an alternative embodiment the melphalan dose is in the range of ~15 to ~50 mg/m2. In an alternative embodiment the melphalan dose is in the range of ~50 to ~70 mg/m2. In an alternative embodiment the melphalan dose is in the range of ~70 to ~200 mg/m2.

In another embodiment the set of drugs that induce oxidative stress includes and inhibitor of glutathione reductase (GR). In one aspect, the GR inhibitor irreversibly inactivates the enzyme.

Examples of irreversible inhibitors include chloroalkylnitrosoureas, for example, in certain embodiments the GR inhibitor is BCNU (carmustine) or CCNU (Lomustine). Combinations of GR inhibitors can also be used.

The dose of the GR inhibitor is chosen to be sufficient to at least an ~50-80% reduction in GR enzyme activity. For example, the dose of BCNU is ~70 to ~100 mg/m2 give IV over ~30 minutes in certain embodiments of the invention. (See: Babson J R, Reed D J.; Biochem Biophys Res Commun. 1978 Jul. 28; 83(2):754-62.; Frischer H, Ahmad T.; J Lab Clin Med. 1977 May; 89(5):1080-91).

In preferred embodiments, a redox cycling drug is administered in conjunction with the GR inhibitor, preferably after the GR inhibitor has had time to react with and deplete GR activity cells in the body or at the same time. For BCNU, this would generally be ~0.25 to 2 hours after BCNU administration.

A large number of drugs can undergo redox cycling and induce oxidative stress. Such drugs are well known to one skilled in the arts. (See: Wondrak G T.; Antioxid Redox Signal. 2009 December; 11(12):3013-69). In a preferred embodiment the redox cycling drug is an anthracycline. In a preferred embodiment it is doxorubicin. In preferred embodiments the doxorubicin is given intravenously (IV) at a dose of ~15 to ~60 mg/m2. In a preferred embodiment the doxorubicin dose is ~30 to ~40 mg/m2.

Methylene Blue

Methylene blue (MB) is another preferred redox cycling agent to be used in conjunction with a glutathione reductase inhibitor to deplete GSH levels and generate oxidative stress. MB undergoes facile 2-electron reduction to give the colorless, neutrally charged, leuco-MB. A wide range of electron donors can reduce MB including NADPH, NADH and GSH. Leuco-MB can in turn reduce oxygen to hydrogen peroxide and convert Fe+3 to Fe+2. Low levels of MB can lead to oxidant stress and the generation of ROS. In cells, the net effect of MB is electron flow from NADPH, NADH, and GSH to molecular oxygen, increased oxygen consumption, increased H2O2 production, and stimulation of the pentose cycle, which generates NADPH. Glutathione peroxidase catalyzed reduction of hydrogen peroxide generated by redox-cycling of MB can deplete GSH. MB can also directly oxidize GSH to GSSG and undergoes redox cycling in the presence of oxygen.

Methylene blue is concentrated by pigmented melanoma cells, which would be advantageous in the treatment of melanoma. Methylene blue is approved for the treatment of methemoglobinemia. The drug has also been used for the treatment of refractory hypotensive shock, malaria, detection of sentinel lymph nodes, and the treatment and prevention of encephalopathy associated with high dose ifosfamide therapy. MB potently inhibits monoamine oxidase, guanylate cyclase and nitric oxide synthase. MB is contraindicated in patients treated with serotonin uptake inhibitors and can precipitate serotonin syndrome, but otherwise has a favorable safety profile. MB alone generally has minimal cytotoxicity for cells.

The dose of IV methylene blue would preferably be in the range of ~1 mg/kg to ~5 mg/kg. In a preferred embodiment the patient would be treated with BCNU and then given IV boluses of ~1 mg/kg of methylene blue until the desired level of oxidative stress and GSH depletion is obtained. In a preferred embodiment the desired level of GSH depletion in peripheral blood cells is 50% or greater.

Oxidative stress and GSH levels can be rapidly measured in peripheral blood cells by a variety of techniques known to one skilled in the arts. (See: May J M, Qu Z C, Whitesell R R.; Biochem Pharmacol; 2003 Sep. 1; 66(5):777-84; Oz M, Lorke D E, Hasan M, Petroianu G A.; Med Res Rev. 2011 January; 31(1):93-117; Biaglow J E, Koch C J, Tuttle S W, Manevich Y, Ayene I S, Bernhard E J, McKenna W G, Kachur A V.; Int J Radiat Oncol Biol Phys. 1998 Nov. 1; 42(4):769-73; Kelner M J, Alexander N M.; J Biol Chem. 1985 Dec. 5; 260(28):15168-71; Link E M, Blower P J, Costa D C, Lane D M, Lui D, Brown R S, Ell P J, Spittle M F.; Eur J Nucl Med. 1998 September; 25(9):1322-9; Pelgrims J, De Vos F, Van den Brande J, Schrijvers D, Prové A, Vermorken J B.; Br J Cancer. 2000 January; 82(2):291-4; Oz M, Lorke D E, Hasan M, Petroianu G A.; Med Res Rev. 2011 January; 31(1):93-117; Sweiss K I, Beri R, Shord S S.; Drug Saf. 2008; 31(11):989-96; Pelgrims J, De Vos F, Van den Brande J, Schrijvers D, Prové A, Vermorken J B.; Br J Cancer. 2000 January; 82(2):291-4; Buehring G C, Jensen H M.; Cancer Res. 1983 December; 43(12 Pt 1):6039-44.; Berger S J, Gosky D, Zborowska E, Willson J K, Berger N A.; Cancer Res. 1994 Aug. 1; 54(15):4077-83; Pastore A, Federici G, Bertini E, Piemonte F; Clin Chim Acta. 2003 Jul. 1; 333(1):19-39; Michaelsen J T, Dehnert S, Giustarini D, Beckmann B, Tsikas D.; J Chromatogr B Analyt Technol Biomed Life Sci. 2009 October 15; 877(28):3405-17.; Halliwell B, Whiteman M.; Br J Pharmacol. 2004 May; 142 (2):231-55).

Proteasome Inhibitors

However, GSH depletion alone may not be sufficient in all cases to adequately sensitize cells to melphalan and overcome drug resistance. Other mechanisms of melphalan resistance must be concurrently addressed. Phase I study of continuous-infusion L-S,R-buthionine sulfoximine with intravenous melphalan.; Bailey H H, Ripple G, Tutsch K D, Arzoomanian R Z, Alberti D, Feierabend C, Mahvi D, Schink J, Pomplun M, Mulcahy R T, Wilding G.; J Natl Cancer Inst. 1997 Dec. 3; 89(23):1789-96; and Phase I trial of buthionine sulfoximine in combination with melphalan in patients with cancer.; O'Dwyer P J, Hamilton T C, LaCreta F P, Gallo J M, Kilpatrick D, Halbherr T, Brennan J, Bookman M A, Hoffman J, Young R C, Comis R L, Ozols R F.; J Clin Oncol. 1996 January; 14(1):249-56; Activation of Nrf2 is required for up-regulation of the π class of glutathione S-transferase in rat primary hepatocytes with L-methionine starvation.; Lin A H, Chen H W, Liu C T, Tsai C W, Lii C K.; J Agric Food Chem. 2012 Jul. 4; 60(26): 6537-45; Transfection of glutathione S-transferase (GST)-pi antisense complementary DNA increases the sensitivity of a colon cancer cell line to adriamycin, cisplatin, melphalan, and etoposide.; Ban N, Takahashi Y, Takayama T, Kura T, Katahira T, Sakamaki S, Niitsu Y.; Cancer Res. 1996 Aug. 1; 56(15):3577-82; Effect of sulforaphane on metallothionein expression and induction of apoptosis in human hepatoma HepG2 cells.; Yeh C T, Yen G C.; Carcinogenesis. 2005 December; 26(12):2138-48; Covalent sequestration of melphalan by metallothionein and selective alkylation of cysteines.; Yu X, Wu Z, Fenselau C.; Biochemistry. 1995 Mar. 14; 34(10):3377-85.

The repair of DNA interstrand crosslinks is mediated by complex biochemical machinery mediate homologous recombination (HR). Multiple steps in the processes of HR and interstrand DNA crosslink repair require proteasome function, directly or indirectly. Proteasome inhibitors have been shown to inhibit HR and sensitize cells to DNA interstrand crosslinking agents such as melphalan. High dose melphan (200 mg/m2) is used in combination with proteasome inhibitors such as Velcade and Kyprolis for the treatment of myeloma in conjunction with hematopoietic stem cell support; however, melphalan resistance is still a problem, and the therapy is not curative. (See: Bortezomib and high-dose melphalan as conditioning regimen before autologous stem cell transplantation in patients with de novo multiple myeloma: a phase 2 study of the Intergroupe Francophone du Myelome (IFM).; Roussel M, Moreau P, Huynh A, Mary J Y, Danho C, Caillot D, Hulin C, Fruchart C, Marit G, Pégourié B, Lenain P, Araujo C, Kolb B, Randriamalala E, Royer B, Stoppa A M, Dib M, Dorvaux V, Garderet L, Mathiot C, Avet-Loiseau H, Harousseau J L, Attal M; Intergroupe Francophone; The proteasome inhibitor PS-341 markedly enhances sensitivity of multiple myeloma tumor cells to chemotherapeutic agents.; Ma M H, Yang H H, Parker K, Manyak S, Friedman J M, Altamirano C, Wu Z Q, Borad M J, Frantzen M, Roussos E, Neeser J, Mikail A, Adams J, Sjak-Shie N, Vescio R A, Berenson J R.; Clin Cancer Res. 2003 March; 9(3):1136-44.; 1. Inhibitors of the proteasome suppress homologous DNA recombination in mammalian cells.; Murakawa Y, Sonoda E, Barber L J, Zeng W, Yokomori K, Kimura H, Niimi A, Lehmann A, Zhao G Y, Hochegger H, Boulton S J, Takeda S.; Cancer Res. 2007 Sep. 15; 67(18):8536-43. Bortezomib-induced "BRCAness" sensitizes multiple myeloma cells to PARP inhibitors; Neri P, Ren L, Gratton K, Stebner E, Johnson J, Klimowicz A, Duggan P, Tassone P, Mansoor A, Stewart D A, Lonial S, Boise L H, Bahlis N J.; Blood. 2011 Dec. 8; 118(24):6368-79; Proteasome function is required for DNA damage response and fanconi anemia pathway activation.; Jacquemont C, Taniguchi T.; Cancer Res. 2007 Aug. 1; 67(15):7395-405; Degradation-linked ubiquitin signal and proteasome are integral components of DNA double strand break repair: New perspectives for anti-cancer therapy.; Ramadan K, Meerang M.; FEBS Lett. 2011 Sep. 16; 585 (18):2868-75. The vital link between the ubiquitin-proteasome pathway and DNA repair: impact on cancer therapy.; Motegi A, Murakawa Y, Takeda S.; Cancer Lett. 2009 Sep. 28; 283(1):1-9.

Treatment of cells with proteasome inhibitors trigger a variety of biochemical processes that can contribute to melphalan resistance. Inhibition of proteasome function activates NRF2 and elevates GSH levels. This effect takes about 2 hours. Activated NRF2 in turn triggers a variety of cellular responses that inhibit the cytotoxic effect of alkylating agents such as melphalan. (See Proteasome inhibition induces glutathione synthesis and protects cells from oxidative stress: relevance to Parkinson disease.; Yamamoto N, Sawada H, Izumi Y, Kume T, Katsuki H, Shimohama S, Akaike A.; J Biol Chem. 2007 Feb. 16; 282(7):4364-72.; Proteasome inhibition induces a p38 MAPK pathway-dependent antiapoptotic program via Nrf2 in thyroid cancer cells.; Du Z X, Yan Y, Zhang H Y, Liu B Q, Gao Y Y, Niu X F, Meng X, Wang H Q.; J Clin Endocrinol Metab. 2011 May; 96(5):E763-71; Increased protein stability as a mechanism that enhances Nrf2-mediated transcriptional activation of the antioxidant response element. Degradation of Nrf2 by the 26 S proteasome.; Nguyen T, Sherratt P J, Huang H C, Yang C S, Pickett C B.; J Biol Chem. 2003 Feb. 14; 278(7):4536-41).

The present invention relates to methods for the treatment of metastatic cancer with melphalan in conjunction with drugs that concurrently address all of the major mechanisms of melphalan resistance. The methods are designed to enable major, potentially curative log-reductions in cancer cell clonogenic survival to be achieved at clinically tolerated doses of melphalan in conjunction with hematopoietic stem cell support.

For example, treatment of melanoma cells with sub-toxic concentrations of carmustine (BCNU) and doxorubicin profoundly sensitize the cells to melphalan. The AUC needed to give a 1-log reduction in clonogenic survival is reduced by a factor of ~15 to 55 fold. (i.e., DMF=15-55). No increase in melphalan cytotoxicity is seen with the combination of BCNU and doxorubicin in normal fibroblasts. This likely reflects the increased level of oxidative stress that is characteristic of cancer cells. See: ROS stress in cancer cells and therapeutic implications.; Pelicano H, Carney D, Huang P.; Drug Resist Updat. 2004 April; 7(2):97-110.

In certain embodiments, the method treats patient with the metastatic cancer after the surgical removal or ablation of bulk tumor. However, in certain situations, the method is used in the neoadjuvant setting to enable surgical resection of an otherwise unresectable tumor.

Prior to being treated with the present method, hematopoietic stem cells would generally be collected from the patient and stored. The technology of hematopoietic stem cell collection, purification, storage and infusion is routinely used in the treatment of myeloma and is well known to one skilled in the arts.

Anticancer drugs that can inhibit the potential for cell proliferation are well known to one skilled in the arts and have been extensively used to treat cancer. However, as previously discussed there are currently no methods for obtaining high rates or high probabilities of CRs and durable, long-term CRs in patients with most types of metastatic cancers and in all types of refractory metastatic cancers.

Metastatic Cancers

Metastatic cancers within the scope of treatment with the current invention include but are not limited to: Acute Lymphoblastic Leukemia (ALL); Acute Myeloid Leukemia (AML); Adrenocortical Carcinoma; Anal Cancer; Appendix Cancer; Basal Cell Carcinoma; Bile Duct Cancer; Bladder Cancer; Breast Cancer; adenocarcinoma of the breast, (ductal and lobular) Bronchial cancer; Burkitt's lymphoma; Carcinoid Tumor; Carcinoma of Unknown Primary; Cervical Cancer; Chronic Lymphocytic Leukemia (CLL); Chronic Myelogenous Leukemia (CML); Colon Cancer; Colorectal Cancer; Cutaneous T-Cell Lymphoma; Embryonal Tumors; Endometrial Cancer; Esophageal Cancer; Esthesioneuroblastoma, Childhood; Ewing Sarcoma; Extracranial Germ Cell Tumor; Extragonadal Germ Cell Tumor; Ocular Melanoma; Retinoblastoma; Malignant Fibrous Histiocytoma of Bone, Osteosarcoma; Gallbladder Cancer; Gastric Cancer; Gastrointestinal Carcinoid Tumor; Gastrointestinal Stromal Tumors (GIST); Germ Cell Tumors; Gestational Trophoblastic Disease; Hairy Cell Leukemia; Head and Neck Cancer; Hepatocellular Cancer; Malignant Histiocytosis; Langerhans Cell cancer; Hodgkin Lymphoma; Hypopharyngeal Cancer; Malignant Islet Cell Tumors, Pancreatic Neuroendocrine Tumors; Kaposi Sarcoma; Kidney cancers; Renal Cell; Wilms Tumor; Langerhans Cell Histiocytosis; Laryngeal Cancer; Leukemia; Lip and Oral Cavity Cancer; Lung Cancer; Non-Small Cell lung cancer; Small cell lung cancer; Lymphoma; AIDS-Related; Non-Hodgkin lymphoma; Macroglobulinemia, Waldenström; Melanoma; Merkel Cell Carcinoma; Mesothelioma; Multiple Myeloma/Plasma Cell cancer; Mycosis Fungoides; Nasal Cavity and Paranasal Sinus Cancer; Nasopharyngeal Cancer; Neuroblastoma; Oral Cancer; Oropharyngeal Cancer; Ovarian Cancer; Pancreatic Cancer; pancreatic adenocarcinoma; Pancreatic Neuroendocrine Tumors; Paranasal Sinus and Nasal Cavity Cancer; Parathyroid Cancer; Penile Cancer; Pharyngeal Cancer; Pheochromocytoma; Prostate Cancer; Prostatic adenocarcinoma; Rectal Cancer; Renal Cell Cancer; Renal Pelvis and Ureter, Transitional Cell Cancer; Retinoblastoma; Rhabdomyosarcoma; Salivary Gland Cancer; Sarcoma; Osteosarcoma; Rhabdomyosarcoma; Merkel Cell Carcinoma; Small Intestine Cancer; Soft Tissue Sarcoma; Squamous Cell Carcinoma; Squamous Neck Cancer with Occult Primary, T-Cell Lymphoma; Testicular Cancer; Thymic Carcinoma; Thyroid Cancer; (papillary, follicular, medullary and anaplastic); Transitional Cell Cancer of the Renal Pelvis and Ureter; Urethral Cancer; Uterine Cancer, Endometrial Uterine Sarcoma; Waldenström Macroglobulinemia; Wilms Tumor; Vaginal Cancer; and Vulvar Cancer; platinum-resistant ovarian cancer; adenocarcinoma of the small intestine; triple-negative breast cancer; and melphalan-resistant myeloma, More detailed descriptions of metastatic cancers, all of which are within the scope of the present invention are provided in the following reference: Holland-Frei Cancer Medicine, 6th edition, Edited by Donald W Kufe, MD, Raphael E Pollock, MD, PhD, Ralph R Weichselbaum, MD, Robert C Bast, Jr, MD, Ted S Gansler, MD, MBA, James F Holland, MD, ScD and Emil Frei, III, MD; BC Decker Inc., Hamilton, Ontario.

EMBODIMENTS OF THE INVENTION

Irreversible inhibition of the potential for cancer cell proliferation is obtained by the first Embodiment of the invention, (E1) a method for the effective treatment of metastatic cancer comprised of the administration of a set of one or more drugs, wherein said set of drugs irreversibly inhibit the potential for cancer cell proliferation.

Prior to being treated with the present method, hematopoietic stem cells would generally be collected from the patient and stored for later infusion to reverse drug induced bone marrow toxicity. The technology of hematopoietic stem cell collection, purification, storage and infusion is routinely used in the treatment of myeloma and is well known to one skilled in the arts. These stem cells would be typically collected prior to the administration of said drugs and infused in the patient after the blood levels of said drugs have reached non-toxic levels. Purified autologous bone marrow stem cells are strongly preferred. However, other allogeneic bone marrow stem cells can also be employed. Technology for hematopoietic stem cell collection, purification and storage is well known to one skilled in the arts. The use of purified stem cell preparations enriched for CD34+ hematopoietic cells and depleted of circulating tumor cells is preferred. See: Mapara M Y, et al.; Exp Hematol. 1999 January; 27(1):169-75; Mohr M, et al.; Clin Cancer Res. 1999 May; 5(5):1035-40; Cellular, Tissue and Gene Therapies Advisory Committee; Meeting Date: Sep. 23, 2011; CliniMACS® CD34 Reagent System; Briefing Package; HUD #04-0146; HDE #BH110018, U.S. Food and Drug Administration.

The methods of the invention are applicable to refractory solid metastatic cancers and refractory liquid metastatic cancers. The methods of the invention include methods of obtaining high rates of CRs and durable, long-term CRs in patients with refractory metastatic cancers.

Embodiment E1

Embodiment E1 of the present invention is a method for obtaining CRs and durable, long-term CRs in patients with refractory metastatic cancers wherein the method is comprised of the administration of a set of one or more drugs that irreversibly inhibit the potential for cancer cell proliferation.

Embodiment Ee1

Embodiment Ee1 of the present invention is a set of drugs for use in a regimen for the treatment of refractory metastatic cancers and to obtain high rates of complete responses and durable, long-term complete responses in patients, wherein said set of drugs irreversibly inhibit the potential for cancer cell proliferation.

E1 can be expressed in an essentially equivalent form, as a method for obtaining high probabilities of a CR and a durable, long-term CR in a patient with refractory metastatic cancer, wherein said method is comprised of the administration of a set of one or more drugs that irreversibly and permanently inhibit the potential for cancer cell proliferation. Non-refractory metastatic cancers are generally sensitive to chemotherapy. While refractory metastatic cancers are generally resistant to chemotherapy. An effective treatment of refractory metastatic cancer would necessarily be an effective treatment for non-refractory metastatic cancer. The evolutionary nature of cancer implies that for a treatment to be effective in a refractory metastatic cancer it must also be effective against non-refractory metastatic cancer of the same type. If there were not the case then cancer cells similar to those in a patient with "non-refractory metastatic cancer" could evolve in a patient with "refractory metastatic cancer" that was treated with "effective therapy" and these cells could evade the "effective therapy" and cause progressive disease, which would leads to the contradiction that "effective therapy" was ineffective.

Embodiment (E2)

Embodiment (E2) of the present invention is a method for the effective treatment of non-refractory metastatic cancer comprised of the administration of a set of one or more drugs, wherein said set of drugs irreversibly inhibits the potential for cancer cell proliferation and wherein said method gives improved patient outcome compared to current established therapies for the particular type of metastatic cancer.

Embodiment Ee2

Embodiment Ee2 of the present invention is a drug or set of drugs that irreversibly inhibit the potential for cancer cell proliferation for use in a regimen for the treatment of non-refractory metastatic cancers to achieve improved patient outcome compared to current established therapies for the particular type of metastatic cancer.

Embodiment E3

Embodiment E3 of the present invention is a method for the effective treatment of metastatic cancer comprised of the administration of a set of one or more drugs, wherein said set of drugs irreversibly inhibits the potential for cancer cell proliferation and wherein said method has improved patient outcome compared to current established therapies for the particular type of metastatic cancer.

Embodiment Ee3

Embodiment Ee3 of the present invention is a drug or set of drugs that irreversibly inhibit the potential for cancer cell proliferation for use in a regimen for the effective treatment of metastatic cancers and to achieve improved patient outcome compared to current established therapies for the particular type of metastatic cancer.

Anticancer drugs that can inhibit the potential for cell proliferation are well known to one skilled in the arts and have been extensively used to treat metastatic cancer. However, as previously discussed there are currently no established methods for obtaining high rates or high probabilities of CRs and durable, long-term CRs in patients with most types of metastatic cancers and in all types of refractory metastatic cancers using drugs that inhibit the potential for cell proliferation (or any other class of drugs).

Metastatic Cancers that Can be Treated with the Present Invention.

Metastatic cancers that can be treated with the current invention, E1 E2, E3, Ee1, Ee2 and Ee3, and all other later embodiments described in this document (unless otherwise restricted in the particular embodiment) include but are not limited to those given in List A:

List A:

Acute Lymphoblastic Leukemia (ALL); Acute Myeloid Leukemia (AML); Adrenocortical Carcinoma; Anal Cancer; Appendix Cancer; Basal Cell Carcinoma; Bile Duct Cancer; Bladder Cancer; Brain cancers; Breast Cancer; adenocarcinoma of the breast, (ductal and lobular) Bronchial cancer; Burkitt's lymphoma; Carcinoid Tumor; Carcinoma of Unknown Primary; Cervical Cancer; Chronic Lymphocytic Leukemia (CLL); Chronic Myelogenous Leukemia (CML); Colon Cancer; Colorectal Cancer; Cutaneous T-Cell Lymphoma; Embryonal Tumors; Endometrial Cancer; Esophageal Cancer; Esthesioneuroblastoma, Childhood; Ewing Sarcoma; Extracranial Germ Cell Tumor; Extragonadal Germ Cell Tumor; Ocular Melanoma; Retinoblastoma; Malignant Fibrous Histiocytoma of Bone, Osteosarcoma; Gallbladder Cancer; Gastric Cancer; Gastrointestinal Carcinoid Tumor; Gastrointestinal Stromal Tumors (GIST); Germ Cell Tumors; Gestational Trophoblastic Disease; Hairy Cell Leukemia; Head and Neck Cancer; Hepatocellular Cancer; Malignant Histiocytosis; Langerhans Cell cancer; Hodgkin Lymphoma; Hypopharyngeal Cancer; Malignant Islet Cell Tumors, Pancreatic Neuroendocrine Tumors; Kaposi Sarcoma; Kidney cancers; Renal Cell; Wilms Tumor; Langerhans Cell Histiocytosis; Laryngeal Cancer; Leukemia; Lip and Oral Cavity Cancer; Lung Cancer; Non-Small Cell lung cancer; Small cell lung cancer; Lymphoma; AIDS-Related; Non-Hodgkin lymphoma; Macroglobulinemia, Waldenström; Melanoma; Merkel Cell Carcinoma; Mesothelioma; Multiple Myeloma/Plasma Cell cancer; Mycosis Fungoides; Nasal Cavity and Paranasal Sinus Cancer; Nasopharyngeal Cancer; Neuroblastoma; Oral Cancer; Oropharyngeal Cancer; Ovarian Cancer; Pancreatic Cancer; pancreatic adenocarcinoma; Pancreatic Neuroendocrine Tumors; Paranasal Sinus and Nasal Cavity Cancer; Parathyroid Cancer; Penile Cancer; Pharyngeal Cancer; Pheochromocytoma; Prostate Cancer; Prostatic adenocarcinoma; Rectal Cancer; Renal Cell Cancer; Renal Pelvis and Ureter, Transitional Cell Cancer; Retinoblastoma; Rhabdomyosarcoma; Salivary Gland Cancer; Sarcoma; Osteosarcoma; Rhabdomyosarcoma; Merkel Cell Carcinoma; Small Intestine Cancer; Soft Tissue Sarcoma; Squamous Cell Carcinoma; Squamous Neck Cancer with Occult Primary, T-Cell Lymphoma; Testicular Cancer; Thymic Carcinoma; Thyroid Cancer; (papillary, follicular, medullary and anaplastic); Transitional Cell Cancer of the Renal Pelvis and Ureter; Urethral Cancer; Uterine Cancer, Endometrial Uterine Sarcoma; Waldenström Macroglobulinemia; Wilms Tumor; Vaginal Cancer; and Vulvar Cancer; platinum-resistant ovarian cancer; adenocarcinoma of the small intestine; triple-negative breast cancer; and melphalan-resistant myeloma, More detailed descriptions of metastatic cancers, all of which are within the scope of the present invention are provided in the following reference: Holland-Frei Cancer Medicine, 6th edition, Edited by Donald W Kufe, MD, Raphael E Pollock, MD, PhD, Ralph R Weichselbaum, MD, Robert C Bast, Jr, MD, Ted S Gansler, MD, MBA, James F Holland, MD, ScD and Emil Frei, III, MD; BC Decker Inc., Hamilton, Ontario.

The general applicability of the present invention to all types of metastatic cancer is due to the fact that the method targets the potential for cell proliferation, which is an essential property of all malignant cells.

The method (or set of drugs) is also applicable to the adjuvant therapy of patients with very high risk cancers that pose a very high risk of progression and mortality. For example, pancreatic cancer, even in the absence of detectable metastatic lesions has a very grim rate of survival.

Preferably the method (or set of drugs) would be used in patients to treat the metastatic cancer after the surgical removal or ablation of bulk tumor. The method can be used in conjunction with surgery, radiation therapy, cryotherapy, high intensity ultrasound, brachytherapy, or other means of local therapy aimed at decreasing localized tumors. For example, proton beam therapy could be used in conjunction with the present methods to treat brain cancers or metastatic lesions to the brain. Techniques for the local therapy of tumors are well known to one skilled in the arts.

The method (or set of drugs) can also be used in the neoadjuvant setting to enable surgical resection of an otherwise unrespectable tumor such as pancreatic cancer with extensive extra-pancreatic tissue invasion.

The required log reductions in cancer cell survival can be obtained by a single intensive treatment (e.g., a treatment that gives 12-log reduction) or multiple less intensive treatments (e.g., 3 treatments that each give a 4-log reduction). A preferred method is to use 2 to 3 course of treatment each of which gives at least a 12-log reduction in cancer cell clonogenic survival.

In an embodiment the set of drugs is administered at doses expected to be sufficient to completely inhibit the potential for cancer cell proliferation in the patient. In a preferred embodiment the set of drugs is administered at doses such that a single administration of the set of drugs can completely inhibit the potential for cancer cell proliferation in the patient.

Clonogenic survival assays can provide approximate estimates of the probability of cancer cell survival for different types of cancers exposed to the anticancer agents at drug concentrations and drug AUC's achievable in patients. Techniques for performing clonogenic survival assays and measuring drug AUCs in patients are well known to one skilled in the arts. (See: Clonogenic assay of cells in vitro. Franken N A, et al.; Nat Protoc. 2006; 1(5):2315-9; Preclinical studies and clinical correlation of the effect of alkylating dose.; Frei E 3rd, Teicher B A, Holden S A, Cathcart K N, Wang Y Y.; Cancer Res. 1988 Nov. 15; 48(22):6417-23).

In other embodiments the set of drugs is administered multiple times (i.e., multiple course) each of which gives approximately an N-log reduction in the potential for cancer cell proliferation in the patient wherein N is in the range of approximately 2 to greater than 15. The number of courses of therapy would generally be in the range of 1 to approximately 4. Multiple courses of the therapy would be required in cases where N is less than that needed to achieve a high probability of long-term CR.

In preferred embodiments patients would receive 2-3 courses of therapy, each of which could provide at least N-log reductions in cancer cell clonogenic survival, where $10^{(N-1)}$ is the estimated number of tumor cell present in the patient at the beginning of the first course of therapy. The purpose of the multiple cycles is to provide a large margin of safety that the required number of log reductions will be achieved in the patient.

In certain cancers, (e.g., some prostate cancer) the disease may be so slowly progressive that complete elimination of all malignant cells is not needed to treat the disease and have excellent patient outcomes, in these cases fewer course of therapy or less intensive therapy could be used.

Embodiments Ee1, Ee2, and Ee3 (Inhibitors of potential for cell proliferation and bone marrow stem cell infusion) (a)

In embodiments of E1, E2 and E3 respectively named E1(a) and E2(a) and E3(a), the set of drugs are administered and the patient is then treated with bone marrow stem cells or other cells that are able to regenerate the patient's bone marrow and thereby reverse bone marrow suppression caused by said drugs.

In embodiments of Ee1, Ee2 and Ee3 respectively named Ee1(a) and Ee2(a) and Ee3(a), the set of drugs are used in a regimen that includes treatment with bone marrow stem cells or other cells that are able to regenerate the patient's bone marrow. Bone marrow stem cell support will generally be needed with the present invention. However, there are exceptions. Stem cell support would not be needed if the requisite log reductions in cancer cell survival could be obtained without causing ablation of the bone marrow and prolonged bone marrow suppression. For example, in patients with a low metastatic tumor cell burden (i.e., micro-metastatic disease) and or in patients with cancers that are especially hypersensitive to the set of drugs.

DNA Crosslinking Agents

DNA strand separation is required for DNA synthesis and cell proliferation. Unrepaired DNA interstrand crosslinks inhibit the potential for cell proliferation profoundly impair clonogenic cell survival. The ability of DNA crosslinking agents to inhibit the potential for cell proliferation in a cell cycle non-specific manner makes said agents highly suited for the use in the present methods.

Embodiments with DNA Crosslinking Agents (b)

In a certain embodiments of E1 and E2 and E3 and E1(a) and E2(a) and E3(a) and Ee1 and Ee2 and Ee3 and Ee1(a) and Ee2(a) and Ee3(a), named respectively E1(b) and E2(b) and E3(b), and E1(a,b) and E2(a,b) and E3(a,b) and Ee1(b) and Ee2(b) and Ee3(b), and Ee1(a,b) and Ee2(a,b) and Ee3(a,b) the set of drugs that irreversibly inhibit the potential for cancer cell proliferation is comprised of a DNA crosslinking agent.

More than one DNA crosslinking agent can be included in the set. In a preferred embodiment the set of drugs is comprised of an electrophilic DNA crosslinking agent. Bifunctional alkylating agents and especially nitrogen mustard analogs are preferred. A wide range of DNA crosslinking agents can be used. Suitable DNA crosslinking agents include but are not limited to: melphalan, chlorambucil, cyclophosphamide, bendamustine, bizelesin, ifosfamide, cisplatin, carboplatin, and oxaliplatin, thiotepa, busulfan, and mitomycin c, mechlorethamine, carmustine, lomustine, cisplatin, carboplatin, nedaplatin, oxaliplatin, satraplatin, picoplatin and busulfan. Analogs, derivatives, and prodrugs of these crosslinking agents are also within the scope of the present method. Additional suitable DNA crosslinking agent are described in the following reference: Rajski S R, Williams R M.; Chem Rev. 1998 Dec. 17; 98(8):2723-2796. Techniques for administering said DNA crosslinking drugs are well known to one skilled in the arts. (See: A Multidisciplinary Approach. Medical, Surgical and Radiation Oncology-13th ed.; by Richard Pazdur et al.; Publisher: Matthews Medical Books 2010).

A wide range of DNA crosslinking agents can be used with the methods of the present invention. The specific chemical nature of the DNA crosslinking agent is not critical to the mechanisms of action of the present invention. Interstrand DNA crosslinks preclude separation of DNA strands and interfere with DNA synthesis. Complex cellular machinery has evolved to repair DNA crosslinks. The methods of the present invention, among other things, are focused on inhibiting cellular machinery that repair DNA crosslinks.

Methods to identify DNA crosslinking agents are known to one skilled in the art. One skilled in the art will recognize and know a large number of DNA crosslinking agents; the use of said crosslinking agents with the present methods is within the scope of the present invention.

Embodiments with Specific DNA Crosslinking Agents (c)

In preferred embodiments of E1(b) and E2(b), and E3(b), and E1(a,b) and E2(a,b) and E3(a,b) and Ee1(b) and Ee2(b) and Ee3(b), and Ee1(a,b) and Ee2(a,b) and Ee3(a,b) named respectively E1(b,cX) and E2(b,cX) and E3(b,cX) and E1(a,b,cX) and E2(a,b,cX) and E3(a,b,cX) and Ee1(b,cX) and Ee2(b,cX) and Ee3(b,cX) and Ee1(a,b,cX) and Ee2(a,b,cX) and Ee3(a,b,cX), wherein X=1, 2, 3 . . . or 22, the DNA crosslinking agent is comprised of: melphalan (X=1), bizelesin (X=2), chlorambucil (X=3), cyclophosphamide (X=4), bendamustine (X=5), ifosfamide (X=6), cisplatin (X=7), carboplatin (X=8), and oxaliplatin (X=9), thiotepa (X=10), busulfan (X=11), and mitomycin c (X=12), mechlorethamine (X=13), carmustine (X=14), lomustine (X=15), cisplatin (X=16), carboplatin (X=17), nedaplatin (X=18), oxaliplatin (X=19), satraplatin (X=20), picoplatin (X=21) and busulfan (X=22).

To illustrate the terminology: E3(a,b,c2) is an embodiment of method E3 in which the set of drugs is comprised of a DNA crosslinking agent (represented by "b"), wherein said crosslinking agent is comprised of bizelesin (represented by "c2" and wherein the patient is then treated with bone marrow stem cells (represented by "a" or other cells that are able to regenerate the patient's bone marrow and thereby reverse bone marrow suppression caused by said drugs.

Alkylating Agents and Log-Linear Dose Response Curve

Bifunctional alkylating agents generally have steep log-linear dose response curves for clonogenic survival fraction verse drug concentration (or drug AUC) and can give major log-reductions in cancer cell survival. (See FIGS. 2A and 2B) (See: Preclinical studies and clinical correlation of the effect of alkylating dose.; Frei E 3rd, Teicher B A, Holden S A, Cathcart K N, Wang Y Y.; Cancer Res. 1988 Nov. 15; 48(22):6417-23.)

The dose of the crosslinking agent is determined by the AUC of said agent that is required in the patient to achieve the desired log reductions in cancer cell clonogenic survival. Techniques for measuring drug AUC and for determining the dose of drug need to approximately achieve a desired drug AUC in patients are well known to one skilled in the arts. Methods for measuring clonogenic cell survival techniques and for measuring and estimating the drug AUC needed to give a 1-log reduction in cancer cell survival (i.e., AUC-1) are also well known to one skilled in the arts. Within the limits of linearity, an AUC=(N×AUC-1) will give approximately an N-log reduction in cancer cell clonogenic survival. When the DNA crosslinking agent is administered as part of a set of drugs that hypersensitize cancer cells to said agent the AUC of the crosslinking agent needed to get a 1-log reduction will be decreased by a factor approximately equal to the dose modification (DMF). It is desirable that the dose of crosslinking agent that is employed exceed that needed to give the desired log reduction.

Bizelesin

Bizelesin is an ultra-potent, cell-cycle independent, irreversible inhibitor of the potential for cell proliferation. The drug is rapidly taken up by cells and binds in the minor groove of AT rich regions of DNA, which play a critical role in cell proliferation. Bizelesin covalently cross-links the DNA in the AT rich regions. Bizelesin-DNA adducts stall replication forks, halt proliferation and abolish colony formation (i.e., abolish clonogenic potential). Bizelesin is able to give major-log reductions in clonogenic cell survival. The dose response curve is log-linear. (See FIG. 2B) The IC90 for inhibition of cancer cell clonogenic survival in sensitive cells is ~2 to 20 pM for a 2 hour exposure, which would correspond to an AUC-1 of ~4 to 40 pM h. In patients given bizelesin at a dose of 1 microgram/m2 the mean Bizelesin AUC was ~840 pM h, which is ~20 to 200 times higher than the drug AUC needed to give a 1-log decrease in clonogenic survival for most types of human cancer cell lines. However, bizelesin is a substrate for the pgp MNDR-1 drug efflux pump and pgp expression can increase the IC90 by up to 250 fold. Bizelesin is active in melphalan, cisplatin, BCNU, and lomustine resistant cell lines.

In clinical two trials bizelesin had minimal to no significant anticancer activity and displayed dose limiting bone marrow toxicity. Clinical development of the drug was abandoned.

Some Bizelesin Embodiments

Embodiments E1(b,a,c2) E2(b,a,c2), E3(b,a,c2), Ee1(b,a,c2), Ee2(b,a,c2), and Ee3(b,a,c2) (Inhibitor of Potential for Cell Proliferation, the DNA Crosslinking Agent Bizelesin and Bone Marrow Stem Cell Infusion)

In embodiments E1(b,a,c2) E2(b,a,c2), E3(b,a,c2), Ee1(b,a,c2), Ee2(b,a,c2), and Ee3(b,a,c2) the set of drugs is comprised of bizelesin and bone marrow stem cell infusion is used to reverse bone marrow toxicity. The dose of bizelesin for IV administration in these embodiments is approximately 1, 2, 3, 4, 5, 6, 7, 8, 10, 15, or 20 micrograms/m². In some embodiments, the dose of bizelesin is approximately 1 micrograms/m² to 2 micrograms/m² or 3 micrograms/m² to 5 micrograms/m² or 5 micrograms/m² to 7 micrograms/m². Bone marrow stem cells would be infused approximately 2 to 3 days after the bizelesin. The bone marrow stem cells can be autologous or allogeneic. The treatment with bizelesin and stem cell infusion can be repeated in approximately 4-8 week intervals, for a total of approximately 2-3 courses. The above embodiments can be used to treat refractory solid metastatic cancers as given in List A. The above embodiment can also be used to treat refractory leukemias, lymphomas, and myeloma. When treating leukemias and lymphomas the use of purified bone marrow stem cells is strongly preferred. Techniques for the purification and depletion of cancer cells from bone marrow stem cell preparations are known to one skilled in the art.

Since bizelesin can permanently inhibit the potential for cell proliferation without killing cells, the CRs are defined in terms of absence of any detectable growth or cancer cell proliferation in tumors and long term progression free survival.

Embodiments E1(b,a,c2,t) E2(b,a,c2,t), E3(b,a,c2,t), Ee1(b,a,c2,t), Ee2(b,a,c2,t), and Ee3(b,a,c2,t) (Inhibitor of Potential for Cell Proliferation, and PgP Inhibitor, the DNA Crosslinking Agent Bizelesin and Bone Marrow Stem Cell Infusion)

In Embodiments E1(b,a,c2,t) E2(b,a,c2,t), E3(b,a,c2,t), Ee1(b,a,c2,t), Ee2(b,a,c2,t), and Ee3(b,a,c2,t) the set of drugs also includes an inhibitor to the pgp pump, MDR-1. Bizelesin is a substrate for the pgp pump and efflux of the drug by said pump can decrease the sensitivity of cancer cells to bizelesin. The dose of bizelesin is as given above. The MDR-1 inhibitor is administered prior to or essentially concurrently with the bizelesin.

A wide range of drugs are known to one skilled in the arts that can inhibit pgp and the efflux of pgp substrates from cells that can be used in the present embodiments. Methods for identifying Pgp inhibitors are known to one skilled in the art. Bizelesin is rapidly taken up by cells and rapidly binds to DNA. Therefore, prolonged inhibition of the pgp is not required; inhibition for a period of approximately 1-6 hours is sufficient. Substrates of the pgp pump can also be used as competitive inhibitors, especially since the bizelesin concentration is so low in patients.

In some embodiments the pgp inhibitor is a drug given in the following List of PGP Inhibitors: 1.) Cyclosporine; 2.) Valspodar; 3.) Tariquidar; 4.) Cefoperazone, 5.) Doxorubicin 6.) Thaliblastin; 7.) Zosuquidar; 8.) Ontogen; 9.) Disulfiram; 10.) Erythromycin 11.) BCNU; 12.) Thiol-reactive compounds; 13.) Ritonavir. 14.) Fluoxetine; 15.) Lipophilic amines such as fluoxetine, toremifine, chloroquine. Lipohilic amines increase the pH of lysosomes and acidic cellular compartments and inhibit recycling of plasma membrane pgp, thereby decreasing pgp mediated drug reflux.

The dose of erythromycin is in the approximate range of 3-5 mg/kg every 6 hours with a maximum of 4 grams/day given IV or by mouth. Generally the patient would be given a dose immediately prior to the administration of the bizelesin. The dose of disulfiram is in the approximate range of 500 mg to 3 grams orally, given approximately 1 hour prior to the bizelesin. The dose of doxorubicin is in the approximate range of 10 mg/m$^2$ to 80 mg/m$^2$; given immediately prior to the bizelesin. The dose of BCNU is approximately 75-300 mg/m$^2$ given approximately 1 hour prior to or at the same time as the bizelesin.

The dose of BCNU and doxorubicin used together are in the following approximate ranges: BCNU 75-300 mg/m$^2$ and doxorubicin 10 mg/m$^2$ to 80 mg/m$^2$. Specific doses are approximately BCNU 100 mg/m$^2$ and doxorubicin 40 mg/m$^2$ or approximately BCNU 150 mg/m$^2$ and doxorubicin 60 mg/m$^2$.

The dose of Valspodar; is approximately 1.5 mg/kg given over 2 hours immediately prior to the bizelesin. The dose of Cefoperazone is approximately 2-4 grams given IV immediately after the bizelesin. The dose of cyclosporine is approximately 6 mg/kg IV over 2 hours followed immediately by to the bizelesin. The Ritonavir dose is 600 to 1200 mg by mouth 2-4 hours prior to the bizelesin. The dose of fluoxetine is approximately in the range of 20 to 80 mg/day and this drug is generally begun 7-14 days prior to the bizelesin. Techniques for the administration of these and other pgp inhibitors are known to one skilled in the arts. Other dosing schedules can also be used provided that the net result is inhibition of bizelesin efflux from cells. Said dosing schedules are within the scope of the present invention.

Pgp ATPase and its pump function are inactivated by thiol reactive agents that covalently modify critical cysteines in Pgp and by oxidative conditions that lead to disulfide bond formation. Disulfiram inhibits pgp by reacting with active thiols in the ATPase of the pgp molecule. Other electrophilic thiol-reactive compounds act similarly. BCNU decomposes into 2-chloroethyl isocyanate, which is highly reactive towards thiols. Based on the chemistry, 2-chloroethyl isocyanate is expected to be a potent irreversible inhibitor of Pgp.

Clinical trials have repeatedly demonstrated minimal to no improvement in patient outcomes with the use of pgp inhibitors in the conjunction with drugs that are effluxed from cancer cells by pgp for the treatment of metastatic cancer. The failure observed in these trials is due to limitations in the log reductions in cancer cell survival that could be obtained with the treatment regimens employed in said trials. The present method is designed to overcome the failure of bizelesin and pgp inhibitors in past clinical trials. (See: Schwartz G H, Patnaik A, Hammond L A, Rizzo J, Berg K, Von Hoff D D, Rowinsky E K; Ann Oncol. 2003 May; 14(5):775-82; Pitot H C, Reid J M, Sloan J A, Ames M M, Adjei A A, Rubin J, Bagniewski P G, Atherton P, Rayson D, Goldberg R M, Erlichman C. Clin Cancer Res. 2002 March; 8(3):712-7; Carter C A, Waud W R, Li L H, DeKoning T F, McGovren J P, Plowman; J. Clin Cancer Res. 1996 July; 2(7):1143-9; Nooter K, Sonneveld P.; Leuk Res. 1994 April; 18(4):233-43; Robey R W et al.; Biochem Pharmacol. 2008 Mar. 15; 75(6):1302-12; Yu M, Ocana A, Tannock I F.; Cancer Metastasis Rev. 2013 June; 32(1-2): 211-27; Van Bambeke F, et al.; J Antimicrob Chemother. 2003 May; 51(5):1067-7; Teodori E, et al.; Farmaco. 2002 May; 57(5):385-415; Ozben T.; FEBS Lett. 2006 May 22; 580(12):2903-9; Gruber A, et al.; Leuk Res. 2003 April; 27(4):323-8; Ozben T.; FEBS Lett. 2006 May 22; 580(12): 2903-9; Gosland M P, et al.; Cancer Res. 1989 Dec. 15; 49(24 Pt 1):6901-5; Borowski E, et al.; Acta Biochim Pol. 2005; 52(3):609-2; Szakács G, et al.; Nat Rev Drug Discov. 2006 March; 5(3):219-34; Bhuyan B K et al.; Cancer Res. 1993 Mar. 15; 53(6):1354-9; Butryn R K, et al.; Cancer Chemother Pharmacol. 1994; 34(1):44-50; Cao P R, McHugh M M, Melendy T, Beerman T; Mol Cancer Ther. 2003 July; 2(7):651-9; Eckford P D, Sharom F J; Chem Rev. 2009 July; 109(7):2989-3011; Sauna Z E, et al.; Mol Pharmacol. 2004 March; 65(3):675-8; al-Shawi M K, Urbatsch I L, Senior A E.; J Biol Chem. 1994 Mar. 25; 269(12):8986-92; Loo T W, Clarke D M.; J Biol Chem. 2000 Jun. 30; 275(26):19435-8; Liu R, Sharom F J.; Biochemistry. 1996 Sep. 10; 35(36):11865-73; Loo T W, Clarke D M.; J Biol Chem. 1995 Sep. 29; 270(39):22957-61; Sauna Z E, Peng X H, Nandigama K, Tekle S, Ambudkar S V.; Mol Pharmacol. 2004 March; 65(3):675-84; Efferth T, Volm M.; Cancer Lett. 1993 Jul. 16; 70(3):197-202); Vacuolar ATPase inactivation blocks recycling to the trans-Golgi network from the plasma membrane; Reaves B, Banting G.; FEBS Lett. 1994 May 23; 345(1):61-6; Experimentally induced changes in the endocytic traffic of P-glycoprotein alter drug resistance of cancer cells.; Kim H, Barroso M, Samanta R, Greenberger L, Sztul E. Am J Physiol. 1997 August; 273(2 Pt 1):C687-702.

Embodiments of E1, E2, E3, Ee1, Ee2, and Ee3 with Melphalan and Doses

In a preferred embodiment the DNA crosslinking agent is melphalan. In embodiments of E1(b,c1) and E1(a,b,c1) and E2(b,c1) and E2(a,b,c1) and E3(b,c1) and E3(a,b,c1) respectively named E1(b, c1,dX) and E1(a,b, c1,dX) and E2(b, c1,dX) and E2(a,b, c1,dX) and E3(b, c1,dX) and E3(a,b,c1, dX) and Ee1(b,c1, dX) and Ee1(a,b,c1, dX) and Ee2(b,c1, dX) and Ee2(a,b,c1, dX) and Ee3(b,c1, dX) where X=1, 2, or 3, the IV melphalan dose is approximately 35 to 50 mg/m$^2$, X=1; or 50 to 70 mg/m$^2$, X=2; or 100-200 mg/m$^2$, X=3.

A major advantage of melphalan is that the drug can be given to patients at high doses, (e.g., two courses each of ~200 mg/m$^2$) and the toxicity is mainly directed to the bone marrow, which can be reversed by the infusion of bone marrow stem cells. At still higher doses gastrointestinal toxicity becomes dose limiting. Importantly, melphalan does not generally cause chronic side effects such as neurotoxicity, peripheral neuropathy, hearing loss, or kidney damage, which frequently occur with high doses of other alkylating agents and platinum drugs. The following reference relates to this matter: Melphalan 200 mg/m$^2$ versus melphalan 100 mg/m$^2$ in newly diagnosed myeloma patients: A prospective, multicenter phase 3 study; Palumbo A, et al.; Blood. 2010 Mar. 11; 115(10):1873-9.

FIGS. 3A,3B, and 3C list the calculated melphalan AUC-1's for a variety of human cancer cell lines and normal bone marrow progenitor cells. The AUC data were calculated based on a melphalan half-life of 1.1 hours in tissue culture media. The calculations are based on the assumption of a linear relationship between the log of the survival fraction and the melphalan concentration and AUC. This assumption is a good approximation. For example, the melphalan AUCs giving a 1-log reduction in clonogenic survival of MCF-7 human breast cancer cells are closely similar for drug exposure times of 1, 2, or 12 hours. (See: Ozawa S, et al.; Cancer Chemother Pharmacol. 1988; 21(3):185-90; Influence of schedule on alkylating agent cytotoxicity in vitro and in vivo.; Teicher B A, Holden S A, Eder J P, Brann T W, Jones S M, Frei E 3rd.; Cancer Res; 1989 Nov. 1; 49(21): 5994-8; Stability of melphalan solutions during preparation and storage.; Bosanquet A G.; J Pharm Sci. 1985 March; 74(3):348-51. The references cited in FIGS. 2A, 2B, 2C and 2D are as follows:

1) Antineoplastic drug cytotoxicity in a human bladder cancer cell line: implications for intravesical chemotherapy. Erlichman C, Vidgen D, Wu A.; Urol Res. 1987; 15(1):13-6.

2) Differential response of cultured human normal and tumor cells to trace element-induced resistance to the alkylating agent melphalan.; Tobey R A, Tesmer J G.; Cancer Res. 1985 June; 45(6):2567-71.

3) Characterization of a human bladder cancer cell line selected for resistance to mitomycin C.; Xu B H, Gupta V, Singh S V.; Int J Cancer. 1994 Sep. 1; 58(5):686-92.

4) Increased sensitivity of human colon cancer cells to DNA cross-linking agents after GRP78 up-regulation.; Belfi C A, Chatterjee S, Gosky D M, Berger S J, Berger N A.; Biochem Biophys Res Commun. 1999 Apr. 13; 257(2):361-8.

5) Effect of hyperthermia and chemotherapeutic agents on TRAIL-induced cell death in human colon cancer cells.; Yoo J, Lee Y J.; J Cell Biochem. 2008 Jan. 1; 103(1):98-109.

6) Estimation of the haematological toxicity of minor groove alkylators using tests on human cord blood cells.; Ghielmini M, Bosshard G, Capolongo L, Geroni M C, Pesenti E, Torri V, D'Incalci M, Cavalli F, Sessa C.; Br J Cancer. 1997; 75(6):878-83.

7) Changes in glutathione content and resistance to anticancer agents in human stomach cancer cells induced by treatments with melphalan in vitro.; Barranco S C, Townsend C M Jr, Weintraub B, Beasley E G, MacLean K K, Shaeffer J, Liu N H, Schellenberg K.; Cancer Res. 1990 Jun. 15; 50(12):3614-8.

8) Nitric oxide enhancement of melphalan-induced cytotoxicity.; Cook J A, Krishna M C, Pacelli R, DeGraff W, Liebmann J, Mitchell J B, Russo A, Wink D A.; Br J Cancer. 1997; 76(3):325-34.

9) Role of cellular glutathione and glutathione S-transferase in the expression of alkylating agent cytotoxicity in human breast cancer cells; Chen G, Waxman D J.; Biochem Pharmacol. 1994 Mar. 15; 47(6):1079-87.

10) Glutathione depletion increases the cytotoxicity of melphalan to PC-3, an androgen-insensitive prostate cancer cell line.; Canada A, Herman L, Kidd K, Robertson C, Trump D.; Cancer Chemother Pharmacol. 1993; 32(1):73-7.

11) Increase in gamma-glutamylcysteine synthetase activity and steady-state messenger RNA levels in melphalan-resistant DU-145 human prostate carcinoma cells expressing elevated glutathione levels.; Bailey H H, Gipp J J, Ripple M, Wilding G, Mulcahy R T.; Cancer Res. 1992 Sep. 15; 52(18):5115-8.

12) Human renal UOK130 tumor cells: a drug resistant cell line with highly selective over-expression of glutathione S-transferase-pi isozyme; Wang W, Liu G, Zheng J.; Eur J Pharmacol. 2007 Jul. 30; 568(1-3):61-7.

13) The response of tumour cells to radiation and cytotoxic drugs—a comparison of clonogenic and isotope uptake assays.; Twentyman P R, Walls G A, Wright K A.; Br J Cancer. 1984 November; 50(5):625-31.

14) Differential cytotoxicity of 19 anticancer agents in wild type and etoposide resistant small cell lung cancer cell lines.; Jensen P B, Christensen I J, Sehested M, Hansen H H, Vindeløv L.; Br J Cancer. 1993 February; 67(2):311-20.

15) Characterization of a human small cell lung carcinoma cell line with acquired resistance to cis-diamminedichloroplatinum(II) in vitro.; Hospers G A, Mulder N H, de Jong B, de Ley L, Uges D R, Fichtinger-Schepman A M, Scheper R J, de Vries E G.; Cancer Res. 1988 Dec. 1; 48(23):6803-7.

16) Up-regulation of gamma-glutamylcysteine synthetase activity in melphalan-resistant human multiple myeloma cells expressing increased glutathione levels.; Mulcahy R T, Bailey H H, Gipp J J.; Cancer Chemother Pharmacol. 1994; 34(1):67-71.

17) Relationship between melanogenesis, glutathione levels and melphalan toxicity in human melanoma cells.; Benathan M, Alvero-Jackson H, Mooy A M, Scaletta C, Frenk E.; Melanoma Res. 1992 December; 2(5-6):305-14.

18) Differential response of cultured human normal and tumor cells to trace element-induced resistance to the alkylating agent melphalan.; Tobey R A, Tesmer J G.; Cancer Res. 1985 June; 45(6):2567-71.

19) Use of nude mouse xenografts as preclinical screens. Characterization of xenograft-derived melanoma cell lines; Taetle R, Jones O W, Honeysett J M, Abramson I, Bradshaw C, Reid S.; Cancer. 1987 Oct. 15; 60(8):1836-41.

20) Melphalan-induced chromosome damage in sensitive and resistant human melanoma cell lines; Parsons P G, Morrison L.; Int J Cancer. 1978 Apr. 15; 21(4):438-43.

21) The effect of hyperthermia and melphalan on survival of human fibroblast strains and melanoma cell lines; Goss P, Parsons P G.; Cancer Res. 1977 January; 37(1):152-6.

22) Melphalan-induced chromosome damage in sensitive and resistant human melanoma cell lines.; Parsons P G, Morrison L.; Int J Cancer. 1978 Apr. 15; 21(4):438-43.

23) The effect of hyperthermia and melphalan on survival of human fibroblast strains and melanoma cell lines.; Goss P, Parsons P G.; Cancer Res. 1977 January; 37(1):152-6.

24) Sensitization of human melanoma cells to the cytotoxic effect of melphalan by the glutathione transferase inhibitor ethacrynic acid.; Hansson J, Berhane K, Castro V M, Jungnelius U, Mannervik B, Ringborg U.; Cancer Res. 1991 Jan. 1; 51(1):94-8.

25) In vitro chemosensitivity tests on xenografted human melanomas.; Bateman A E, Selby P J, Steel G G, Towse G D. Br J Cancer. 1980 February; 41(2):189-98.

26) Sensitization of human melanoma cells to melphalan cytotoxicity by adriamycin and carmustine; Jevtović-Todorović V, Guenthner T M.; J Cancer Res Clin Oncol. 1991; 117(4):313-20.

27) Cross-resistance and glutathione-S-transferase-pi levels among four human melanoma cell lines selected for alkylating agent resistance. Wang Y Y, Teicher B A, Shea T C, Holden S A, Rosbe K W, al-Achi A, Henner W D.; Cancer Res. 1989 Nov. 15; 49(22):6185-92.

28) Resistance to cytotoxic drugs in DNA mismatch repair-deficient cells.; Aebi S, Fink D, Gordon R, Kim H K, Zheng H, Fink J L, Howell S B.; Clin Cancer Res. 1997 October; 3(10):1763-7.

29) Effects of L-phenylalanine mustard and L-buthionine sulfoximine on murine and human hematopoietic progenitor cells in vitro.; Du D L, Volpe D A, Grieshaber C K, Murphy M J Jr.; Cancer Res. 1990 Jul. 1; 50(13):4038-43.

30) Estimation of the haematological toxicity of minor groove alkylators using tests on human cord blood cells.; Ghielmini M, Bosshard G, Capolongo L, Geroni M C, Pesenti E, Toni V, D'Incalci M, Cavalli F, Sessa C.; Br J Cancer. 1997; 75(6):878-83.

31) Assays of drug sensitivity for cells from human tumours: in vitro and in vivo tests on a xenografted tumour; Bateman A E, Peckham M J, Steel G G.; Br J Cancer. 1979 July; 40(1):81-8.

32) The response to chemotherapy of a variety of human tumour xenografts; Steel G G, Courtenay V D, Peckham M J.; Br J Cancer. 1983 January; 47(1):1-13.

33) Cell survival in four ovarian carcinoma xenografts following in vitro exposure to melphalan, cisplatin and cis-diammine-1,1-cyclobutane dicarboxylate platinum II (CBDCA,JM8).; Jones A C, Wilson P A, Steel G G.; Cancer Chemother Pharmacol. 1984; 13(2):109-13.

34) Characterization of a chlorambucil-resistant human ovarian carcinoma cell line overexpressing glutathione S-transferase mu.; Horton J K, Roy G, Piper J T, Van Houten B, Awasthi Y C, Mitra S, Alaoui-Jamali M A, Boldogh I, Singhal S S.; Biochem Pharmacol. 1999 Aug. 15; 58(4):693-702.

35) Flow cytometric analysis of DNA damage and repair in the cells resistant to alkylating agents.; Frankfurt O S, Seckinger D, Sugarbaker E V.; Cancer Res. 1990 Aug. 1; 50(15):4453-7.

36) The use of an image analyzer in human tumour clonogenic assays; Kahn E, Benard J, Di Paola R.; Cytometry. 1986 July; 7(4):313-7.

37) A comparison of two in vitro assays of cell response following in vitro drug and radiation exposures of human tumour xenograft cells.; Hanson J A, Bean E A, Coombs A M, Moore J L. Br J Cancer. 1985 October; 52(4):637-40.

38) Enhanced melphalan cytotoxicity in human ovarian cancer in vitro and in tumor-bearing nude mice by buthionine sulfoximine depletion of glutathione; Ozols R F, Louie K G, Plowman J, Behrens B C, Fine R L, Dykes D, Hamilton T C.; Biochem Pharmacol. 1987 Jan. 1; 36(1):147-53.

39) Potentiation of melphalan cytotoxicity in human ovarian cancer cell lines by glutathione depletion.; Green J A, Vistica D T, Young R C, Hamilton T C, Rogan A M, Ozols R F.; Cancer Res. 1984 November; 44(11):5427-31.

40) Differential sensitization of human ovarian carcinoma and mouse L1210 cells to cisplatin and melphalan by glutathione depletion; Andrews P A, Murphy M P, Howell S B.; Mol Pharmacol. 1986 December; 30(6):643-50.

41) Characterization of cisplatin-resistant COLO 316 human ovarian carcinoma cells.; Andrews P A, Murphy M P, Howell S B.; Eur J Cancer Clin Oncol. 1989 April; 25(4):619-25.

42) The relationship between nuclear glutathione levels and resistance to melphalan in human ovarian tumour cells.; Britten R A, Green J A, Broughton C, Browning P G, White R, Warenius H M.; Biochem Pharmacol. 1991 Feb. 15; 41(4):647-9.

43) Mechanism of cross-resistance to a camptothecin analogue (CPT-11) in a human ovarian cancer cell line selected by cisplatin.; Niimi S, Nakagawa K, Sugimoto Y, Nishio K, Fujiwara Y, Yokoyama S, Terashima Y, Saijo N.; Cancer Res. 1992 Jan. 15; 52(2):328-33.

44) Potentiation of melphalan cytotoxicity in human ovarian cancer cell lines by glutathione depletion.; Green J A, Vistica D T, Young R C, Hamilton T C, Rogan A M, Ozols R F.; Cancer Res. 1984 November; 44(11):5427-31.

45) As discussed previously, high dose melphalan (e.g., 200 mg/m^2) in conjunction with bone marrow support has been generally ineffective in the treatment of solid metastatic cancers. At maximal clinically tolerated melphalan doses the melphalan AUC achieved in patients (~40 microM h) is insufficient to give the 11-12 log reduction needed in cancer cell clonogenic survival to get high rates of durable, long-term CRs for most types of metastatic cancers.

Melphalan alone would be an effective treatment for metastatic cancers that have defects in the Fanconi/BRCA pathways and that are hypersensitive to melphalan. In such cases the melphalan AUC-1 can be in the range of ~0.5 to 1 microM h and clinically achievable dose of melphalan could provide far in excess of that needed to achieve the 12-log reduction needed to get high rates of durable complete responses. Approximate melphalan AUCs achieved with different doses of melphalan in patients are shown in FIG. 3. A melphalan dose of 70 mg/m$^2$ gives an AUC of ~13 microM h.

Fanconi/BRCA Defective Cancers

Embodiment E4

Embodiment E4 of the invention is a method for the effective treatment of metastatic cancers that have defects in the function of the Fanconi/BRCA pathways of DNA repair, wherein said method is comprised of the administration of a DNA crosslinking agent that irreversibly inhibit the potential for cancer cell proliferation in the patient.

Embodiment Ee4

Embodiment Ee4 is a set of drugs for use in a regimen for the effective treatment of metastatic cancers that have defects in the function of the Fanconi/BRCA pathways of DNA repair; wherein said set is comprised of a DNA crosslinking agent that irreversibly inhibits the potential for cancer cell proliferation in the patient.

DNA crosslinking agents have been used to treat cancers with defects in the Fanconi/BRCA pathways, however, the established methods are generally ineffective and do not give high rates of CRs, and durable CRs. For example, cisplatin and oxaliplatin are DNA crosslinking agent that have been used in conjunction with other drugs to treat BRCA-2 associated metastatic pancreatic cancer; the results have been generally dismal. The median progression free survival time in 12 patients with BRCA-associated pancreatic cancer treated with a platinum-based therapy was 90 days. The five year event free survival in women with BRCA1 and BRCA2-associate ovarian cancer was approximately 20%, (at least 84% of the women received platinum-based chemotherapy). In women with BRCA1-associated stage IV breast cancer treated with cisplatin the probability of survival was 20% at 3.5 years.

The following reference relates to this matter: An emerging entity: pancreatic adenocarcinoma associated with a known BRCA mutation: clinical descriptors, treatment implications, and future direction; Lowery M A, et al.; Oncologist. 2011; 16(10):1397-402; BRCA-associated pancreatic cancer: the evolving management.; Leung K, Saif M W.; JOP. 2013 Mar. 10; 14(2):149-51; Clinical characteristics and outcomes of BRCA-associated ovarian cancer: genotype and survival.; Liu J, et al.; Cancer Genet. 2012 January-February; 205(1-2):34-41; Results of a phase II open-label, non-randomized trial of cisplatin chemotherapy in patients with BRCA1-positive metastatic breast cancer; Byrski T et al.; Breast Cancer Res. 2012 Jul. 20; 14(4):R110.

The present invention also relates to a method for obtaining high rates of CRs and durable long-term CRs in patients with metastatic cancers that have defects in Fanconi/BRCA pathways of DNA repair. The Fanconi/BRCA pathways are critical to homologous recombination and the repair of DNA interstrand crosslinks. Methods for identifying patients with inherited mutation in Fanconi/BRCA pathway genes that result or predispose to functional defects in said pathway are well known to one skilled in the arts. Method for analyzing cancers for genetic, epigenetic, and functional defects in said pathway defects are also well known to one skilled in the arts.

Genetic defects in the Fanconi/BRCA pathways make cells hypersensitive to melphalan and other DNA crosslinking agents. Inherited BRCA1 and BRCA2 mutations markedly increase the risk of developing a number of types of cancer including breast cancer, ovarian cancer, and pancreatic cancer. The inherited mutations play a mechanistic role in the evolution of these cancers. Loss or inactivation of the wild type allele of the mutated gene generally occurs at an early stage in the evolution of the cancers and results in an evolutionary population of cells with defective DNA repair and increased genetic instability. The increased genetic instability accelerates the rate of evolution and cancer development. An important consequence is the emergence of a population of cancer cells that have defects in homologous recombination, which confers a profound hypersensitivity to DNA crosslinking agents. Acquired defects in the Fanconi/BRCA pathways are common in the evolution of cancers and have been reported in 20% of lung cancers.

Embodiment E4(c1) and Ee4(c1), (The Set of Drugs is Comprised of Melphalan)

In an embodiment of E4 and Ee4, named E4(c1) and Ee4(c1), the set of drugs is comprised of melphalan. The method (or set of drugs) is generally applicable to cancers with defective Fanconi/BRCA pathways of DNA repair, including but not limited to cancers associated with germ line mutations in BRCA1, BRCA2, and PALB2. The scope of the method (or set of drugs) includes the treatment of metastatic: breast cancer, ovarian cancer, pancreatic cancer, melanoma, colon cancer, fallopian tube cancer, prostate cancer, lung cancer, renal cancer, liver, nasopharyngeal cancer, salivary gland cancer, gastric cancer and all other cancers arising in other tissues in the setting the aforementioned germ line mutations. The method (or set of drugs) is also applicable to cancers that evolve in the absence of a germ line mutation, but which have defects in the Fanconi/BRCA pathways, such cancer can be identified by assessment of FANCD2 nuclear foci formation in pathological specimens, and with other methods known to one skilled in the art.

The following references relate to this matter: The Fanconi anaemia/BRCA pathway; D'Andrea A D, Grompe M.; Nat Rev Cancer. 2003 January; 3(1):23-34; Susceptibility of Fanconi's anemia lymphoblasts to DNA-cross-linking and alkylating agents.; Ishida R, Buchwald M.; Cancer Res. 1982 October; 42(10):4000-6.; The ERCC1/XPF endonuclease is required for completion of homologous recombination at DNA replication forks stalled by inter-strand cross-links; Al-Minawi A Z, Lee Y F, Håkansson D, Johansson F, Lundin C, Saleh-Gohari N, Schultz N, Jenssen D, Bryant H E, Meuth M, Hinz J M, Helleday T.; Nucleic Acids Res. 2009 October; 37(19):6400-13; A syngeneic variance library for functional annotation of human variation: application to BRCA2; Hucl T, Rago C, Gallmeier E, Brody J R, Gorospe M, Kern S E.; Cancer Res. 2008 Jul. 1; 68(13): 5023-30; A high-throughput pharmaceutical screen identifies compounds with specific toxicity against BRCA2-deficient tumors.; Evers B, Schut E, van der Burg E, Braumuller T M, Egan D A, Holstege H, Edser P, Adams D J, Wade-Martins R, Bouwman P, Jonkers J.; Clin Cancer Res. 2010 Jan. 1; 16(1):99-108; Assessment of FANCD2 nuclear foci formation in paraffin-embedded tumors: a potential patient-enrichment strategy for treatment with DNA interstrand crosslinking agents.; Duan W, et al.; Transl Res. 2012 Oct. 11.

The melphalan AUC needed to give a 1-log reduction in clonogenic survival of BRCA2 deficient cells is ~0.5-1 microM h. Intermediate dose melphalan (i.e., 70 mg/m2) will give a melphalan AUC of ~13 microM h. Two courses of intermediate dose melphalan would provide far in excess of a 12-log reduction in the probability of BRCA2 deficient cancer cell clonogenic survival.

In an embodiments of E4(c1), and Ee4(c1), named E4(c1, dX) and Ee4(c1,dX) where X=1, 2, or 3, the IV melphalan dose is approximately 35 to 50 mg/m$^2$, X=1; or 50 to 70 mg/m$^2$, X=2; or 70-200 mg/m$^2$, X=3.

In embodiments of E4(c1,d1) and E4(c1,d2) and E4(c1, d3), and Ee4(c1,d1) and Ee4(c1,d2) and Ee4(c1,d3), named respectively, E4(a, c1,d1) and E4(a, c1,d2) and E4(a,c1,d3), and Ee4(a, c1,d1) and Ee4(a, c1,d2) and Ee4(a,c1,d3), the treatment regimen includes the administration of bone marrow stem cells to the patient after the melphalan to reverse bone marrow toxicity.

Techniques for the collection, purification, storage and administration of bone marrow stem cells following the administration of melphalan are well known to one skilled in the arts. The bone marrow stem cells can be autologous or allogeneic.

The melphalan dose is in the range of ~15 to ~200 mg/m2 and is administered intravenously (IV) over ~30 to ~60 minutes. In an embodiments the melphalan dose is in the range of ~15 to ~50 mg/m2, ~50 to ~70 mg/m2 or ~70 to ~200 mg/m2. Techniques for the systemic administration of melphalan are well known to one skilled in the arts.

In practice, one to two additional doses would generally be administered with approximately 6-8 weeks intervals between the doses. Prior to the administration of the melphalan autologous bone marrow stem cells would generally be collected and stored for possible infusion to reverse bone marrow toxicity. Melphalan at a dose of up to 70 mg/m$^2$ is not myeloablative and can generally be safely administered without bone marrow stem cell infusion. However, in some patients delayed bone marrow recovery can occur, in which cases the stem cell infusions would be warranted. Alternatively the stem cell infusion can be used to speed up the bone marrow recovery. Patients would generally also receive a granulocyte colony-stimulating factor preparation such as Pegfilgrastim to accelerate bone marrow recovery. Techniques and protocols for the administration of IV melphalan at doses of 70 mg/m$^2$ are well known to one skilled in the arts and have been used to treat myeloma as is the required supportive medical care.

Embodiment E5

Embodiment E5 of the invention is a method for the treatment of metastatic cancers that have defects in the function of the Fanconi/BRCA pathways of repair, wherein said method is comprised of the administration of the DNA melphalan. In embodiments of E5, named E5(dX), where X=1, 2, or 3, the melphalan is administered IV at a dose of approximately: 35 to 50 mg/m$^2$, X=1; or 50 to 70 mg/m$^2$, X=2; or 100-200 mg/m$^2$, X=3. In embodiments of E5(d1) and E5(d2) and E5(d3), named respectively, E5(a, d1) and E5(a, d2) and E5(a, d3), bone marrow stem cells are administered to the patient after the melphalan to reverse bone marrow toxicity.

Embodiment Ee5

Embodiment Ee5 is a set of drugs comprised of melphalan for use in a regimen for the treatment of metastatic cancers that have defects in the function of the Fanconi/BRCA pathways of repair. In embodiments of Ee5, named Ee5(dX), where X=1, 2, or 3, the melphalan dose is approximately: 35 to 50 mg/m$^2$, X=1; or 50 to 70 mg/m$^2$, X=2; or 100-200 mg/m$^2$, X=3. In embodiments of Ee5(d1) and Ee5(d2) and Ee5(d3), named respectively, Ee5(a, d1) and Ee5(a, d2) and Ee5(a, d3), the regimen includes the administration of bone marrow stem cells to the patient after the melphalan to reverse bone marrow toxicity.
BRCA1 and BRCA2 Associated-Cancers Embodiment E6

Embodiment E6 of the invention is a method for the treatment of metastatic cancers that have defects in the function of the Fanconi/BRCA pathways of DNA repair, wherein said method is comprised of the administration of melphalan. An embodiment of E6, named E6(dX), where X=1, 2, or 3, is a method wherein the melphalan is administered IV at a dose of approximately 35 to 50 mg/m$^2$, X=1; or 50 to 70 mg/m$^2$, X=2; or 100-200 mg/m$^2$, X=3. In preferred embodiments of E6(d1) and E6(d2) and E6(d3) and E6(a, d1) and E6(a, d2) and E6(a, d3), respectively named E6(d1,eX) and E6(d2,eX) and E6(d3,eX) and E6(a, d1,eX) and E6(a, d2,eX) and E6(a, d3,eX) where X=1, 2 the metastatic cancer is a BRAC1-associated, X=1; or a BRCA2-associated cancer, X=2. In preferred embodiments of E6(d1,e1) and E6(d2,e1) and E6(d3,e1) and E5(a, d1,e1) and E6(a, d2,e1) and E6(a, d3,e1) and E6(d1,e2) and E6(d2, e2) and E6(d3,e2) and E6(a, d1,e2) and E6(a, d2,e2) and E6(a, d3,e2) named respectively E6(d1,e1,fX) and E6(d2, e1,fX) and E6(d3,e1,fX) and E6(a, d1,e1,fX) and E6(a, d2,e1,fX) and E6(a, d3,e1,fX) and E6(d1,e2,fX) and E6(d2, e2,fX) and E6(d3,e2,fX) and E6(a, d1,e2,fX) and E6(a, d2,e2,fX) and E6(a, d3,e2,fX) where X=1, 2, 3, 4, 5, 6, 7, 8, 9, 10, 11, 12, 13, or 14, the metastatic cancer is of following type: breast, X=1; ovarian X=2, pancreatic, X=3, melanoma, X=4; colon cancer, X=5; fallopian tube cancer, X=6; prostate cancer, X=7; lung cancer, X=8; renal cancer, X=9, or liver cancer, X=10; salivary gland cancer X=11; nasopharyngeal cancer X=12; bone cancer, X=13; or another type of cancer X=14.

Embodiment Ee6

Embodiment Ee6 is a set of drugs comprised of melphalan for use in a regimen to treat metastatic cancers that have defects in the function of the Fanconi/BRCA pathways of DNA repair. An embodiment of Ee6, named Ee6(dX), where X=1, 2, or 3, the IV melphalan dose is approximately 35 to 50 mg/m$^2$, X=1; or 50 to 70 mg/m$^2$, X=2; or 100-200 mg/m$^2$, X=3. In preferred embodiments of Ee6(d1) and Ee6(d2) and Ee6(d3) and Ee6(a, d1) and Ee6(a, d2) and Ee6(a, d3), respectively named Ee6(d1,eX) and Ee6(d2,eX) and Ee6(d3,eX) and Ee6(a, d1,eX) and Ee6(a, d2,eX) and Ee6(a, d3,eX) where X=1, 2 the metastatic cancer is a BRAC1-associated, X=1; or a BRCA2-associated cancer, X=2. In preferred embodiments of Ee6(d1,e1) and Ee6(d2, e1) and Ee6(d3,e1) and Ee5(a, d1,e1) and Ee6(a, d2,e1) and Ee6(a, d3,e1) and Ee6(d1,e2) and Ee6(d2,e2) and Ee6(d3, e2) and Ee6(a, d1,e2) and Ee6(a, d2,e2) and Ee6(a, d3,e2) named respectively Ee6(d1,e1,fX) and Ee6(d2,e1,fX) and Ee6(d3,e1,fX) and Ee6(a, d1,e1,fX) and Ee6(a, d2,e1,fX) and Ee6(a, d3,e1,fX) and Ee6(d1,e2,fX) and Ee6(d2,e2,fX) and Ee6(d3,e2,fX) and Ee6(a, d1,e2,fX) and Ee6(a, d2,e2, fX) and Ee6(a, d3,e2,fX) where X=1, 2, 3, 4, 5, 6, 7, 8, 9, 10, 11, 12, 13, or 14, the metastatic cancer is the of following type: breast, X=1; ovarian X=2, pancreatic, X=3, melanoma, X=4; colon cancer, X=5; fallopian tube cancer, X=6; prostate cancer, X=7; lung cancer, X=8; renal cancer, X=9, or liver cancer, X=10; salivary gland cancer X=11; nasopharyngeal cancer X=12; bone cancer, X=13; or another type of cancer X=14. As discussed previously, the presence of "a" in the embodiment name means that the method includes bone marrow stem cell infusion to reverse bone marrow toxicity.

Embodiment E7

Embodiment E7 of the invention is a method for the treatment of metastatic cancers that have defects in the function of the Fanconi/BRCA pathways of DNA repair, wherein said method is comprised of the administration of melphalan and said method gives high rates of CR and durable CRs. Embodiment E7(dX) of the invention where X=1, 2, or 3, is a method for the treatment of metastatic cancers that have defects in the function of the Fanconi/ BRCA pathways of DNA repair, wherein said method is comprised of the administration of melphalan and wherein the melphalan is administered IV at a dose of approximately 35 to 50 mg/m$^2$, X=1; or 50 to 70 mg/m$^2$, X=2; or 100-200 mg/m$^2$, X=3. In preferred embodiments of E7(d1) and E7(d2) and E7(d3), named respectively E7(a, d1) and E7(a, d2) and E7(a, d3), bone marrow stem cells are administered to the patient after the melphalan to reverse bone marrow toxicity. In preferred embodiments of E7(d1) and E7(d2) and E7(d3) and E7(a, d1) and E7(a, d2) and E7(a, d3), respectively named E7(d1,eX) and E7(d2,eX) and E7(d3,eX) and E7(a, d1,eX) and E7(a, d2,eX) and E7(a, d3,eX) where X=1 or 2, the metastatic cancer is a BRAC1-associated, X=1; or a BRCA2-associated cancer, X=2. In preferred embodiments of E7(d1,e1) and E7(d2,e1) and E7(d3,e1) and E7(a, d1,e1) and E7(a, d2,e1) and E7(a, d3,e1) and E7(d1,e2) and E7(d2,e2) and E7(d3,e2) and E7(a, d1,e2) and E7(a, d2,e2) and E7(a, d3,e2) named respectively E7(d1,e1,fX) and E7(d2,e1,fX) and E7(d3,e1,fX) and E7(a, d1,e1,fX) and E7(a, d2,e1,fX) and E7(a, d3,e1,fX) and E7(d1,e2,fX) and E7(d2,e2,fX) and E7(d3,e2,fX) and E7(a, d1,e2,fX) and E7(a, d2,e2,fX) and E7(a, d3,e2,fX) where X=1, 2, 3, 4, 5, 6, 7, 8, 9, 10, 11, 12, 13, or 14, the metastatic cancer is the of following type: breast, X=1; ovarian X=2, pancreatic, X=3, melanoma, X=4; colon cancer, X=5; fallopian tube cancer, X=6; prostate cancer, X=7; lung cancer, X=8; renal cancer, X=9, or another type, X=10; or liver cancer, X=10; salivary gland cancer X=11; nasopharyngeal cancer X=12; bone cancer, X=13; or another type of cancer X=14.

Embodiment Ee7

Embodiment Ee7 is a set of drugs comprised of melphalan for use in a regimen to treat metastatic cancers that have defects in the function of the Fanconi/BRCA pathways of DNA repair, wherein said regimen gives high rates of CR and durable CRs. In embodiment Ee7(dX) of the invention where X=1, 2, or 3, the IV melphalan dose is approximately 35 to 50 mg/m$^2$, X=1; or 50 to 70 mg/m$^2$, X=2; or 100-200 mg/m^2, X=3. In embodiments of Ee7(d1) and Ee7(d2) and Ee7(d3), named respectively Ee7(a, d1) and Ee7(a, d2) and Ee7(a, d3), the regimen includes the administration of bone marrow stem cells after the melphalan to reverse bone marrow toxicity. In preferred embodiments of Ee7(d1) and Ee7(d2) and Ee7(d3) and Ee7(a, d1) and Ee7(a, d2) and Ee7(a, d3), respectively named Ee7(d1,eX) and Ee7(d2,eX) and Ee7(d3,eX) and Ee7(a, d1,eX) and Ee7(a, d2,eX) and Ee7(a, d3,eX) where X=1 or 2, the metastatic cancer is a BRAC1-associated, X=1; or a BRCA2-associated cancer, X=2. In preferred embodiments of Ee7(d1,e1) and Ee7(d2, e1) and Ee7(d3,e1) and Ee7(a, d1,e1) and Ee7(a, d2,e1) and Ee7(a, d3,e1) and Ee7(d1,e2) and Ee7(d2,e2) and E7(d3,e2) and Ee7(a, d1,e2) and Ee7(a, d2,e2) and Ee7(a, d3,e2) named respectively Ee7(d1,e1,fX) and Ee7(d2,e1,fX) and Ee7(d3,e1,fX) and Ee7(a, d1,e1,fX) and Ee7(a, d2,e1,fX) and Ee7(a, d3,e1,fX) and Ee7(d1,e2,fX) and Ee7(d2,e2,fX) and Ee7(d3,e2,fX) and Ee7(a, d1,e2,fX) and Ee7(a, d2,e2, fX) and Ee7(a, d3,e2,fX) where X=1, 2, 3, 4, 5, 6, 7, 8, 9, 10, 11, 12, 13, or 14, the metastatic cancer is the of following type: breast, X=1; ovarian X=2, pancreatic, X=3, melanoma, X=4; colon cancer, X=5; fallopian tube cancer, X=6; prostate cancer, X=7; lung cancer, X=8; renal cancer, X=9, or another type, X=10; or liver cancer, X=10; salivary gland cancer X=11; nasopharyngeal cancer X=12; bone cancer, X=13; or another type of cancer X=14.

The following references relate to this matter: Lokhorst H M, Sonneveld P, Wijermans P W, van Marwijk Kooy M, Meuwissen O J, van Oers R H, van der Griend R, Dekker A W.; Br J Haematol. 1996 January; 92(1):44-8; Intermediate-dose melphalan compared with myeloablative treatment in multiple myeloma: long-term follow-up of the Dutch Cooperative Group HOVON 24 trial.; Sonneveld P, van der Holt B, Segeren C M, Vellenga E, Croockewit A J, Verhoe G E, Cornelissen J J, Schaafsma M R, van Oers M H, Wijermans P W, Westveer P H, Lokhorst H M; Dutch-Belgian Hemato-Oncology Cooperative Group (HOVON); Haematologica. 2007 July; 92(7):928-35.; Overall and event-free survival are not improved by the use of myeloablative therapy following intensified chemotherapy in previously untreated patients with multiple myeloma: a prospective randomized phase 3 study; Segeren C M, Sonneveld P, van der Holt B, Vellenga E, Croockewit A J, Verhoef G E, Cornelissen J J, Schaafsma M R, van Oers M H, Wijermans P W, Fibbe W E, Wittebol S, Schouten H C, van Marwijk Kooy M, Biesma D H, Baars J W, Slater R, Steijaert M M, Buijt I, Lokhorst H M; Dutch-Belgian Hemato-Oncology Cooperative Study Group.; Blood. 2003 Mar. 15; 101(6):2144-51.

Secondary mutations can lead to the emergence of cancer cells that regain proficiency in Fanconi/BRCA pathway and proficient in the repair of DNA crosslinks. This occurs with a probability of approximately 1 per 10^6 cell divisions and can lead to the development of drug resistance. The following reference relates to this matter: Secondary mutations as a mechanism of cisplatin resistance in BRCA2-mutated cancers; Sakai W, et al.; Nature. 2008 Feb. 28; 451(7182): 1116-20.

For example, a drug naïve patient with pancreatic cancer in the setting of an inherited BRCA2 mutation, and a tumor cell burden of ~$10^{10}$ cell would be expected to initially have ~$10^4$ BRCA2 proficient cancer cells. An advantage of melphalan is that the drug has significant activity against BRCA2 proficient cells, including pancreatic cancer cells, which at the levels used would be adequate to eradicate this small population of BRCA2 proficient cells. The following reference relates to this matter: Assays of drug sensitivity for cells from human tumours: in vitro and in vivo tests on a xenografted tumour; Bateman A E, Peckham M J, Steel G G.; Br J Cancer. 1979 July; 40(1):81-8.

Intrinsic and Acquired Drug Resistance

To effectively treat most types of cancer it is necessary to address the problems of intrinsic and acquired drug resistance. Resistance and failure in the ability of DNA cross-linking agents to inhibit clonogenic cancer cell survival can result from: insufficient drug levels at the site of the tumor; decreased drug uptake into the cells; increased drug efflux from the cells; increased detoxification of the drug; increased excision and repair of DNA-drug mono-adducts; and increased repair of DNA interstrand crosslinks. The present invention involves the administration of a set of drugs according to any of the embodiments and aspects recited herein that address these issues.

Drug Penetration Into Tumors

The drugs employed in the present invention can be low molecular weight compounds that rapidly distributed into the extravascular space and penetrate well into tumors. The doses are selected to provide drug levels that far exceed those needed to achieve the desired log reductions in cancer cell clonogenic survival. In addition, the treatment would generally be administered to patients after the surgical removal of all resectable bulk tumor. The purpose of this is to reduce the total tumor cell burden in the patient and thereby decrease the required log-reductions needed, to lessen the risk of bleeding and other complications resulting from drug induced destruction of bulk tumor, and to remove large necrotic regions present in bulk tumors that are have poor accessibility to drugs.

Embodiments with Drugs that Hypersensitize Cancer Cells to DNA Crosslinkers

In preferred embodiments of the invention the set of drugs is comprised of a DNA crosslinking agent and one or more additional drugs that hypersensitize cancer cells to said DNA crosslinking agent.

DMF

The degree of hypersensitization is quantitatively expressed by the dose modification factor (DMF).

DMF=[AUC-1 of DNA crosslinking agent alone] divided by [AUC-1 of DNA crosslinking agent with the other drugs]

For example, a DMF=5 means that the dose of the crosslinking agent (as reflected by drug AUC) needed to get a 1-log reduction in cancer cell clonogenic survival is 5 times lower for with the set of drugs than for the crosslinking agent by itself. Since the dose response curve for DNA crosslinking agents are log-linear, within the limits of linearity, a given dose of crosslinking agent (in conjunction with the other drugs) would give a 5 times greater log reduction in cancer cell clonogenic survival than the crosslinking agent alone.

A Note on Nomenclature of Embodiments for E and Ee

To save space Fx( . . . ) will be used to refer to the set of $\{Ex(...)$ and $Eex(...)\}$, where $X=1, 2, 3 \ldots$. For example, F2(a,b.g) refers to E2(a,b.g) and Ee2(a,b.g).

E #( )=method embodiment wherein #=1, 2, 3, . . .

Ee #( )=composition of matter embodiment that corresponds to E #( ) wherein #=1, 2, 3, . . .

The following summarizes the meaning of symbols within ( . . . )

a=with bone marrow stem cell infusion b=DNA crosslinker in set of drugs cX=specifies the particular DNA crosslinker; melphalan (X=1), bizelesin (X=2), chlorambucil (X=3), cyclophosphamide (X=4), bendamustine (X=5), ifosfamide (X=6), cisplatin (X=7), carboplatin (X=8), and oxaliplatin (X=9), thiotepa (X=10), busulfan (X=11), and mitomycin c (X=12), mechlorethamine (X=13), carmustine (X=14), lomustine (X=15), cisplatin (X=16), carboplatin (X=17), nedaplatin (X=18), oxaliplatin (X=19), satraplatin (X=20), picoplatin (X=21) and busulfan (X=22)

dX=specifies the melphalan dose, where X=1, 2, or 3, approximately 35 to 50 mg/m$^2$, X=1; or 50 to 70 mg/m$^2$, X=2; or 100-200 mg/m$^2$, X=3 eX=refers to the type of BRCA mutation, where X=1, 2 the metastatic cancer is a BRAC1-associated, X=1; or a BRCA2-associated cancer, X=2 f X=wherein the type of BRCA 1 or BRCA2 cancer is where X=1, 2, 3, 4, 5, 6, 7, 8, 9, 10, 11, 12, 13, or 14, the metastatic cancer is the of following type: breast, X=1; ovarian X=2, pancreatic, X=3, melanoma, X=4; colon cancer, X=5; fallopian tube cancer, X=6; prostate cancer, X=7; lung cancer, X=8; renal cancer, X=9, or another type, X=10; or liver cancer, X=10; salivary gland cancer X=11; nasopharyngeal cancer X=12; bone cancer, X=13; or another type of cancer X=14 g=wherein one of the drugs hypersensitize cancer cells to DNA crosslinking agent.

h=wherein one or more of said additional drugs decrease the detoxification of the crosslinking agent i=wherein one or more of said drugs decrease GSH-mediated detoxification of the crosslinking agent.

j=wherein one of the drugs in the set reacts with thiols or generates a thiol-reactive species k1=wherein said thiol reactive drug is BCNU k2=wherein said thiol reactive drug is CCNU l=wherein one or more of said drugs is an inhibitor of glutathione reductase.

m=and a drug that decreases intracellular GSH levels by oxidizing GSSG to GSSG n=wherein said drug is a redox cycling agent.

n1=wherein said redox cycling agent is an anthracyline n2=wherein said redox cycling agent is doxorubicin n3=wherein said redox cycling agent is methylene blue o=wherein one or more drugs in the set inhibit NER p=and one or more additional drugs that that increase the intracellular GSSG/2GSH reduction potential in cancer cells during at least part of the time when the cells are exposed to said crosslinking agent.

q=wherein one or more of said drugs is an inhibitor of Thioredoxin reductase.

r=wherein in a drug causes oxidative stress s=wherein a drug in the set is a proteasome inhibitor s1=wherein the set of drugs includes carfilzomib s2=wherein the set of drugs includes bortezomib t=MDR1 pgp inhibitor in the set of drugs Embodiments with DNA Crosslinking Agent, Drugs that Hypersensitize to DNA Crosslinkers (g)

In embodiments of the invention given below in List 1, the set of drugs is comprised of a DNA crosslinking agent and one or more additional drugs that hypersensitize cancer cells to said DNA crosslinking agent. The names of the new embodiments are given in List 2.

List 1:

F1(b) and F2(b) and F3(b), and F1(a,b) and F2(a,b) and F3(a,b) and {F1(b,cX) and F2(b,cX) and F3(b,cX) and F1(a,b,cX) and F2(a,b,cX) and F3(a,b,cX) wherein X=1, 2, 3 . . . or 22} and {F1(b, c1,dX) and F1(a,b, c1,dX) and F2(b, c1,dX) and F2(a,b, c1,dX) and F3(b, c1,dX) and F3(a,b,c1, dX) where X=1, 2, or 3} and F4 and F4(c1) and F4(c,d1) and F4(c,d2) and F4(c,d3) and F4(a, c1,d1) and F4(a, c1,d2) and F4(a,c1,d3) and F5(d1) and F5(d2) and F5(d3), and F5(a, d1) and F5(a, d2) and F5(a, d3) and F6(d1) and F6(d2) and F6(d3) and F6(a, d1) and F6(a, d2) and F6(a, d3), and F6(d1,e1) and F6(d2,e1) and F6(d3,e1) and F6(a, d1,e1) and F6(a, d2,e1) and F6(a, d3,e1) and F6(d1,e2) and F6(d2,e2) and F6(d3,e2) and F6(a, d1,e2) and F6(a, d2,e2) and F6(a, d3,e2) and F7 and F7(d1) and F7(d2) and F7(d3) and F7(a, d1) and F7(a, d2) and F7(a, d3) and F7(d1,e1) and F7(d2,e1) and F7(d3,e1) and F7(a, d1,e1) and F7(a, d2,e1) and F7(a, d3,e1) and F7(d1,e2) and F7(d2,e2) and F7(d3,e2) and F7(a, d1,e2) and F7(a, d2,e2) and F7(a, d3,e2) and {F6(d1,e1,fX) and F6(d2,e1,fX) and F6(d3,e1,fX) and F6(a, d1,e1,fX) and F6(a, d2,e1,fX) and F6(a, d3,e1,fX) and F6(d1,e2,fX) and F6(d2,e2,fX) and F6(d3,e2,fX) and F6(a, d1,e2,fX) and F6(a, d2,e2,fX) and F6(a, d3,e2,fX) and F7(d1,e1,fX) and F7(d2,e1,fX) and F7(d3,e1,fX) and F7(a, d1,e1,fX) and F7(a, d2,e1,fX) and F7(a, d3,e1,fX) and F7(d1,e2,fX) and F7(d2,e2,fX) and F7(d3,e2,fX) and F7(a, d1,e2,fX) and F7(a, d2,e2,fX) and F7(a, d3,e2,fX) where X=1, 2, 3, 4, 5, 6, 7, 8, 9, 10, 11, 12, 13, or 14}.

List 2:

These new embodiments are respectively named:

F1(b,g) and F2(b,g) and F3(b,g), and F1(a,b,g) and F2(a,b,g) and F3(a,b,g) and {F1(b,cX,g) and F2(b,cX,g) and F3(b,cX,g) and F1(a,b,cX,g) and F2(a,b,cX,g) and F3(a,b,cX,g) wherein X=1, 2, 3 . . . or 22} and {F1(b, c1,dX,g) and F1(a,b, c1,dX,g) and F2(b, c1,dX,g) and F2(a,b, c1,dX,g) and F3(b, c1,dX,g) and F3(a,b,c1,dX,g) where X=1, 2, or 3} and F4 and F4(c1,g) and F4(c,d1,g) and F4(c,d2,g) and F4(c,d3,g) and F4(a, c1,d1,g) and F4(a, c1,d2,g) and F4(a, c1,d3,g) and F5(d1,g) and F5(d2,g) and F5(d3,g), and F5(a, d1,g) and F5(a, d2,g) and F5(a, d3,g) and F6(d1,g) and F6(d2,g) and F6(d3,g) and F6(a, d1,g) and F6(a, d2,g) and F6(a, d3,g), and F6(d1,e1,g) and F6(d2,e1,g) and F6(d3,e1, g) and F6(a, d1,e1,g) and F6(a, d2,e1,g) and F6(a, d3,e1,g) and F6(d1,e2,g) and F6(d2,e2,g) and F6(d3,e2,g) and F6(a, d1,e2,g) and F6(a, d2,e2,g) and F6(a, d3,e2,g) and F7 and F7(d1,g) and F7(d2,g) and F7(d3,g) and F7(a, d1,g) and F7(a, d2,g) and F7(a, d3,g) and F7(d1,e1,g) and F7(d2,e1,g) and F7(d3,e1,g) and F7(a, d1,e1,g) and F7(a, d2,e1,g) and F7(a, d3,e1,g) and F7(d1,e2,g) and F7(d2,e2,g) and F7(d3,e2,g) and F7(a, d1,e2,g) and F7(a, d2,e2,g) and F7(a, d3,e2, g) and {F6(d1,e1,fX,g) and F6(d2,e1,fX,g) and F6(d3,e1,fX,g) and F6(a, d1,e1,fX,g) and F6(a, d2,e1,fX,g) and F6(a, d3,e1,fX,g) and F6(d1,e2,fX,g) and F6(d2,e2,fX,g) and F6(d3,e2,fX,g) and F6(a, d1,e2,fX,g) and F6(a, d2,e2,fX,g) and F6(a, d3,e2,fX,g) and F7(d1,e1,fX,g) and F7(d2,e1,fX, g) and F7(d3,e1,fX,g) and F7(a, d1,e1,fX,g) and F7(a, d2,e1,fX,g) and F7(a, d3,e1,fX,g) and F7(d1,e2,fX,g) and F7(d2,e2,fX,g) and F7(d3,e2,fX,g) and F7(a, d1,e2,fX,g) and F7(a, d2,e2,fX,g) and F7(a, d3,e2,fX,g) where X=1, 2, 3, 4, 5, 6, 7, 8, 9, 10, 11, 12, 13, or 14}

In embodiments of the present invention said additional drugs and their doses are selected to give a dose modification factor for the DNA crosslinking greater than approximately 3, 5, 10, 15, 20, 25, 30, 35, 40, or 50.

The required DMF is determined by the AUC of the crosslinking drug that will be achieved in the patient, the desired log in cancer cell clonogenic survival, and the crosslinking agent AUC-1 for the particular type of metastatic cancer. For example, consider a patient with metastatic melanoma that has $10^{10}$ cancer cells, to achieve a high probability of a long-term CR requires achieving ~12-log reduction. A reasonable estimate for melphalan AUC-1 for melanoma cell is ~20 microM h. (See FIG. 3) A single dose of melphalan at 70 mg/m$^2$ gives an AUC in patients of ~13 microM h. Three doses would give a total melphalan AUC of ~39 microM h. To achieve a 6-log reduction in each of the three cycles the AUC-1 of melphalan (in combination with the hypersensitizing drugs) would need to be reduced to a value of ~2 microM h, which would require a set of drugs that can give a DMF of ~10.

The ability of DNA crosslinking agents to inhibit clonogenic cell survival is a function of the number of DNA crosslinks formed in the cell. The relationship between clonogenic survival fraction and the maximal number of crosslinks per cell is log-linear. Doubling the number of crosslinks doubles the log reduction in clonogenic survival. The following reference relates to this matter: Formation and removal of DNA cross-links induced by melphalan and nitrogen mustard in relation to drug-induced cytotoxicity in human melanoma cells.; Hansson J, Lewensohn R, Ringborg U, Nilsson B.; Cancer Res. 1987 May 15; 47(10):2631-7.

Embodiments with DNA Crosslinking Agent, Drugs that Hypersensitize to DNA Crosslinkers and Decrease Detoxification (h).

In an embodiment one or more of said additional drugs in the set decrease the detoxification of the crosslinking agent by cancer cells and thereby increase DNA crosslinking.

In embodiments of the invention given in List 2, the set of drugs is comprised of a DNA crosslinking agent and one or more additional drugs that hypersensitize cancer cells to said DNA crosslinking agent, wherein one or more of said additional drugs decrease the detoxification of the crosslinking agent. These new embodiments are respectively named and given in List 3.

List 3:

F1(b,g,h) and F2(b,g,h) and F3(b,g,h), and F1(a,b,g,h) and F2(a,b,g,h) and F3(a,b,g,h) and {F1(b,cX,g,h) and F2(b,cX,g,h) and F3(b,cX,g,h) and F1(a,b,cX,g,h) and F2(a,b,cX,g,h) and F3(a,b,cX,g,h) wherein X=1, 2, 3 . . . or 22} and {F1(b, c1,dX,g,h) and F1(a,b, c1,dX,g,h) and F2(b, c1,dX,g,h) and F2(a,b, c1,dX,g,h) and F3(b, c1,dX,g,h) and F3(a, b,c1,dX,g,h) where X=1, 2, or 3} and F4 and F4(c1,g,h) and F4(c,d1,g,h) and F4(c,d2,g,h) and F4(c,d3,g,h) and F4(a, c1,d1,g,h) and F4(a, c1,d2,g,h) and F4(a,c1,d3,g,h) and F5(d1,g,h) and F5(d2,g,h) and F5(d3,g,h), and F5(a, d1,g,h) and F5(a, d2,g,h) and F5(a, d3,g,h) and F6(d1,g,h) and F6(d2,g,h) and F6(d3,g,h) and F6(a, d1,g,h) and F6(a, d2,g, h) and F6(a, d3,g,h), and F6(d1,e1,g,h) and F6(d2,e1,g,h) and F6(d3,e1,g,h) and F6(a, d1,e1,g,h) and F6(a, d2,e1,g,h) and F6(a, d3,e1,g,h) and F6(d1,e2,g,h) and F6(d2,e2,g,h) and F6(d3,e2,g,h) and F6(a, d1,e2,g,h) and F6(a, d2,e2,g,h) and F6(a, d3,e2,g,h) and F7 and F7(d1,g,h) and F7(d2,g,h) and F7(d3,g,h) and F7(a, d1,g,h) and F7(a, d2,g,h) and F7(a, d3,g,h) and F7(d1,e1,g,h) and F7(d2,e1,g,h) and F7(d3,e1,g,h) and F7(a, d1,e1,g,h) and F7(a, d2,e1,g,h) and F7(a, d3,e1,g,h) and F7(d1,e2,g,h) and F7(d2,e2,g,h) and F7(d3,e2,g,h) and F7(a, d1,e2,g,h) and F7(a, d2,e2,g,h) and F7(a, d3,e2,g,h) and {F6(d1,e1,fX,g,h) and F6(d2,e1,fX,g,h) and F6(d3,e1,fX,g,h) and F6(a, d1,e1,fX,g,h) and F6(a, d2,e1, fX,g,h) and F6(a, d3,e1,fX,g,h) and F6(d1,e2,fX,g,h) and F6(d2,e2,fX,g,h) and F6(d3,e2,fX,g,h) and F6(a, d1,e2,fX, g,h) and F6(a, d2,e2,fX,g,h) and F6(a, d3,e2,fX,g,h) and F7(d1,e1,fX,g,h) and F7(d2,e1,fX,g,h) and F7(d3,e1,fX,g,h) and F7(a, d1,e1,fX,g,h) and F7(a, d2,e1,fX,g,h) and F7(a, d3,e1,fX,g,h) and F7(d1,e2,fX,g,h) and F7(d2,e2,fX,g,h) and F7(d3,e2,fX,g,h) and F7(a, d1,e2,fX,g,h) and F7(a, d2,e2,fX,g,h) and F7(a, d3,e2,fX,g,h) where X=1, 2, 3, 4, 5, 6, 7, 8, 9, 10, 11, 12, 13, or 14}.

Decreased GSH-Mediated Detoxification of the Crosslinking Agent

In general, DNA crosslinking agents are electrophilic compounds or generate electrophilic species that can react with nucleophilic sites on DNA and other molecules. The maximal number of DNA crosslinks formed in a cell is determined by the partioning of the electrophilic crosslinking agent between DNA and other nucleophiles. A common and general mechanism of the detoxification of electrophilic compounds involves spontaneous or enzymatic reaction with intracellular thiols, principally glutathione (GSH). Elevated levels of intracellular thiols, especially GSH enhance the detoxification of electrophilic DNA crosslinking agents and decrease the maximal number of DNA crosslinks per cell. Conversely, decreasing GSH and GSH mediated detoxification results in an increase in DNA crosslink formation.

The following references relate to this matter: Cellular pharmacokinetics of the phenylalanine mustards; Vistica D T.; Pharmacol Ther. 1983; 22(3):379-406; Relationship between melanogenesis, glutathione levels and melphalan toxicity in human melanoma cells.; Benathan M, Alvero-Jackson H, Mooy A M, Scaletta C, Frenk E.; Melanoma Res. 1992 December; 2(5-6):305-14; Effect of D,L-buthionine-S,R-sulfoximine on cytotoxicity and DNA cross-linking induced by bifunctional DNA-reactive cytostatic drugs in human melanoma cells.; Hansson J, Edgren M, Ehrsson H, Ringborg U, Nilsson B.; Cancer Res. 1988 Jan. 1; 48(1): 19-26.

In an embodiment one or more of said drugs decrease GSH-mediated detoxification of the crosslinking agent. The decrease in GSH-mediated detoxification can be the result of decreased activity of GSH transferases (GSTs), decreased GSH levels or both.

Decreased crosslinker detoxification would be reflected in an increased maximal number of DNA-drug mono adducts and interstrand crosslinks. Methods for measuring DNA-drug monoadducts and crosslinks are known top one skilled in the art. See: Gene-specific formation and repair of DNA monoadducts and interstrand cross-links after therapeutic exposure to nitrogen mustards.; Souliotis V L, et al.; Clin Cancer Res. 2003 Oct. 1; 9(12):4465-74; Nucleotide excision repair of melphalan monoadducts.; Grant D F, Bessho T, Reardon J T.; Cancer Res. 1998 Nov. 15; 58(22):5196-200; Association between transcriptional activity, local chromatin structure, and the efficiencies of both sub-pathways of nucleotide excision repair of melphalan adducts; Episkopou H, et al.; Cancer Res. 2009 May 15; 69(10):4424-33.

Embodiments with DNA Crosslinking Agent, Drugs that Hypersensitize to DNA Crosslinkers and Decrease GSH-Mediated Detoxification (i)

In embodiments of the invention given in List 3, the set of drugs is comprised of a DNA crosslinking agent, and one or more additional drugs that hypersensitize cancer cells to said DNA crosslinking agent, wherein one or more of said additional drugs decrease the detoxification of the crosslinking agent, and wherein one or more of said drugs decrease GSH-mediated detoxification of the crosslinking agent. The new embodiments are respectively named and given in List 4.

List 4:

F1(b,g,h,i) and F2(b,g,h,i) and F3(b,g,h,i), and F1(a,b,g,h,i) and F2(a,b,g,h,i) and F3(a,b,g,h,i) and {F1(b,cX,g,h,i) and F2(b,cX,g,h,i) and F3(b,cX,g,h,i) and F1(a,b,cX,g,h,i) and F2(a,b,cX,g,h,i) and F3(a,b,cX,g,h,i) wherein X=1, 2, 3 . . . or 22} and {F1(b, c1,dX,g,h,i) and F1(a,b, c1,dX,g,h,i) and F2(b, c1,dX,g,h,i) and F2(a,b, c1,dX,g,h,i) and F3(b, c1,dX,g,h,i) and F3(a,b,c1,dX,g,h,i) where X=1, 2, or 3} and F4 and F4(c1,g,h,i) and F4(c,d1,g,h,i) and F4(c,d2,g,h,i) and F4(c,d3,g,h,i) and F4(a, c1,d1,g,h,i) and F4(a, c1,d2,g,h,i) and F4(a,c1,d3,g,h,i) and F5(d1,g,h,i) and F5(d2,g,h,i) and F5(d3,g,h,i), and F5(a, d1,g,h,i) and F5(a, d2,g,h,i) and F5(a, d3,g,h,i) and F6(d1,g,h,i) and F6(d2,g,h,i) and F6(d3,g,h,i) and F6(a, d1,g,h,i) and F6(a, d2,g,h,i) and F6(a, d3,g,h,i), and F6(d1,e1,g,h,i) and F6(d2,e1,g,h,i) and F6(d3,e1,g,h,i) and F6(a, d1,e1,g,h,i) and F6(a, d2,e1,g,h,i) and F6(a, d3,e1,g,h,i) and F6(d1,e2,g,h,i) and F6(d2,e2,g,h,i) and F6(d3,e2,g,h,i) and F6(a, d1,e2,g,h,i) and F6(a, d2,e2,g,h,i) and F6(a, d3,e2,g,h,i) and F7 and F7(d1,g,h,i) and F7(d2,g,h,i) and F7(d3,g,h,i) and F7(a, d1,g,h,i) and F7(a, d2,g,h,i) and F7(a, d3,g,h,i) and F7(d1,e1,g,h,i) and F7(d2,e1,g,h,i) and F7(d3,e1,g,h,i) and F7(a, d1,e1,g,h,i) and F7(a, d2,e1,g,h,i) and F7(a, d3,e1,g,h,i) and F7(d1,e2,g,h,i) and F7(d2,e2,g,h,i) and F7(d3,e2,g,h,i) and F7(a, d1,e2,g,h,i) and F7(a, d2,e2,g,h,i) and F7(a, d3,e2,g,h,i) and {F6(d1,e1,fX,g,h,i) and F6(d2,e1,fX,g,h,i) and F6(d3,e1,fX,g,h,i) and F6(a, d1,e1,fX,g,h,i) and F6(a, d2,e1,fX,g,h,i) and F6(a, d3,e1,fX,g,h,i) and F6(d1,e2,fX,g,h,i) and F6(d2,e2,fX,g,h,i) and F6(d3,e2,fX,g,h,i) and F6(a, d1,e2,fX,g,h,i) and F6(a, d2,e2,fX,g,h,i) and F6(a, d3,e2,fX,g,h,i) and F7(d1,e1,fX,g,h,i) and F7(d2,e1,fX,g,h,i) and F7(d3,e1,fX,g,h,i) and F7(a, d1,e1,fX,g,h,i) and F7(a, d2,e1,fX,g,h,i) and F7(a, d3,e1,fX,g,h,i) and F7(d1,e2,fX,g,h,i) and F7(d2,e2,fX,g,h,i) and F7(d3,e2,fX,g,h,i) and F7(a, d1,e2,fX,g,h,i) and F7(a, d2,e2,fX,g,h,i) and F7(a, d3,e2,fX,g,h,i) where X=1, 2, 3, 4, 5, 6, 7, 8, 9, 10, 11, 12, 13, or 14}.

Elevated levels of Glutathione-S-transferase-π (GST-π) have been associated with resistance to DNA crosslinking agents. Inhibition of GST results in ~2 fold increase in DMF for melphalan. GST-π activity has an acidic cysteine-SH group with a pKa of ~4.2 that is critical for enzyme activity and which is highly reactive with electrophilic agents that inhibit the enzyme. The enzyme is also redox sensitive and is inhibited under oxidative conditions. In an embodiment one of the drugs in the set reacts with thiols or generates a thiol-reactive species. In a preferred embodiment said drug is BCNU. BCNU spontaneously decomposes to generate 2-chloroethyl isocyanate which is highly reactive towards thiols. In an embodiment of the invention one or more of the drugs of the set inhibits GST activity. In an embodiment said drug is BCNU.

A large number of electrophilic, thiol reactive compounds are well known to one skilled in the arts that can covalently modify reactive protein thiols that could be used in this method; said compounds are within the scope of the present invention. Methods to identify thiol-reactive compounds are known to one skilled in the art.

Embodiments with DNA Crosslinking Agent, Drugs that Hypersensitize to DNA Crosslinkers and Thiol-Reactive Drugs(j)

In embodiments of the invention in List 4, the set of drugs is comprised of a DNA crosslinking agent, and one or more additional drugs that hypersensitize cancer cells to said DNA crosslinking agent, wherein one or more of said additional drugs decrease the detoxification of the crosslinking agent and wherein one or more of said drugs decrease GSH-mediated detoxification of the crosslinking agent (i), and wherein one of the drugs in the set reacts with thiols or generates a thiol-reactive species (j). The new embodiments are respectively named and given in List 5.

List 5:

F1(b,g,h,i,j) and F2(b,g,h,i,j) and F3(b,g,h,i,j), and F1(a,b,g,h,i,j) and F2(a,b,g,h,i,j) and F3(a,b,g,h,i,j) and {F1(b, cX,g,h,i,j) and F2(b,cX,g,h,i,j) and F3(b,cX,g,h,i,j) and F1(a,b,cX,g,h,i,j) and F2(a,b,cX,g,h,i,j) and F3(a,b,cX,g,h,i,j) wherein X=1, 2, 3 . . . or 22} and {F1(b, c1,dX,g,h,i,j) and F1(a,b, c1,dX,g,h,i,j) and F2(b, c1,dX,g,h,i,j) and F2(a, b, c1,dX,g,h,i,j) and F3(b, c1,dX,g,h,i,j) and F3(a,b,c1,dX, g,h,i,j) where X=1, 2, or 3} and F4 and F4(c1,g,h,i,j) and F4(c,d1,g,h,i,j) and F4(c,d2,g,h,i,j) and F4(c,d3,g,h,i,j) and F4(a, c1,d1,g,h,i,j) and F4(a, c1,d2,g,h,i,j) and F4(a,c1,d3, g,h,i,j) and F5(d1,g,h,i,j) and F5(d2,g,h,i,j) and F5(d3,g,h,i,j), and F5(a, d1,g,h,i,j) and F5(a, d2,g,h,i,j) and F5(a, d3,g,h,i,j) and F6(d1,g,h,i,j) and F6(d2,g,h,i,j) and F6(d3,g,h,i,j) and F6(a, d1,g,h,i,j) and F6(a, d2,g,h,i,j) and F6(a, d3,g,h,i,j), and F6(d1,e1,g,h,i,j) and F6(d2,e1,g,h,i,j) and F6(d3,e1,g,h,i,j) and F6(a, d1,e1,g,h,i,j) and F6(a, d2,e1,g,h,i,j) and F6(a, d3,e1,g,h,i,j) and F6(d1,e2,g,h,i,j) and F6(d2,e2,g,h,i,j) and F6(d3,e2,g,h,i,j) and F6(a, d1,e2,g,h,i,j) and F6(a, d2,e2,g,h,i,j) and F6(a, d3,e2,g,h,i,j) and F7 and F7(d1,g,h,i,j) and F7(d2,g,h,i,j) and F7(d3,g,h,i,j) and F7(a, d1,g,h,i,j) and F7(a, d2,g,h,i,j) and F7(a, d3,g,h,i,j) and F7(d1,e1,g,h,i,j) and F7(d2,e1,g,h,i,j) and F7(d3,e1,g,h,i,j) and F7(a, d1,e1,g,h,i,j) and F7(a, d2,e1,g,h,i,j) and F7(a, d3,e1,g,h,i,j) and F7(d1,e2,g,h,i,j) and F7(d2,e2,g,h,i,j) and F7(d3,e2,g,h,i,j) and F7(a, d1,e2,g,h,i,j) and F7(a, d2,e2,g,h,i,j) and F7(a, d3,e2,g,h,i,j) and {F6(d1,e1,fX,g,h,i,j) and F6(d2,e1,fX,g,h,i,j) and F6(d3,e1,fX,g,h,i,j) and F6(a, d1,e1,fX,g,h,i,j) and F6(a, d2,e1,fX,g,h,i,j) and F6(a, d3,e1,fX,g,h,i,j) and F6(d1,e2,fX,g,h,i,j) and F6(d2,e2,fX,g,h,i,j) and F6(d3,e2,fX,g,h,i,j) and F6(a, d1,e2,fX,g,h,i,j) and F6(a, d2,e2,fX,g,h,i,j) and F6(a, d3,e2,fX,g,h,i,j) and F7(d1,e1,fX,g,h,i,j) and F7(d2,e1,fX,g,h,i,j) and F7(d3,e1,fX,g,h,i,j) and F7(a, d1,e1,fX,g,h,i,j) and F7(a, d2,e1,fX,g,h,i,j) and F7(a, d3,e1,fX,g,h,i,j) and F7(d1,e2,fX,g,h,i,j) and F7(d2,e2,fX,g,h,i,j) and F7(d3,e2,fX,g,h,i,j) and F7(a, d1,e2,fX,g,h,i,j) and F7(a, d2,e2,fX,g,h,i,j) and F7(a, d3,e2,fX,g,h,i,j) where X=1, 2, 3, 4, 5, 6, 7, 8, 9, 10, 11, 12, 13, or 14}.

The following references relate to this matter: Modulation of class Pi glutathione transferase activity by sulfhydryl group modification; Shen H X, Tamai K, Satoh K, Hatayama I, Tsuchida S, Sato K.; Arch Biochem Biophys. 1991 April; 286(1):178-82; Sensitization of human melanoma cells to the cytotoxic effect of melphalan by the glutathione transferase inhibitor ethacrynic acid; Hansson J, et al.; Cancer Res. 1991 Jan. 1; 51(1):94-8.; Structural and functional consequences of inactivation of human glutathione S-transferase P1-1 mediated by the catechol metabolite of equine estrogens, 4-hydroxyequilenin.; Chang M, Shin Y G, van Breemen R B, Blond S Y, Bolton J L.; Biochemistry. 2001 Apr. 17; 40(15):4811-20; Inactivation of glutathione reductase by 2-chloroethyl nitrosourea-derived isocyanates.; Babson J R, Reed D J.; Biochem Biophys Res Commun. 1978 Jul. 28; 83(2):754-62; Measurement and estimation of electrophilic reactivity for predictive toxicology; Schwöbel J A, et al.; Chem Rev. 2011 Apr. 13; 111(4):2562-96; Class-pi glutathione S-transferase is unable to regain its native conformation after oxidative inactivation by hydrogen peroxide; Sluis-Cremer N, Naidoo N, Dirr H.; Eur J Biochem. 1996 Dec. 1; 242(2):301-7; Inactivation of mouse liver glutathione S-transferase YfYf (Pi class) by ethacrynic acid and 5,5'-dithiobis-(2-nitrobenzoic acid).; Phillips M F, Mantle T J.; Biochem J. 1993 Aug. 15; 294 (Pt 1):57-62; Identifying and characterizing binding sites on the irreversible inhibition of human glutathione S-transferase P1-1 by S-thiocarbamoylation.; Quesada-Soriano I, et al.; Chembiochem. 2012 Jul. 23; 13(11):1594-604.

Embodiments with DNA Crosslinking Agent and Drugs that Hypersensitize to DNA Crosslinkers with BCNU (k1)

In embodiments of the invention in List 5, the set of drugs is comprised of a DNA crosslinking agent, and one or more additional drugs that hypersensitize cancer cells to said DNA crosslinking agent, wherein one or more of said additional drugs decrease the detoxification of the crosslinking agent, and wherein one or more of said drugs decrease GSH-mediated detoxification of the crosslinking agent, and wherein one of the drugs in the set is reacts with thiols or generates a thiol-reactive species, wherein said drug is BCNU. The new embodiments are respectively named and given in List 6

List 6:

F1(b,g,h,i,j,k1) and F2(b,g,h,i,j,k1) and F3(b,g,h,i,j,k1), and F1(a,b,g,h,i,j,k1) and F2(a,b,g,h,i,j,k1) and F3(a,b,g,h,i,j,k1) and {F1(b,cX,g,h,i,j,k1) and F2(b,cX,g,h,i,j,k1) and F3(b,cX,g,h,i,j,k1) and F1(a,b,cX,g,h,i,j,k1) and F2(a,b,cX,g,h,i,j,k1) and F3(a,b,cX,g,h,i,j,k1) wherein X=1, 2, 3 . . . or 22} and {F1(b, c1,dX,g,h,i,j,k1) and F1(a,b, c1,dX,g,h,i,j,k1) and F2(b, c1,dX,g,h,i,j,k1) and F2(a,b, c1,dX,g,h,i,j,k1) and F3(b, c1,dX,g,h,i,j,k1) and F3(a,b,c1,dX,g,h,i,j,k1) where X=1, 2, or 3} and F4 and F4(c1,g,h,i,j,k1) and F4(c,d1,g,h,i,j,k1) and F4(c,d2,g,h,i,j,k1) and F4(c,d3,g,h,i,j,k1) and F4(a, c1,d1,g,h,i,j,k1) and F4(a, c1,d2,g,h,i,j,k1) and F4(a,c1,d3,g,h,i,j,k1) and F5(d1,g,h,i,j,k1) and F5(d2,g,h,i,j,k1) and F5(d3,g,h,i,j,k1), and F5(a, d1,g,h,i,j,k1) and F5(a, d2,g,h,i,j,k1) and F5(a, d3,g,h,i,j,k1) and F6(d1,g,h,i,j,k1) and F6(d2,g,h,i,j,k1) and F6(d3,g,h,i,j,k1) and F6(a, d1,g,h,i,j,k1) and F6(a, d2,g,h,i,j,k1) and F6(a, d3,g,h,i,j,k1), and F6(d1,e1,g,h,i,j,k1) and F6(d2,e1,g,h,i,j,k1) and F6(d3,e1,g,h,i,j,k1) and F6(a, d1,e1,g,h,i,j,k1) and F6(a, d2,e1,g,h,i,j,k1) and F6(a, d3,e1,g,h,i,j,k1) and F6(d1,e2,g,h,i,j,k1) and F6(d2,e2,g,h,i,j,k1) and F6(d3,e2,g,h,i,j,k1) and F6(a, d1,e2,g,h,i,j,k1) and F6(a, d2,e2,g,h,i,j,k1) and F6(a, d3,e2,g,h,i,j,k1) and F7 and F7(d1,g,h,i,j,k1) and F7(d2,g,h,i,j,k1) and F7(d3,g,h,i,j,k1) and F7(a, d1,g,h,i,j,k1) and F7(a, d2,g,h,i,j,k1) and F7(a, d3,g,h,i,j,k1) and F7(d1,e1,g,h,i,j,k1) and F7(d2,e1,g,h,i,j,k1) and F7(d3,e1,g,h,i,j,k1) and F7(a, d1,e1,g,h,i,j,k1) and F7(a, d2,e1,g,h,i,j,k1) and F7(a, d3,e1,g,h,i,j,k1) and F7(d1,e2,g,h,i,j,k1) and F7(d2,e2,g,h,i,j,k1) and F7(d3,e2,g,h,i,j,k1) and F7(a, d1,e2,g,h,i,j,k1) and F7(a, d2,e2,g,h,i,j,k1) and F7(a, d3,e2,g,h,i,j,k1) and {F6(d1,e1,fX,g,h,i,j,k1) and F6(d2,e1,fX,g,h,i,j,k1) and F6(d3,e1,fX,g,h,i,j,k1) and F6(a, d1,e1,fX,g,h,i,j,k1) and F6(a, d2,e1,fX,g,h,i,j,k1) and F6(a, d3,e1,fX,g,h,i,j,k1) and F6(d1,e2,fX,g,h,i,j,k1) and F6(d2,e2,fX,g,h,i,j,k1) and F6(d3,e2,fX,g,h,i,j,k1) and F6(a, d1,e2,fX,g,h,i,j,k1) and F6(a, d2,e2,fX,g,h,i,j,k1) and F6(a, d3,e2,fX,g,h,i,j,k1) and F7(d1,e1,fX,g,h,i,j,k1) and F7(d2,e1,fX,g,h,i,j,k1) and F7(d3,e1,fX,g,h,i,j,k1) and F7(a, d1,e1,fX,g,h,i,j,k1) and F7(a, d2,e1,fX,g,h,i,j,k1) and F7(a, d3,e1,fX,g,h,i,j,k1) and F7(d1,e2,fX,g,h,i,j,k1) and F7(d2,e2,fX,g,h,i,j,k1) and F7(d3,e2,fX,g,h,i,j,k1) and F7(a, d1,e2,fX,g,h,i,j,k1) and F7(a, d2,e2,fX,g,h,i,j,k1) and F7(a, d3,e2,fX,g,h,i,j,k1) where X=1, 2, 3, 4, 5, 6, 7, 8, 9, 10, 11, 12, 13, or 14}.

Embodiments with DNA Crosslinking Agent and Drugs that Hypersensitize to DNA Crosslinkers with CCNU (k2)

In embodiments of the invention in List 5, the set of drugs is comprised of a DNA crosslinking agent, and one or more additional drugs that hypersensitize cancer cells to said DNA crosslinking agent, wherein one or more of said additional drugs decrease the detoxification of the crosslinking agent, and wherein one or more of said drugs decrease GSH-mediated detoxification of the crosslinking agent, and wherein one of the drugs in the set is reacts with thiols or generates a thiol-reactive species, wherein said drug is CCNU. The new embodiments are respectively named and given in List 7.

List 7:

F1(b,g,h,i,j,k2) and F2(b,g,h,i,j,k2) and F3(b,g,h,i,j,k2), and F1(a,b,g,h,i,j,k2) and F2(a,b,g,h,i,j,k2) and F3(a,b,g,h,i,j,k2) and {F1(b,cX,g,h,i,j,k2) and F2(b,cX,g,h,i,j,k2) and F3(b,cX,g,h,i,j,k2) and F1(a,b,cX,g,h,i,j,k2) and F2(a,b,cX,g,h,i,j,k2) and F3(a,b,cX,g,h,i,j,k2) wherein X=1, 2, 3 . . . or 22} and {F1(b, c1,dX,g,h,i,j,k2) and F1(a,b, c1,dX,g,h,i,j,k2) and F2(b, c1,dX,g,h,i,j,k2) and F2(a,b, c1,dX,g,h,i,j,k2) and F3(b, c1,dX,g,h,i,j,k2) and F3(a,b,c1,dX,g,h,i,j,k2) where X=1, 2, or 3} and F4 and F4(c1,g,h,i,j,k2) and F4(c,d1,g,h,i,j,k2) and F4(c,d2,g,h,i,j,k2) and F4(c,d3,g,h,i,j,k2) and F4(a, c1,d1,g,h,i,j,k2) and F4(a, c1,d2,g,h,i,j,k2) and F4(a,c1,d3,g,h,i,j,k2) and F5(d1,g,h,i,j,k2) and F5(d2,g,h,i,j,k2) and F5(d3,g,h,i,j,k2), and F5(a, d1,g,h,i,j,k2) and F5(a, d2,g,h,i,j,k2) and F5(a, d3,g,h,i,j,k2) and F6(d1,g,h,i,j,k2) and F6(d2,g,h,i,j,k2) and F6(d3,g,h,i,j,k2) and F6(a, d1,g,h,i,j,k2) and F6(a, d2,g,h,i,j,k2) and F6(a, d3,g,h,i,j,k2), and F6(d1,e1,g,h,i,j,k2) and F6(d2,e1,g,h,i,j,k2) and F6(d3,e1,g,h,i,j,k2) and F6(a, d1,e1,g,h,i,j,k2) and F6(a, d2,e1,g,h,i,j,k2) and F6(a, d3,e1,g,h,i,j,k2) and F6(d1,e2,g,h,i,j,k2) and F6(d2,e2,g,h,i,j,k2) and F6(d3,e2,g,h,i,j,k2) and F6(a, d1,e2,g,h,i,j,k2) and F6(a, d2,e2,g,h,i,j,k2) and F6(a, d3,e2,g,h,i,j,k2) and F7 and F7(d1,g,h,i,j,k2) and F7(d2,g,h,i,j,k2) and F7(d3,g,h,i,j,k2) and F7(a, d1,g,h,i,j,k2) and F7(a, d2,g,h,i,j,k2) and F7(a, d3,g,h,i,j,k2) and F7(d1,e1,g,h,i,j,k2) and F7(d2,e1,g,h,i,j,k2) and F7(d3,e1,g,h,i,j,k2) and F7(a, d1,e1,g,h,i,j,k2) and F7(a, d2,e1,g,h,i,j,k2) and F7(a, d3,e1,g,h,i,j,k2) and F7(d1,e2,g,h,i,j,k2) and F7(d2,e2,g,h,i,j,k2) and F7(d3,e2,g,h,i,j,k2) and F7(a, d1,e2,g,h,i,j,k2) and F7(a, d2,e2,g,h,i,j,k2) and F7(a, d3,e2,g,h,i,j,k2) and {F6(d1,e1,fX,g,h,i,j,k2) and F6(d2,e1,fX,g,h,i,j,k2) and F6(d3,e1,fX,g,h,i,j,k2) and F6(a, d1,e1,fX,g,h,i,j,k2) and F6(a, d2,e1,fX,g,h,i,j,k2) and F6(a, d3,e1,fX,g,h,i,j,k2) and F6(d1,e2,fX,g,h,i,j,k2) and F6(d2,e2,fX,g,h,i,j,k2) and F6(d3,e2,fX,g,h,i,j,k2) and F6(a, d1,e2,fX,g,h,i,j,k2) and F6(a, d2,e2,fX,g,h,i,j,k2) and F6(a, d3,e2,fX,g,h,i,j,k2) and F7(d1,e1,fX,g,h,i,j,k2) and F7(d2,e1,fX,g,h,i,j,k2) and F7(d3,e1,fX,g,h,i,j,k2) and F7(a, d1,e1,fX,g,h,i,j,k2) and F7(a, d2,e1,fX,g,h,i,j,k2) and F7(a, d3,e1,fX,g,h,i,j,k2) and F7(d1,e2,fX,g,h,i,j,k2) and F7(d2,e2,fX,g,h,i,j,k2) and F7(d3,e2,fX,g,h,i,j,k2) and F7(a, d1,e2,fX,g,h,i,j,k2) and F7(a, d2,e2,fX,g,h,i,j,k2) and F7(a, d3,e2,fX,g,h,i,j,k2) where X=1, 2, 3, 4, 5, 6, 7, 8, 9, 10, 11, 12, 13, or 14}.

GSH is one of the major redox buffers in cells. The intracellular concentration of GSH is generally maintained in the 0.5 to 10 mM range. The rate limiting step in the denovo synthesis of GSH is γ-glutamylcysteine synthetase (GCS) activity. Intracellular GSH levels are determined by the balance between GSH consumption, regeneration and denovo synthesis, Oxidizing agents (e.g., ROS) convert GSH to give GSSG. GSH is then regenerated by GR catalyzed reduction of GSSH with NADPH as the reducing agent. The system is robust and highly dynamic. Treatment of cells with a high concentration of the oxidizing agent diamide rapidly depletes cells of GSH. Within minutes after removal of the diamide the GSH levels can be restored to normal levels by GR mediated reduction of GSSG. The following references relates to this matter:" Imaging in real-time with FRET the redox response of tumorigenic cells to glutathione perturbations in a microscale flow; Lin C, et al.; Integr Biol (Camb). 2011 March; 3(3):208-17; Glutathione; Meister A, Anderson M E.; Annu Rev Biochem. 1983; 52:711-60.

Inhibition of GCS by buthionine sulfoximine (BSO) results in profound depletion of GSH. However, the kinetics of GSH depletion in cells in treated patients treated with BSO is slow; 24 to 48 hours are needed to obtain major reductions in GSH levels. During this time a number of compensatory mechanisms are triggered in BSO treated cells that counteract the potentiating effects of GSH depletion on the inhibition of clonogenic cell survival by DNA crosslinking agents. For example, Nuclear factor-erythroid 2 p45-related factor 2 (NRF2) is activated in BSO treated cells. NrF2 is a transcription factor that increases the expression of a wide range of genes involved in the detoxification of reactive electrophilic species (including DNA crosslinking agents) and ROS. GSH depletion with BSO generally gives results in a DMF of ~2 to 6 for DNA crosslinking agents such as melphalan or cisplatin. In clinical trials, the method of GSH depletion with BSO followed by melphalan was ineffective and did not give high rates of CRs in patients with metastatic cancer, bone marrow toxicity was dose limiting. (See: Phase I trial of buthionine sulfoximine in combination with melphalan in patients with cancer; O'Dwyer P J, et al; J Clin Oncol. 1996 January; 14(1):249-56; Phase I study of continuous-infusion L-S,R-buthionine sulfoximine with intravenous melphalan; Bailey H H, et al.; J Natl Cancer Inst. 1997 Dec. 3; 89(23):1789-96).

At the present time there are no effective methods for the treatment of metastatic cancer involving a DNA crosslinking agent in combination with drugs that decrease GSH in cancer cells and thereby decrease the intracellular detoxification of said crosslinking agent. (DNA crosslinking agents react with GSH, however, even high doses of these drugs do not generally result in major decreases in intracellular GSH levels in patients.) The following reference relates to this matter: The effect of treatment with high dose melphalan, cisplatin or carboplatin on levels of glutathione in plasma, erythrocytes, mononuclear cells and urine.; Hogarth L, English M, Price L, Wyllie R, Pearson A D, Hall A G.; Cancer Chemother Pharmacol. 1996; 37(5):479-85 The problem cannot be safely and reliably solved by merely increasing the dose of the crosslinking agent.

In order to be able to reliably obtain major-log reduction in cancer cell survival with (electrophilic) DNA crosslinking agents the problem of GSH-mediated detoxification needs to be addressed. Genetic mutations that confer resistance to alkylating agents are infrequent. For example, the frequency of melphalan resistance in CHO cells is ~10-7 per cell division. However, resistance to melphalan and other DNA crosslinking agents can be mediated by a rapid inducible metabolic response to a wide range of factors and occurs with high frequency. A single dose of melphalan given to mice with human ovarian cancer xenografts induces drug resistance with a 2-fold decrease in the tumor cell sensitivity to melphalan. This resistance is associated with a 2-fold increase in GSH levels and is prevented by BSO. Major resistance to melphalan has also been observed in breast cancer tumors in mice 5 days after a single dose of melphalan. (The first dose gave a 2.5 log reduction versus <1-log reduction for the second dose of melphalan.)

The following references relates to this matter: Rapid development of drug resistance in human ovarian tumor xenografts after a single treatment with melphalan in Vivo.; Caffrey P B, Zhang Y, Frenkel G D.; Anticancer Res. 1998 July-August; 18(4C):3021-5; Acute in vivo resistance in high-dose therapy.; Teicher B A, Ara G, Keyes S R, Herbst R S, Frei E 3rd.; Clin Cancer Res. 1998 February; 4(2):483-91; Rapid development of glutathione-S-transferase-dependent drug resistance in vitro and its prevention by ethacrynic acid; Caffrey P B, et al.; Cancer Lett. 1999 Feb. 8; 136(1): 47-52.

Up-regulation of GSH and other protective thiols is inducible by a wide range of alkylating agents, anticancer drugs, heavy metals, electrophiles and agents that induce oxidative stress. Sulforaphane, which is present in cruciferous vegetable such as broccoli elevates GSH levels. These effects can be mediated by activation of Nrf2 (Nuclear factor-erythroid 2 p45-related factor 2). NrF2 is a transcription factor that increases the expression of a wide range of genes involved in glutathione synthesis and metabolism and detoxification of reactive oxygen species (ROS).

The following references relate to this matter: Differential effect of covalent protein modification and glutathione depletion on the transcriptional response of Nrf2 and NF-kappaB; Chia A J, Goldring C E, Kitteringham N R, Wong S Q, Morgan P, Park B K.; Biochem Pharmacol. 2010 Aug. 1; 80(3):410-2; Transcription factor Nrf2 mediates an adaptive response to sulforaphane that protects fibroblasts in vitro against the cytotoxic effects of electrophiles, peroxides and redox-cycling agents; Higgins L G, Kelleher M O, Eggleston I M, Itoh K, Yamamoto M, Hayes J D.; Toxicol Appl Pharmacol. 2009 Jun. 15; 237(3):267-80.

Embodiments with DNA Crosslinking Agent and Glutathione Reductase Inhibitor (l)

In a preferred embodiment the set of drugs is comprised of a DNA crosslinking agent and a second drug that is an inhibitor of glutathione reductase (GR).

In embodiments of the invention given in List 2, the set of drugs is comprised of a DNA crosslinking agent and one or more additional drugs that hypersensitize cancer cells to said DNA crosslinking agent, wherein one or more of said drugs is an inhibitor of glutathione reductase. The new embodiments are respectively named and given in List 8.

List 8:

F1(b,g,l) and F2(b,g,l) and F3(b,g,l), and F1(a,b,g,l) and F2(a,b,g,l) and F3(a,b,g,l) and {F1(b,cX,g,l) and F2(b,cX,g,l) and F3(b,cX,g,l) and F1(a,b,cX,g,l) and F2(a,b,cX,g,l) and F3(a,b,cX,g,l) wherein X=1, 2, 3 . . . or 22} and {F1(b, c1,dX,g,l) and F1(a,b, c1,dX,g,l) and F2(b, c1,dX,g,l) and F2(a,b, c1,dX,g,l) and F3(b, c1,dX,g,l) and F3(a,b,c1,dX,g,l) where X=1, 2, or 3} and F4 and F4(c1,g,l) and F4(c,d1,g,l) and F4(c,d2,g,l) and F4(c,d3,g,l) and F4(a, c1,d1,g,l) and F4(a, c1,d2,g,l) and F4(a,c1,d3,g,l) and F5(d1,g,l) and F5(d2,g,l) and F5(d3,g,l), and F5(a, d1,g,l) and F5(a, d2,g,l) and F5(a, d3,g,l) and F6(d1,g,l) and F6(d2,g,l) and F6(d3, g,l) and F6(a, d1,g,l) and F6(a, d2,g,l) and F6(a, d3,g,l), and F6(d1,e1,g,l) and F6(d2,e1,g,l) and F6(d3,e1,g,l) and F6(a, d1,e1,g,l) and F6(a, d2,e1,g,l) and F6(a, d3,e1,g,l) and F6(d1,e2,g,l) and F6(d2,e2,g,l) and F6(d3,e2,g,l) and F6(a, d1,e2,g,l) and F6(a, d2,e2,g,l) and F6(a, d3,e2,g,l) and F7 and F7(d1,g,l) and F7(d2,g,l) and F7(d3,g,l) and F7(a, d1,g,l) and F7(a, d2,g,l) and F7(a, d3,g,l) and F7(d1,e1,g,l) and F7(d2,e1,g,l) and F7(d3,e1,g,l) and F7(a, d1,e1,g,l) and F7(a, d2,e1,g,l) and F7(a, d3,e1,g,l) and F7(d1,e2,g,l) and F7(d2,e2,g,l) and F7(d3,e2,g,l) and F7(a, d1,e2,g,l) and F7(a, d2,e2,g,l) and F7(a, d3,e2,g,l) and {F6(d1,e1,fX,g,l) and F6(d2,e1,fX,g,l) and F6(d3,e1,fX,g,l) and F6(a, d1,e1, fX,g,l) and F6(a, d2,e1,fX,g,l) and F6(a, d3,e1,fX,g,l) and F6(d1,e2,fX,g,l) and F6(d2,e2,fX,g,l) and F6(d3,e2,fX,g,l) and F6(a, d1,e2,fX,g,l) and F6(a, d2,e2,fX,g,l) and F6(a, d3,e2,fX,g,l) and F7(d1,e1,fX,g,l) and F7(d2,e1,fX,g,l) and F7(d3,e1,fX,g,l) and F7(a, d1,e1,fX,g,l) and F7(a, d2,e1,fX, g,l) and F7(a, d3,e1,fX,g,l) and F7(d1,e2,fX,g,l) and F7(d2, e2,fX,g,l) and F7(d3,e2,fX,g,l) and F7(a, d1,e2,fX,g,l) and F7(a, d2,e2,fX,g,l) and F7(a, d3,e2,fX,g,l), wherein X=1, 2, 3, 4, 5, 6, 7, 8, 9, 10, 11, 12, 13, or 14}

Embodiments with DNA Crosslinking Agent and the Glutathione Reductase Inhibitor BCNU (l1)

In embodiments of the invention given in List 8, the set of drugs is comprised of a DNA crosslinking agent and one or more additional drugs that hypersensitize cancer cells to said DNA crosslinking agent, wherein one or more of said drugs is an inhibitor of glutathione reductase and wherein said GR inhibitor is BCNU. The new embodiments are respectively named and given in List 9. The analogous embodiments in which BCNU is replaced CCNU is provided in List 10.

List 9:

F1(b,g,l,l1) and F2(b,g,l,l1) and F3(b,g,l,l1), and F1(a,b, g,l,l1) and F2(a,b,g,l,l1) and F3(a,b,g,l,l1) and {F1(b,cX,g, l,l1) and F2(b,cX,g,l,l1) and F3(b,cX,g,l,l1) and F1(a,b,cX, g,l,l1) and F2(a,b,cX,g,l,l1) and F3(a,b,cX,g,l,l1) wherein X=1, 2, 3 . . . or 22} and {F1(b, c1,dX,g,l,l1) and F1(a,b, c1,dX,g,l,l1) and F2(b, c1,dX,g,l,l1) and F2(a,b, c1,dX,g,l, l1) and F3(b, c1,dX,g,l,l1) and F3(a,b,c1,dX,g,l,l1) where X=1, 2, or 3} and F4 and F4(c1,g,l,l1) and F4(c,d1,g,l,l1) and F4(c,d2,g,l,l1) and F4(c,d3,g,l,l1) and F4(a, c1,d1,g,l,l1) and F4(a, c1,d2,g,l,l1) and F4(a,c1,d3,g,l,l1) and F5(d1,g,l, l1) and F5(d2,g,l,l1) and F5(d3,g,l,l1), and F5(a, d1,g,l,l1) and F5(a, d2,g,l,l1) and F5(a, d3,g,l,l1) and F6(d1,g,l,l1) and F6(d2,g,l,l1) and F6(d3,g,l,l1) and F6(a, d1,g,l,l1) and F6(a, d2,g,l,l1) and F6(a, d3,g,l,l1), and F6(d1,e1,g,l,l1) and F6(d2,e1,g,l,l1) and F6(d3,e1,g,l,l1) and F6(a, d1,e1,g,l,l1) and F6(a, d2,e1,g,l,l1) and F6(a, d3,e1,g,l,l1) and F6(d1,e2, g,l,l1) and F6(d2,e2,g,l,l1) and F6(d3,e2,g,l,l1) and F6(a, d1,e2,g,l,l1) and F6(a, d2,e2,g,l,l1) and F6(a, d3,e2,g,l,l1) and F7 and F7(d1,g,l,l1) and F7(d2,g,l,l1) and F7(d3,g,l,l1) and F7(a, d1,g,l,l1) and F7(a, d2,g,l,l1) and F7(a, d3,g,l,l1) and F7(d1,e1,g,l,l1) and F7(d2,e1,g,l,l1) and F7(d3,e1,g,l,l1) and F7(a, d1,e1,g,l,l1) and F7(a, d2,e1,g,l,l1) and F7(a, d3,e1,g,l,l1) and F7(d1,e2,g,l,l1) and F7(d2,e2,g,l,l1) and F7(d3,e2,g,l,l1) and F7(a, d1,e2,g,l,l1) and F7(a, d2,e2,g,l, l1) and F7(a, d3,e2,g,l,l1) and {F6(d1,e1,fX,g,l,l1) and F6(d2,e1,fX,g,l,l1) and F6(d3,e1,fX,g,l,l1) and F6(a, d1,e1, fX,g,l,l1) and F6(a, d2,e1,fX,g,l,l1) and F6(a, d3,e1,fX,g, l1) and F6(d1,e2,fX,g,l,l1) and F6(d2,e2,fX,g,l,l1) and F6(d3,e2,fX,g,l,l1) and F6(a, d1,e2,fX,g,l,l1) and F6(a, d2,e2,fX,g,l,l1) and F6(a, d3,e2,fX,g,l,l1) and F7(d1,e1,fX, g,l,l1) and F7(d2,e1,fX,g,l,l1) and F7(d3,e1,fX,g,l,l1) and F7(a, d1,e1,fX,g,l,l1) and F7(a, d2,e1,fX,g,l,l1) and F7(a, d3,e1,fX,g,l,l1) and F7(d1,e2,fX,g,l,l1) and F7(d2,e2,fX,g, l,l1) and F7(d3,e2,fX,g,l,l1) and F7(a, d1,e2,fX,g,l,l1) and F7(a, d2,e2,fX,g,l,l1) and F7(a, d3,e2,fX,g,l,l1), wherein X=1, 2, 3, 4, 5, 6, 7, 8, 9, 10, 11, 12, 13, or 14}.

List 10:

F1(b,g,l,l1,l2) and F2(b,g,l,l1,l2) and F3(b,g,l,l1,l2), and F1(a,b,g,l,l1,l2) and F2(a,b,g,l,l1,l2) and F3(a,b,g,l,l1,l2) and {F1(b,cX,g,l,l1,l2) and F2(b,cX,g,l,l1,l2) and F3(b,cX, g,l,l1,l2) and F1(a,b,cX,g,l,l1,l2) and F2(a,b,cX,g,l,l1,l2) and F3(a,b,cX,g,l,l1,l2) wherein X=1, 2, 3 . . . or 22} and {F1(b, c1,dX,g,l,l1,l2) and F1(a,b, c1,dX,g,l,l1,l2) and F2(b, c1,dX,g,l,l1,l2) and F2(a,b, c1,dX,g,l,l1,l2) and F3(b, c1,dX, g,l,l1,l2) and F3(a,b,c1,dX,g,l,l1,l2) where X=1, 2, or 3} and F4 and F4(c1,g,l,l1,l2) and F4(c,d1,g,l,l1,l2) and F4(c,d2,g, l,l1,l2) and F4(c,d3,g,l,l1,l2) and F4(a, c1,d1,g,l,l1,l2) and F4(a, c1,d2,g,l,l1,l2) and F4(a,c1,d3,g,l,l1,l2) and F5(d1,g, l,l1,l2) and F5(d2,g,l,l1,l2) and F5(d3,g,l,l1,l2), and F5(a, d1,g,l,l1,l2) and F5(a, d2,g,l,l1,l2) and F5(a, d3,g,l,l1,l2) and F6(d1,g,l,l1,l2) and F6(d2,g,l,l1,l2) and F6(d3,g,l,l1,l2) and F6(a, d1,g,l,l1,l2) and F6(a, d2,g,l,l1,l2) and F6(a, d3,g,l,l1, l2), and F6(d1,e1,g,l,l1,l2) and F6(d2,e1,g,l,l1,l2) and F6(d3,e1,g,l,l1,l2) and F6(a, d1,e1,g,l,l1,l2) and F6(a, d2,e1, g,l,l1,l2) and F6(a, d3,e1,g,l,l1,l2) and F6(d1,e2,g,l,l1,l2) and F6(d2,e2,g,l,l1,l2) and F6(d3,e2,g,l,l1,l2) and F6(a, d1,e2,g,l,l1,l2) and F6(a, d2,e2,g,l,l1,l2) and F6(a, d3,e2,g, l,l1,l2) and F7 and F7(d1,g,l,l1,l2) and F7(d2,g,l,l1,l2) and F7(d3,g,l,l1,l2) and F7(a, d1,g,l,l1,l2) and F7(a, d2,g,l,l1,l2) and F7(a, d3,g,l,l1,l2) and F7(d1,e1,g,l,l1,l2) and F7(d2,e1, g,l,l1,l2) and F7(d3,e1,g,l,l1,l2) and F7(a, d1,e1,g,l,l1,l2) and F7(a, d2,e1,g,l,l1,l2) and F7(a, d3,e1,g,l,l1,l2) and F7(d1,e2,g,l,l1,l2) and F7(d2,e2,g,l,l1,l2) and F7(d3,e2,g, l1,l2) and F7(a, d1,e2,g,l,l1,l2) and F7(a, d2,e2,g,l,l1,l2) and F7(a, d3,e2,g,l,l1,l2) and {F6(d1,e1,fX,g,l,l1,l2) and F6(d2, e1,fX,g,l,l1,l2) and F6(d3,e1,fX,g,l,l1,l2) and F6(a, d1,e1, fX,g,l,l1,l2) and F6(a, d2,e1,fX,g,l,l1,l2) and F6(a, d3,e1, fX,g,l,l1,l2) and F6(d1,e2,fX,g,l,l1,l2) and F6(d2,e2,fX,g, l1,l2) and F6(d3,e2,fX,g,l,l1,l2) and F6(a, d1,e2,fX,g,l,l1,l2) and F6(a, d2,e2,fX,g,l,l1,l2) and F6(a, d3,e2,fX,g,l,l1,l2) and F7(d1,e1,fX,g,l,l1,l2) and F7(d2,e1,fX,g,l,l1,l2) and F7(d3,e1,fX,g,l,l1,l2) and F7(a, d1,e1,fX,g,l,l1,l2) and F7(a, d2,e1,fX,g,l,l1,l2) and F7(a, d3,e1,fX,g,l,l1,l2) and F7(d1, e2,fX,g,l,l1,l2) and F7(d2,e2,fX,g,l,l1,l2) and F7(d3,e2,fX, g,l,l1,l2) and F7(a, d1,e2,fX,g,l,l1,l2) and F7(a, d2,e2,fX,g, l,l1,l2) and F7(a, d3,e2,fX,g,l,l1,l2), wherein X=1, 2, 3, 4, 5, 6, 7, 8, 9, 10, 11, 12, 13, or 14}.

In an embodiment the set of drugs is comprised of a DNA crosslinking agent and a second drug that is an inhibitor of glutathione reductase (GR). In a preferred embodiment said drugs is BCNU. In embodiments BCNU is administered at an intravenous dose of approximately 50-300 mg/m$^2$. (body surface area). In embodiments the BCNU dose is approximately 50, 75, 100, 125, 150, 175, 200, 225, 250, 275, 300, or 350 mg/m$^2$. Techniques for the administration of BCNU to patients are well known to one skilled in the arts. See: Carmustine infusion reactions are more common with rapid administration; Janson B, Van Koeverden P, Yip S W, Thakerar A, Mellor J D.; Support Care Cancer. 2012 October; 20(10):2531-5.

A wide range of compounds are known that can inhibit GR and can be also; these include but not limited to: 2-chloroethylisocyanate; cyclohexyl isocyanate; N,N'-bis (trans-4-hydroxycyclohexyl)-N'-nitrosourea N,N'-bis(trans-4-hydroxycyclohexyl)-N'-nitrosourea; 2,4-dihydroxybenzylamine; 2-acetylamino-3-[4-(2-acetylamino-2-carboxyethylsulfanylthiocarbonylamino)-phenylthiocarbamoylsulfanyl] propionic acid (2-AAPA); 1-(2-chloruethyl)-3-cyclohexyl-nitrosourea (CCNU);

hydroxymethylacylfulvene (HMAF); 4,5-dichloro-N-octyl-isothiazol-3-one (DCOIT); [1-phenyl-2,5-di(2-pyridyl)-phosphole}AuCl]; S—(N-[2-chloroethyl]carbamoyl)gluta-thione; S—(N-methylcarbamoyl)glutathione; N-alkymaleimides; S—(N-[2-chloroethyl]carbamoyl)cyste-ine; and isocyanates.

One skilled in the arts will know a large number of suitable compounds that inhibit GR. The use of said compounds is within scope of the present method.

In the presence of NADPH, GR has a reactive cysteine thiolate group that is essential for catalytic activity. Covalent modification of this thiolate group will irreversibly inhibit GR activity. A large number of thiol reactive compounds are well known to one skilled in the arts that can modify said thiolate group and irreversibly inhibit GR, use of such compounds are within the scope of the present invention.

The following references relate to this matter: Inactivation of glutathione reductase by 2-chloroethyl nitrosourea-derived isocyanates; Babson J R, Reed D J.; Biochem Biophys Res Commun. 1978 Jul. 28; 83(2):754-62; Inhibition of human glutathione reductase by the nitrosourea drugs 1,3-bis(2-chloroethyl)-1-nitrosourea and 1-(2-chloroethyl)-3-(2-hydroxyethyl)-1-nitrosourea. A crystallographic analysis; Karplus P A, Krauth-Siegel R L, Schirmer R H, Schulz G E.; Eur J Biochem. 1988 Jan. 15; 171(1-2):193-8. Depletion of cellular glutathione by N,N'-bis(trans-4-hydroxycyclo-hexyl)-N'-nitrosourea as a determinant of sensitivity of K562 human leukemia cells to 4-hydroperoxycyclophosph-amide.; Chresta C M, Crook T R, Souhami R L; Cancer Res. 1990 Jul. 1; 50(13):4067-71; 2,4-Dihydroxybenzylamine: a specific inhibitor of glutathione reductase.; FitzGerald G B, Bauman C, Hussoin M S, Wick M M.; Biochem Pharmacol. 1991 Jan. 15; 41(2):185-90; Characterization of a novel dithiocarbamate glutathione reductase inhibitor and its use as a tool to modulate intracellular glutathione; Seefeldt T, Zhao Y, Chen W, Raza A S, Carlson L, Herman J, Stoebner A, Hanson S, Foll R, Guan X.; J Biol Chem. 2009 Jan. 30; 284(5):2729-37; Profiling patterns of glutathione reductase inhibition by the natural product illudin S and its acylfulvene analogues; Liu X, Sturla S J.; Mol Biosyst. 2009 September; 5(9):1013-24; Structure-activity relationships for the impact of selected isothiazol-3-one biocides on glutathione metabolism and glutathione reductase of the human liver cell line Hep G2; Arning J, et al.; Toxicology. 2008 Apr. 18; 246(2-3):203-12; Mechanistic studies on a novel, highly potent gold-phosphole inhibitor of human glutathione reductase; Deponte M, et al.; J Biol Chem. 2005 May 27; 280(21):20628-37; Selective and irreversible inhibition of gluta-thione reductase in vitro by carbamate thioester conjugates of methyl isocyanate; Jochheim C M, Baillie T A.; Biochem Pharmacol. 1994 Mar. 29; 47(7):1197-206;

Simultaneous inactivation of the catalytic activities of yeast glutathione reductase by N-alkylmaleimides.; Dubler R E, Anderson B M; Biochim Biophys Acta. 1981 May 14; 659(1):70-85; Effect of carbamate thioester derivatives of methyl- and 2-chloroethyl isocyanate on glutathione levels and glutathione reductase activity in isolated rat hepato-cytes.; Kassahun K, et al.; Biochem Pharmacol. 1994 Aug. 3; 48(3):587-94.

Embodiments with a DNA Crosslinking Agent and a Thioredoxin Reductase Inhibitor (q)

Thioredoxin (Trx) is a class of oxidoreductase proteins that can reduce disulfides in proteins and other biomolecules (e.g., GSSG) by thiol-disulfide exchange. In the process the reduced form of Trx(red), which has two thiol groups is converted into the oxidized disulfide form Trx(ox). Trx (red) serves as the reductant for peroxiredoxins, which catalyze the reduction of hydrogen peroxide; ribonucleotide reductase, which catalyzes the formation of deoxyribonucle-otides from ribonucleotide; Trx is also involved in multiple cellular processes. Thioredoxin reductase (TrxR) is a sele-noprotein oxidoreductase that catalyzes the NADPH-dependent reduction of Trx(ox) to Trx(red). TrxR also catalyzes the reduction of a large number of other compounds such as peroxides and dehydroascorbic acid. Like glutathione reductase, TrxR has an active thiol that is essential for enzyme activity. BCNU and other thiol-reactive agents and electrophilic compounds irreversibly inhibit TrxR. BCNU decomposes to 2-chloroethyl isocyanate, which can rapidly carbamoylate and irreversibly inactivate enzymes with critical thiol groups such as glutathione reductase and thioredoxin reductase.

TrxR can catalyze the NADPD dependent reduction of GSSG. Inhibition of TrxR would decrease the regeneration of GSH from GSSG, especially in the setting of GR inhibition.

In an embodiment of the present invention the set of drugs includes an inhibitor of TrxR. In another embodiment the set of drugs includes an inhibitor of GR and an inhibitor of TrxR, which can be one and the same. BCNU and CCNU are suitable inhibitors for both GR and TrxR. Gold drugs such as auranofin, aurothiomalate, aurothioglucose and aurothio-propanol sulfonate are also suitable TxrR inhibitors. A large number of other thiol reactive compounds are well known to one skilled in the arts that can modify said thiolate group and irreversibly inhibit TxrR, use of such compounds are within the scope of the present invention. These thiol-reactive agents include drugs that generate nitric oxide and reactive nitrogen species.

The following references relate to this matter: Reactive oxygen species, antioxidants, and the mammalian thiore-doxin system.; Nordberg J, Arnér E S.; Free Radic Biol Med. 2001 Dec. 1; 31(11):1287-312; Redox control systems in the nucleus: mechanisms and functions; Go Y M, Jones D P; Antioxid Redox Signal. 2010 Aug. 15; 13(4):489-509; The thioredoxin system of the malaria parasite Plasmodium falciparum. Glutathione reduction revisited; Kanzok S M et al.; J Biol Chem. 2000 Dec. 22; 275(51):40180-6; Human placenta thioredoxin reductase. Isolation of the selenoen-zyme, steady state kinetics, and inhibition by therapeutic gold compounds; Gromer S, et al.; J Biol Chem. 1998 Aug. 7; 273(32):20096-101; Miersch S., et. al., Clin. Biochem September; 38 89): 777-91 (2005); Hess D. T., et al., Nat. Rev. Mol. cell Biol. fe:6(2):150-66 (2005)).

Embodiments with a DNA Crosslinking Agent and a Thioredoxin Reductase Inhibitor (q)

In embodiments of the invention given in List 2 and List 8, the set of drugs is comprised of a DNA crosslinking agent and one or more additional drugs that hypersensitize cancer cells to said DNA crosslinking agent, wherein one or more of said drugs is an inhibitor of Thioredoxin Reductase. The new embodiments are respectively named and given in List 2b and List 8b. In List 8b the set of drugs includes both GR and TxrR inhibitor.

List 2b:

F1(b,g,q) and F2(b,g,q) and F3(b,g,q), and F1(a,b,g,q) and F2(a,b,g,q) and F3(a,b,g,q) and {F1(b,cX,g,q) and F2(b, cX,g,q) and F3(b,cX,g,q) and F1(a,b,cX,g,q) and F2(a,b,cX, g,q) and F3(a,b,cX,g,q) wherein X=1, 2, 3 . . . or 22} and {F1(b, c1,dX,g,q) and F1(a,b, c1,dX,g,q) and F2(b, c1,dX, g,q) and F2(a,b, c1,dX,g,q) and F3(b, c1,dX,g,q) and F3(a, b,c1,dX,g,q) where X=1, 2, or 3} and F4 and F4(c1,g,q) and F4(c,d1,g,q) and F4(c,d2,g,q) and F4(c,d3,g,q) and F4(a, c1,d1,g,q) and F4(a, c1,d2,g,q) and F4(a,c1,d3,g,q) and F5(d1,g,q) and F5(d2,g,q) and F5(d3,g,q), and F5(a, d1,g,q) and F5(a, d2,g,q) and F5(a, d3,g,q) and F6(d1,g,q) and F6(d2,g,q) and F6(d3,g,q) and F6(a, d1,g,q) and F6(a, d2,g,q) and F6(a, d3,g,q), and F6(d1,e1,g,q) and F6(d2,e1,g,q) and F6(d3,e1,g,q) and F6(a, d1,e1,g,q) and F6(a, d2,e1,g,q) and F6(a, d3,e1,g,q) and F6(d1,e2,g,q) and F6(d2,e2,g,q) and F6(d3,e2,g,q) and F6(a, d1,e2,g,q) and F6(a, d2,e2,g,q) and F6(a, d3,e2,g,q) and F7 and F7(d1,g,q) and F7(d2,g,q) and F7(d3,g,q) and F7(a, d1,g,q) and F7(a, d2,g,q) and F7(a, d3,g,q) and F7(d1,e1,g,q) and F7(d2,e1,g,q) and F7(d3,e1, g,q) and F7(a, d1,e1,g,q) and F7(a, d2,e1,g,q) and F7(a, d3,e1,g,q) and F7(d1,e2,g,q) and F7(d2,e2,g,q) and F7(d3, e2,g,q) and F7(a, d1,e2,g,q) and F7(a, d2,e2,g,q) and F7(a, d3,e2,g,q) and {F6(d1,e1,fX,g,q) and F6(d2,e1,fX,g,q) and F6(d3,e1,fX,g,q) and F6(a, d1,e1,fX,g,q) and F6(a, d2,e1, fX,g,q) and F6(a, d3,e1,fX,g,q) and F6(d1,e2,fX,g,q) and F6(d2,e2,fX,g,q) and F6(d3,e2,fX,g,q) and F6(a, d1,e2,fX, g,q) and F6(a, d2,e2,fX,g,q) and F6(a, d3,e2,fX,g,q) and F7(d1,e1,fX,g,q) and F7(d2,e1,fX,g,q) and F7(d3,e1,fX,g,q) and F7(a, d1,e1,fX,g,q) and F7(a, d2,e1,fX,g,q) and F7(a, d3,e1,fX,g,q) and F7(d1,e2,fX,g,q) and F7(d2,e2,fX,g,q) and F7(d3,e2,fX,g,q) and F7(a, d1,e2,fX,g,q) and F7(a, d2,e2,fX,g,q) and F7(a, d3,e2,fX,g,q), wherein X=1, 2, 3, 4, 5, 6, 7, 8, 9, 10, 11, 12, 13, or 14}

List 8b

F1(b,g,l,q) and F2(b,g,l,q) and F3(b,g,l,q), and F1(a,b, l,q) and F2(a,b,g,l,q) and F3(a,b,g,l,q) and {F1(b,cX,g,l,q) and F2(b,cX,g,l,q) and F3(b,cX,g,l,q) and F1(a,b,cX,g,l,q) and F2(a,b,cX,g,l,q) and F3(a,b,cX,g,l,q) wherein X=1, 2, 3 . . . or 22} and {F1(b, c1,dX,g,l,q) and F1(a,b, c1,dX,g,l,q) and F2(b, c1,dX,g,l,q) and F2(a,b, c1,dX,g,l,q) and F3(b, c1,dX,g,l,q) and F3(a,b,c1,dX,g,l,q) where X=1, 2, or 3} and F4 and F4(c1,g,l,q) and F4(c,d1,g,l,q) and F4(c,d2,g,l,q) and F4(c,d3,g,l,q) and F4(a, c1,d1,g,l,q) and F4(a, c1,d2,g,l,q) and F4(a,c1,d3,g,l,q) and F5(d1,g,l,q) and F5(d2,g,l,q) and F5(d3,g,l,q), and F5(a, d1,g,l,q) and F5(a, d2,g,l,q) and F5(a, d3,g,l,q) and F6(d1,g,l,q) and F6(d2,g,l,q) and F6(d3,g,l,q) and F6(a, d1,g,l,q) and F6(a, d2,g,l,q) and F6(a, d3,g,l,q), and F6(d1,e1,g,l,q) and F6(d2,e1,g,l,q) and F6(d3,e1,g,l,q) and F6(a, d1,e1,g,l,q) and F6(a, d2,e1,g,l,q) and F6(a, d3,e1, g,l,q) and F6(d1,e2,g,l,q) and F6(d2,e2,g,l,q) and F6(d3,e2, g,l,q) and F6(a, d1,e2,g,l,q) and F6(a, d2,e2,g,l,q) and F6(a, d3,e2,g,l,q) and F7 and F7(d1,g,l,q) and F7(d2,g,l,q) and F7(d3,g,l,q) and F7(a, d1,g,l,q) and F7(a, d2,g,l,q) and F7(a, d3,g,l,q) and F7(d1,e1,g,l,q) and F7(d2,e1,g,l,q) and F7(d3, e1,g,l,q) and F7(a, d1,e1,g,l,q) and F7(a, d2,e1,g,l,q) and F7(a, d3,e1,g,l,q) and F7(d1,e2,g,l,q) and F7(d2,e2,g,l,q) and F7(d3,e2,g,l,q) and F7(a, d1,e2,g,l,q) and F7(a, d2,e2, g,l,q) and F7(a, d3,e2,g,l,q) and {F6(d1,e1,fX,g,l,q) and F6(d2,e1,fX,g,l,q) and F6(d3,e1,fX,g,l,q) and F6(a, d1,e1, fX,g,l,q) and F6(a, d2,e1,fX,g,l,q) and F6(a, d3,e1,fX,g,l,q) and F6(d1,e2,fX,g,l,q) and F6(d2,e2,fX,g,l,q) and F6(d3,e2, fX,g,l,q) and F6(a, d1,e2,fX,g,l,q) and F6(a, d2,e2,fX,g,l,q) and F6(a, d3,e2,fX,g,l,q) and F7(d1,e1,fX,g,l,q) and F7(d2, e1,fX,g,l,q) and F7(d3,e1,fX,g,l,q) and F7(a, d1,e1,fX,g,l,q) and F7(a, d2,e1,fX,g,l,q) and F7(a, d3,e1,fX,g,l,q) and F7(d1,e2,fX,g,l,q) and F7(d2,e2,fX,g,l,q) and F7(d3,e2,fX, g,l,q) and F7(a, d1,e2,fX,g,l,q) and F7(a, d2,e2,fX,g,l,q) and F7(a, d3,e2,fX,g,l,q), wherein X=1, 2, 3, 4, 5, 6, 7, 8, 9, 10, 11, 12, 13, or 14}

Embodiments with a DNA Crosslinking Agent, and Inhibitor of GR and a Drug that Decreases Intracellular GSH Levels (m)

Inhibition of GR prevents the efficient regeneration of GSH from GSSG. However, the effect of GR inhibition on GSH levels is variable and depends upon the rate at which GSH is oxidized in the cell. Treatment with oxidizing agents in the setting of GR inhibition can profoundly depress intracellular GSH levels.

In an embodiment the set of drugs is comprised of a DNA crosslinking agent, an inhibitor of GR and also a drug that decreases intracellular GSH levels in cancer cells by oxidizing GSH to GSSG. In embodiments said decreases in GSH levels are approximately 20%, 30%, 40%, 50%, 60%, 70, 80%, 90% or 95% of the pretreatment values.

Drugs and agents that oxidize GSH to GSSG are known to one skilled in the art. Methods for identifying said drugs are also known to one skilled in the art.

Embodiments with a DNA Crosslinking Agent, a GR Inhibitor, and a Drug that Decreases Intracellular GSH Levels by Oxidizing GSSG to GSSG (m)

In embodiments of those given in List 8, List 9, and List 10; the set of drugs is comprised of a DNA crosslinking agent, a GR inhibitor, and a drug that decreases intracellular GSH levels by oxidizing GSSG to GSSG. The new embodiments are respectively named and given in List 8.1, List 9.1, and List 10.1, respectively.

List 8.1

F1(b,g,l,m) and F2(b,g,l,m) and F3(b,g,l,m), and F1(a,b, g,l,m) and F2(a,b,g,l,m) and F3(a,b,g,l,m) and {F1(b,cX,g, l,m) and F2(b,cX,g,l,m) and F3(b,cX,g,l,m) and F1(a,b,cX, g,l,m) and F2(a,b,cX,g,l,m) and F3(a,b,cX,g,l,m) wherein X=1, 2, 3 . . . or 22} and {F1(b, c1,dX,g,l,m) and F1(a,b, c1,dX,g,l,m) and F2(b, c1,dX,g,l,m) and F2(a,b, c1,dX,g,l, m) and F3(b, c1,dX,g,l,m) and F3(a,b,c1,dX,g,l,m) where X=1, 2, or 3} and F4 and F4(c1,g,l,m) and F4(c,d1,g,l,m) and F4(c,d2,g,l,m) and F4(c,d3,g,l,m) and F4(a, c1,d1,g,l,m) and F4(a, c1,d2,g,l,m) and F4(a,c1,d3,g,l,m) and F5(d1,g,l, m) and F5(d2,g,l,m) and F5(d3,g,l,m), and F5(a, d1,g,l,m) and F5(a, d2,g,l,m) and F5(a, d3,g,l,m) and F6(d1,g,l,m) and F6(d2,g,l,m) and F6(d3,g,l,m) and F6(a, d1,g,l,m) and F6(a, d2,g,l,m) and F6(a, d3,g,l,m), and F6(d1,e1,g,l,m) and F6(d2,e1,g,l,m) and F6(d3,e1,g,l,m) and F6(a, d1,e1,g,l,m) and F6(a, d2,e1,g,l,m) and F6(a, d3,e1,g,l,m) and F6(d1,e2, g,l,m) and F6(d2,e2,g,l,m) and F6(d3,e2,g,l,m) and F6(a, d1,e2,g,l,m) and F6(a, d2,e2,g,l,m) and F6(a, d3,e2,g,l,m) and F7 and F7(d1,g,l,m) and F7(d2,g,l,m) and F7(d3,g,l,m) and F7(a, d1,g,l,m) and F7(a, d2,g,l,m) and F7(a, d3,g,l,m) and F7(d1,e1,g,l,m) and F7(d2,e1,g,l,m) and F7(d3,e1,g,l,m) and F7(a, d1,e1,g,l,m) and F7(a, d2,e1,g,l,m) and F7(a, d3,e1,g,l,m) and F7(d1,e2,g,l,m) and F7(d2,e2,g,l,m) and F7(d3,e2,g,l,m) and F7(a, d1,e2,g,l,m) and F7(a, d2,e2,g,l, m) and F7(a, d3,e2,g,l,m) and {F6(d1,e1,fX,g,l,m) and F6(d2,e1,fX,g,l,m) and F6(d3,e1,fX,g,l,m) and F6(a, d1,e1, fX,g,l,m) and F6(a, d2,e1,fX,g,l,m) and F6(a, d3,e1,fX,g,l, m) and F6(d1,e2,fX,g,l,m) and F6(d2,e2,fX,g,l,m) and F6(d3,e2,fX,g,l,m) and F6(a, d1,e2,fX,g,l,m) and F6(a, d2,e2,fX,g,l,m) and F6(a, d3,e2,fX,g,l,m) and F7(d1,e1,fX, g,l,m) and F7(d2,e1,fX,g,l,m) and F7(d3,e1,fX,g,l,m) and F7(a, d1,e1,fX,g,l,m) and F7(a, d2,e1,fX,g,l,m) and F7(a, d3,e1,fX,g,l,m) and F7(d1,e2,fX,g,l,m) and F7(d2,e2,fX,g, l,m) and F7(d3,e2,fX,g,l,m) and F7(a, d1,e2,fX,g,l,m) and F7(a, d2,e2,fX,g,l,m) and F7(a, d3,e2,fX,g,l,m), wherein X=1, 2, 3, 4, 5, 6, 7, 8, 9, 10, 11, 12, 13, or 14}.

List 9.1:

F1(b,g,l,l1,m) and F2(b,g,l,l1,m) and F3(b,g,l,l1,m), and F1(a,b,g,l,l1,m) and F2(a,b,g,l,l1,m) and F3(a,b,g,l,l1,m) and {F1(b,cX,g,l,l1,m) and F2(b,cX,g,l,l1,m) and F3(b,cX, g,l,l1,m) and F1(a,b,cX,g,l,l1,m) and F2(a,b,cX,g,l,l1,m) and F3(a,b,cX,g,l,l1,m) wherein X=1, 2, 3 . . . or 22} and {F1(b, c1,dX,g,l,l1,m) and F1(a,b, c1,dX,g,l,l1,m) and F2(b, c1,dX,g,l,l1,m) and F2(a,b, c1,dX,g,l,l1,m) and F3(b, c1,dX, g,l,l1,m) and F3(a,b,c1,dX,g,l,l1,m) where X=1, 2, or 3} and F4 and F4(c1,g,l,l1,m) and F4(c,d1,g,l,l1,m) and F4(c,d2,g,l,l1,m) and F4(c,d3,g,l,l1,m) and F4(a, c1,d1,g,l,l1,m) and F4(a, c1,d2,g,l,l1,m) and F4(a,c1,d3,g,l,l1,m) and F5(d1,g,l,l1,m) and F5(d2,g,l,l1,m) and F5(d3,g,l,l1,m) and F5(a, d1,g,l,l1,m) and F5(a, d2,g,l,l1,m) and F5(a, d3,g,l,l1,m) and F6(d1,g,l,l1,m) and F6(d2,g,l,l1,m) and F6(d3,g,l,l1,m) and F6(a, d1,g,l,l1,m) and F6(a, d2,g,l,l1,m) and F6(a, d3,g,l,l1,m), and F6(d1,e1,g,l,l1,m) and F6(d2,e1,g,l,l1,m) and F6(d3,e1,g,l,l1,m) and F6(a, d1,e1,g,l,l1,m) and F6(a, d2,e1,g,l,l1,m) and F6(a, d3,e1,g,l,l1,m) and F6(d1,e2,g,l,l1,m) and F6(d2,e2,g,l,l1,m) and F6(d3,e2,g,l,l1,m) and F6(a, d1,e2,g,l,l1,m) and F6(a, d2,e2,g,l,l1,m) and F6(a, d3,e2,l,l1,m) and F7 and F7(d1,g,l,l1,m) and F7(d2,g,l,l1,m) and F7(d3,g,l,l1,m) and F7(a, d1,g,l,l1,m) and F7(a, d2,g,l,l1,m) and F7(a, d3,g,l,l1,m) and F7(d1,e1,g,l,l1,m) and F7(d2,e1,g,l,l1,m) and F7(d3,e1,g,l,l1,m) and F7(a, d1,e1,g,l,l1,m) and F7(a, d2,e1,g,l,l1,m) and F7(a, d3,e1,g,l,l1,m) and F7(d1,e2,g,l,l1,m) and F7(d2,e2,g,l,l1,m) and F7(d3,e2,g,l,l1,m) and F7(a, d1,e2,g,l,l1,m) and F7(a, d2,e2,g,l,l1,m) and F7(a, d3,e2,g,l,l1,m) and {F6(d1,e1,fX,g,l,l1,m) and F6(d2,e1,fX,g,l,l1,m) and F6(d3,e1,fX,g,l,l1,m) and F6(a, d1,e1,fX,g,l,l1,m) and F6(a, d2,e1,fX,g,l,l1,m) and F6(a, d3,e1,fX,g,l,l1,m) and F6(d1,e2,fX,g,l,l1,m) and F6(d2,e2,fX,g,l,l1,m) and F6(d3,e2,fX,g,l,l1,m) and F6(a, d1,e2,fX,g,l,l1,m) and F6(a, d2,e2,fX,g,l,l1,m) and F6(a, d3,e2,fX,g,l,l1,m) and F7(d1,e1,fX,g,l,l1,m) and F7(d2,e1,fX,g,l,l1,m) and F7(d3,e1,fX,g,l,l1,m) and F7(a, d1,e1,fX,g,l,l1,m) and F7(a, d2,e1,fX,g,l,l1,m) and F7(a, d3,e1,fX,g,l,l1,m) and F7(d1,e2,fX,g,l,l1,m) and F7(d2,e2,fX,g,l,l1,m) and F7(d3,e2,fX,g,l,l1,m) and F7(a, d1,e2,fX,g,l,l1,m) and F7(a, d2,e2,fX,g,l,l1,m) and F7(a, d3,e2,fX,g,l,l1,m), wherein X=1, 2, 3, 4, 5, 6, 7, 8, 9, 10, 11, 12, 13, or 14}.

List 10.1

F1(b,g,l,l1,l2,m) and F2(b,g,l,l1,l2,m) and F3(b,g,l,l1,l2,m), and F1(a,b,g,l,l1,l2,m) and F2(a,b,g,l,l1,l2,m) and F3(a,b,g,l,l1,l2,m) and {F1(b,cX,g,l,l1,l2,m) and F2(b,cX,g,l,l1,l2,m) and F3(b,cX,g,l,l1,l2,m) and F1(a,b,cX,g,l,l1,l2,m) and F2(a,b,cX,g,l,l1,l2,m) and F3(a,b,cX,g,l,l1,l2,m) wherein X=1, 2, 3 . . . or 22} and {F1(b, c1,dX,g,l,l1,l2,m) and F1(a,b, c1,dX,g,l,l1,l2,m) and F2(b, c1,dX,g,l,l1,l2,m) and F2(a,b, c1,dX,g,l,l1,l2,m) and F3(b, c1,dX,g,l,l1,l2,m) and F3(a,b,c1,dX,g,l,l1,l2,m) where X=1, 2, or 3} and F4 and F4(c1,g,l,l1,l2,m) and F4(c,d1,g,l,l1,l2,m) and F4(c,d2,g,l,l1,l2,m) and F4(c,d3,g,l,l1,l2,m) and F4(a, c1,d1,g,l,l1,l2,m) and F4(a, c1,d2,g,l,l1,l2,m) and F4(a,c1,d3,g,l,l1,l2,m) and F5(d1,g,l,l1,l2,m) and F5(d2,g,l,l1,l2,m) and F5(d3,g,l,l1,l2,m), and F5(a, d1,g,l,l1,l2,m) and F5(a, d2,g,l,l1,l2,m) and F5(a, d3,g,l,l1,l2,m) and F6(d1,g,l,l1,l2,m) and F6(d2,g,l,l1,l2,m) and F6(d3,g,l,l1,l2,m) and F6(a, d1,g,l,l1,l2,m) and F6(a, d2,g,l,l1,l2,m) and F6(a, d3,g,l,l1,l2,m), and F6(d1,e1,g,l,l1,l2,m) and F6(d2,e1,g,l,l1,l2,m) and F6(d3,e1,g,l,l1,l2,m) and F6(a, d1,e1,g,l,l1,l2,m) and F6(a, d2,e1,g,l,l1,l2,m) and F6(a, d3,e1,g,l,l1,l2,m) and F6(d1,e2,g,l,l1,l2,m) and F6(d2,e2,g,l,l1,l2,m) and F6(d3,e2,g,l,l1,l2,m) and F6(a, d1,e2,g,l,l1,l2,m) and F6(a, d2,e2,g,l,l1,l2,m) and F6(a, d3,e2,g,l,l1,l2,m) and F7 and F7(d1,g,l,l1,l2,m) and F7(d2,g,l,l1,l2,m) and F7(d3,g,l,l1,l2,m) and F7(a, d1,g,l,l1,l2,m) and F7(a, d2,g,l,l1,l2,m) and F7(a, d3,g,l,l1,l2,m) and F7(d1,e1,g,l,l1,l2,m) and F7(d2,e1,g,l,l1,l2,m) and F7(d3,e1,g,l,l1,l2,m) and F7(a, d1,e1,g,l,l1,l2,m) and F7(a, d2,e1,g,l,l1,l2,m) and F7(a, d3,e1,g,l,l1,l2,m) and F7(d1,e2,g,l,l1,l2,m) and F7(d2,e2,g,l,l1,l2,m) and F7(d3,e2,g,l,l1,l2,m) and F7(a, d1,e2,g,l,l1,l2,m) and F7(a, d2,e2,g,l,l1,l2,m) and F7(a, d3,e2,g,l,l1,l2,m) and {F6(d1,e1,fX,g,l,l1,l2,m) and F6(d2,e1,fX,g,l,l1,l2,m) and F6(d3,e1,fX,g,l,l1,l2,m) and F6(a, d1,e1,fX,g,l,l1,l2,m) and F6(a, d2,e1,fX,g,l,l1,l2,m) and F6(a, d3,e1,fX,g,l,l1,l2,m) and F6(d1,e2,fX,g,l,l1,l2,m) and F6(d2,e2,fX,g,l,l1,l2,m) and F6(d3,e2,fX,g,l,l1,l2,m) and F6(a, d1,e2,fX,g,l,l1,l2,m) and F6(a, d2,e2,fX,g,l,l1,l2,m) and F6(a, d3,e2,fX,g,l,l1,l2,m) and F7(d1,e1,fX,g,l,l1,l2,m) and F7(d2,e1,fX,g,l,l1,l2,m) and F7(a, d1,e1,fX,g,l,l1,l2,m) and F7(a, d2,e1,fX,g,l,l1,l2,m) and F7(a, d3,e1,fX,g,l,l1,l2,m) and F7(d1,e2,fX,g,l,l1,l2,m) and F7(d2,e2,fX,g,l,l1,l2,m) and F7(d3,e2,fX,g,l,l1,l2,m) and F7(a, d1,e2,fX,g,l,l1,l2,m) and F7(a, d2,e2,fX,g,l,l1,l2,m) and F7(a, d3,e2,fX,g,l,l1,l2,m), wherein X=1, 2, 3, 4, 5, 6, 7, 8, 9, 10, 11, 12, 13, or 14}.

Redox Cycling Embodiments (n)

Redox cycling drugs engage in the following cyclic processes:

The oxidized form of the drug is reduced by electron transfer from intracellular reducing agents (e.g., NADH, NADPH, ascorbic acid).

The reduced form of the drug is oxidized by molecular oxygen, which regenerates the oxidized from of the drug and reduces oxygen.

The cycle repeats multiple times.

Redox cycling agents that engage in one electron transfer reactions generally proceed by means of free radical intermediates and reduce oxygen to superoxide. (Superoxide dismutase catalyzes the conversion of 2 molecules of superoxide into oxygen and hydrogen peroxide.) While recycling redox agents that engage in two electron transfer reactions reduce oxygen to hydrogen peroxide. The net result in both cases is that a catalytic amount of the redox cycling drug can consume large quantities of cellular reducing equivalents and generate large quantities of hydrogen peroxide. Superoxide and hydrogen peroxide are ROS and can participate in a complex range of reactions with cellular components both directly and indirectly by free radical intermediates.

Glutathione peroxidase catalyzes the reduction of H2O2 into 2 H2O with the concomitant oxidation of 2 GSH into glutathione disulfide (GSSG). Glutathione reductase converts NADPH and GSSG into 2 GSH and NADP. NADP can be reduced to NADPH principally by the pentose phosphate pathway. However, in the setting of GR inhibition, GSSG accumulates, GSH levels plummet, the intracellular GSSG/2GSH reduction potential increases, and ROS levels increase. The net result is that the redox cycling agent causes oxidative stress which profoundly hypersensitize cancer cells to DNA crosslinking agents.

A dose modification factor (DMF) of up to 55 has been achieved for melphalan in the setting of GR inhibitor (BCNU) and a redox cycling agent (doxorubicin). The BCNU and doxorubicin were used at sub-toxic doses. In human melanoma cells the AUC-1 for melphalan alone ranged from ~5.5 to 22 microM h. In cells concomitantly treated with sub-toxic concentrations of BCNU and doxorubicin the AUC-1 was ~0.4 to 0.5 microM h. (See FIG. 4). See: Jevtovic-Todoroviv, Vesna; 1990, Ph.D. Dissertation, University of Illinois at Chicago, Health Sciences Center; Depletion of a discrete nuclear glutathione pool by oxidative stress, but not by buthionine sulfoximine. Correlation with enhanced alkylating agent cytotoxicity to human melanoma cells in vitro; Jevtović-Todorović V, Guenthner T M.; Biochem Pharmacol. 1992 Oct. 6; 44(7):1383-93; Sensitization of human melanoma cells to melphalan cytotoxicity by adriamycin and carmustine.; Jevtović-Todorović V, Guenthner T M.; J Cancer Res Clin Oncol. 1991; 117(4): 313-20. See: Role of the glutathione-glutathione peroxidase cycle in the cytotoxicity of the anticancer quinones.; Doroshow J H, Akman S, Chu F F, Esworthy S.; Pharmacol Ther. 1990; 47(3):359-70; Metabolism and reactions of quinoid anticancer agents.; Powis G.; Pharmacol Ther. 1987; 35(1-

2):57-162; Enzymatic activation and binding of adriamycin to nuclear DNA.; Sinha B K, Trush M A, Kennedy K A, Mimnaugh E G; Cancer Res. 1984 July; 44(7):2892-6; Doxorubicin (adriamycin): a critical review of free radical-dependent mechanisms of cytotoxicity.; Keizer H G, Pinedo H M, Schuurhuis G J, Joenje H.; Pharmacol Ther. 1990; 47(2):219-31; Changes in mitochondrial redox state, membrane potential and calcium precede mitochondrial dysfunction in doxorubicin-induced cell death.; Kuznetsov A V, Margreiter R, Amberger A, Saks V, Grimm M.; Biochim Biophys Acta. 2011 June; 1813(6):1144-52; Free radicals and anticancer drug resistance: oxygen free radicals in the mechanisms of drug cytotoxicity and resistance by certain tumors.; Sinha B K, Mimnaugh E G.; Free Radic Biol Med. 1990; 8(6):567-81. Redox cycling of anthracyclines by cardiac mitochondria. II. Formation of superoxide anion, hydrogen peroxide, and hydroxyl radical.; Doroshow J H, Davies K J.; J Biol Chem. 1986 Mar. 5; 261(7):3068-74; NADPH cytochrome P-450 reductase activation of quinone anticancer agents to free radicals.; Bachur N R, Gordon S L, Gee M V, Kon H.; Proc Natl Acad Sci USA. 1979 February; 76(2):954-7; Cellular and molecular actions of Methylene Blue in the nervous system.; Oz M, Lorke D E, Hasan M, Petroianu G A.; Med Res Rev. 2011 January; 31(1):93-117; Free radicals, metals and antioxidants in oxidative stress-induced cancer; Valko M, Rhodes C J, Moncol J, Izakovic M, Mazur M; Chem Biol Interact. 2006 Mar. 10; 160(1):1-40.

In an embodiment the set of drugs is comprised of a DNA crosslinking agent, an inhibitor of GR and a redox cycling drug. More than one redox cycling agent can be used together. Suitable redox cycling agents include: Anthracyclines such as doxorubicin, idarubicin, epirubicin, daunorubicin; Motexafin gadolinium; compounds with quinone pharmacophores and precursors of such menadione (2-methylnaphthalene-1,4-dione, vitamin K3; compounds with a 3,7-diaminophenothiazinium pharmacophores including methylene blue and toluidine blue; Disulfiram [Bis(N,N-(diethylthiocarbamoyl) disulfide] in association with Cu (II); Polysulfides; Mitomycin C; Carbazilquinone; Aclacinomycin A; Glendananmycin; Plumbagen; Bleomycin; beta-lapachone; Azo compounds;

Aromatic nitro compounds such as nitrofurantoin, metronidazole, and misomidazole; metal chelate complexes; hydroxylamines and nitroxides; and procarbazine; and nitropusside.

Many other compounds are known to one skilled in the arts that undergo redox cycling that could be used in the present invention are known to one skilled in the arts. The use of these compounds is with scope of the present invention. Techniques for identifying redox cycling agents are also known to one skilled in the arts. See: Overview of enzyme systems involved in bio-reduction of drugs and in redox cycling; Kappus H., Biochem Pharmacol. 1986 Jan. 1; 35(1):1-6; Free radical mediated cell toxicity by redox cycling chemicals; Cohen G M, d'Arcy Doherty M; Br J Cancer Suppl. 1987 June; 8:46-52. Redox and addition chemistry of quinoid compounds and its biological implications; Brunmark A, Cadenas E; Free Radic Biol Med. 1989; 7(4):435-77

Embodiments with a DNA Crosslinking Agent, a GR Inhibitor, and a Redox Cycling Agents (n)

In embodiments of those given in List 8.1, List 9.1, and List 10.1 the set of drugs is comprised of a DNA crosslinking agent, a GR inhibitor, and a drug that decreases intracellular GSH levels by oxidizing GSH to GSSG wherein said drug is a redox cycling agent. The new embodiments are respectively named and given in List 8.2, List 9.2, and List 10.2, respectively.

List 8.2

F1(b,g,l,m,n) and F2(b,g,l,m,n) and F3(b,g,l,m,n), and F1(a,b,g,l,m,n) and F2(a,b,g,l,m,n) and F3(a,b,g,l,m,n) and {F1(b,cX,g,l,m,n) and F2(b,cX,g,l,m,n) and F3(b,cX,g,l,m,n) and F1(a,b,cX,g,l,m,n) and F2(a,b,cX,g,l,m,n) and F3(a,b,cX,g,l,m,n) wherein X=1, 2, 3 . . . or 22} and {F1(b, c1,dX,g,l,m,n) and F1(a,b, c1,dX,g,l,m,n) and F2(b, c1,dX,g,l,m,n) and F2(a,b, c1,dX,g,l,m,n) and F3(b, c1,dX,g,l,m,n) and F3(a,b,c1,dX,g,l,m,n) where X=1, 2, or 3} and F4 and F4(c1,g,l,m,n) and F4(c,d1,g,l,m,n) and F4(c,d2,g,l,m,n) and F4(c,d3,g,l,m,n) and F4(a, c1,d1,g,l,m,n) and F4(a, c1,d2,g,l,m,n) and F4(a,c1,d3,g,l,m,n) and F5(d1,g,l,m,n) and F5(d2,g,l,m,n) and F5(d3,g,l,m,n), and F5(a, d1,g,l,m,n) and F5(a, d2,g,l,m,n) and F5(a, d3,g,l,m,n) and F6(d1,g,l,m,n) and F6(d2,g,l,m,n) and F6(d3,g,l,m,n) and F6(a, d1,g,l,m,n) and F6(a, d2,g,l,m,n) and F6(a, d3,g,l,m,n), and F6(d1,e1,g,l,m,n) and F6(d2,e1,g,l,m,n) and F6(d3,e1,g,l,m,n) and F6(a, d1,e1,g,l,m,n) and F6(a, d2,e1,g,l,m,n) and F6(a, d3,e1,g,l,m,n) and F6(d1,e2,g,l,m,n) and F6(d2,e2,g,l,m,n) and F6(d3,e2,g,l,m,n) and F6(a, d1,e2,g,l,m,n) and F6(a, d2,e2,g,l,m,n) and F6(a, d3,e2,g,l,m,n) and F7 and F7(d1,g,l,m,n) and F7(d2,g,l,m,n) and F7(d3,g,l,m,n) and F7(a, d1,g,l,m,n) and F7(a, d2,g,l,m,n) and F7(a, d3,g,l,m,n) and F7(d1,e1,g,l,m,n) and F7(d2,e1,g,l,m,n) and F7(d3,e1,g,l,m,n) and F7(a, d1,e1,g,l,m,n) and F7(a, d2,e1,g,l,m,n) and F7(a, d3,e1,g,l,m,n) and F7(d1,e2,g,l,m,n) and F7(d2,e2,g,l,m,n) and F7(d3,e2,g,l,m,n) and F7(a, d1,e2,g,l,m,n) and F7(a, d2,e2,g,l,m,n) and F7(a, d3,e2,g,l,m,n) and {F6(d1,e1,fX,g,l,m,n) and F6(d2,e1,fX,g,l,m,n) and F6(d3,e1,fX,g,l,m,n) and F6(a, d1,e1,fX,g,l,m,n) and F6(a, d2,e1,fX,g,l,m,n) and F6(a, d3,e1,fX,g,l,m,n) and F6(d1,e2,fX,g,l,m,n) and F6(d2,e2,fX,g,l,m,n) and F6(d3,e2,fX,g,l,m,n) and F6(a, d1,e2,fX,g,l,m,n) and F6(a, d2,e2,fX,g,l,m,n) and F6(a, d3,e2,fX,g,l,m,n) and F7(d1,e1,fX,g,l,m,n) and F7(d2,e1,fX,g,l,m,n) and F7(d3,e1,fX,g,l,m,n) and F7(a, d1,e1,fX,g,l,m,n) and F7(a, d2,e1,fX,g,l,m,n) and F7(a, d3,e1,fX,g,l,m,n) and F7(d1,e2,fX,g,l,m,n) and F7(d2,e2,fX,g,l,m,n) and F7(d3,e2,fX,g,l,m,n) and F7(a, d1,e2,fX,g,l,m,n) and F7(a, d2,e2,fX,g,l,m,n) and F7(a, d3,e2,fX,g,l,m,n), wherein X=1, 2, 3, 4, 5, 6, 7, 8, 9, 10, 11, 12, 13, or 14}.

List 9.2:

F1(b,g,l,l1,m,n) and F2(b,g,l,l1,m,n) and F3(b,g,l,l1,m,n), and F1(a,b,g,l,l1,m,n) and F2(a,b,g,l,l1,m,n) and F3(a,b,g,l,l1,m,n) and {F1(b,cX,g,l,l1,m,n) and F2(b,cX,g,l,l1,m,n) and F3(b,cX,g,l,l1,m,n) and F1(a,b,cX,g,l,l1,m,n) and F2(a,b,cX,g,l,l1,m,n) and F3(a,b,cX,g,l,l1,m,n) wherein X=1, 2, 3 . . . or 22} and {F1(b, c1,dX,g,l,l1,m,n) and F1(a,b, c1,dX,g,l,l1,m,n) and F2(b, c1,dX,g,l,l1,m,n) and F2(a,b, c1,dX,g,l,l1,m,n) and F3(b, c1,dX,g,l,l1,m,n) and F3(a,b,c1, dX,g,l,l1,m,n) where X=1, 2, or 3} and F4 and F4(c1,g,l,l1,m,n) and F4(c,d1,g,l,l1,m,n) and F4(c,d2,g,l,l1,m,n) and F4(c,d3,g,l,l1,m,n) and F4(a, c1,d1,g,l,l1,m,n) and F4(a, c1,d2,g,l,l1,m,n) and F4(a,c1,d3,g,l,l1,m,n) and F5(d1,g,l,l1,m,n) and F5(d2,g,l,l1,m,n) and F5(d3,g,l,l1,m,n), and F5(a, d1,g,l,l1,m,n) and F5(a, d2,g,l,l1,m,n) and F5(a, d3,g,l,l1,m,n) and F6(d1,g,l,l1,m,n) and F6(d2,g,l,l1,m,n) and F6(d3,g,l,l1,m,n) and F6(a, d1,g,l,l1,m,n) and F6(a, d2,g,l,l1,m,n) and F6(a, d3,g,l,l1,m,n), and F6(d1,e1,g,l,l1,m,n) and F6(d2,e1,g,l,l1,m,n) and F6(d3,e1,g,l,l1,m,n) and F6(a, d1,e1,g,l,l1,m,n) and F6(a, d2,e1,g,l,l1,m,n) and F6(a, d3,e1,g,l,l1,m,n) and F6(d1,e2,g,l,l1,m,n) and F6(d2,e2,g,l,l1,m,n) and F6(d3,e2,g,l,l1,m,n) and F6(a, d1,e2,g,l,l1,m,n) and F6(a, d2,e2,g,l,l1,m,n) and F6(a, d3,e2,g,l,l1,m,n) and F7 and F7(d1,g,l,l1,m,n) and F7(d2,g,l,l1,m,n) and F7(d3,g,l,l1,m,n) and F7(a, d1,g,l,l1,m,n) and F7(a, d2,g,l,l1,m,n) and F7(a, d3,g,l,l1,m,n) and F7(d1,e1,g,l,l1,m,n) and F7(d2,e1,g,l,l1,m,n) and F7(d3,e1,g,l,l1,m,n) and F7(a, d1,e1,g,l,l1,m,n) and F7(a, d2,e1,g,l,l1,m,n) and F7(a, d3,e1,g,l,l1,m,n) and F7(d1,e2,g,l,l1,m,n) and F7(d2,e2,g,l,l1,m,n) and F7(d3,e2,g,l,l1,m,n) and F7(a, d1,e2,g,l,l1,m,n) and F7(a, d2,e2,g,l,l1,m,n) and F7(a, d3,e2,g,l,l1,m,n) and {F6(d1,e1,fX,g,l,l1,m,n) and F6(d2,e1,fX,g,l,l1,m,n) and F6(d3,e1,fX,g,l,l1,m,n) and F6(a, d1,e1,fX,g,l,l1,m,n) and F6(a, d2,e1,fX,g,l,l1,m,n) and F6(a, d3,e1,fX,g,l,l1,m,n) and F6(d1,e2,fX,g,l,l1,m,n) and F6(d2,e2,fX,g,l,l1,m,n) and F6(d3,e2,fX,g,l,l1,m,n) and F6(a, d1,e2,fX,g,l,l1,m,n) and F6(a, d2,e2,fX,g,l,l1,m,n) and F6(a, d3,e2,fX,g,l,l1,m,n) and F7(d1,e1,fX,g,l,l1,m,n) and F7(d2,e1,fX,g,l,l1,m,n) and F7(d3,e1,fX,g,l,l1,m,n) and F7(a, d1,e1,fX,g,l,l1,m,n) and F7(a, d2,e1,fX,g,l,l1,m,n) and F7(a, d3,e1,fX,g,l,l1,m,n) and F7(d1,e2,fX,g,l,l1,m,n) and F7(d2,e2,fX,g,l,l1,m,n) and F7(d3,e2,fX,g,l,l1,m,n) and F7(a, d1,e2,fX,g,l,l1,m,n) and F7(a, d2,e2,fX,g,l,l1,m,n) and F7(a, d3,e2,fX,g,l,l1,m,n), wherein X=1, 2, 3, 4, 5, 6, 7, 8, 9, 10, 11, 12, 13, or 14}.

List 10.2

F1(b,g,l,l1,l2,m,n) and F2(b,g,l,l1,l2,m,n) and F3(b,g,l,l1,l2,m,n), and F1(a,b,g,l,l1,l2,m,n) and F2(a,b,g,l,l1,l2,m,n) and F3(a,b,g,l,l1,l2,m,n) and {F1(b,cX,g,l,l1,l2,m,n) and F2(b,cX,g,l,l1,l2,m,n) and F3(b,cX,g,l,l1,l2,m,n) and F1(a,b,cX,g,l,l1,l2,m,n) and F2(a,b,cX,g,l,l1,l2,m,n) and F3(a,b,cX,g,l,l1,l2,m,n) wherein X=1, 2, 3 . . . or 22} and {F1(b, c1,dX,g,l,l1,l2,m,n) and F1(a,b, c1,dX,g,l,l1,l2,m,n) and F2(b, c1,dX,g,l,l1,l2,m,n) and F2(a,b, c1,dX,g,l,l1,l2,m,n) and F3(b, c1,dX,g,l,l1,l2,m,n) and F3(a,b,c1,dX,g,l,l1,l2,m,n) where X=1, 2, or 3} and F4 and F4(c1,g,l,l1,l2,m,n) and F4(c,d1,g,l,l1,l2,m,n) and F4(c,d2,g,l,l1,l2,m,n) and F4(c,d3,g,l,l1,l2,m,n) and F4(a, c1,d1,g,l,l1,l2,m,n) and F4(a, c1,d2,g,l,l1,l2,m,n) and F4(a,c1,d3,g,l,l1,l2,m,n) and F5(d1, g,l,l1,l2,m,n) and F5(d2,g,l,l1,l2,m,n) and F5(d3,g,l,l1,l2,m,n), and F5(a, d1,g,l,l1,l2,m,n) and F5(a, d2,g,l,l1,l2,m,n) and F5(a, d3,g,l,l1,l2,m,n) and F6(d1,g,l,l1,l2,m,n) and F6(d2,g,l,l1,l2,m,n) and F6(d3,g,l,l1,l2,m,n) and F6(a, d1,g,l,l1,l2,m,n) and F6(a, d2,g,l,l1,l2,m,n) and F6(a, d3,g,l,l1,l2,m,n), and F6(d1,e1,g,l,l1,l2,m,n) and F6(d2,e1,g,l,l1,l2,m,n) and F6(d3,e1,g,l,l1,l2,m,n) and F6(a, d1,e1,g,l,l1,l2,m,n) and F6(a, d2,e1,g,l,l1,l2,m,n) and F6(a, d3,e1,g,l,l1,l2,m,n) and F6(d1,e2,g,l,l1,l2,m,n) and F6(d2,e2,g,l,l1,l2,m,n) and F6(d3,e2,g,l,l1,l2,m,n) and F6(a, d1,e2,g,l,l1,l2,m,n) and F6(a, d2,e2,g,l,l1,l2,m,n) and F6(a, d3,e2,g,l,l1,l2,m,n) and F7 and F7(d1,g,l,l1,l2,m,n) and F7(d2,g,l,l1,l2,m,n) and F7(d3,g,l,l1,l2,m,n) and F7(a, d1,g,l,l1,l2,m,n) and F7(a, d2,g,l,l1,l2,m,n) and F7(a, d3,g,l,l1,l2,m,n) and F7(d1,e1,g,l,l1,l2,m,n) and F7(d2,e1,g,l,l1,l2,m,n) and F7(d3,e1,g,l,l1,l2,m,n) and F7(a, d1,e1,g,l,l1,l2,m,n) and F7(a, d2,e1,g,l,l1,l2,m,n) and F7(a, d3,e1,g,l,l1,l2,m,n) and F7(d1,e2,g,l,l1,l2,m,n) and F7(d2,e2,g,l,l1,l2,m,n) and F7(d3,e2,g,l,l1,l2,m,n) and F7(a, d1,e2,g,l,l1,l2,m,n) and F7(a, d2,e2,g,l,l1,l2,m,n) and F7(a, d3,e2,g,l,l1,l2,m,n) and {F6(d1,e1,fX,g,l,l1,l2,m,n) and F6(d2,e1,fX,g,l,l1,l2,m,n) and F6(d3,e1,fX,g,l,l1,l2,m,n) and F6(a, d1,e1,fX,g,l,l1,l2,m,n) and F6(a, d2,e1,fX,g,l,l1,l2,m,n) and F6(a, d3,e1,fX,g,l,l1,l2,m,n) and F6(d1,e2,fX,g,l,l1,l2,m,n) and F6(d2,e2,fX,g,l,l1,l2,m,n) and F6(d3,e2,fX,g,l,l1,l2,m,n) and F6(a, d1,e2,fX,g,l,l1,l2,m,n) and F6(a, d2,e2,fX,g,l,l1,l2,m,n) and {F6(a, d3,e2,fX,g,l,l1,l2,m,n) and F7(d1,e 1,fX,g,l,l1,l2,m,n) and F7(d2,e1,fX,g,l,l1,l2,m,n) and F7(d3,e1,fX,g,l,l1,l2,m,n) and F7(a, d1,e1,fX,g,l,l1,l2,m,n) and F7(a, d2,e1,fX,g,l,l1,l2,m,n) and F7(a, d3,e1,fX,g,l,l1,l2,m,n) and F7(d1,e2,fX,g,l,l1,l2,m,n) and F7(d2,e2,fX,g,l,l1,l2,m,n) and F7(d3,e2,fX,g,l,l1,l2,m,n) and F7(a, d1,e2,fX,g,l,l1,l2,m,n) and F7(a, d2,e2,fX,g,l,l1,l2,m,n) and F7(a, d3,e2,fX,g,l,l1,l2,m,n), wherein X=1, 2, 3, 4, 5, 6, 7, 8, 9, 10, 11, 12, 13, or 14}.

A large number of drugs and compounds that can engage in redox cycling are well known to one skilled in the arts and can be employed with the present method. And are within the scope of the present invention. Suitable redox cycling agents include but are not limited to: anthracyclines such as doxorubicin, idarubicin, epirubicin, daunorubicin; Motexafin gadolinium; Compounds with quinone pharmacophores and precursors of such menadione (2-methylnaphthalene-1,4-dione, vitamin K3; Compounds with a 3,7-diaminophenothiazinium pharmacophores including methylene blue and toluidine blue; Disulfiram [Bis(N,N-(diethylthiocarbamoyl) disulfide] in association with Cu (II); Cu(II) and chelation complexes of Cu(II); Polysulfides; Mitomycin C; Carbazilquinone; Aclacinomycin A; Glendananmycin; Plumbagen; Etoposide; Bleomycin; beta-lapachone; azo compounds; Aromatic nitro compounds such as nitrofurantoin, metronidazole, misomidazole; Metal chelate complexes; Hydroxylamines and nitroxides; Procarbazine; nitropusside; sanguinarine and chelerythrine; 8-nitroguanosine and polyphenolic compounds. See: Biochemistry of reduction of nitro heterocycles; Biaglow J E, et al.; Biochem Pharmacol. 1986 Jan. 1; 35(1):77-90.; Ascorbate potentiates the cytotoxicity of menadione leading to an oxidative stress that kills cancer cells by a non-apoptotic caspase-3 independent form of cell death.; Verrax J, et al.; Apoptosis. 2004 March; 9(2):223-33.; Autoxidation of extracellular hydroquinones is a causative event for the cytotoxicity of menadione and DMNQ in A549-S cells.; Watanabe N, Forman H J.; Arch Biochem Biophys. 2003 Mar. 1; 411(1):145-57; Free radical mediated cell toxicity by redox cycling chemicals;

Cohen G M, d'Arcy Doherty M.; Br J Cancer Suppl. 1987 June; 8:46-52.; Generation of reactive oxygen species by the redox cycling of nitroprusside.;

Ramakrishna Rao D N, Cederbaum A I; Biochim Biophys Acta. 1996 Mar. 15; 1289(2):195-202; Overview of enzyme systems involved in bio-reduction of drugs and in redox cycling.; Kappus H.; Biochem Pharmacol. 1986 Jan. 1; 35(1):1-6.; Production of hydrogen peroxide and redox cycling can explain how sanguinarine and chelerythrine induce rapid apoptosis.; Matkar S S, Wrischnik L A, Hellmann-Blumberg U.; Arch Biochem Biophys. 2008 Sep. 1; 477(1):43-52; Redox and addition chemistry of quinoid compounds and its biological implications; Brunmark A, Cadenas E.; Free Radic Biol Med. 1989; 7(4):435-77; Redox cycling by motexafin gadolinium enhances cellular response to ionizing radiation by forming reactive oxygen species.; Magda D, et al.; Int J Radiat Oncol Biol Phys. 2001 Nov. 15; 51(4):1025-36; Redox cycling of radical anion metabolites of toxic chemicals and drugs and the Marcus theory of electron transfer.; Mason R P.; Environ Health Perspect. 1990 July; 87:237-43.; Redox properties and thiol reactivity of geldanamycin and its analogues in aqueous solutions.; Samuni A, Goldstein S.; J Phys Chem B. 2012 Jun. 7; 116(22):6404-10; Geldanamycin leads to superoxide formation by enzymatic and non-enzymatic redox cycling. Implications for studies of Hsp90 and endothelial cell nitric-oxide synthase; Dikalov S, Landmesser U, Harrison D G.; J Biol Chem. 2002 Jul. 12; 277(28):25480-5.; Superoxide generation mediated by 8-nitroguanosine, a highly redox-active nucleic acid derivative.; Sawa T, et al.; Biochem Biophys Res Commun. 2003 Nov. 14; 311(2):300-6; The metabolism of quinone-containing alkylating agents: free radical production and measurement; Gutierrez P L.; Front Biosci. 2000 Jul. 1; 5:D629-38; Adriamycin activation and oxygen free radical formation in human breast tumor cells: protective role of glutathione peroxidase in adriamycin resistance; Sinha B K, Mimnaugh E G, Rajagopalan S, Myers C E.; Cancer Res. 1989 Jul. 15; 49(14):3844-8; Generation of free radicals and lipid peroxidation by redox cycling of adriamycin and daunomycin; Goodman J, Hochstein P.; Biochem Biophys Res Commun. 1977 Jul. 25; 77(2):797-803.

In an embodiment the redox cycling agent is an anthracyline drug or analog thereof. See: Anthracycline Chemistry and Biology I, Biological Occurrence and Biosynthesis, Synthesis and Chemistry; Volume I; Editor: Karsten Krohn, 2008 Springer-Verlag Berlin Heidelberg.

In a preferred embodiment said anthracyline drug is doxorubicin. In preferred embodiments the IV doxorubicin dose is approximately 10 to 80 mg/m$^2$. In preferred embodiments the doxorubicin dose is approximately 10, 15, 20, 25, 30, 35, 40, 45, 50, 55, 60, 65, 70, 75, or 80 mg/m$^2$. Preferably the drug is administered immediately after the GR inhibitor or at essentially the same time as the GR inhibitor or within approximately 1 hour of administering the GR inhibitor. The DNA crosslinking agent is administered simultaneously with or such that the cells are exposed to the crosslinking agent during the period of GSH decrease. In other preferred embodiments the drug is idarubicin, epirubicin, aclarubicin, or daunorubicin. Techniques for the administration of these drugs to patients are well known to one skilled in the arts and given in the FDA package labeling information.

Embodiments with a DNA Crosslinking Agent, a GR Inhibitor, and an Anthracycline as Redox Cycling Agent (n1)

In embodiments of those given in List 8.2, List 9.2, and List 10.2 the set of drugs is comprised of a DNA crosslinking agent, a GR inhibitor, and a drug that decreases intracellular GSH levels by oxidizing GSSG, wherein said drug is a redox cycling agent and wherein said redox cycling agent is an anthracyline. The new embodiments are respectively named and given in List 8.3, List 9.3, and List 10.3, respectively.

List 8.3

F1(b,g,l,m,n1) and F2(b,g,l,m,n1) and F3(b,g,l,m,n1), and F1(a,b,g,l,m,n1) and F2(a,b,g,l,m,n1) and F3(a,b,g,l,m,n1) and {F1(b,cX,g,l,m,n1) and F2(b,cX,g,l,m,n1) and F3(b,cX,g,l,m,n1) and F1(a,b,cX,g,l,m,n1) and F2(a,b,cX,g,l,m,n1) and F3(a,b,cX,g,l,m,n1) wherein X=1, 2, 3 . . . or 22} and {F1(b, c1,dX,g,l,m,n1) and F1(a,b, c1,dX,g,l,m,n1) and F2(b, c1,dX,g,l,m,n1) and F2(a,b, c1,dX,g,l,m,n1) and F3(b, c1,dX,g,l,m,n1) and F3(a,b,c1,dX,g,l,m,n1) where X=1, 2, or 3} and F4 and F4(c1,g,l,m,n1) and F4(c,d1,g,l,m,n1) and F4(c,d2,g,l,m,n1) and F4(c,d3,g,l,m,n1) and F4(a, c1,d1,g,l,m,n1) and F4(a, c1,d2,g,l,m,n1) and F4(a,c1,d3,g,l,m,n1) and F5(d1,g,l,m,n1) and F5(d2,g,l,m,n1) and F5(d3,g,l,m,n1), and F5(a, d1,g,l,m,n1) and F5(a, d2,g,l,m,n1) and F5(a, d3,g,l,m,n1) and F6(d1,g,l,m,n1) and F6(d2,g,l,m,n1) and F6(d3,g,l,m,n1) and F6(a, d1,g,l,m,n1) and F6(a, d2,g,l,m,n1) and F6(a, d3,g,l,m,n1), and F6(d1,e1,g,l,m,n1) and F6(d2,e1,g,l,m,n1) and F6(d3,e1,g,l,m,n1) and F6(a, d1,e1,g,l,m,n1) and F6(a, d2,e1,g,l,m,n1) and F6(a, d3,e1,g,l,m,n1) and F6(d1,e2,g,l,m,n1) and F6(d2,e2,g,l,m,n1) and F6(d3,e2,g,l,m,n1) and F6(a, d1,e2,g,l,m,n1) and F6(a, d2,e2,g,l,m,n1) and F6(a, d3,e2,g,l,m,n1) and F7 and F7(d1,g,l,m,n1) and F7(d2,g,l,m,n1) and F7(d3,g,l,m,n1) and F7(a, d1,g,l,m,n1) and F7(a, d2,g,l,m,n1) and F7(a, d3,g,l,m,n1) and F7(d1,e1,g,l,m,n1) and F7(d2,e1,g,l,m,n1) and F7(d3,e1,g,l,m,n1) and F7(a, d1,e1,g,l,m,n1) and F7(a, d2,e1,g,l,m,n1) and F7(a, d3,e1,g,l,m,n1) and F7(d1,e2,g,l,m,n1) and F7(d2,e2,g,l,m,n1) and F7(d3,e2,g,l,m,n1) and F7(a, d1,e2,g,l,m,n1) and F7(a, d2,e2,g,l,m,n1) and F7(a, d3,e2,g,l,m,n1) and {F6(d1,e1,fX,g,l,m,n1) and F6(d2,e1,fX,g,l,m,n1) and F6(d3,e1,fX,g,l,m,n1) and F6(a, d1,e1,fX,g,l,m,n1) and F6(a, d2,e1,fX,g,l,m,n1) and F6(a, d3,e1,fX,g,l,m,n1) and F6(d1,e2,fX,g,l,m,n1) and F6(d2,e2,fX,g,l,m,n1) and F6(d3,e2,fX,g,l,m,n1) and F6(a, d1,e2,fX,g,l,m,n1) and F6(a, d2,e2,fX,g,l,m,n1) and F6(a, d3,e2,fX,g,l,m,n1) and F7(d1,e1,fX,g,l,m,n1) and F7(d2,e1,fX,g,l,m,n1) and F7(d3,e1,fX,g,l,m,n1) and F7(a, d1,e1,fX,g,l,m,n1) and F7(a, d2,e1,fX,g,l,m,n1) and F7(a, d3,e1,fX,g,l,m,n1) and F7(d1,e2,fX,g,l,m,n1) and F7(d2,e2,fX,g,l,m,n1) and F7(d3,e2,fX,g,l,m,n1) and F7(a, d1,e2,fX,g,l,m,n1) and F7(a, d2,e2,fX,g,l,m,n1) and F7(a, d3,e2,fX,g,l,m,n1), wherein X=1, 2, 3, 4, 5, 6, 7, 8, 9, 10, 11, 12, 13, or 14}.

List 9.3:

F1(b,g,l,l1,m,n1) and F2(b,g,l,l1,m,n1) and F3(b,g,l,l1,m,n1), and F1(a,b,g,l,l1,m,n1) and F2(a,b,g,l,l1,m,n1) and F3(a,b,g,l,l1,m,n1) and {F1(b,cX,g,l,l1,m,n1) and F2(b,cX,g,l,l1,m,n1) and F3(b,cX,g,l,l1,m,n1) and F1(a,b,cX,g,l,l1,m,n1) and F2(a,b,cX,g,l,l1,m,n1) and F3(a,b,cX,g,l,l1,m,n1) wherein X=1, 2, 3 . . . or 22} and {F1(b, c1,dX,g,l,l1,m,n1) and F1(a,b, c1,dX,g,l,l1,m,n1) and F2(b, c1,dX,g,l,l1,m,n1) and F2(a,b, c1,dX,g,l,l1,m,n1) and F3(b, c1,dX,g,l,l1,m,n1) and F3(a,b,c1,dX,g,l,l1,m,n1) where X=1, 2, or 3} and F4 and F4(c1,g,l,l1,m,n1) and F4(c,d1,g,l,l1,m,n1) and F4(c,d2,g,l,l1,m,n1) and F4(c,d3,g,l,l1,m,n1) and F4(a, c1,d1,g,l,l1,m,n1) and F4(a, c1,d2,g,l,l1,m,n1) and F4(a,c1,d3,g,l,l1,m,n1) and F5(d1,g,l,l1,m,n1) and F5(d2,g,l,l1,m,n1) and F5(d3,g,l,l1,m,n1), and F5(a, d1,g,l,l1,m,n1) and F5(a, d2,g,l,l1,m,n1) and F5(a, d3,g,l,l1,m,n1) and F6(d1,g,l,l1,m,n1) and F6(d2,g,l,l1,m,n1) and F6(d3,g,l,l1,m,n1) and F6(a, d1,g,l,l1,m,n1) and F6(a, d2,g,l,l1,m,n1) and F6(a, d3,g,l,l1,m,n1), and F6(d1,e1,g,l,l1,m,n1) and F6(d2,e1,g,l,l1,m,n1) and F6(d3,e1,g,l,l1,m,n1) and F6(a, d1,e1,g,l,l1,m,n1) and F6(a, d2,e1,g,l,l1,m,n1) and F6(a, d3,e1,g,l,l1,m,n1) and F6(d1,e2,g,l,l1,m,n1) and F6(d2,e2,g,l,l1,m,n1) and F6(d3,e2,g,l,l1,m,n1) and F6(a, d1,e2,g,l,l1,m,n1) and F6(a, d2,e2,g,l,l1,m,n1) and F6(a, d3,e2,g,l,l1,m,n1) and F7 and F7(d1,g,l,l1,m,n1) and F7(d2,g,l,l1,m,n1) and F7(d3,g,l,l1,m,n1) and F7(a, d1,g,l,l1,m,n1) and F7(a, d2,g,l,l1,m,n1) and F7(a, d3,g,l,l1,m,n1) and F7(d1,e1,g,l,l1,m,n1) and F7(d2,e1,g,l,l1,m,n1) and F7(d3,e1,g,l,l1,m,n1) and F7(a, d1,e1,g,l,l1,m,n1) and F7(a, d2,e1,g,l,l1,m,n1) and F7(a, d3,e1,g,l,l1,m,n1) and F7(d1,e2,g,l,l1,m,n1) and F7(d2,e2,g,l,l1,m,n1) and F7(d3,e2,g,l,l1,m,n1) and F7(a, d1,e2,g,l,l1,m,n1) and F7(a, d2,e2,g,l,l1,m,n1) and F7(a, d3,e2,g,l,l1,m,n1) and {F6(d1,e1,fX,g,l,l1,m,n1) and F6(d2,e1,fX,g,l,l1,m,n1) and F6(d3,e1,fX,g,l,l1,m,n1) and F6(a, d1,e1,fX,g,l,l1,m,n1) and F6(a, d2,e1,fX,g,l,l1,m,n1) and F6(a, d3,e1,fX,g,l,l1,m,n1) and F6(d1,e2,fX,g,l,l1,m,n1) and F6(d2,e2,fX,g,l,l1,m,n1) and F6(d3,e2,fX,g,l,l1,m,n1) and F6(a, d1,e2,fX,g,l,l1,m,n1) and F6(a, d2,e2,fX,g,l,l1,m,n1) and F6(a, d3,e2,fX,g,l,l1,m,n1) and F7(d1,e1,fX,g,l,l1,m,n1) and F7(d2,e1,fX,g,l,l1,m,n1) and F7(d3,e1,fX,g,l,l1,m,n1) and F7(a, d1,e1,fX,g,l,l1,m,n1) and F7(a, d2,e1,fX,g,l,l1,m,n1) and F7(a, d3,e1,fX,g,l,l1,m,n1) and F7(d1,e2,fX,g,l,l1,m,n1) and F7(d2,e2,fX,g,l,l1,m,n1) and F7(d3,e2,fX,g,l,l1,m,n1) and F7(a, d1,e2,fX,g,l,l1,m,n1) and F7(a, d2,e2,fX,g,l,l1,m,n1) and F7(a, d3,e2,fX,g,l,l1,m,n1), wherein X=1, 2, 3, 4, 5, 6, 7, 8, 9, 10, 11, 12, 13, or 14}.

List 10.3

F1(b,g,l,l1,l2,m,n1) and F2(b,g,l,l1,l2,m,n1) and F3(b,g,l,l1,l2,m,n1), and F1(a,b,g,l,l1,l2,m,n1) and F2(a,b,g,l,l1,l2,m,n1) and F3(a,b,g,l,l1,l2,m,n1) and {F1(b,cX,g,l,l1,l2,m,n1) and F2(b,cX,g,l,l1,l2,m,n1) and F3(b,cX,g,l,l1,l2,m,n1) and F1(a,b,cX,g,l,l1,l2,m,n1) and F2(a,b,cX,g,l,l1,l2,m,n1) and F3(a,b,cX,g,l,l1,l2,m,n1) wherein X=1, 2, 3 . . . or 22} and {F1(b, c1,dX,g,l,l1,l2,m,n1) and F1(a,b, c1,dX,g,l,l1,l2,m,n1) and F2(b, c1,dX,g,l,l1,l2,m,n1) and F2(a,b, c1,dX,g, l,l1,l2,m,n1) and F3(b, c1,dX,g,l,l1,l2,m,n1) and F3(a,b,c1, dX,g,l,l1,l2,m,n1) where X=1, 2, or 3} and F4 and F4(c1, g,l,l1,l2,m,n1) and F4(c,d1,g,l,l1,l2,m,n1) and F4(c,d2,g,l, l1,l2,m,n1) and F4(c,d3,g,l,l1,l2,m,n1) and F4(a, c1,d1,g,l, l1,l2,m,n1) and F4(a, c1,d2,g,l,l1,l2,m,n1) and F4(a,c1,d3, g,l,l1,l2,m,n1) and F5(d1,g,l,l1,l2,m,n1) and F5(d2,g,l,l1,l2, m,n1) and F5(d3,g,l,l1,l2,m,n1), and F5(a, d1,g,l,l1,l2,m,n1) and F5(a, d2,g,l,l1,l2,m,n1) and F5(a, d3,g,l,l1,l2,m,n1) and F6(d1,g,l,l1,l2,m,n1) and F6(d2,g,l,l1,l2,m,n1) and F6(d3,g, l,l1,l2,m,n1) and F6(a, d1,g,l,l1,l2,m,n1) and F6(a, d2,g,l,l1, l2,m,n1) and F6(a, d3,g,l,l1,l2,m,n1), and F6(d1,e1,g,l,l1,l2, m,n1) and F6(d2,e1,g,l,l1,l2,m,n1) and F6(d3,e1,g,l,l1,l2,m, n1) and F6(a, d1,e1,g,l,l1,l2,m,n1) and F6(a, d2,e1,g,l,l1,l2, m,n1) and F6(a, d3,e1,g,l,l1,l2,m,n1) and F6(d1,e2,g,l,l1,l2, m,n1) and F6(d2,e2,g,l,l1,l2,m,n1) and F6(d3,e2,g,l,l1,l2,m, n1) and F6(a, d1,e2,g,l,l1,l2,m,n1) and F6(a, d2,e2,g,l,l1,l2, m,n1) and F6(a, d3,e2,g,l,l1,l2,m,n1) and F7 and F7(d1,g,l, l1,l2,m,n1) and F7(d2,g,l,l1,l2,m,n1) and F7(d3,g,l,l1,l2,m, n1) and F7(a, d1,g,l,l1,l2,m,n1) and F7(a, d2,g,l,l1,l2,m,n1) and F7(a, d3,g,l,l1,l2,m,n1) and F7(d1,e1,g,l,l1,l2,m,n1) and F7(d2,e1,g,l,l1,l2,m,n1) and F7(d3,e1,g,l,l1,l2,m,n1) and F7(a, d1,e1,g,l,l1,l2,m,n1) and F7(a, d2,e1,g,l,l1,l2,m,n1) and F7(a, d3,e1,g,l,l1,l2,m,n1) and F7(d1,e2,g,l,l1,l2,m,n1) and F7(d2,e2,g,l,l1,l2,m,n1) and F7(d3,e2,g,l,l1,l2,m,n1) and F7(a, d1,e2,g,l,l1,l2,m,n1) and F7(a, d2,e2,g,l,l1,l2,m, n1) and F7(a, d3,e2,g,l,l1,l2,m,n1) and {F6(d1,e1,fX,g,l,l1,l2,m,n1) and F6(d2,e1,fX,g,l,l1,l2,m, n1) and F6(d3,e1,fX,g,l,l1,l2,m,n1) and F6(a, d1,e1,fX,g,l, l1,l2,m,n1) and F6(a, d2,e1,fX,g,l,l1,l2,m,n1) and F6(a, d3,e1,fX,g,l,l1,l2,m,n1) and F6(d1,e2,fX,g,l,l1,l2,m,n1) and F6(d2,e2,fX,g,l,l1,l2,m,n1) and F6(d3,e2,fX,g,l,l1,l2,m,n1) and F6(a, d1,e2,fX,g,l,l1,l2,m,n1) and F6(a, d2,e2,fX,g,l,l1, l2,m,n1) and F6(a, d3,e2,fX,g,l,l1,l2,m,n1) and F7(d1,e1,fX, g,l,l1,l2,m,n1) and F7(d2,e1,fX,g,l,l1,l2,m,n1) and F7(d3, e1,fX,g,l,l1,l2,m,n1) and F7(a, d1,e1,fX,g,l,l1,l2,m,n1) and F7(a, d2,e1,fX,g,l,l1,l2,m,n1) and F7(a, d3,e1,fX,g,l,l1,l2,m, n1) and F7(d1,e2,fX,g,l,l1,l2,m,n1) and F7(d2,e2,fX,g,l,l1, l2,m,n1) and F7(d3,e2,fX,g,l,l1,l2,m,n1) and F7(a, d1,e2,fX, g,l,l1,l2,m,n1) and F7(a, d2,e2,fX,g,l,l1,l2,m,n1) and F7(a, d3,e2,fX,g,l,l1,l2,m,n1), wherein X=1, 2, 3, 4, 5, 6, 7, 8, 9, 10, 11, 12, 13, or 14}.

Embodiments with a DNA Crosslinking Agent, a GR Inhibitor, and an Doxorubicin as Redox Cycling Agent (n2)

In embodiments of those given in List 8.3, List 9.3, and List 10.3 the set of drugs is comprised of a DNA crosslinking agent, a GR inhibitor, and a drug that decreases intracellular GSH levels by oxidizing GSSG, wherein said drug is a redox cycling agent and wherein said redox cycling agent is a doxorubicin. The new embodiments are respectively named and given in List 8.4, List 9.4, and List 10.4, respectively.

List 8.4

F1(b,g,l,m,n2) and F2(b,g,l,m,n2) and F3(b,g,l,m,n2), and F1(a,b,g,l,m,n2) and F2(a,b,g,l,m,n2) and F3(a,b,g,l,m,n2) and {F1(b,cX,g,l,m,n2) and F2(b,cX,g,l,m,n2) and F3(b,cX, g,l,m,n2) and F1(a,b,cX,g,l,m,n2) and F2(a,b,cX,g,l,m,n2) and F3(a,b,cX,g,l,m,n2) wherein X=1, 2, 3 . . . or 22} and {F1(b, c1,dX,g,l,m,n2) and F1(a,b, c1,dX,g,l,m,n2) and F2(b, c1,dX,g,l,m,n2) and F2(a,b, c1,dX,g,l,m,n2) and F3(b, c1,dX,g,l,m,n2) and F3(a,b,c1,dX,g,l,m,n2) where X=1, 2, or 3} and F4 and F4(c1,g,l,m,n2) and F4(c,d1,g,l,m,n2) and F4(c,d2,g,l,m,n2) and F4(c,d3,g,l,m,n2) and F4(a, c1,d1,g, l,m,n2) and F4(a, c1,d2,g,l,m,n2) and F4(a,c1,d3,g,l,m,n2) and F5(d1,g,l,m,n2) and F5(d2,g,l,m,n2) and F5(d3,g,l,m, n2), and F5(a, d1,g,l,m,n2) and F5(a, d2,g,l,m,n2) and F5(a, d3,g,l,m,n2) and F6(d1,g,l,m,n2) and F6(d2,g,l,m,n2) and F6(d3,g,l,m,n2) and F6(a, d1,g,l,m,n2) and F6(a, d2,g,l,m, n2) and F6(a, d3,g,l,m,n2), and F6(d1,e1,g,l,m,n2) and F6(d2,e1,g,l,m,n2) and F6(d3,e1,g,l,m,n2) and F6(a, d1,e1, g,l,m,n2) and F6(a, d2,e1,g,l,m,n2) and F6(a, d3,e1,g,l,m, n2) and F6(d1,e2,g,l,m,n2) and F6(d2,e2,g,l,m,n2) and F6(a, d1,e2,g,l,m,n2) and F6(a, d1,e2,g,l,m,n2) and F6(a, d2,e2,g,l,m,n2) and F6(a, d3,e2,g,l,m,n2) and F7 and F7(d1, g,l,m,n2) and F7(d2,g,l,m,n2) and F7(d3,g,l,m,n2) and F7(a, d1,g,l,m,n2) and F7(a, d2,g,l,m,n2) and F7(a, d3,g,l,m,n2) and F7(d1,e1,g,l,m,n2) and F7(d2,e1,g,l,m,n2) and F7(d3, e1,g,l,m,n2) and F7(a, d1,e1,g,l,m,n2) and F7(a, d2,e1,g,l, m,n2) and F7(a, d3,e1,g,l,m,n2) and F7(d1,e2,g,l,m,n2) and F7(d2,e2,g,l,m,n2) and F7(d3,e2,g,l,m,n2) and F7(a, d1,e2, g,l,m,n2) and F7(a, d2,e2,g,l,m,n2) and F7(a, d3,e2,g,l,m, n2) and {F6(d1,e1,fX,g,l,m,n2) and F6(d2,e1,fX,g,l,m,n2) and F6(d3,e1,fX,g,l,m,n2) and F6(a, d1,e1,fX,g,l,m,n2) and F6(a, d2,e1,fX,g,l,m,n2) and F6(a, d3,e1,fX,g,l,m,n2) and F6(d1,e2,fX,g,l,m,n2) and F6(d2,e2,fX,g,l,m,n2) and F6(d3, e2,fX,g,l,m,n2) and F6(a, d1,e2,fX,g,l,m,n2) and F6(a, d2,e2,fX,g,l,m,n2) and F6(a, d3,e2,fX,g,l,m,n2) and F7(d1, e1,fX,g,l,m,n2) and F7(d2,e1,fX,g,l,m,n2) and F7(d3,e1,fX, g,l,m,n2) and F7(a, d1,e1,fX,g,l,m,n2) and F7(a, d2,e1,fX, g,l,m,n2) and F7(a, d3,e1,fX,g,l,m,n2) and F7(d1,e2,fX,g,l, m,n2) and F7(d2,e2,fX,g,l,m,n2) and F7(d3,e2,fX,g,l,m,n2) and F7(a, d1,e2,fX,g,l,m,n2) and F7(a, d2,e2,fX,g,l,m,n2) and F7(a, d3,e2,fX,g,l,m,n2), wherein X=1, 2, 3, 4, 5, 6, 7, 8, 9, 10, 11, 12, 13, or 14}.

List 9.4:

F1(b,g,l,l1,m,n2) and F2(b,g,l,l1,m,n2) and F3(b,g,l,l1,m, n2), and F1(a,b,g,l,l1,m,n2) and F2(a,b,g,l,l1,m,n2) and F3(a,b,g,l,l1,m,n2) and {F1(b,cX,g,l,l1,m,n2) and F2(b,cX, g,l,l1,m,n2) and F3(b,cX,g,l,l1,m,n2) and F1(a,b,cX,g,l,l1, m,n2) and F2(a,b,cX,g,l,l1,m,n2) and F3(a,b,cX,g,l,l1,m,n2) wherein X=1, 2, 3 . . . or 22} and {F1(b, c1,dX,g,l,l1,m,n2) and F1(a,b, c1,dX,g,l,l1,m,n2) and F2(b, c1,dX,g,l,l1,m,n2) and F2(a,b, c1,dX,g,l,l1,m,n2) and F3(b, c1,dX,g,l,l1,m,n2) and F3(a,b,c1,dX,g,l,l1,m,n2) where X=1, 2, or 3} and F4 and F4(c1,g,l,l1,m,n2) and F4(c,d1,g,l,l1,m,n2) and F4(c,d2, g,l,l1,m,n2) and F4(c,d3,g,l,l1,m,n2) and F4(a, c1,d1,g,l,l1, m,n2) and F4(a, c1,d2,g,l,l1,m,n2) and F4(a,c1,d3,g,l,l1,m, n2) and F5(d1,g,l,l1,m,n2) and F5(d2,g,l,l1,m,n2) and F5(d3,g,l,l1,m,n2), and F5(a, d1,g,l,l1,m,n2) and F5(a, d2,g, l,l1,m,n2) and F5(a, d3,g,l,l1,m,n2) and F6(d1,g,l,l1,m,n2) and F6(d2,g,l,l1,m,n2) and F6(d3,g,l,l1,m,n2) and F6(a, d1,g,l,l1,m,n2) and F6(a, d2,g,l,l1,m,n2) and F6(a, d3,g,l,l1, m,n2), and F6(d1,e1,g,l,l1,m,n2) and F6(d2,e1,g,l,l1,m,n2) and F6(d3,e1,g,l,l1,m,n2) and F6(a, d1,e1,g,l,l1,m,n2) and F6(a, d2,e1,g,l,l1,m,n2) and F6(a, d3,e1,g,l,l1,m,n2) and F6(d1,e2,g,l,l1,m,n2) and F6(d2,e2,g,l,l1,m,n2) and F6(d3, e2,g,l,l1,m,n2) and F6(a, d1,e2,g,l,l1,m,n2) and F6(a, d2,e2, g,l,l1,m,n2) and F6(a, d3,e2,g,l,l1,m,n2) and F7 and F7(d1, g,l,l1,m,n2) and F7(d2,g,l,l1,m,n2) and F7(d3,g,l,l1,m,n2) and F7(a, d1,g,l,l1,m,n2) and F7(a, d2,g,l,l1,m,n2) and F7(a, d3,g,l,l1,m,n2) and F7(d1,e1,g,l,l1,m,n2) and F7(d2,e1,g,l, l1,m,n2) and F7(d3,e1,g,l,l1,m,n2) and F7(a, d1,e1,g,l,l1,m, n2) and F7(a, d2,e1,g,l,l1,m,n2) and F7(a, d3,e1,g,l,l1,m,n2) and F7(d1,e2,g,l,l1,m,n2) and F7(d2,e2,g,l,l1,m,n2) and F7(d3,e2,g,l,l1,m,n2) and F7(a, d1,e2,g,l,l1,m,n2) and F7(a, d2,e2,g,l,l1,m,n2) and F7(a, d3,e2,g,l,l1,m,n2) and {F6(d1, e1,fX,g,l,l1,m,n2) and F6(d2,e1,fX,g,l,l1,m,n2) and F6(d3, e1,fX,g,l,l1,m,n2) and F6(a, d1,e1,fX,g,l,l1,m,n2) and F6(a, d2,e1,fX,g,l,l1,m,n2) and F6(a, d3,e1,fX,g,l,l1,m,n2) and F6(d1, e2,fX,g,l,l1,m,n2) and F6(d2,e2,fX,g,l,l1,m,n2) and F6(d3,e2,fX,g,l,l1,m,n2) and F6(a, d1,e2,fX,g,l,l1,m,n2) and F6(a, d2,e2,fX,g,l,l1,m,n2) and F6(a, d3,e2,fX,g,l,l1,m,n2) and F7(d1, e1,fX,g,l,l1,m,n2) and F7(d2,e1,fX,g,l,l1,m,n2) and F7(d3,e1,fX,g,l,l1,m,n2) and F7(a, d1,e1,fX,g,l,l1,m,n2) and F7(a, d2,e1,fX,g,l,l1,m,n2) and F7(a, d3,e1,fX,g,l,l1,m, n2) and F7(d1, e2,fX,g,l,l1,m,n2) and F7(d2,e2,fX,g,l,l1,m, n2) and F7(d3,e2,fX,g,l,l1,m,n2) and F7(a, d1,e2,fX,g,l,l1, m,n2) and F7(a, d2,e2,fX,g,l,l1,m,n2) and F7(a, d3,e2,fX,g, l,l1,m,n2), wherein X=1, 2, 3, 4, 5, 6, 7, 8, 9, 10, 11, 12, 13, or 14}.

List 10.4

F1(b,g,l,l1,l2,m,n2) and F2(b,g,l,l1,l2,m,n2) and F3(b,g, l,l1,l2,m,n2), and F1(a,b,g,l,l1,l2,m,n2) and F2(a,b,g,l,l1,l2, m,n2) and F3(a,b,g,l,l1,l2,m,n2) and {F1(b,cX,g,l,l1,l2,m, n2) and F2(b,cX,g,l,l1,l2,m,n2) and F3(b,cX,g,l,l1,l2,m,n2) and F1(a,b,cX,g,l,l1,l2,m,n2) and F2(a,b,cX,g,l,l1,l2,m,n2) and F3(a,b,cX,g,l,l1,l2,m,n2) wherein X=1, 2, 3 . . . or 22} and {F1(b, c1,dX,g,l,l1,l2,m,n2) and F1(a,b, c1,dX,g,l,l1,l2, m,n2) and F2(b, c1,dX,g,l,l1,l2,m,n2) and F2(a,b, c1,dX,g, l,l1,l2,m,n2) and F3(b, c1,dX,g,l,l1,l2,m,n2) and F3(a,b,c1, dX,g,l,l1,l2,m,n2) where X=1, 2, or 3} and F4 and F4(c1, g,l,l1,l2,m,n2) and F4(c,d1,g,l,l1,l2,m,n2) and F4(c,d2,g,l, l1,l2,m,n2) and F4(c,d3,g,l,l1,l2,m,n2) and F4(a, c1,d1,g,l, l1,l2,m,n2) and F4(a, c1,d2,g,l,l1,l2,m,n2) and F4(a,c1,d3, g,l,l1,l2,m,n2) and F5(d1,g,l,l1,l2,m,n2) and F5(d2,g,l,l1,l2, m,n2) and F5(d3,g,l,l1,l2,m,n2), and F5(a, d1,g,l,l1,l2,m,n2) and F5(a, d2,g,l,l1,l2,m,n2) and F5(a, d3,g,l,l1,l2,m,n2) and F6(d1,g,l,l1,l2,m,n2) and F6(d2,g,l,l1,l2,m,n2) and F6(d3,g, l,l1,l2,m,n2) and F6(a, d1,g,l,l1,l2,m,n2) and F6(a, d2,g,l,l1, l2,m,n2) and F6(a, d3,g,l,l1,l2,m,n2), and F6(d1,e1,g,l,l1,l2, m,n2) and F6(d2,e1,g,l,l1,l2,m,n2) and F6(d3,e1,g,l,l1,l2,m, n2) and F6(a, d1,e1,g,l,l1,l2,m,n2) and F6(a, d2,e1,g,l,l1,l2, m,n2) and F6(a, d3,e1,g,l,l1,l2,m,n2) and F6(d1,e2,g,l,l1,l2, m,n2) and F6(d2,e2,g,l,l1,l2,m,n2) and F6(d3,e2,g,l,l1,l2,m, n2) and F6(a, d1,e2,g,l,l1,l2,m,n2) and F6(a, d2,e2,g,l,l1,l2, m,n2) and F6(a, d3,e2,g,l,l1,l2,m,n2) and F7 and F7(d1,g,l, l1,l2,m,n2) and F7(d2,g,l,l1,l2,m,n2) and F7(d3,g,l,l1,l2,m, n2) and F7(a, d1,g,l,l1,l2,m,n2) and F7(a, d2,g,l,l1,l2,m,n2) and F7(a, d3,g,l,l1,l2,m,n2) and F7(d1,e1,g,l,l1,l2,m,n2) and F7(d2,e1,g,l,l1,l2,m,n2) and F7(d3,e1,g,l,l1,l2,m,n2) and F7(a, d1,e1,g,l,l1,l2,m,n2) and F7(a, d2,e1,g,l,l1,l2,m,n2) and F7(a, d3,e1,g,l,l1,l2,m,n2) and F7(d1,e2,g,l,l1,l2,m,n2) and F7(d2,e2,g,l,l1,l2,m,n2) and F7(d3,e2,g,l,l1,l2,m,n2) and F7(a, d1,e2,g,l,l1,l2,m,n2) and F7(a, d2,e2,g,l,l1,l2,m, n2) and F7(a, d3,e2,g,l,l1,l2,m,n2) and {F6(d1,e1,fX,g,l,l1, l2,m,n2) and F6(d2,e1,fX,g,l,l1,l2,m,n2) and F6(d3,e1,fX,g, l,l1,l2,m,n2) and F6(a, d1,e1,fX,g,l,l1,l2,m,n2) and F6(a, d2,e1,fX,g,l,l1,l2,m,n2) and F6(a, d3,e1,fX,g,l,l1,l2,m,n2) and F6(d1,e2,fX,g,l,l1,l2,m,n2) and F6(d2,e2,fX,g,l,l1,l2,m, n2) and F6(d3,e2,fX,g,l,l1,l2,m,n2) and F6(a, d1,e2,fX,g,l, l1,l2,m,n2) and F6(a, d2,e2,fX,g,l,l1,l2,m,n2) and F6(a, d3,e2,fX,g,l,l1,l2,m,n2) and F7(d1,e1,fX,g,l,l1,l2,m,n2) and F7(d2,e1,fX,g,l,l1,l2,m,n2) and F7(d3,e1,fX,g,l,l1,l2,m,n2) and F7(a, d1,e1,fX,g,l,l1,l2,m,n2) and F7(a, d2,e1,fX,g,l,l1, l2,m,n2) and F7(a, d3,e1,fX,g,l,l1,l2,m,n2) and F7(d1,e2,fX, g,l,l1,l2,m,n2) and F7(d2,e2,fX,g,l,l1,l2,m,n2) and F7(d3, e2,fX,g,l,l1,l2,m,n2) and F7(a, d1,e2,fX,g,l,l1,l2,m,n2) and F7(a, d2,e2,fX,g,l,l1,l2,m,n2) and F7(a, d3,e2,fX,g,l,l1,l2,m, n2), wherein X=1, 2, 3, 4, 5, 6, 7, 8, 9, 10, 11, 12, 13, or 14}.

Methylene Blue as a Redox Cycling Agent (n3)

Methylene blue (MB) can be used in in conjunction with a GR inhibitor to deplete GSH levels and generate oxidative stress. MB undergoes facile 2-electron reduction to give the colorless, neutrally charged, leuco-MB. A wide range of electron donors can reduce MB including NADPH, NADH and GSH. Leuco-MB can in turn reduce oxygen to hydrogen peroxide and also convert $Fe^{+3}$ to $Fe^{+2}$. Low levels of MB can lead to oxidant stress and the generation of ROS.

In cells, the net effect of MB is electron flow from NADPH, NADH, and GSH to molecular oxygen, increased oxygen consumption, increased $H_2O_2$ production, and stimulation of the pentose cycle, which generates NADPH. Glutathione peroxidase catalyzed reduction of hydrogen peroxide generated by redox-cycling of MB can deplete GSH. MB can also directly oxidize GSH to GSSG and undergoes redox cycling in the presence of oxygen. Methylene blue is approved for the treatment of methemoglobinemia. The drug has also been used for the treatment of refractory hypotensive shock, malaria, detection of sentinel lymph nodes, and the treatment and prevention of encephalopathy associated with high dose ifosfamide therapy. MB potently inhibits monoamine oxidase, guanylate cyclase and nitric oxide synthase. MB is contraindicated in patients treated with serotonin uptake inhibitors and can precipitate serotonin syndrome, but otherwise has a favorable safety profile. MB generally has minimal cytotoxicity for cells.

Methylene blue would be useful in patients with brain cancer or metastatic lesions to the brain as a component of the set, as MB penetrates well into the brain. See: Generation of oxidant stress in cultured endothelial cells by methylene blue: protective effects of glucose and ascorbic acid.; May J M, Qu Z C, Whitesell R R.; Biochem Pharmacol. 2003 Sep. 1; 66(5):777-84.; Methylene blue directly oxidizes glutathione without the intermediate formation of hydrogen peroxide.; Kelner M J, Alexander N M.; J Biol Chem. 1985 Dec. 5; 260(28):15168-71; The measurement of bioreductive capacity of tumor cells using methylene blue.; Biaglow J E, et al.; Int J Radiat Oncol Biol Phys. 1998 Nov. 1; 42(4):769-73; Methylene blue in the treatment and prevention of ifosfamide-induced encephalopathy: report of 12 cases and a review of the literature.; Pelgrims J, et al.; Br J Cancer. 2000 January; 82(2):291-4; Cellular and molecular actions of Methylene Blue in the nervous system.; Oz M, Lorke D E, Hasan M, Petroianu G A.; Med Res Rev. 2011 January; 31(1):93-117; Encephalopathy after high-dose Ifosfamide: a retrospective cohort study and review of the literature; Sweiss K I, et al.; Drug Saf. 2008; 31(11):989-96; Methylene blue in the treatment and prevention of ifosfamide-induced encephalopathy: report of 12 cases and a review of the literature.; Pelgrims J, et al.; Br J Cancer. 2000 January; 82(2):291-4; Lack of toxicity of methylene blue chloride to supravitally stained human mammary tissues.; Buehring G C, Jensen H M.; Cancer Res. 1983 December; 43(12 Pt 1):6039-44; Interactions of methylene blue with human disulfide reductases and their orthologues from Plasmodium falciparum; Buchholz K, et al.; Antimicrob Agents Chemother. 2008 January; 52(1):183-91.

Embodiment with Methylene Blue as Redox Cycling Agent (n3)

In embodiments of those given in List 8.2, List 9.2, and List 10.2 the set of drugs is comprised of a DNA crosslinking agent, a GR inhibitor, and a drug that decreases intracellular GSH levels by oxidizing GSSG, wherein said drug is a redox cycling agent and wherein said redox cycling agent is methylene blue. The new embodiments are respectively named and given in List 8.5, List 9.5, and List 10.5, respectively.

List 8.5

F1(b,g,l,m,n3) and F2(b,g,l,m,n3) and F3(b,g,l,m,n3), and F1(a,b,g,l,m,n3) and F2(a,b,g,l,m,n3) and F3(a,b,g,l,m,n3) and {F1(b,cX,g,l,m,n3) and F2(b,cX,g,l,m,n3) and F3(b,cX, g,l,m,n3) and F1(a,b,cX,g,l,m,n3) and F2(a,b,cX,g,l,m,n3) and F3(a,b,cX,g,l,m,n3) wherein X=1, 2, 3 . . . or 22} and {F1(b, c1,dX,g,l,m,n3) and F1(a,b, c1,dX,g,l,m,n3) and F2(b, c1,dX,g,l,m,n3) and F2(a,b, c1,dX,g,l,m,n3) and F3(b, c1,dX,g,l,m,n3) and F3(a,b,c1,dX,g,l,m,n3) where X=1, 2, or 3} and F4 and F4(c1,g,l,m,n3) and F4(c,d1,g,l,m,n3) and F4(c,d2,g,l,m,n3) and F4(c,d3,g,l,m,n3) and F4(a, c1,d1,g, l,m,n3) and F4(a, c1,d2,g,l,m,n3) and F4(a,c1,d3,g,l,m,n3)

and F5(d1,g,l,m,n3) and F5(d2,g,l,m,n3) and F5(d3,g,l,m,n3), and F5(a, d1,g,l,m,n3) and F5(a, d2,g,l,m,n3) and F5(a, d3,g,l,m,n3) and F6(d1,g,l,m,n3) and F6(d2,g,l,m,n3) and F6(d3,g,l,m,n3) and F6(a, d1,g,l,m,n3) and F6(a, d2,g,l,m,n3) and F6(a, d3,g,l,m,n3), and F6(d1,e1,g,l,m,n3) and F6(d2,e1,g,l,m,n3) and F6(d3,e1,g,l,m,n3) and F6(a, d1,e1,g,l,m,n3) and F6(a, d2,e1,g,l,m,n3) and F6(a, d3,e1,g,l,m,n3) and F6(d1,e2,g,l,m,n3) and F6(d2,e2,g,l,m,n3) and F6(d3,e2,g,l,m,n3) and F6(a, d1,e2,g,l,m,n3) and F6(a, d2,e2,g,l,m,n3) and F6(a, d3,e2,g,l,m,n3) and F7 and F7(d1,g,l,m,n3) and F7(d2,g,l,m,n3) and F7(d3,g,l,m,n3) and F7(a, d1,g,l,m,n3) and F7(a, d2,g,l,m,n3) and F7(a, d3,g,l,m,n3) and F7(d1,e1,g,l,m,n3) and F7(d2,e1,g,l,m,n3) and F7(d3,e1,g,l,m,n3) and F7(a, d1,e1,g,l,m,n3) and F7(a, d2,e1,g,l,m,n3) and F7(a, d3,e1,g,l,m,n3) and F7(d1,e2,g,l,m,n3) and F7(d2,e2,g,l,m,n3) and F7(d3,e2,g,l,m,n3) and F7(a, d1,e2,g,l,m,n3) and F7(a, d2,e2,g,l,m,n3) and F7(a, d3,e2,g,l,m,n3) and {F6(d1,e1,fX,g,l,m,n3) and F6(d2,e1,fX,g,l,m,n3) and F6(d3,e1,fX,g,l,m,n3) and F6(a, d1,e1,fX,g,l,m,n3) and F6(a, d2,e1,fX,g,l,m,n3) and F6(a, d3,e1,fX,g,l,m,n3) and F6(d1,e2,fX,g,l,m,n3) and F6(d2,e2,fX,g,l,m,n3) and F6(d3,e2,fX,g,l,m,n3) and F6(a, d1,e2,fX,g,l,m,n3) and F6(a, d2,e2,fX,g,l,m,n3) and F6(a, d3,e2,fX,g,l,m,n3) and F7(d1,e1,fX,g,l,m,n3) and F7(d2,e1,fX,g,l,m,n3) and F7(d3,e1,fX,g,l,m,n3) and F7(a, d1,e1,fX,g,l,m,n3) and F7(a, d2,e1,fX,g,l,m,n3) and F7(a, d3,e1,fX,g,l,m,n3) and F7(d1,e2,fX,g,l,m,n3) and F7(d2,e2,fX,g,l,m,n3) and F7(d3,e2,fX,g,l,m,n3) and F7(a, d1,e2,fX,g,l,m,n3) and F7(a, d2,e2,fX,g,l,m,n3) and F7(a, d3,e2,fX,g,l,m,n3), wherein X=1, 2, 3, 4, 5, 6, 7, 8, 9, 10, 11, 12, 13, or 14}.

List 9.5:

F1(b,g,l,l1,m,n3) and F2(b,g,l,l1,m,n3) and F3(b,g,l,l1,m,n3), and F1(a,b,g,l,l1,m,n3) and F2(a,b,g,l,l1,m,n3) and F3(a,b,g,l,l1,m,n3) and {F1(b,cX,g,l,l1,m,n3) and F2(b,cX,g,l,l1,m,n3) and F3(b,cX,g,l,l1,m,n3) and F1(a,b,cX,g,l,l1,m,n3) and F2(a,b,cX,g,l,l1,m,n3) and F3(a,b,cX,g,l,l1,m,n3) wherein X=1, 2, 3 . . . or 22} and {F1(b, c1,dX,g,l,l1,m,n3) and F1(a,b, c1,dX,g,l,l1,m,n3) and F2(b, c1,dX,g,l,l1,m,n3) and F2(a,b, c1,dX,g,l,l1,m,n3) and F3(b, c1,dX,g,l,l1,m,n3) and F3(a,b,c1,dX,g,l,l1,m,n3) where X=1, 2, or 3} and F4 and F4(c1,g,l,l1,m,n3) and F4(c,d1,g,l,l1,m,n3) and F4(c,d2,g,l,l1,m,n3) and F4(c,d3,g,l,l1,m,n3) and F4(a, c1,d1,g,l,l1,m,n3) and F4(a, c1,d2,g,l,l1,m,n3) and F4(a,c1,d3,g,l,l1,m,n3) and F5(d1,g,l,l1,m,n3) and F5(d2,g,l,l1,m,n3) and F5(d3,g,l,l1,m,n3), and F5(a, d1,g,l,l1,m,n3) and F5(a, d2,g,l,l1,m,n3) and F5(a, d3,g,l,l1,m,n3) and F6(d1,g,l,l1,m,n3) and F6(d2,g,l,l1,m,n3) and F6(d3,g,l,l1,m,n3) and F6(a, d1,g,l,l1,m,n3) and F6(a, d2,g,l,l1,m,n3) and F6(a, d3,g,l,l1,m,n3), and F6(d1,e1,g,l,l1,m,n3) and F6(d2,e1,g,l,l1,m,n3) and F6(d3,e1,g,l,l1,m,n3) and F6(a, d1,e1,g,l,l1,m,n3) and F6(a, d2,e1,g,l,l1,m,n3) and F6(a, d3,e1,g,l,l1,m,n3) and F6(d1,e2,g,l,l1,m,n3) and F6(d2,e2,g,l,l1,m,n3) and F6(d3,e2,g,l,l1,m,n3) and F6(a, d1,e2,g,l,l1,m,n3) and F6(a, d2,e2,g,l,l1,m,n3) and F6(a, d3,e2,g,l,l1,m,n3) and F7 and F7(d1,g,l,l1,m,n3) and F7(d2,g,l,l1,m,n3) and F7(d3,g,l,l1,m,n3) and F7(a, d1,g,l,l1,m,n3) and F7(a, d2,g,l,l1,m,n3) and F7(a, d3,g,l,l1,m,n3) and F7(d1,e1,g,l,l1,m,n3) and F7(d2,e1,g,l,l1,m,n3) and F7(d3,e1,g,l,l1,m,n3) and F7(a, d1,e1,g,l,l1,m,n3) and F7(a, d2,e1,g,l,l1,m,n3) and F7(a, d3,e1,g,l,l1,m,n3) and F7(d1,e2,g,l,l1,m,n3) and F7(d2,e2,g,l,l1,m,n3) and F7(d3,e2,g,l,l1,m,n3) and F7(a, d1,e2,g,l,l1,m,n3) and F7(a, d2,e2,g,l,l1,m,n3) and F7(a, d3,e2,g,l,l1,m,n3) and {F6(d1,e1,fX,g,l,l1,m,n3) and F6(d2,e1,fX,g,l,l1,m,n3) and F6(d3,e1,fX,g,l,l1,m,n3) and F6(a, d1,e1,fX,g,l,l1,m,n3) and F6(a, d2,e1,fX,g,l,l1,m,n3) and F6(a, d3,e1,fX,g,l,l1,m,n3) and F6(d1,e2,fX,g,l,l1,m,n3) and F6(d2,e2,fX,g,l,l1,m,n3) and F6(d3,e2,fX,g,l,l1,m,n3) and F6(a, d1,e2,fX,g,l,l1,m,n3) and F6(a, d2,e2,fX,g,l,l1,m,n3) and F6(a, d3,e2,fX,g,l,l1,m,n3) and F7(d1,e1,fX,g,l,l1,m,n3) and F7(d2,e1,fX,g,l,l1,m,n3) and F7(d3,e1,fX,g,l,l1,m,n3) and F7(a, d1,e1,fX,g,l,l1,m,n3) and F7(a, d2,e1,fX,g,l,l1,m,n3) and F7(a, d3,e1,fX,g,l,l1,m,n3) and F7(d1,e2,fX,g,l,l1,m,n3) and F7(d2,e2,fX,g,l,l1,m,n3) and F7(d3,e2,fX,g,l,l1,m,n3) and F7(a, d1,e2,fX,g,l,l1,m,n3) and F7(a, d2,e2,fX,g,l,l1,m,n3) and F7(a, d3,e2,fX,g,l,l1,m,n3), wherein X=1, 2, 3, 4, 5, 6, 7, 8, 9, 10, 11, 12, 13, or 14}.

List 10.5

F1(b,g,l,l1,l2,m,n3) and F2(b,g,l,l1,l2,m,n3) and F3(b,g,l,l1,l2,m,n3), and F1(a,b,g,l,l1,l2,m,n3) and F2(a,b,g,l,l1,l2,m,n3) and F3(a,b,g,l,l1,l2,m,n3) and {F1(b,cX,g,l,l1,l2,m,n3) and F2(b,cX,g,l,l1,l2,m,n3) and F3(b,cX,g,l,l1,l2,m,n3) and F1(a,b,cX,g,l,l1,l2,m,n3) and F2(a,b,cX,g,l,l1,l2,m,n3) and F3(a,b,cX,g,l,l1,l2,m,n3) wherein X=1, 2, 3 . . . or 22} and {F1(b, c1,dX,g,l,l1,l2,m,n3) and F1(a,b, c1,dX,g,l,l1,l2,m,n3) and F2(b, c1,dX,g,l,l1,l2,m,n3) and F2(a,b, c1,dX,g,l,l1,l2,m,n3) and F3(b, c1,dX,g,l,l1,l2,m,n3) and F3(a,b,c1,dX,g,l,l1,l2,m,n3) where X=1, 2, or 3} and F4 and F4(c1,g,l,l1,l2,m,n3) and F4(c,d1,g,l,l1,l2,m,n3) and F4(c,d2,g,l,l1,l2,m,n3) and F4(c,d3,g,l,l1,l2,m,n3) and F4(a, c1,d1,g,l,l1,l2,m,n3) and F4(a, c1,d2,g,l,l1,l2,m,n3) and F4(a,c1,d3,g,l,l1,l2,m,n3) and F5(d1,g,l,l1,l2,m,n3) and F5(d2,g,l,l1,l2,m,n3) and F5(d3,g,l,l1,l2,m,n3), and F5(a, d1,g,l,l1,l2,m,n3) and F5(a, d2,g,l,l1,l2,m,n3) and F5(a, d3,g,l,l1,l2,m,n3) and F6(d1,g,l,l1,l2,m,n3) and F6(d2,g,l,l1,l2,m,n3) and F6(d3,g,l,l1,l2,m,n3) and F6(a, d1,g,l,l1,l2,m,n3) and F6(a, d2,g,l,l1,l2,m,n3) and F6(a, d3,g,l,l1,l2,m,n3), and F6(d1,e1,g,l,l1,l2,m,n3) and F6(d2,e1,g,l,l1,l2,m,n3) and F6(d3,e1,g,l,l1,l2,m,n3) and F6(a, d1,e1,g,l,l1,l2,m,n3) and F6(a, d2,e1,g,l,l1,l2,m,n3) and F6(a, d3,e1,g,l,l1,l2,m,n3) and F6(d1,e2,g,l,l1,l2,m,n3) and F6(d2,e2,g,l,l1,l2,m,n3) and F6(d3,e2,g,l,l1,l2,m,n3) and F6(a, d1,e2,g,l,l1,l2,m,n3) and F6(a, d2,e2,g,l,l1,l2,m,n3) and F6(a, d3,e2,g,l,l1,l2,m,n3) and F7 and F7(d1,g,l,l1,l2,m,n3) and F7(d2,g,l,l1,l2,m,n3) and F7(d3,g,l,l1,l2,m,n3) and F7(a, d1,g,l,l1,l2,m,n3) and F7(a, d2,g,l,l1,l2,m,n3) and F7(a, d3,g,l,l1,l2,m,n3) and F7(d1,e1,g,l,l1,l2,m,n3) and F7(d2,e1,g,l,l1,l2,m,n3) and F7(d3,e1,g,l,l1,l2,m,n3) and F7(a, d1,e1,g,l,l1,l2,m,n3) and F7(a, d2,e1,g,l,l1,l2,m,n3) and F7(a, d3,e1,g,l,l1,l2,m,n3) and F7(d1,e2,g,l,l1,l2,m,n3) and F7(d2,e2,g,l,l1,l2,m,n3) and F7(d3,e2,g,l,l1,l2,m,n3) and F7(a, d1,e2,g,l,l1,l2,m,n3) and F7(a, d2,e2,g,l,l1,l2,m,n3) and F7(a, d3,e2,g,l,l1,l2,m,n3) and {F6(d1,e1,fX,g,l,l1,l2,m,n3) and F6(d2,e1,fX,g,l,l1,l2,m,n3) and F6(d3,e1,fX,g,l,l1,l2,m,n3) and F6(a, d1,e1,fX,g,l,l1,l2,m,n3) and F6(a, d2,e1,fX,g,l,l1,l2,m,n3) and F6(a, d3,e1,fX,g,l,l1,l2,m,n3) and F6(d1,e2,fX,g,l,l1,l2,m,n3) and F6(d2,e2,fX,g,l,l1,l2,m,n3) and F6(d3,e2,fX,g,l,l1,l2,m,n3) and F6(a, d1,e2,fX,g,l,l1,l2,m,n3) and F6(a, d2,e2,fX,g,l,l1,l2,m,n3) and F6(a, d3,e2,fX,g,l,l1,l2,m,n3) and F7(d1,e1,fX,g,l,l1,l2,m,n3) and F7(d2,e1,fX,g,l,l1,l2,m,n3) and F7(d3,e1,fX,g,l,l1,l2,m,n3) and F7(a, d1,e1,fX,g,l,l1,l2,m,n3) and F7(a, d2,e1,fX,g,l,l1,l2,m,n3) and F7(a, d3,e1,fX,g,l,l1,l2,m,n3) and F7(d1,e2,fX,g,l,l1,l2,m,n3) and F7(d2,e2,fX,g,l,l1,l2,m,n3) and F7(d3,e2,fX,g,l,l1,l2,m,n3) and F7(a, d1,e2,fX,g,l,l1,l2,m,n3) and F7(a, d2,e2,fX,g,l,l1,l2,m,n3) and F7(a, d3,e2,fX,g,l,l1,l2,m,n3), wherein X=1, 2, 3, 4, 5, 6, 7, 8, 9, 10, 11, 12, 13, or 14}.

In a preferred embodiments the dose of IV methylene blue is approximately 1 mg/kg to 5 mg/kg. Methods for the IV administration of methylene blue are known to one skilled in the arts and given in the FDA package label. The GR inhibitor would generally be administered approximately 5 to 60 minutes prior to the methylene blue, which would then be followed immediately by the DNA crosslinking agent. However, the drugs can also be given at essentially the same time.

Leucomethylene blue can be used in place of methylene blue.

Inhibition of NER

The interaction of melphalan with DNA proceeds in a stepwise fashion with the rapid formation of mono-adducts and the slower development of interstrand DNA crosslinks (ICLs). In cells peak levels of melphalan-DNA mono-adducts form at ~2 hours and peak levels of ICLs form at ~8 hours post melphalan exposure. Interstrand crosslinking of DNA oligo-nucleotides in vitro by melphalan proceeds with a half-life of ~3 hours. See: Gene-specific formation and repair of DNA monoadducts and interstrand cross-links after therapeutic exposure to nitrogen mustards.; Souliotis V L, et al.; Clin Cancer Res. 2003 Oct. 1; 9(12):4465-74; Specificity and kinetics of interstrand and intrastrand bifunctional alkylation by nitrogen mustards at a G-G-C sequence.; Bauer G B, Povirk L F; Nucleic Acids Res. 1997 Mar. 15; 25(6): 1211-8.

Excision of DNA-drug mono-adducts of crosslinking agents plays a major role in decreasing DNA crosslink formation. In melphalan treated cells the majority of monoadducts are excised and do not result in DNA crosslink formation. Nucleotide excision repair is the major mechanism by which these mono-adducts are excised. Melphalan-DNA mono-adducts can be very rapidly removed in normal cells with a T½ ranging from <15 minutes to ~2 hours for different genes. By contrast, NER deficient, xeroderma pigmentosum group A protein (XP-A) cells failed to remove the mono-adducts, (even after 8 hours). The level of interstrand DNA crosslinks (ICLs) closely parallel those seen for mono-adducts. Cell deficient in NER are hypersensitive to melphalan. Since NER can profoundly decrease the level of mono-adducts and ICls that are formed in cells, inhibition of NER will sensitize cells to melphalan. Only a brief time period of NER inhibition (e.g., 0 to 6 hours post melphalan exposure) would be needed to sensitize cells to melphalan, since peak ICL formation occurs in cell by ~8 hours and most ICLs are formed by 6 hours.

Methods for measuring NER and its inhibition are well known to one skilled in the arts. See: Gene-specific formation and repair of DNA monoadducts and interstrand crosslinks after therapeutic exposure to nitrogen mustards.; Souliotis V L, et al.; Clin Cancer Res. 2003 Oct. 1; 9(12):4465-74; Nucleotide excision repair of melphalan monoadducts.; Grant D F, Bessho T, Reardon J T.; Cancer Res. 1998 Nov. 15; 58(22):5196-200; Association between transcriptional activity, local chromatin structure, and the efficiencies of both sub-pathways of nucleotide excision repair of melphalan adducts; Episkopou H, et al.; Cancer Res. 2009 May 15; 69(10):4424-33; Sensitivity of CHO mutant cell lines with specific defects in nucleotide excision repair to different anti-cancer agents.; Damia G, Imperatori L, Stefanini M, D'Incalci M.; Int J Cancer. 1996 Jun. 11; 66(6):779-83.

At least 30 different proteins are required for NER. A number of these proteins have thiol groups that are redox sensitive, highly reactive with electrophilic compounds, and essential for function. These proteins include: replication protein A (RPA), XPA, XPF, ubiquitin-activating enzymes (E1), ubiquitin-conjugating enzymes (E2) and E3 ubiquitin ligases, and 4A-based ubiquitin E3 ligase, DDB1-CUL4ADDB2. XPA has a zinc finger motif that is essential to DNA binding and which is susceptible to oxidation and glutathionylation. RPA also has an oxidation-sensitive zinc finger. Oxidative stress induced by hydrogen peroxide exposure results in a GSH dependent inhibition of NER, which is likely due to glutathionylation of critical proteins involved in NER. See: Episkopou H, et al.; Cancer Res. 2009 May 15; 69(10):4424-33; Quantitative electrospray ionization mass spectrometry of zinc finger oxidation: the reaction of XPA zinc finger with H(2)O(2).; Smirnova J, et al.; Anal Biochem. 2007 Oct. 15; 369(2):226-31; Reaction of the XPA zinc finger with S-nitrosoglutathione.; Smirnova J, et al.; Chem Res Toxicol. 2008 February; 21(2):386-92.; Zinc finger of replication protein A, a non-DNA binding element, regulates its DNA binding activity through redox.; Park J S, Wang M, Park S J, Lee S H.; J Biol Chem. 1999 Oct. 8; 274(41):29075-80; Zinc finger of replication protein A, a non-DNA binding element, regulates its DNA binding activity through redox.; Park J S, Wang M, Park S J, Lee S H.; J Biol Chem. 1999 Oct. 8; 274(41):29075-80; Functions of human replication protein A (RPA): from DNA replication to DNA damage and stress responses.; Zou Y, Liu Y, Wu X, Shell S M.; J Cell Physiol. 2006 August; 208(2):267-73; Multiple roles of ubiquitination in the control of nucleotide excision repair.; Nouspikel T.; Mech; Ageing Dev. 2011 August; 132(8-9):355-65; Cellular ubiquitination and proteasomal functions positively modulate mammalian nucleotide excision repair.; Wang Q E, Wani M A, et al; Mol Carcinog. 2005 January; 42(1):53-64.; Cullin 4A-mediated proteolysis of DDB2 protein at DNA damage sites regulates in vivo lesion recognition by XPC.; El-Mahdy M A, Zhu Q, Wang Q E, Wani G, Praetorius-Ibba M, Wani A A.; J Biol Chem. 2006 May 12; 281(19):13404-11; The DDB1-CUL4ADDB2 ubiquitin ligase is deficient in xeroderma pigmentosum group E and targets histone H2A at UV-damaged DNA sites.; Kapetanaki M G, et al.; Proc Natl Acad Sci USA. 2006 Feb. 21; 103(8):2588-93; Regulation of ubiquitin-conjugating enzymes by glutathione following oxidative stress.; Jahngen-Hodge et al.; J Biol Chem. 1997 Nov. 7; 272(45):28218-26; Redox regulation of ubiquitin-conjugating enzymes: mechanistic insights using the thiol-specific oxidant diamide.; Obin M, Shang F, Gong X, Handelman G, Blumberg J, Taylor A.; FASEB J. 1998 May; 12(7):561-9; The role of glutathione in the regulation of nucleotide excision repair during oxidative stress.; Langie S A, et al.; Toxicol Lett. 2007 Feb. 5; 168(3):302-9; Diverse functional roles of reactive cysteines.; Pace N J, Weerapana E.; ACS Chem Biol. 2013 Feb. 15; 8(2):283-96; Redox-dependent formation of disulfide bonds in human replication protein A.; Men L, Roginskaya M, Zou Y, Wang Y.; Rapid Commun Mass Spectrom. 2007; 21(16):2743-9.

In an embodiment the set of drug is comprised of a DNA crosslinking agent and one or more drugs that inhibit NER. In an embodiment said drugs inhibit NER by directly or indirectly modifying redox active thiol groups in proteins involved in NER either by changing the oxidation state of the thiol or by covalent modification. A direct action would involve covalent modification or oxidation of said thiols by the drug. An indirect action would represent modification of said thiol groups by either a spontaneous degradation product of the drug, a metabolite or as a result of a perturbation in the cell induced buy the drug, such as the production of ROS, oxidative stress, or alterations in the intracellular GSSG/2GSH reduction potential or increased S-protein glutathionylation. Suitable drugs that can modify active thiols have been described previously in the section on GR inhibitors. Suitable drugs that can cause oxidative stress and increase the GSSG/2GSH reduction potential were describe previously in the section on redox cycling. The timing of the administration of said drugs is important. They preferably are given within ~0.25 to 2 hours prior or at the same times as the DNA crosslinking agent so that NER is inhibited at the time of DNA crosslinking drug exposure. The ER inhibitor can also be given at the same time as the DNA crosslinking agent.

Embodiments with a DNA Crosslinking Agent and an Inhibitor of NER (o)

In embodiments of the invention given below in List 2, the set of drugs is comprised of a DNA crosslinking agent and one or more additional drugs that hypersensitize cancer cells to said DNA crosslinking agent, wherein one or more of said drugs inhibits NER. The new embodiments are respectively named and given in List 11.

List 11:

F1(b,g,o) and F2(b,g,o) and F3(b,g,o), and F1(a,b,g,o) and F2(a,b,g,o) and F3(a,b,g,o) and {F1(b,cX,g,o) and F2(b,cX,g,o) and F3(b,cX,g,o) and F1(a,b,cX,g,o) and F2(a,b,cX,g,o) and F3(a,b,cX,g,o) wherein X=1, 2, 3 . . . or 22} and {F1(b, c1,dX,g,o) and F1(a,b, c1,dX,g,o) and F2(b, c1,dX,g,o) and F2(a,b, c1,dX,g,o) and F3(b, c1,dX,g,o) and F3(a,b,c1,dX,g,o) where X=1, 2, or 3} and F4 and F4(c1,g,o) and F4(c,d1,g,o) and F4(c,d2,g,o) and F4(c,d3,g,o) and F4(a, c1,d1,g,o) and F4(a, c1,d2,g,o) and F4(a,c1,d3,g,o) and F5(d1,g,o) and F5(d2,g,o) and F5(d3,g,o), and F5(a, d1,g,o) and F5(a, d2,g,o) and F5(a, d3,g,o) and F6(d1,g,o) and F6(d2,g,o) and F6(d3,g,o) and F6(a, d1,g,o) and F6(a, d2,g, o) and F6(a, d3,g,o), and F6(d1,e1,g,o) and F6(d2,e1,g,o) and F6(d3,e1,g,o) and F6(a, d1,e1,g,o) and F6(a, d2,e1,g,o) and F6(a, d3,e1,g,o) and F6(d1,e2,g,o) and F6(d2,e2,g,o) and F6(d3,e2,g,o) and F6(a, d1,e2,g,o) and F6(a, d2,e2,g,o) and F6(a, d3,e2,g,o) and F7 and F7(d1,g,o) and F7(d2,g,o) and F7(d3,g,o) and F7(a, d1,g,o) and F7(a, d2,g,o) and F7(a, d3,g,o) and F7(d1,e1,g,o) and F7(d2,e1,g,o) and F7(d3,e1, g,o) and F7(a, d1,e1,g,o) and F7(a, d2,e1,g,o) and F7(a, d3,e1,g,o) and F7(d1,e2,g,o) and F7(d2,e2,g,o) and F7(d3, e2,g,o) and F7(a, d1,e2,g,o) and F7(a, d2,e2,g,o) and F7(a, d3,e2,g,o) and {F6(d1,e1,fX,g,o) and F6(d2,e1,fX,g,o) and F6(d3,e1,fX,g,o) and F6(a, d1,e1,fX,g,o) and F6(a, d2,e1, fX,g,o) and F6(a, d3,e1,fX,g,o) and F6(d1,e2,fX,g,o) and F6(d2,e2,fX,g,o) and F6(d3,e2,fX,g,o) and F6(a, d1,e2,fX, g,o) and F6(a, d2,e2,fX,g,o) and F6(a, d3,e2,fX,g,o) and F7(d1,e1,fX,g,o) and F7(d2,e1,fX,g,o) and F7(d3,e1,fX,g,o) and F7(a, d1,e1,fX,g,o) and F7(a, d2,e1,fX,g,o) and F7(a, d3,e1,fX,g,o) and F7(d1,e2,fX,g,o) and F7(d2,e2,fX,g,o) and F7(d3,e2,fX,g,o) and F7(a, d1,e2,fX,g,o) and F7(a, d2,e2,fX,g,o) and F7(a, d3,e2,fX,g,o) where X=1, 2, 3, 4, 5, 6, 7, 8, 9, 10, 11, 12, 13, or 14}

In embodiments of the invention given in List 4, the set of drugs is comprised of a DNA crosslinking agent, and one or more additional drugs that hypersensitize cancer cells to said DNA crosslinking agent, wherein one or more of said additional drugs decrease the detoxification of the crosslinking agent, and wherein one or more of said drugs decrease GSH-mediated detoxification of the crosslinking agent and wherein one or more of said drugs inhibits NER. The new embodiments are respectively named and given in List 12.

List 12:

F1(b,g,h,i,o) and F2(b,g,h,i,o) and F3(b,g,h,i,o), and F1(a, b,g,h,i,o) and F2(a,b,g,h,i,o) and F3(a,b,g,h,i,o) and {F1(b, cX,g,h,i,o) and F2(b,cX,g,h,i,o) and F3(b,cX,g,h,i,o) and F1(a,b,cX,g,h,i,o) and F2(a,b,cX,g,h,i,o) and F3(a,b,cX,g,h, i,o) wherein X=1, 2, 3 . . . or 22} and {F1(b, c1,dX,g,h,i,o) and F1(a,b, c1,dX,g,h,i,o) and F2(b, c1,dX,g,h,i,o) and F2(a, b, c1,dX,g,h,i,o) and F3(b, c1,dX,g,h,i,o) and F3(a,b,c1,dX, g,h,i,o) where X=1, 2, or 3} and F4 and F4(c1,g,h,i,o) and F4(c,d1,g,h,i,o) and F4(c,d2,g,h,i,o) and F4(c,d3,g,h,i,o) and F4(a, c1,d1,g,h,i,o) and F4(a, c1,d2,g,h,i,o) and F4(a,c1,d3, g,h,i,o) and F5(d1,g,h,i,o) and F5(d2,g,h,i,o) and F5(d3,g,h, i,o), and F5(a, d1,g,h,i,o) and F5(a, d2,g,h,i,o) and F5(a, d3,g,h,i,o) and F6(d1,g,h,i,o) and F6(d2,g,h,i,o) and F6(d3, g,h,i,o) and F6(a, d1,g,h,i,o) and F6(a, d2,g,h,i,o) and F6(a, d3,g,h,i,o), and F6(d1,e1,g,h,i,o) and F6(d2,e1,g,h,i,o) and F6(d3,e1,g,h,i,o) and F6(a, d1,e1,g,h,i,o) and F6(a, d2,e1,g, h,i,o) and F6(a, d3,e1,g,h,i,o) and F6(d1,e2,g,h,i,o) and F6(d2,e2,g,h,i,o) and F6(d3,e2,g,h,i,o) and F6(a, d1,e2,g,h, i,o) and F6(a, d2,e2,g,h,i,o) and F6(a, d3,e2,g,h,i,o) and F7 and F7(d1,g,h,i,o) and F7(d2,g,h,i,o) and F7(d3,g,h,i,o) and F7(a, d1,g,h,i,o) and F7(a, d2,g,h,i,o) and F7(a, d3,g,h,i,o) and F7(d1,e1,g,h,i,o) and F7(d2,e1,g,h,i,o) and F7(d3,e1, g,h,i,o) and F7(a, d1,e1,g,h,i,o) and F7(a, d2,e1,g,h,i,o) and F7(a, d3,e1,g,h,i,o) and F7(d1,e2,g,h,i,o) and F7(d2,e2,g,h, i,o) and F7(d3,e2,g,h,i,o) and F7(a, d1,e2,g,h,i,o) and F7(a, d2,e2,g,h,i,o) and F7(a, d3,e2,g,h,i,o) and F6(d1,e1,fX,g,h, i,o) and F6(d2,e1,fX,g,h,i,o) and F6(d3,e1,fX,g,h,i,o) and F6(a, d1,e1,fX,g,h,i,o) and F6(a, d2,e1,fX,g,h,i,o) and F6(a, d3,e1,fX,g,h,i,o) and F6(d1,e2,fX,g,h,i,o) and F6(d2,e2,fX, g,h,i,o) and F6(d3,e2,fX,g,h,i,o) and F6(a, d1,e2,fX,g,h,i,o) and F6(a, d2,e2,fX,g,h,i,o) and F6(a, d3,e2,fX,g,h,i,o) and F7(d1,e1,fX,g,h,i,o) and F7(d2,e1,fX,g,h,i,o) and F7(d3,e1, fX,g,h,i,o) and F7(a, d1,e1,fX,g,h,i,o) and F7(a, d2,e1,fX,g, h,i,o) and F7(a, d3,e1,fX,g,h,i,o) and F7(d1,e2,fX,g,h,i,o) and F7(d2,e2,fX,g,h,i,o) and F7(d3,e2,fX,g,h,i,o) and F7(a, d1,e2,fX,g,h,i,o) and F7(a, d2,e2,fX,g,h,i,o) and F7(a, d3,e2, fX,g,h,i,o) where X=1, 2, 3, 4, 5, 6, 7, 8, 9, 10, 11, 12, 13, or 14}.

In a preferred embodiment the DNA crosslinking agent is melphalan and the drug that inhibits NER is comprised of BCNU. In an even more preferred embodiment doxorubicin is added. Suitable doses and timing of the drugs are as previously described in the section on redox cycling and elsewhere in this description.

Increasing the Intracellular GSSG/2GSH Reduction Potential (p)

Multiple steps required for the repair of DNA-drug monoadducts and DNA interstrand crosslinks are redox sensitive and are inhibited by increase in the intracellular GSSG/2GSH reduction potential. An increase the GSSG/2GSH reduction potential inhibition can inhibit proteins involved in DNA repair by a variety of mechanisms including: S-glutathionylation of the proteins, intermolecular disulfide formation, intramolecular disulfide formation, and by impairing the detoxification of ROS, which causes an increase levels of ROS that oxidize critical protein thiols. See: Cooper A J, Pinto J T, Callery P S.; Expert Opin Drug Metab Toxicol. 2011 July; 7(7):891-910.

Proteins and mechanisms involved in DNA repair that are inhibited by an increase in the GSSG/2GSH reduction potential and oxidative stress include: NF-κB DNA binding and activity; Ubiquitin ligase and conjugating activity; ubiquitination of multiple proteins; Nonhomologous end joining (NHEJ) Repair of DNA DSBs; Topoisomerase II; SUMOylation of multiple proteins; XPA and RPA.

Details are provided below:

NF-κB strongly enhances the removal of DNA double stranded breaks by stimulating homologous recombination. See: Cooperation of protein disulfide isomerase and redox environment in the regulation of NF-kappaB and AP1 binding to DNA; Clive D R, Greene J J.; Cell Biochem Funct. 1996; NF-κB regulates DNA double-strand break repair in conjunction with BRCA1-CtIP complexes; Volcic M, et al.; Nucleic Acids Res. 2012 January; 40(1):181-95.

Multiple steps in DNA repair including in NER, HR, and trans-lesion synthesis involve ubiquitination. Inhibition of RNF8 ubiquinating activity inhibits NHEJ by preventing the removal of Ku 80. Ubiquitin ligase activity is needed for BRCA1. The absence of Ubc13 activity profoundly sensitizes cells to DNA crosslinking agents and DNA DSBs. Recruitment and activation of the E3 Ub ligase function of BRCA1 and the subsequent formation of the Rad51 nucleoprotein filament at DSBs are abolished, and HR is inhibited. See: Multiple roles of ubiquitination in the control of nucleotide excision repair.; Nouspikel T; Mech; Ageing Dev. 2011 August; 132(8-9):355-65; Degradation-linked ubiquitin signal and proteasome are integral components of DNA double strand break repair: New perspectives for anti-cancer therapy.; Ramadan K, Meerang M.; FEBS Lett. 2011 Sep. 16; 585(18):2868-75; The ubiquitin- and SUMO-dependent signaling response to DNA double-strand breaks.; Bekker-Jensen S, Mailand N.; FEBS Lett. 2011 Sep. 16; 585(18): 2914-9; The ubiquitous role of ubiquitin in the DNA damage response.; Al-Hakim A, et al.; DNA Repair (Amst). 2010 Dec. 10; 9(12):1229-40; Dynamic regulation of PCNA ubiquitylation/deubiquitylation.; Fox J T, Lee K Y, Myung K.; FEBS Lett. 2011 Sep. 16; 585(18):2780-5.; The E3 ligase RNF8 regulates KU80 removal and NHEJ repair.; Feng L, Chen J.; Nat Struct Mol Biol. 2012 Jan. 22; 19(2):201-6. A critical role for the ubiquitin-conjugating enzyme Ubc13 in initiating homologous recombination.; Zhao G Y, et al.; Mol Cell. 2007 Mar. 9; 25(5):663-75; Redox regulation of ubiquitin-conjugating enzymes: mechanistic insights using the thiol-specific oxidant diamide; Obin M, et al.; FASEB J. 1998 May; 12(7):561-9.

Ku protein is required for the NHEJ repair of DNA double stranded breaks (DSBs) and is redox sensitive. Oxidative stress also inhibits DNA-dependent protein kinase (DNA-PKcs) and inhibits the localization of DNA-PKcspThr2609 at DSBs and impairs repair. See: Zhang W W, Yaneva M.; Biochem J. 1993 Aug. 1; 293 (Pt 3):769-74; Induction and repair of DNA double strand breaks: the increasing spectrum of non-homologous end joining pathways.; Mladenov E, Iliakis G.; Mutat Res. 2011 Jun. 3; 711(1-2):61-72; Modulation of DNA-dependent protein kinase activity in chlorambucil-treated cells.; Bacsi A, Kannan S, Lee M S, Hazra T K, Boldogh I.; Free Radic Biol Med. 2005 Dec. 15; 39(12): 1650-9; Reduced DNA double strand breaks in chlorambucil resistant cells are related to high DNA-PKcs activity and low oxidative stress.; Boldogh I, et al.; Toxicology. 2003 Nov. 15; 193(1-2):137-52.

Topoisomerase II is involved in DNA unwinding and is involved in multiple steps of DNA repair. Increased Topoisomerase II levels contribute to melphalan resistance and inhibition decrease the rate of DNA crosslink removal. See: Activation of topoisomerase II-mediated excision of chromosomal DNA loops during oxidative stress.; Li T K, Chen A Y, Yu C, Mao Y, Wang H, Liu L F.; Genes Dev. 1999 Jun. 15; 13(12):1553-60; Stimulation of topoisomerase II-mediated DNA damage via a mechanism involving protein thiolation.; Wang H, Mao Y, Chen A Y, Zhou N, LaVoie E J, Liu L F.; Biochemistry. 2001 Mar. 20; 40(11):3316-23.; Induction of apoptosis by plumbagin through reactive oxygen species-mediated inhibition of topoisomerase II.; Kawiak A, al.; Toxicol Appl Pharmacol. 2007 Sep. 15; 223(3):267-76; Induction of alkylator (melphalan) resistance in HL60 cells is accompanied by increased levels of topoisomerase II expression and function.; Pu Q Q, Bezwoda W R.; Mol Pharmacol. 1999 July; 56(1):147-53.

Sumoylation is involved in multiple steps in DNA repair. See: Regulation of DNA Damage Responses by Ubiquitin and SUMO; Jackson S P, Durocher D.; Mol Cell. 2013 Feb. 12. S1097-2765; The ubiquitin- and SUMO-dependent signaling response to DNA double-strand breaks.; Bekker-Jensen S, Mailand N.; FEBS Lett. 2011 Sep. 16; 585(18): 2914-9; A PIAS-ed view of DNA double strand break repair focuses on SUMO.; Zlatanou A, Stewart G S.; DNA Repair (Amst). 2010 May 4; 9(5):588-92; Mammalian SUMO E3-ligases PIAS1 and PIAS4 promote responses to DNA double-strand breaks.; Galanty Y, et al.; Nature. 2009 Dec. 17; 462(7275):935-9.

As previously discussed XPA is required for NER and, XPA deficiency sensitizes cells to melphalan. See: Quantitative electrospray ionization mass spectrometry of zinc finger oxidation: the reaction of XPA zinc finger with $H(2)O(2)$.; Smirnova J, et al.; Anal Biochem. 2007 Oct. 15; 369(2):226-31; Reaction of the XPA zinc finger with S-nitrosoglutathione.; Smirnova J et al.; Chem Res Toxicol. 2008 February; 21(2):386-92.

RPA is required for all major DNA repair pathways. See: Functions of human replication protein A (RPA): from DNA replication to DNA damage and stress responses.; Zou Y, Liu Y, Wu X, Shell S M.; J Cell Physiol. 2006 August; 208(2): 267-73; Zinc finger of replication protein A, a non-DNA binding element, regulates its DNA binding activity through redox.; Park J S, Wang M, Park S J, Lee S H.; J Biol Chem. 1999 Oct. 8; 274(41):29075-80; Role of zinc-finger motif in redox regulation of human replication protein A.; Wang M, You J S, Lee S H.; Antioxid Redox Signal. 2001 August; 3(4):657-69; Reversible and irreversible protein glutathionylation: biological and clinical aspects; Cooper A J, Pinto J T, Callery P S.; Expert Opin Drug Metab Toxicol. 2011 July; 7(7):891-910. Epub 2011 May 11.

Cancer cells generally have increased basal rates of ROS production that make the cells more susceptible to agents that increase ROS levels and more susceptible to increases in the GSSG/2GSH reduction potential. For example GSH levels are profoundly decreased in melanoma cells treated with BCNU and doxorubicin; by contrast GSH levels in normal fibroblasts remain normal.

See: Sensitization of Human Melanoma Cells to Melphalan Cytoxicity by Adriamycin and Carmustine; Jevtovic-Todoroviv, Vesna; 1990, Ph.D. Dissertation, University of Illinois at Chicago, Health Sciences Center; ROS stress in cancer cells and therapeutic implications.; Pelicano H, Carney D, Huang P.; Drug Resist Updat. 2004 April; 7(2):97-110; Production of large amounts of hydrogen peroxide by human tumor cells.; Szatrowski T P, Nathan C F.; Cancer Res. 1991 Feb. 1; 51(3):794-8; Production of superoxide by human malignant melanoma cells.; Bittinger F, al.; Melanoma Res. 1998 October; 8(5):381-7; Aiding and abetting roles of NOX oxidases in cellular transformation; Block K, Gorin Y.; Nat Rev Cancer. 2012 September; 12(9):627-37; Mechanisms associated with mitochondrial-generated reactive oxygen species in cancer.; Verschoor M L, Wilson L A, Singh G.; Can J Physiol Pharmacol. 2010 March; 88(3): 204-19.

The scope of the present invention includes a method for the effective treatment of metastatic cancer that is comprised of the administration of a set of drugs that increase the intracellular GSSG/2GSH reduction potential in cancer cells and a DNA crosslinking drug. Suitable DNA crosslinking agents are as described for previous embodiments. In embodiments the reduction potential is increased by approximately 15%, 20%, 25%, 30%, 40%, 50%, 60%, or greater.

In preferred embodiments the drugs that increase the intracellular GSSG/2GSH reduction potential are comprised of a GR inhibitor and a redox cycling agent. The DNA crosslinking agent is administered during the time, or at least during part of the time, of increased GSSG/2GSH reduction potential. However, it is not necessary that the reduction potential be increased during the entire time of crosslinker exposure. In an embodiment the GR inhibitor is BCNU and the redox cycling agent is doxorubicin. A preferred DNA crosslinking agent is melphalan. In embodiments the BCNU dose is approximately 50, 75, 100, 125, 150, 175, 200, 225, 250, 275, 300, or 350 mg/m$^2$; the doxorubicin dose is approximately 10, 15, 20, 25, 30, 35, 40, 45, 50, 55, 60, 65, 70, 75, or 80 mg/m$^2$; and the melphalan dose is approximately 20, 25, 30, 35, 40, 45, 50, 55, 60, 65, 70, 75, 80, 85, 90, 95, 100, 125, 150, 175, or 200 mg/m$^2$. In a preferred embodiment the BCNU dose is approximately 150 mg/m$^2$, the doxorubicin dose is approximately 50 mg/m$^2$, and the melphalan dose is approximately 70 mg/m$^2$.

Embodiments with a crosslinking agent and one or more additional drugs that that increase the intracellular GSSG/2GSH reduction potential (p).

In embodiments of the invention given in List 1, the set of drugs is comprised of a DNA crosslinking agent and one or more additional drugs that that increase the intracellular GSSG/2GSH reduction potential in cancer cells during at least part of the time that the cells are exposed to the crosslinking agent. The respective names of the new embodiments are given in List 1.1

List 1.1:

F1(b,p) and F2(b,p) and F3(b,p), and F1(a,b,p) and F2(a,b,p) and F3(a,b,p) and {F1(b,cX,p) and F2(b,cX,p) and F3(b,cX,p) and F1(a,b,cX,p) and F2(a,b,cX,p) and F3(a,b,cX,p) wherein X=1, 2, 3 . . . or 22} and {F1(b, c1,dX,p) and F1(a,b, c1,dX,p) and F2(b, c1,dX,p) and F2(a,b, c1,dX,p) and F3(b, c1,dX,p) and F3(a,b,c1,dX,p) where X=1, 2, or 3} and F4 and F4(c1,p) and F4(c,d1,p) and F4(c,d2,p) and F4(c,d3,p) and F4(a, c1,d1,p) and F4(a, c1,d2,p) and F4(a, c1,d3,p) and F5(d1,p) and F5(d2,p) and F5(d3,p), and F5(a, d1,p) and F5(a, d2,p) and F5(a, d3,p) and F6(d1,p) and F6(d2,p) and F6(d3,p) and F6(a, d1,p) and F6(a, d2,p) and F6(a, d3,p), and F6(d1,e1,p) and F6(d2,e1,p) and F6(d3,e1,p) and F6(a, d1,e1,p) and F6(a, d2,e1,p) and F6(a, d3,e1,p) and F6(d1,e2,p) and F6(d2,e2,p) and F6(d3,e2,p) and F6(a, d1,e2,p) and F6(a, d2,e2,p) and F6(a, d3,e2,p) and F7 and F7(d1,p) and F7(d2,p) and F7(d3,p) and F7(a, d1,p) and F7(a, d2,p) and F7(a, d3,p) and F7(d1,e1,p) and F7(d2,e1,p) and F7(d3,e1,p) and F7(a, d1,e1,p) and F7(a, d2,e1,p) and F7(a, d3,e1,p) and F7(d1,e2,p) and F7(d2,e2,p) and F7(d3,e2,p) and F7(a, d1,e2,p) and F7(a, d2,e2,p) and F7(a, d3,e2,p) and {F6(d1,e1,fX,p) and F6(d2,e1,fX,p) and F6(d3,e1,fX,p) and F6(a, d1,e1,fX,p) and F6(a, d2,e1,fX,p) and F6(a, d3,e1,fX,p) and F6(d1,e2,fX,p) and F6(d2,e2,fX,p) and F6(d3,e2,fX,p) and F6(a, d1,e2,fX,p) and F6(a, d2,e2,fX,p) and F6(a, d3,e2,fX,p) and F7(d1,e1,fX,p) and F7(d2,e1,fX,p) and F7(d3,e1,fX,p) and F7(a, d1,e1,fX,p) and F7(a, d2,e1,fX,p) and F7(a, d3,e1,fX,p) and F7(d1,e2,fX,p) and F7(d2,e2,fX,p) and F7(d3,e2,fX,p) and F7(a, d1,e2,fX,p) and F7(a, d2,e2,fX,p) and F7(a, d3,e2,fX,p) where X=1, 2, 3, 4, 5, 6, 7, 8, 9, 10, 11, 12, 13, or 14}.

Embodiments with Melphalan and One or More Additional Drugs that that Increase the Intracellular GSSG/2GSH Reduction Potential (p)

In embodiments of the invention given in List 1, the set of drugs is comprised of the DNA crosslinking agent melphalan and one or more additional drugs that that increase the intracellular GSSG/2GSH reduction potential in cancer cells during at least part of the time of melphalan exposure. The names of the new embodiments are given in List 1.2

List 1.2:

F1(b,p) and F2(b,p) and F3(b,p), and F1(a,b,p) and F2(a,b,p) and F3(a,b,p) and F1(b,c1,p) and F2(b,c1,p) and F3(b,c1,p) and F1(a,b,c1,p) and F2(a,b,c1,p) and F3(a,b,c1,p) and F1(b, c1,d1,p) and F1(a,b, c1,d1,p) and F2(b, c1,d1,p) and F2(a,b, c1,d1,p) and F3(b, c1,d1,p) and F3(a,b,c1,d1,p) and F1(b, c1,d2,p) and F1(a,b, c1,d2,p) and F2(b, c1,d2,p) and F2(a,b, c1,d2,p) and F3(b, c1,d2,p) and F3(a,b,c1,d2,p) and F1(b, c1,d3,p) and F1(a,b, c1,d3,p) and F2(b, c1,d3,p) and F2(a,b, c1,d3,p) and F3(b, c1,d3,p) and F3(a,b,c1,d3,p), and F4 and F4(c1,p) and F4(c,d1,p) and F4(c,d2,p) and F4(c,d3,p) and F4(a, c1,d1,p) and F4(a, c1,d2,p) and F4(a,c1,d3,p) and F5(d1,p) and F5(d2,p) and F5(d3,p), and F5(a, d1,p) and F5(a, d2,p) and F5(a, d3,p) and F6(d1,p) and F6(d2,p) and F6(d3,p) and F6(a, d1,p) and F6(a, d2,p) and F6(a, d3,p), and F6(d1,e1,p) and F6(d2,e1,p) and F6(d3,e1,p) and F6(a, d1,e1,p) and F6(a, d2,e1,p) and F6(a, d3,e1,p) and F6(d1,e2,p) and F6(d2,e2,p) and F6(d3,e2,p) and F6(a, d1,e2,p) and F6(a, d2,e2,p) and F6(a, d3,e2,p) and F7 and F7(d1,p) and F7(d2,p) and F7(d3,p) and F7(a, d1,p) and F7(a, d2,p) and F7(a, d3,p) and F7(d1,e1,p) and F7(d2,e1,p) and F7(d3,e1,p) and F7(a, d1,e1,p) and F7(a, d2,e1,p) and F7(a, d3,e1,p) and F7(d1,e2,p) and F7(d2,e2,p) and F7(d3,e2,p) and F7(a, d1,e2,p) and F7(a, d2,e2,p) and F7(a, d3,e2,p) and {F6(d1,e1,fX,p) and F6(d2,e1,fX,p) and F6(d3,e1,fX,p) and F6(a, d1,e1,fX,p) and F6(a, d2,e1,fX,p) and F6(a, d3,e1,fX,p) and F6(d1,e2,fX,p) and F6(d2,e2,fX,p) and F6(d3,e2,fX,p) and F6(a, d1,e2,fX,p) and F6(a, d2,e2,fX,p) and F6(a, d3,e2,fX,p) and F7(d1,e1,fX,p) and F7(d2,e1,fX,p) and F7(d3,e1,fX,p) and F7(a, d1,e1,fX,p) and F7(a, d2,e1,fX,p) and F7(a, d3,e1,fX,p) and F7(d1,e2,fX,p) and F7(d2,e2,fX,p) and F7(d3,e2,fX,p) and F7(a, d1,e2,fX,p) and F7(a, d2,e2,fX,p) and F7(a, d3,e2,fX,p) where X=1, 2, 3, 4, 5, 6, 7, 8, 9, 10, 11, 12, 13, or 14}.

Embodiments with Specified DNA Crosslinkers and One or More Additional Drugs that that Increase the Intracellular GSSG/2GSH Reduction Potential (p)

In embodiments of the invention given in List 1, the set of drugs is comprised of the specified DNA crosslinking agent and one or more additional drugs that that increase the intracellular GSSG/2GSH reduction potential in cancer cells during at least part of the time of crosslinker exposure. The names of the new embodiments are given in List 1.3

List 1.3:

F1(b,p) and F2(b,p) and F3(b,p), and F1(a,b,p) and F2(a,b,p) and F3(a,b,p) and F1(b,cx,p) and F2(b,cX,p) and F3(b,cX,p) and F1(a,b,cX,p) and F2(a,b,cX,p) and F3(a,b,cX,p) and F4 and F4(cX,p) and wherein X=1, 2, 3 . . . or 22, the DNA crosslinking agent is comprised of: melphalan (X=1), bizelesin (X=2), chlorambucil (X=3), cyclophosphamide (X=4), bendamustine (X=5), ifosfamide (X=6), cisplatin (X=7), carboplatin (X=8), and oxaliplatin (X=9), thiotepa (X=10), busulfan (X=11), and mitomycin c (X=12), mechlorethamine (X=13), carmustine (X=14), lomustine (X=15), cisplatin (X=16), carboplatin (X=17), nedaplatin (X=18), oxaliplatin (X=19), satraplatin (X=20), picoplatin (X=21) and busulfan (X=22).

An increased intracellular GSSG/GSH reduction potential inhibits the repair of DNA damage by crosslinking agents and hypersensitizes cancer cells to said agents. A large number of drugs are known to one skilled in the arts that can increase the intracellular GSSG/GSH reduction potential; said drugs can be used in the present methods and are within the scope of the present invention. Methods for measuring the GSSG/2GSH reduction potential in cells and for identifying drugs that increase the reduction potential are known to one skilled in the arts.

Oxidative Stress
Embodiments with a DNA Crosslinking Agent and Drugs that Cause Oxidative Stress (r)

As discussed previously, oxidative stress and increased levels of ROS inhibit multiple steps in the repair of DNA damage caused by DNA crosslinking agents.

In an embodiment one or more drugs of the set generate increased oxidative stress in cancer cells and thereby hypersensitize cancer cells to the DNA crosslinking agent. A number of drugs that cause oxidative stress, such as redox cycling agents have already been discussed. The cause of the oxidative stress is not critical to the mechanism of action of the present method in which oxidative stress hypersensitizes cancer cells to DNA crosslinking agents by inhibiting detoxification and repair of DNA damage caused by said crosslinking agent.

A large number of drugs, agents and mechanisms are known that cause oxidative stress in cancer cells that can be used with the present method and use of said drugs and agents in the present methods are within the scope of the present invention. Methods for detecting and measuring oxidative stress and increased levels of ROS are known to one skilled in the arts. The following reference relates to this matter and is hereby incorporated in its: entirety: ROS stress in cancer cells and therapeutic implications.; Pelicano H, Carney D, Huang P.; Drug Resist Updat. 2004 April; 7(2): 97-110.

Embodiments with a DNA Crosslinking Agent and Drugs that Cause Oxidative Stress (r)

In embodiments of the invention given in List 1, the set of drugs is comprised of a DNA crosslinking agent and one or more additional drugs that cause oxidative stress in cancer cells during at least part of the time that the cells are exposed to the crosslinking agent. The respective names of the new embodiments are given in List 1.4

List 1.4:

F1(b,r) and F2(b,r) and F3(b,r), and F1(a,b,r) and F2(a,b,r) and F3(a,b,r) and {F1(b,cX,r) and F2(b,cX,r) and F3(b,cX,r) and F1(a,b,cX,r) and F2(a,b,cX,r) and F3(a,b,cX,r) wherein X=1, 2, 3 . . . or 22} and {F1(b, c1,dX,r) and F1(a,b, c1,dX,r) and F2(b, c1,dX,r) and F2(a,b, c1,dX,r) and F3(b, c1,dX,r) and F3(a,b,c1,dX,r) where X=1, 2, or 3} and F4 and F4(c1,r) and F4(c,d1,r) and F4(c,d2,r) and F4(c,d3,r) and F4(a, c1,d1,r) and F4(a, c1,d2,r) and F4(a,c1,d3,r) and F5(d1,r) and F5(d2,r) and F5(d3,r), and F5(a, d1,r) and F5(a, d2,r) and F5(a, d3,r) and F6(d1,r) and F6(d2,r) and F6(d3,r) and F6(a, d1,r) and F6(a, d2,r) and F6(a, d3,r), and F6(d1,e1,r) and F6(d2,e1,r) and F6(d3,e1,r) and F6(a, d1,e1,r) and F6(a, d2,e1,r) and F6(a, d3,e1,r) and F6(d1,e2,r) and F6(d2,e2,r) and F6(d3,e2,r) and F6(a, d1,e2,r) and F6(a, d2,e2,r) and F6(a, d3,e2,r) and F7 and F7(d1,r) and F7(d2,r) and F7(d3,r) and F7(a, d1,r) and F7(a, d2,r) and F7(a, d3,r) and F7(d1,e1,r) and F7(d2,e1,r) and F7(d3,e1,r) and F7(a, d1,e1, r) and F7(a, d2,e1,r) and F7(a, d3,e1,r) and F7(d1,e2,r) and F7(d2,e2,r) and F7(d3,e2,r) and F7(a, d1,e2,r) and F7(a, d2,e2,r) and F7(a, d3,e2,r) and {F6(d1,e1,fX,r) and F6(d2,e1,fX,r) and F6(d3,e1,fX,r) and F6(a, d1,e1,fX,r) and F6(a, d2,e1,fX,r) and F6(a, d3,e1,fX,r) and F6(d1,e2,fX,r) and F6(d2,e2,fX,r) and F6(d3,e2,fX,r) and F6(a, d1,e2,fX,r) and F6(a, d2,e2,fX,r) and F6(a, d3,e2,fX,r) and F7(d1,e1,fX,r) and F7(d2,e1,fX,r) and F7(d3,e1,fX,r) and F7(a, d1,e1,fX,r) and F7(a, d2,e1,fX,r) and F7(a, d3,e1,fX,r) and F7(d1,e2,fX,r) and F7(d2,e2,fX,r) and F7(d3,e2,fX,r) and F7(a, d1,e2,fX,r) and F7(a, d2,e2,fX,r) and F7(a, d3,e2,fX,r) where X=1, 2, 3, 4, 5, 6, 7, 8, 9, 10, 11, 12, 13, or 14}.

In an embodiment the DNA crosslinking agent is administered during the period of increased oxidative stress caused by said drugs. In preferred embodiments said drugs increase oxidative stress by increasing the production and/or levels of superoxide and/or hydrogen peroxide in cancer cells. In an embodiment the oxidative stress is caused by the administration of an inhibitor of glutathione reductase in conjunction with an agent that undergoes redox cycling. In an embodiment the glutathione reductase inhibitor is BCNU and the redox cycling agent is doxorubicin. In another embodiment the glutathione reductase inhibitor is a BCNU and the redox cycling agent is methylene blue.

In an embodiment the glutathione reductase inhibitor is BCNU, the redox cycling agent is doxorubicin and the DNA crosslinking agent is melphalan.

In an embodiment BCNU is administered at an intravenous dose of approximately 50-300 mg/m$^2$. (body surface area). In preferred embodiments the BCNU dose is approximately 50, 75, 100, 125, 150, 175, 200, 225, 250, 275, 300, or 350 mg/m$^2$. In preferred embodiments the IV doxorubicin dose is approximately 10 to 80 mg/m$^2$. In preferred embodiments the doxorubicin dose is approximately 10, 15, 20, 25, 30, 35, 40, 45, 50, 55, 60, 65, 70, 75, or 80 mg/m$^2$. In preferred embodiments the IV melphalan dose is approximately 20 to 200 mg/m$^2$. In preferred embodiments the melphalan dose is approximately 20, 25, 30, 35, 40, 45, 50, 55, 60, 65, 70, 75, 80, 85, 90, 95, 100, 125, 150, 175, or 200 mg/m$^2$.

In an embodiment the BCNU dose is approximately 75-125 mg/m$^2$, the doxorubicin dose is approximately 40 to 60 mg/m$^2$, and the melphalan dose is approximately 50 to 100 mg/m$^2$.

In an embodiment the BCNU dose is approximately 100 mg/m$^2$, the doxorubicin dose is approximately 40 mg/m$^2$, and the melphalan dose is approximately 70 mg/m$^2$.

In an embodiment the BCNU dose is approximately 100 mg/m$^2$, the doxorubicin dose is approximately 40 mg/m$^2$, and the melphalan dose is approximately 70 mg/m$^2$ and Kyprolis (carfilzomib) is administered at an IV dose of approximately 20 mg/m$^2$.

In preferred embodiments the BCNU dose is approximately 50, 75, 100, 125, 150, 175, 200, 225, 250, 275, 300, or 350 mg/m$^2$. In preferred embodiments the IV doxorubicin dose is approximately 10 to 80 mg/m$^2$. In preferred embodiments the doxorubicin dose is approximately 10, 15, 20, 25, 30, 35, 40, 45, 50, 55, 60, 65, 70, 75, or 80 mg/m$^2$. In preferred embodiments the IV melphalan dose is approximately 20 to 200 mg/m$^2$. In preferred embodiments the melphalan dose is approximately 20, 25, 30, 35, 40, 45, 50, 55, 60, 65, 70, 75, 80, 85, 90, 95, 100, 125, 150, 175, or 200 mg/m$^2$. In an embodiment Kyprolis (carfilzomib) is also administered at an IV dose of approximately 10 to 60 mg/m$^2$.

In preferred embodiments the BCNU, doxorubicin, and melphalan are administered approximately at the same time and the Kyprolis is administered approximately 2-6 hours after the melphalan. In an embodiment a second dose of Kyprolis is given approximately 24 hours later. In an embodiment the BCNU is administered at time T=0 over approximately 30 minutes, then the doxorubicin is administered at approximately T=30 minutes over approximately 15 minutes, then the melphalan is administered at approximately T=45 minutes over approximately 30 minutes, then Kyprolis is administered at approximately T=5 hours over approximately 30 minutes and repeated approximately 24 hours later.

In an embodiment the glutathione reductase inhibitor is BCNU, the redox cycling agent is methylene blue and the DNA crosslinking agent is melphalan.

In an embodiment the dose of IV methylene blue is approximately 1 mg/kg to 5 mg/kg.

In preferred embodiments the BCNU dose is approximately 50, 75, 100, 125, 150, 175, 200, 225, 250, 275, 300, or 350 mg/m² and the dose of IV methylene blue is approximately 1 mg/kg to 5 mg/kg, and the melphalan dose is approximately 20, 25, 30, 35, 40, 45, 50, 55, 60, 65, 70, 75, 80, 85, 90, 95, 100, 125, 150, 175, or 200 mg/m^2. In an embodiment Kyprolis (carfilzomib) is also administered at an IV dose of approximately 10 to 60 mg/m². In preferred embodiments the Kyprolis dose is approximately 10, 15, 20, 25, 30, 35, 40, 45, 50, 55, or 60 mg/m².

In an embodiment the BCNU is administered at time T=0 over approximately 30 minutes, then the methylene blue is administered at approximately T=30 minutes over approximately 15 minutes, then the melphalan is administered at approximately T=45 minutes over approximately 30 minutes, then Kyprolis is administered at approximately T=5 hours over approximately 30 minutes and repeated approximately 24 hours later. In alternate preferred embodiments bortezomib is used in place of Kyprolis. The dose of bortezomib is approximately 1 to 1.3 mg/M² given approximately 6-24 hours after the melphalan.

Inhibition of the Repair of DNA Interstrand Crosslinks

The ability of DNA crosslinking agents to inhibit cancer cell clonogenic survival is dependent upon the number of unrepaired DNA interstrand crosslinks (ICLs). Approximately 8000 ICLs/cell are formed in lymphocytes from patients treated with 200 mg/m² of melphalan. The vast majority of ICLs, are repaired over the course of about 48 hours. Enhanced removal of ICLs is a major mechanism of melphalan resistance in multiple types of cancer cells.

The following references relate to this matter and are hereby incorporated in their entirety: Melphalan-induced DNA damage in vitro as a predictor for clinical outcome in multiple myeloma; Dimopoulos M A, et al.; Haematologica. 2007 November; 92(11):1505-12.; Formation and removal of DNA cross-links induced by melphalan and nitrogen mustard in relation to drug-induced cytotoxicity in human melanoma cells.; Hansson J, Lewensohn R, Ringborg U, Nilsson B.; Cancer Res. 1987 May 15; 47(10):2631-7.; Enhanced DNA cross-link removal: the apparent mechanism of resistance in a clinically relevant melphalan-resistant human breast cancer cell line; Batist G, et al.; Mol Pharmacol. 1989 August; 36(2):224-30.; The FA/BRCA pathway is involved in melphalan-induced DNA interstrand cross-link repair and accounts for melphalan resistance in multiple myeloma cells.; Chen Q, et al.; Blood. 2005 Jul. 15; 106 (2):698-705; Repair of DNA interstrand crosslinks as a mechanism of clinical resistance to melphalan in multiple myeloma.; Spanswick V J, et al.; Blood. 2002 Jul. 1; 100(1):224-9; The FA/BRCA pathway is involved in melphalan-induced DNA interstrand cross-link repair and accounts for melphalan resistance in multiple myeloma cells.; Chen Q, Van der Sluis P C, Boulware D, Hazlehurst L A, Dalton W S.; Blood. 2005 Jul. 15; 106(2):698-705; Gene-specific formation and repair of DNA monoaducts and interstrand cross-links after therapeutic exposure to nitrogen mustards.; Souliotis V L, Dimopoulos M A, Sfikakis P P.; Clin Cancer Res. 2003 Oct. 1; 9(12):4465-74; Dependence on treatment time of melphalan resistance and DNA cross-linking in human melanoma cell line.; Parsons P G.; Cancer Res. 1984 July; 44(7):2773-8.

A preferred embodiment for the effective treatment of metastatic cancer is comprised of the administration of set of drugs comprised of a DNA crosslinking agent, and additional drugs that decrease GSH-mediated detoxification of said crosslinking agent, decrease NER-mediated removal of DNA-mono-adducts, and decrease removal of DNA interstrand crosslinks.

Homologous recombination is critical to the repair of DNA interstrand crosslinks. Cells deficient in the BRCA/Fanconi pathway have defective repair and are hypersensitive to melphalan and other DNA crosslinking agents. Conversely, cells with hyperactive BRCA/Fanconi pathway function have enhanced ability to repair DNA ICLs and exhibit resistance to alkylating agents and DNA crosslinking agents.

The following references relate to this matter and are hereby incorporated in their entirety: DNA interstrand crosslink repair in mammalian cells: step by step.; Muniandy P A, Liu J, Majumdar A, Liu S T, Seidman M M.; Crit Rev Biochem Mol Biol. 2010 February; 45(1):23-49; DNA interstrand crosslink repair and cancer.; Deans A J, West S C.; Nat Rev Cancer. 2011 Jun. 24; 11(7):467-80; A high-throughput pharmaceutical screen identifies compounds with specific toxicity against BRCA2-deficient tumors.; Evers B, Schut E, van der Burg E, Braumuller T M, Egan D A, Holstege H, Edser P, Adams D J, Wade-Martins R, Bouwman P, Jonkers J.; Clin Cancer Res. 2010 Jan. 1; 16(1):99-108; A syngeneic variance library for functional annotation of human variation: application to BRCA2.; Hucl T, Rago C, Gallmeier E, Brody J R, Gorospe M, Kern S E.; Cancer Res. 2008 Jul. 1; 68(13):5023-30.

The repair of DNA interstrand crosslinks is mediated by complex biochemical machinery mediate homologous recombination (HR). Multiple steps in the processes of HR and interstrand DNA crosslink repair require proteasome function, directly or indirectly. Proteasome inhibitors have been shown to inhibit HR and sensitize cells to DNA interstrand crosslinking agents such as melphalan. High dose melphan (200 mg/m2) is used in combination with proteasome inhibitors such as Velcade for the treatment of myeloma in conjunction with hematopoietic stem cell support; however, melphalan resistance is still a problem, and the therapy is not generally not curative. The CR rate in patients with myeloma treated with high dose melphalan, Velcade and bone marrow stem cell infusion was 30%. The CR rate in 29 patients with non-small cell lung cancer treated with Velcade, carboplatin, and gemcitabine was 0%. The CR rate in 21 patients with platinum-resistant ovarian cancer treated with Velcade and carboplatin was 0%.

The following references relate to this matter and are hereby incorporated in their entirety: Bortezomib salvage followed by a Phase I/II study of bortezomib plus high-dose melphalan and tandem autologous transplantation for patients with primary resistant myeloma; Nishihori T, et al.; Br J Haematol. 2012 June; 157(5):553-63; Bortezomib and high-dose melphalan as conditioning regimen before autologous stem cell transplantation in patients with de novo multiple myeloma: a phase 2 study of the Intergroupe Francophone du Myeloma (IFM).; Roussel M, et al.; The proteasome inhibitor PS-341 markedly enhances sensitivity of multiple myeloma tumor cells to chemotherapeutic agents.; Ma M H, et al.; Clin Cancer Res. 2003 March; 9(3):1136-44.; Inhibitors of the proteasome suppress homologous DNA recombination in mammalian cells; Murakawa Y et al.; Cancer Res. 2007 Sep. 15; 67(18):8536-43.; Bortezomib-induced "BRCAness" sensitizes multiple myeloma cells to PARP inhibitors; Neri P, et al.; Blood. 2011 Dec. 8; 118(24):6368-79; Proteasome function is required for DNA damage response and Fanconi anemia pathway activation.; Jacquemont C, Taniguchi T.; Cancer Res. 2007 Aug. 1; 67(15):7395-405; Degradation-linked ubiquitin signal and proteasome are integral components of DNA double strand break repair: New perspectives for anti-cancer therapy.; Ramadan K, Meerang M.; FEBS Lett. 2011 Sep. 16; 585(18):2868-75. The vital link between the ubiquitin-proteasome pathway and DNA repair: impact on cancer therapy; Motegi A, Murakawa Y, Takeda S.; Cancer Lett. 2009 Sep. 28; 283(1):1-9; The proteasome inhibitor bortezomib in combination with gemcitabine and carboplatin in advanced non-small cell lung cancer: a California Cancer Consortium Phase I study; Davies A M, et al.; J Thorac Oncol. 2008 January; 3(1):68-74; Phase I trial of the proteasome inhibitor bortezomib in combination with carboplatin in patients with platinum- and taxane-resistant ovarian cancer; Ramirez P T, Landen C N Jr, Coleman R L, Milam M R, Levenback C, Johnston T A, Gershenson D M.; Gynecol Oncol. 2008 January; 108(1):68-71.

Proteasome inhibition alone is not sufficient to adequately sensitize cells to DNA crosslinking agents and overcome drug resistance. Other mechanisms of melphalan resistance must be concurrently addressed.

The time of proteasome inhibition is important. Treatment of cells with proteasome inhibitors trigger a variety of biochemical processes that can contribute to melphalan resistance. Inhibition of proteasome function activates NRF2 and elevates GSH levels. This effect takes about 2 hours. Activated NRF2 in turn triggers a variety of cellular responses that inhibit the cytotoxic effect of alkylating agents such as melphalan.

Proteasome inhibition induces glutathione synthesis and protects cells from oxidative stress: relevance to Parkinson disease.; Yamamoto N, Sawada H, Izumi Y, Kume T, Katsuki H, Shimohama S, Akaike A.; J Biol Chem. 2007 Feb. 16; 282(7):4364-72.; Proteasome inhibition induces a p38 MAPK pathway-dependent antiapoptotic program via Nrf2 in thyroid cancer cells.; Du Z X, Yan Y, Zhang H Y, Liu B Q, Gao Y Y, Niu X F, Meng X, Wang H Q.; J Clin Endocrinol Metab. 2011 May; 96(5):E763-71; Increased protein stability as a mechanism that enhances Nrf2-mediated transcriptional activation of the antioxidant response element. Degradation of Nrf2 by the 26 S proteasome.; Nguyen T, Sherratt P J, Huang H C, Yang C S, Pickett C B.; J Biol Chem. 2003 Feb. 14; 278(7):4536-41

A preferred embodiment for the effective treatment of metastatic cancer is comprised of the administration of set of drugs comprised of a DNA crosslinking agent, and additional drugs that decrease GSH-mediated detoxification of said crosslinking agent, decrease NER-mediated removal of DNA-mono-adducts, and inhibit homologous recombination (HR) and thereby decrease removal of DNA interstrand crosslinks. In a preferred embodiment the set of drugs includes a proteasome inhibitor. In a preferred embodiment said proteasome inhibitor is the drug carfilzomib (Kyprolis). In another preferred embodiment it is bortezomib (Velcade). In a preferred embodiment said proteasome inhibitor is administered after the DNA crosslinking agent. A large number of drugs and agents that inhibit proteasome function are known to one skilled in the arts and can be used in the present method and are within the scope of the present invention.

In embodiments the Kyprolis dose is approximately 10, 15, 20, 25, 30, 35, 40, 45, 50, 55, or 60 mg/m$^2$ and it is given approximately 1-24 hours after the melphalan. Preferably a second dose is given approximately 24 hours later.

The irreversible proteasome inhibitor Kyprolis is preferably administered at a dose of ~20 to 27 mg/m2 beginning ~2-6 hours after the melphalan is administered with a second dose ~24 hours later.

The reversible proteasome inhibitor Velcade is preferably administered at a dose of ~1.3 mg/m2 beginning ~2-4 hours after the melphalan is administered with a second dose given ~72 hours later.

In alternate preferred embodiments bortezomib is administered at a dose of approximately 1 to 1.3 mg/M$^2$.

Embodiments with a DNA Crosslinking Agent and Proteasome Inhibitor (s)

In all embodiments of the invention previously given the set of drugs can include a proteasome inhibitor. In preferred embodiments the proteasome inhibitor is carfilzomib. In other preferred embodiments the proteasome inhibitor is bortezomib.

In embodiments of those given in the following lists: List 1; List 2; List 3; List 4; List 5; List 6; List 7; List 8; List 9; List 10; List 2b; List 8b; List 8.1; List 9.1; List 10.1; List 8.2; List 9.2; List 10.2; List 8.3; List 9.3; List 10.3; List 8.4; List 9.4; List 10.4; List 8.5; List 9.5; List 10.5; List 11; List 12; List 1.1; List 1.2; List 1.3; and List 1.4, the set of drugs includes a proteasome inhibitor. These new embodiments are herein explicitly described and named. The name of the new embodiments are respectively given by adding the letter, ",s" before the ")" in the names given in the said Lists. For example, F1(b) in List 1 would become F1(b,s), which corresponds to E1(b,s) and Ee1(b,s).

In embodiments of those given in the following lists: List 1; List 2; List 3; List 4; List 5; List 6; List 7; List 8; List 9; List 10; List 2b; List 8b; List 8.1; List 9.1; List 10.1; List 8.2; List 9.2; List 10.2; List 8.3; List 9.3; List 10.3; List 8.4; List 9.4; List 10.4; List 8.5; List 9.5; List 10.5; List 11; List 12; List 1.1; List 1.2; List 1.3; and List 1.4, the set of drugs includes the proteasome inhibitor carfilzomib. These new embodiments are herein explicitly described and named. The name of the new embodiments are respectively given by adding ",s1" before the ")" in the names given in said Lists. For example, E1(b) in List 1 would become E1(b,s1).

In embodiments of those given in the following lists: List 1; List 2; List 3; List 4; List 5; List 6; List 7; List 8; List 9; List 10; List 2b; List 8b; List 8.1; List 9.1; List 10.1; List 8.2; List 9.2; List 10.2; List 8.3; List 9.3; List 10.3; List 8.4; List 9.4; List 10.4; List 8.5; List 9.5; List 10.5; List 11; List 12; List 1.1; List 1.2; List 1.3; and List 1.4, the set of drugs includes the proteasome inhibitor bortezomib. These new embodiments are herein explicitly described and named. The name of the new embodiments are respectively given by adding ",s2" before the ")" in the names given in said Lists. For example, E1(b) in List 1 would become E1(b,s2).

The methods given by all of embodiments listed above or described above can be used to treat the types of cancers given in List A, (unless the embodiment is stated to apply to a specified type of cancer.) For example E7(d3,e2,f3) is an embodiment that applies to BRCA2-associated pancreatic cancer.

Embodiment E8 (Oxidative Stress and DNA Crosslinker)

Embodiment E8 is a method for the treatment of refractory metastatic cancer comprised of the following steps:
1. Administering a set of drugs that induce oxidative stress in cancer cells
2. Administering a DNA crosslinking agent during the period of oxidative stress Embodiment Ee8 (Oxidative Stress and DNA Crosslinker)

Embodiment Ee8 is a set of drugs for use in a regimen to treat refractory metastatic cancer comprised of one or more drugs that induce oxidative stress in cancer cells and a DNA crosslinking agent, wherein the regimen is comprised of the following steps:
1. Administering a set of drugs that induce oxidative stress in cancer cells
2. Administering a DNA crosslinking agent during the period of oxidative stress

Embodiment E9 (Oxidative Stress and DNA Crosslinker and Proteasome Inhibitor)

Embodiment E9 is a method for the treatment of refractory metastatic cancer comprised of the following steps:
1. Administering a set of drugs that induce oxidative stress in cancer cells
2. Administering a DNA crosslinking agent during the period of oxidative stress
3. Administering a proteasome inhibitor

Embodiment Ee9 (Oxidative Stress, DNA Crosslinker, Proteasome Inhibitor)

Embodiment Ee9 is a set of drugs for use in a regimen to treat refractory metastatic cancer comprised of one or more drugs that induce oxidative stress in cancer cells and a DNA crosslinking agent and a proteasome inhibitor, wherein the regimen is comprised of the following steps:
1. Administering a set of drugs that induce oxidative stress in cancer cells
2. Administering a DNA crosslinking agent during the period of oxidative stress
3. Administering a proteasome inhibitor

Embodiment E10 (Oxidative Stress, DNA Crosslinker, Proteasome Inhibitor and Bone Marrow Stem Cell Infusion)

Embodiment E10 is a method for the treatment of refractory metastatic cancer comprised of the following steps:
1. Administering a set of drugs that induce oxidative stress in cancer cells
2. Administering a DNA crosslinking agent during the period of oxidative stress
3. Administering the proteasome inhibitor
4. Administering an infusion of hematopoietic stem cells

Embodiment Ee10 (Oxidative Stress, DNA Crosslinker, Proteasome Inhibitor and Bone Marrow Stem Cell Infusion)

Embodiment Ee10 is a set of drugs for use in a regimen to treat refractory metastatic cancer comprised of one or more drugs that induce oxidative stress in cancer cells and a DNA crosslinking agent and a proteasome inhibitor, wherein the regimen is comprised of the following steps:
1. Administering a set of drugs that induce oxidative stress in cancer cells
2. Administering a DNA crosslinking agent during the period of oxidative stress
3. Administering the proteasome inhibitor
4. Administering an infusion of hematopoietic stem cells

Embodiment E11 (Oxidative Stress and DNA Crosslinker, and High CRs)

Embodiment E11 is a method for the treatment of refractory metastatic cancer and to obtain high rates of complete responses and durable complete responses in patients comprised of the following steps:
1. Administering a set of drugs that induce oxidative stress in cancer cells
2. Administering a DNA crosslinking agent during the period of oxidative stress

Embodiment Ee11 (Oxidative Stress, DNA Crosslinker and High CRs)

Embodiment Ee11 is a set of drugs for use in a regimen to treat refractory metastatic cancer and to obtain high rates of complete responses and durable complete responses in patients, comprised of one or more drugs that induce oxidative stress in cancer cells and a DNA crosslinking agent, wherein the regimen is comprised of the following steps:
1. Administering a set of drugs that induce oxidative stress in cancer cells
2. Administering a DNA crosslinking agent during the period of oxidative stress

Embodiment E12 (Oxidative Stress and DNA Crosslinker and Proteasome Inhibitor)

Embodiment E12 is a method for the treatment of refractory metastatic cancer and to obtain high rates of complete responses and durable complete responses in patients comprised of the following steps:
1. Administering a set of drugs that induce oxidative stress in cancer cells
2. Administering a DNA crosslinking agent during the period of oxidative stress
3. Administering a proteasome inhibitor

Embodiment Ee12 (Oxidative Stress, DNA Crosslinker, Proteasome Inhibitor, and High Rates of CRs)

Embodiment is a set of drugs for use in a regimen to treat refractory metastatic cancer and to obtain high rates of complete responses and durable complete responses in patients, comprised of one or more drugs that induce oxidative stress in cancer cells and a DNA crosslinking agent and a proteasome inhibitor, wherein the regimen is comprised of the following steps:
1. Administering a set of drugs that induce oxidative stress in cancer cells
2. Administering a DNA crosslinking agent during the period of oxidative stress
3. Administering a proteasome inhibitor

Embodiment E13 (Oxidative Stress, DNA Crosslinker, Proteasome Inhibitor, Bone Marrow Stem Cell Infusion, and High Rate of CRs)

Embodiment E13 is a method for the treatment of refractory metastatic cancer and to obtain high rates of complete responses and durable complete responses in patients, comprised of the following steps:
1. Administering a set of drugs that induce oxidative stress in cancer cells
2. Administering a DNA crosslinking agent during the period of oxidative stress
3. Administering the proteasome inhibitor
4. Administering an infusion of hematopoietic stem cells

Embodiment Ee13 (Oxidative Stress, DNA Crosslinker, Proteasome Inhibitor, Bone Marrow Stem Cell Infusion, and High Rate of CRs)

Embodiment Ee13 is a set of drugs for use in a regimen to treat refractory metastatic cancer and to obtain high rates of complete responses and durable complete responses in patients, comprised of one or more drugs that induce oxidative stress in cancer cells and a DNA crosslinking agent and a proteasome inhibitor, wherein the regimen is comprised of the following steps:
1. Administering a set of drugs that induce oxidative stress in cancer cells
2. Administering a DNA crosslinking agent during the period of oxidative stress
3. Administering the proteasome inhibitor
4. Administering an infusion of hematopoietic stem cells Embodiment E14 (pgp Inhibitor, Oxidative Stress, DNA Crosslinker, Bone Marrow Stem Cell Infusion, and High Rate of CRs)

Embodiment E14 is a method for the treatment of refractory metastatic cancer and to obtain high rates of complete responses and durable complete responses in patients comprised of the following steps:
1. Administering an inhibitor of the MDR1 pgp efflux pump
2. Administering a set of drugs that induce oxidative stress in cancer cells
3. Administering a DNA crosslinking agent during the period of oxidative stress
4. Administering an infusion of hematopoietic stem cells Embodiment Ee14 (pgp Inhibitor, Oxidative Stress, DNA Crosslinker, Bone Marrow Stem Cell Infusion, and High Rate of CRs)

Embodiment Ee14 is a set of drugs for use in a regimen for the treatment of refractory metastatic cancer, and to obtain high rates of complete responses and durable complete responses in patients, wherein the set is comprised of a pgp inhibitor, one or more drugs that induce oxidative stress, and a DNA crosslinking agent, wherein the regimen is comprised of the following steps:
1. Administering an inhibitor of the MDR1 pgp efflux pump
2. Administering a set of drugs that induce oxidative stress in cancer cells
3. Administering a DNA crosslinking agent during the period of oxidative stress
4. Administering an infusion of hematopoietic stem cells Embodiment E15 (pgp Inhibitor, Oxidative Stress, DNA Crosslinker, Proteasome Inhibitor, Bone Marrow Stem Cell Infusion, and High Rate of CRs)

Embodiment E15 is a method for the treatment of refractory metastatic cancer and to obtain high rates of complete responses and durable complete responses in patients comprised of the following steps:
1. Administering an inhibitor of the MDR1 pgp efflux pump
2. Administering a set of drugs that induce oxidative stress in cancer cells
3. Administering a DNA crosslinking agent during the period of oxidative stress
4. Administering a proteasome inhibitor
5. Administering an infusion of hematopoietic stem cells Embodiment Ee15 (pgp Inhibitor, Oxidative Stress, DNA Crosslinker, Proteasome Inhibitor, Bone Marrow Stem Cell Infusion, and High Rate of CRs)

Embodiment Ee15 is a set of drugs for use in a regimen for the treatment of refractory metastatic cancer, and to obtain high rates of complete responses and durable complete responses in patients, wherein the set is comprised of a pgp inhibitor, one or more drugs that induce oxidative stress, and a DNA crosslinking agent, and a proteasome inhibitor wherein the regimen is comprised of the following steps:
1. Administering an inhibitor of the pgp inhibitor
2. Administering a set of drugs that induce oxidative stress in cancer cells
3. Administering a DNA crosslinking agent during the period of oxidative stress
4. Administering a proteasome inhibitor
5. Administering an infusion of hematopoietic stem cells Embodiment E16 Increase the GSSG/GSH2 Reduction Potential Embodiment E16 (Increased Intracellular (GSSG)/(GSH)2 Reduction Potential and DNA Crosslinker)

Embodiment E16 is a method for the treatment of refractory metastatic cancer comprised of the following steps:
1. Administering a set of drugs that induce increased intracellular GSSG)/(GSH)2 reduction potential in cancer cells
2. Administering a DNA crosslinking agent during the period of increased intracellular (GSSG)/(GSH)2 reduction potential in cancer cells Embodiment Ee16 (Increased Intracellular (GSSG)/(GSH)2 Reduction Potential and DNA Crosslinker)

Embodiment Ee16 is a set of drugs for use in a regimen to treat refractory metastatic cancer comprised of one or more drugs that induce increased intracellular (GSSG)/(GSH)2 reduction potential in cancer cells and a DNA crosslinking agent, wherein the regimen is comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells Embodiment E17 (Increased Intracellular (GSSG)/(GSH)2 Reduction Potential and DNA Crosslinker and Proteasome Inhibitor)

Embodiment E17 is a method for the treatment of refractory metastatic cancer comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells
3. Administering a proteasome inhibitor

Embodiment Ee17 (Increased Intracellular (GSSG)/(GSH)2 Reduction Potential, DNA Crosslinker, Proteasome Inhibitor)

Embodiment Ee17 is a set of drugs for use in a regimen to treat refractory metastatic cancer comprised of one or more drugs that induce increased intracellular (GSSG)/(GSH)2 reduction potential in cancer cells and a DNA crosslinking agent and a proteasome inhibitor, wherein the regimen is comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells
3. Administering a proteasome inhibitor

Embodiment E18 (Increased Intracellular (GSSG)/(GSH)2 Reduction Potential, DNA Crosslinker, Proteasome Inhibitor and Bone Marrow Stem Cell Infusion)

Embodiment E18 is a method for the treatment of refractory metastatic cancer comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells
3. Administering the proteasome inhibitor
4. Administering an infusion of hematopoietic stem cells

Embodiment Ee19 (Increased Intracellular (GSSG)/(GSH)2 Reduction Potential, DNA Crosslinker, Proteasome Inhibitor and Bone Marrow Stem Cell Infusion)

Embodiment Ee19 is a set of drugs for use in a regimen to treat refractory metastatic cancer comprised of one or more drugs that induce increased intracellular (GSSG)/(GSH)2 reduction potential in cancer cells and a DNA crosslinking agent and a proteasome inhibitor, wherein the regimen is comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells
3. Administering the proteasome inhibitor
4. Administering an infusion of hematopoietic stem cells

Embodiment E20 (Increased Intracellular (GSSG)/(GSH)2 Reduction Potential and DNA Crosslinker, and High CRs)

Embodiment E20 is a method for the treatment of refractory metastatic cancer and to obtain high rates of complete responses and durable complete responses in patients comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells

Embodiment Ee21 (Increased Intracellular (GSSG)/(GSH)2 Reduction Potential, DNA Crosslinker and High CRs)

Embodiment Ee21 is a set of drugs for use in a regimen to treat refractory metastatic cancer and to obtain high rates of complete responses and durable complete responses in patients, comprised of one or more drugs that induce increased intracellular (GSSG)/(GSH)2 reduction potential in cancer cells and a DNA crosslinking agent, wherein the regimen is comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells

Embodiment E22 (Increased Intracellular (GSSG)/(GSH)2 Reduction Potential and DNA Crosslinker and Proteasome Inhibitor)

Embodiment E22 is a method for the treatment of refractory metastatic cancer and to obtain high rates of complete responses and durable complete responses in patients comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells
3. Administering a proteasome inhibitor

Embodiment Ee22 (Increased Intracellular (GSSG)/(GSH)2 Reduction Potential, DNA Crosslinker, Proteasome Inhibitor, and High Rates of CRs)

Embodiment Ee22 is a set of drugs for use in a regimen to treat refractory metastatic cancer and to obtain high rates of complete responses and durable complete responses in patients, comprised of one or more drugs that induce increased intracellular (GSSG)/(GSH)2 reduction potential in cancer cells and a DNA crosslinking agent and a proteasome inhibitor, wherein the regimen is comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells
3. Administering a proteasome inhibitor

Embodiment E23 (Increased Intracellular (GSSG)/(GSH)2 Reduction Potential, DNA Crosslinker, Proteasome Inhibitor, Bone Marrow Stem Cell Infusion, and High Rate of CRs)

Embodiment E23 is a method for the treatment of refractory metastatic cancer and to obtain high rates of complete responses and durable complete responses in patients, comprised of the following steps:

1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells
3. Administering the proteasome inhibitor
4. Administering an infusion of hematopoietic stem cells Embodiment Ee23 (Increased Intracellular (GSSG)/(GSH)2 Reduction Potential, DNA Crosslinker, Proteasome Inhibitor, Bone Marrow Stem Cell Infusion, and High Rate of CRs)

Embodiment Ee23 is a set of drugs for use in a regimen to treat refractory metastatic cancer and to obtain high rates of complete responses and durable complete responses in patients, comprised of one or more drugs that induce increased intracellular (GSSG)/(GSH)2 reduction potential in cancer cells and a DNA crosslinking agent and a proteasome inhibitor, wherein the regimen is comprised of the following steps:
1. Administering a set of drugs that induce increased intracellular (GSSG)/(GSH)2 reduction potential in cancer cells
2. Administering a DNA crosslinking agent during the period of increased intracellular (GSSG)/(GSH)2 reduction potential in cancer cells
3. Administering the proteasome inhibitor
4. Administering an infusion of hematopoietic stem cells Embodiment E24 (pgp Inhibitor, Increased Intracellular (GSSG)/(GSH)2 Reduction Potential, DNA Crosslinker, Bone Marrow Stem Cell Infusion, and High Rate of CRs)

Embodiment E24 is a method for the treatment of refractory metastatic cancer and to obtain high rates of complete responses and durable complete responses in patients comprised of the following steps:
1. Administering an inhibitor of the MDR1 pgp efflux pump
2. Administering a set of drugs that induce increased intracellular (GSSG)/(GSH)2 reduction potential in cancer cells
3. Administering a DNA crosslinking agent during the period of increased intracellular (GSSG)/(GSH)2 reduction potential in cancer cells
4. Administering an infusion of hematopoietic stem cells Embodiment Ee24 (pgp Inhibitor, Increased Intracellular (GSSG)/(GSH)2 Reduction Potential, DNA Crosslinker, Bone Marrow Stem Cell Infusion, and High Rate of CRs)

Embodiment Ee24 is a set of drugs for use in a regimen for the treatment of refractory metastatic cancer, and to obtain high rates of complete responses and durable complete responses in patients, wherein the set is comprised of a pgp inhibitor, one or more drugs that induce increased intracellular (GSSG)/(GSH)2 reduction potential, and a DNA crosslinking agent, wherein the regimen is comprised of the following steps:
1. Administering an inhibitor of the MDR1 pgp efflux pump
2. Administering a set of drugs that induce increased intracellular (GSSG)/(GSH)2 reduction potential in cancer cells
3. Administering a DNA crosslinking agent during the period of increased intracellular (GSSG)/(GSH)2 reduction potential in cancer cells
4. Administering an infusion of hematopoietic stem cells Embodiment E25 (pgp Inhibitor, Increased Intracellular (GSSG)/(GSH)2 Reduction Potential, DNA Crosslinker, Proteasome Inhibitor, Bone Marrow Stem Cell Infusion, and High Rate of CRs)

Embodiment E25 is a method for the treatment of refractory metastatic cancer and to obtain high rates of complete responses and durable complete responses in patients comprised of the following steps:
1. Administering an inhibitor of the MDR1 pgp efflux pump
2. Administering a set of drugs that induce increased intracellular (GSSG)/(GSH)2 reduction potential in cancer cells
3. Administering a DNA crosslinking agent during the period of increased intracellular (GSSG)/(GSH)2 reduction potential in cancer cells
4. Administering a proteasome inhibitor
5. Administering an infusion of hematopoietic stem cells Embodiment Ee25 (pgp Inhibitor, Increased Intracellular (GSSG)/(GSH)2 Reduction Potential, DNA Crosslinker, Proteasome Inhibitor, Bone Marrow Stem Cell Infusion, and High Rate of CRs)

Embodiment Ee25 is a set of drugs for use in a regimen for the treatment of refractory metastatic cancer, and to obtain high rates of complete responses and durable complete responses in patients, wherein the set is comprised of a pgp inhibitor, one or more drugs that induce increased intracellular (GSSG)/(GSH)2 reduction potential, and a DNA crosslinking agent, and a proteasome inhibitor wherein the regimen is comprised of the following steps:
1. Administering an inhibitor of the MDR1 pgp efflux pump
2. Administering a set of drugs that induce increased intracellular (GSSG)/(GSH)2 reduction potential in cancer cells
3. Administering a DNA crosslinking agent during the period of increased intracellular (GSSG)/(GSH)2 reduction potential in cancer cells
4. Administering a proteasome inhibitor
5. Administering an infusion of hematopoietic stem cells GR Inhibitor and Redox Cycling Agent Embodiment E26 (GR Inhibitor and Redox Cycling Agent and DNA Crosslinker)

Embodiment E26 is a method for the treatment of refractory metastatic cancer comprised of the following steps:
1. Administering a set of drugs that include a GR inhibitor and a redox cycling agent
2. Administering a DNA crosslinking agent Embodiment Ee26 (GR Inhibitor and Redox Cycling Agent and DNA Crosslinker)

Embodiment Ee26 is a set of drugs for use in a regimen to treat refractory metastatic cancer comprised of one or more drugs that include a GR inhibitor and a redox cycling agent and a DNA crosslinking agent, wherein the regimen is comprised of the following steps:
1. Administering a set of drugs that include a GR inhibitor and a redox cycling agent
2. Administering a DNA crosslinking agent Embodiment E27 (GR Inhibitor and Redox Cycling Agent and DNA Crosslinker and Proteasome Inhibitor)

Embodiment E27 is a method for the treatment of refractory metastatic cancer comprised of the following steps:
1. Administering a set of drugs that include a GR inhibitor and a redox cycling agent
2. Administering a DNA crosslinking agent
3. Administering a proteasome inhibitor Embodiment Ee27 (GR Inhibitor and Redox Cycling Agent, DNA Crosslinker, Proteasome Inhibitor)

Embodiment Ee27 is a set of drugs for use in a regimen to treat refractory metastatic cancer comprised of one or more drugs that include a GR inhibitor and a redox cycling agent and a DNA crosslinking agent and a proteasome inhibitor, wherein the regimen is comprised of the following steps:
1. Administering a set of drugs that include a GR inhibitor and a redox cycling agent
2. Administering a DNA crosslinking agent
3. Administering a proteasome inhibitor Embodiment E28 (GR Inhibitor and Redox Cycling Agent, DNA Crosslinker, Proteasome Inhibitor and Bone Marrow Stem Cell Infusion)

Embodiment E28 is a method for the treatment of refractory metastatic cancer comprised of the following steps:
1. Administering a set of drugs that include a GR inhibitor and a redox cycling agent
2. Administering a DNA crosslinking agent
3. Administering the proteasome inhibitor
4. Administering an infusion of hematopoietic stem cells Embodiment Ee29 (GR Inhibitor and Redox Cycling Agent, DNA Crosslinker, Proteasome Inhibitor and Bone Marrow Stem Cell Infusion)

Embodiment Ee29 is a set of drugs for use in a regimen to treat refractory metastatic cancer comprised of one or more drugs that include a GR inhibitor and a redox cycling agent and a DNA crosslinking agent and a proteasome inhibitor, wherein the regimen is comprised of the following steps:
1. Administering a set of drugs that include a GR inhibitor and a redox cycling agent
2. Administering a DNA crosslinking agent
3. Administering the proteasome inhibitor
4. Administering an infusion of hematopoietic stem cells Embodiment E30 (GR Inhibitor and Redox Cycling Agent and DNA Crosslinker, and High CRs)

Embodiment E30 is a method for the treatment of refractory metastatic cancer and to obtain high rates of complete responses and durable complete responses in patients comprised of the following steps:
1. Administering a set of drugs that include a GR inhibitor and a redox cycling agent
2. Administering a DNA crosslinking agent Embodiment Ee31 (GR Inhibitor and Redox Cycling Agent, DNA Crosslinker and High CRs)

Embodiment Ee31 is a set of drugs for use in a regimen to treat refractory metastatic cancer and to obtain high rates of complete responses and durable complete responses in patients, comprised of one or more drugs that include a GR inhibitor and a redox cycling agent and a DNA crosslinking agent, wherein the regimen is comprised of the following steps:
1. Administering a set of drugs that include a GR inhibitor and a redox cycling agent
2. Administering a DNA crosslinking agent Embodiment E32 (GR Inhibitor and Redox Cycling Agent and DNA Crosslinker and Proteasome Inhibitor)

Embodiment E32 is a method for the treatment of refractory metastatic cancer and to obtain high rates of complete responses and durable complete responses in patients comprised of the following steps:
1. Administering a set of drugs that include a GR inhibitor and a redox cycling agent
2. Administering a DNA crosslinking agent
3. Administering a proteasome inhibitor Embodiment Ee32 (GR Inhibitor and Redox Cycling Agent, DNA Crosslinker, Proteasome Inhibitor, and High Rates of CRs)

Embodiment Ee32 is a set of drugs for use in a regimen to treat refractory metastatic cancer and to obtain high rates of complete responses and durable complete responses in patients, comprised of one or more drugs that include a GR inhibitor and a redox cycling agent and a DNA crosslinking agent and a proteasome inhibitor, wherein the regimen is comprised of the following steps:
1. Administering a set of drugs that include a GR inhibitor and a redox cycling agent
2. Administering a DNA crosslinking agent
3. Administering a proteasome inhibitor Embodiment E33 (GR Inhibitor and Redox Cycling Agent, DNA Crosslinker, Proteasome Inhibitor, Bone Marrow Stem Cell Infusion, and High Rate of CRs)

Embodiment E33 is a method for the treatment of refractory metastatic cancer and to obtain high rates of complete responses and durable complete responses in patients, comprised of the following steps:
1. Administering a set of drugs that include a GR inhibitor and a redox cycling agent
2. Administering a DNA crosslinking agent
3. Administering the proteasome inhibitor
4. Administering an infusion of hematopoietic stem cells Embodiment Ee33 (GR Inhibitor and Redox Cycling Agent, DNA Crosslinker, Proteasome Inhibitor, Bone Marrow Stem Cell Infusion, and High Rate of CRs)

Embodiment Ee33 is a set of drugs for use in a regimen to treat refractory metastatic cancer and to obtain high rates of complete responses and durable complete responses in patients, comprised of one or more drugs that include a GR inhibitor and a redox cycling agent and a DNA crosslinking agent and a proteasome inhibitor, wherein the regimen is comprised of the following steps:
1. Administering a set of drugs that include a GR inhibitor and a redox cycling agent
2. Administering a DNA crosslinking agent
3. Administering the proteasome inhibitor
4. Administering an infusion of hematopoietic stem cells Embodiment E34 (pgp Inhibitor, GR Inhibitor and Redox Cycling Agent, DNA Crosslinker, Bone Marrow Stem Cell Infusion, and High Rate of CRs)

Embodiment E34 is a method for the treatment of refractory metastatic cancer and to obtain high rates of complete responses and durable complete responses in patients comprised of the following steps:
1. Administering an inhibitor of the MDR1 pgp efflux pump
2. Administering a set of drugs that include a GR inhibitor and a redox cycling agent
3. Administering a DNA crosslinking agent
4. Administering an infusion of hematopoietic stem cells Embodiment Ee34 (pgp Inhibitor, GR Inhibitor and Redox Cycling Agent, DNA Crosslinker, Bone Marrow Stem Cell Infusion, and High Rate of CRs)

Embodiment Ee34 is a set of drugs for use in a regimen for the treatment of refractory metastatic cancer, and to obtain high rates of complete responses and durable complete responses in patients, wherein the set is comprised of a pgp inhibitor, one or more drugs that include GR inhibitor and redox cycling agent, and a DNA crosslinking agent, wherein the regimen is comprised of the following steps:
1. Administering an inhibitor of the MDR1 pgp efflux pump
2. Administering a set of drugs that include a GR inhibitor and a 3. redox cycling agent in cancer cells
4. Administering a DNA crosslinking agent
5. Administering an infusion of hematopoietic stem cells Embodiment E35 (pgp Inhibitor, GR Inhibitor and Redox Cycling Agent, DNA Crosslinker, Proteasome Inhibitor, Bone Marrow Stem Cell Infusion, and High Rate of CRs)

Embodiment E35 is a method for the treatment of refractory metastatic cancer and to obtain high rates of complete responses and durable complete responses in patients comprised of the following steps:
1. Administering an inhibitor of the MDR1 pgp efflux pump
2. Administering a set of drugs that include a GR inhibitor and a redox cycling agent
3. Administering a DNA crosslinking agent
4. Administering a proteasome inhibitor
5. Administering an infusion of hematopoietic stem cells Embodiment Ee35 (pgp Inhibitor, GR Inhibitor and Redox Cycling Agent, DNA Crosslinker, Proteasome Inhibitor, Bone Marrow Stem Cell Infusion, and High Rate of CRs)

Embodiment Ee35 is a set of drugs for use in a regimen for the treatment of refractory metastatic cancer, and to obtain high rates of complete responses and durable complete responses in patients, wherein the set is comprised of a pgp inhibitor, one or more drugs that include GR inhibitor and redox cycling agent, and a DNA crosslinking agent, and a proteasome inhibitor wherein the regimen is comprised of the following steps:
1. Administering an inhibitor of the MDR1 pgp efflux pump
2. Administering a set of drugs that include a GR inhibitor and a redox cycling agent
3. Administering a DNA crosslinking agent
4. Administering a proteasome inhibitor
5. Administering an infusion of hematopoietic stem cells NER Inhibitor Embodiments Embodiment E36 (NER Inhibitor and DNA Crosslinker)

Embodiment E36 is a method for the treatment of refractory metastatic cancer comprised of the following steps:
1. Administering a nucleotide excision repair inhibitor
2. Administering a DNA crosslinking agent Embodiment Ee36 (A Nucleotide Excision Repair Inhibitor and DNA Crosslinker)

Embodiment Ee36 is a set of drugs for use in a regimen to treat refractory metastatic cancer comprised of an inhibitor of nucleotide excision repair and a DNA crosslinking agent, wherein the regimen is comprised of the following steps:
1. Administering the inhibitor of nucleotide excision repair
2. Administering the DNA crosslinking agent Embodiment E37 (A Nucleotide Excision Repair Inhibitor and DNA Crosslinker and Proteasome Inhibitor)

Embodiment E37 is a method for the treatment of refractory metastatic cancer comprised of the following steps:
1. Administering an inhibitor of nucleotide excision repair
2. Administering a DNA crosslinking agent
3. Administering a proteasome inhibitor Embodiment Ee37 (A Nucleotide Excision Repair Inhibitor, DNA Crosslinker, Proteasome Inhibitor)

Embodiment Ee37 is a set of drugs for use in a regimen to treat refractory metastatic cancer comprised of an inhibitor of nucleotide excision repair and a DNA crosslinking agent and a proteasome inhibitor, wherein the regimen is comprised of the following steps:
1. Administering the inhibitor of nucleotide excision repair
2. Administering the DNA crosslinking agent
3. Administering the proteasome inhibitor Embodiment E38 (A Nucleotide Excision Repair Inhibitor, DNA Crosslinker, Proteasome Inhibitor and Bone Marrow Stem Cell Infusion)

Embodiment E28 is a method for the treatment of refractory metastatic cancer comprised of the following steps:
1. Administering an inhibitor of nucleotide excision repair
2. Administering a DNA crosslinking agent
3. Administering a proteasome inhibitor
4. Administering an infusion of bone marrow stem cells

Embodiment Ee38 (A Nucleotide Excision Repair Inhibitor, DNA Crosslinker, Proteasome Inhibitor and Bone Marrow Stem Cell Infusion)

Embodiment Ee38 is a set of drugs for use in a regimen to treat refractory metastatic cancer comprised of an inhibitor of nucleotide excision repair and a DNA crosslinking agent and a proteasome inhibitor, wherein the regimen is comprised of the following steps:
1. Administering the inhibitor of nucleotide excision repair
2. Administering the DNA crosslinking agent
3. Administering the proteasome inhibitor
4. Administering an infusion of bone marrow stem cells Inhibitor of DNA Crosslink Repair or Homologous Recombination Embodiments

Embodiment E39 (Inhibitor of DNA Interstrand Crosslink Repair or an Inhibitor of HR and a DNA Crosslinker)

Embodiment E36 is a method for the treatment of refractory metastatic cancer comprised of the following steps:
1. Administering a DNA crosslinking agent
2. Administering an inhibitor of DNA interstrand crosslink repair or an inhibitor of HR

Embodiment Ee39 (Inhibitor of DNA Interstrand Crosslink Repair or an Inhibitor of HR and a DNA Crosslinker)

Embodiment Ee39 is a set of drugs for use in a regimen to treat refractory metastatic cancer comprised of an inhibitor of DNA interstrand crosslink repair or an inhibitor of HR and a DNA crosslinking agent, wherein the regimen is comprised of the following steps:
1. Administering the DNA crosslinking agent
2. Administering an inhibitor of DNA interstrand crosslink repair or inhibitor of HR

Embodiment E40 (A Nucleotide Excision Repair Inhibitor and DNA Crosslinker and an Inhibitor of DNA Interstrand Crosslink Repair or an Inhibitor of HR)

Embodiment E40 is a method for the treatment of refractory metastatic cancer comprised of the following steps:
1. Administering an inhibitor of nucleotide excision repair
2. Administering a DNA crosslinking agent
3. Administering an inhibitor of DNA interstrand crosslink repair or an inhibitor of HR

Embodiment Ee40 (A Nucleotide Excision Repair Inhibitor and DNA Crosslinker and an Inhibitor of DNA Interstrand Crosslink Repair or an Inhibitor of HR)

Embodiment Ee40 is a set of drugs for use in a regimen to treat refractory metastatic cancer comprised of an inhibitor of nucleotide excision repair and a DNA crosslinking agent and an inhibitor of DNA interstrand crosslink repair or an inhibitor of HR, wherein the regimen is comprised of the following steps:
1. Administering the inhibitor of nucleotide excision repair
2. Administering the DNA crosslinking agent
3. Administering the inhibitor of DNA interstrand crosslink repair or an inhibitor of HR

Embodiment E41 (A Nucleotide Excision Repair Inhibitor, DNA Crosslinker, an Inhibitor of DNA Interstrand Crosslink Repair or Inhibitor of HR and Bone Marrow Stem Cell Infusion)

Embodiment E41 is a method for the treatment of refractory metastatic cancer comprised of the following steps:
1. Administering an inhibitor of nucleotide excision repair
2. Administering a DNA crosslinking agent
3. Administering an inhibitor of DNA interstrand crosslink repair or an inhibitor of HR
4. Administering an infusion of bone marrow stem cells

Embodiment Ee41 (A Nucleotide Excision Repair Inhibitor, DNA Crosslinker, an Inhibitor of DNA Interstrand Crosslink Repair or an Inhibitor of HR and Bone Marrow Stem Cell Infusion)

Embodiment Ee41 is a set of drugs for use in a regimen to treat refractory metastatic cancer comprised of an inhibitor of nucleotide excision repair and a DNA crosslinking agent and an inhibitor of DNA interstrand crosslink repair or an inhibitor of HR, wherein the regimen is comprised of the following steps:
I. Administering the inhibitor of nucleotide excision repair
II. Administering the DNA crosslinking agent
III. Administering the inhibitor of DNA interstrand crosslink repair or the inhibitor of HR
IV. Administering an infusion of bone marrow stem cells In embodiments of EN and EeN for N=1, 23, 4, . . . 41 respectively named EN(cX) and EeN(cX) wherein X=1, 2, 3 . . . 22, the DNA crosslinking agent is comprised of the DNA crosslinking agent is comprised of: melphalan (X=1), bizelesin (X=2), chlorambucil (X=3), cyclophosphamide (X=4), bendamustine (X=5), ifosfamide (X=6), cisplatin (X=7), carboplatin (X=8), and oxaliplatin (X=9), thiotepa (X=10), busulfan (X=11), and mitomycin c (X=12), mechlorethamine (X=13), carmustine (X=14), lomustine (X=15), cisplatin (X=16), carboplatin (X=17), nedaplatin (X=18), oxaliplatin (X=19), satraplatin (X=20), picoplatin (X=21) and busulfan (X=22).

In embodiments of EN(cX) and EeN(cX), for N=26, 27, 28, 29, 30, 31, 32, 33, 34, and 35 and X=1, 2, 3, 4, . . . 22, respectively named EN(cX,k1,nY) and EeN(cX,k1,nY), the GR inhibitor is BCNU and the redox cycling agent is an anthracycline Y=1; doxorubicin Y=2; methylene blue Y=3, epirubicin Y=4, and daunorubicin Y=5.

In embodiments of EN, EeN, EN(cX), EeN(cX), EN(cX, K1), EeN(cX, K1), EN(cX,k1,nY), EeN(cX,k1,nY), wherein N=1, 23, 4, . . . 41 and X=1, 2, 3 . . . 22 and Y=1, 2, 3, 4, and 5; respectively named of EN(sZ), EeN(sZ), EN(cX, sZ), EeN(cX, sZ), EN(cX, K1, sZ), EeN(cX, K1, sZ), EN(cX,k1,nY, sZ), EeN(cX,k1,nY, sZ), wherein N=1, 23, 4, . . . 41 and X=1, 2, 3 . . . 22 and Y=1, 2, 3, 4, and 5; and Z=1, and 2; when said embodiments include a proteasome inhibitor the proteasome inhibitor is carfilzomib Z=1; or bortezomib Z=2.

Embodiment E42 (BCNU, Doxorubicin and Melphalan and Optionally a Proteasome Inhibitor)

Embodiment E42 is a method for the treatment of metastatic cancer or refractory metastatic cancer in a subject; comprised of administering the drugs BCNU, doxorubicin, and melphalan simultaneously or within a 6 hour time period and optionally administering a proteasome inhibitor within said 6 hour time period or within the following 24 hours; and wherein the melphalan dose is in the range of 20 to 200 mg/m^2. In Embodiment E42(s1) the methods includes administration of the proteasome inhibitor is carfilzomib. In Embodiment E42(s2) the methods includes administration of the proteasome inhibitor is bortezomib.

Embodiment Ee42 is a set of drugs method for use in a regimen to treat metastatic cancer or refractory metastatic cancer in a subject; comprised of BCNU, doxorubicin, and melphalan and optionally a proteasome inhibitor; wherein said method is comprised of the administration of BCNU, doxorubicin, and melphalan within said 6 hour time period and optionally said proteasome inhibitor within said 6 hour time period or within the following 24 hours; and wherein the melphalan dose is in the range of 20 to 200 mg/m^2. In Embodiment Ee42(s1) the set includes the proteasome inhibitor carfilzomib. In Embodiment Ee42(s2) the set includes the proteasome inhibitor bortezomib.

Embodiment E43 is a method for the effective treatment of metastatic cancer or refractory metastatic cancer in a subject; comprised of administering the drugs BCNU, doxorubicin, and melphalan and optionally administering a proteasome inhibitor. In Embodiment E43(s1) the set includes the proteasome inhibitor carfilzomib. In Embodiment E43(s2) the set includes the proteasome inhibitor bortezomib.

Embodiment Ee43 is a set of drugs for use in a regimen for the effective treatment of a subject with metastatic cancer or refractory metastatic cancer wherein said set is comprised of BCNU, doxorubicin, and melphalan and optionally administering a proteasome inhibitor. In Embodiment Ee43(s1) the set includes the proteasome inhibitor carfilzomib. In Embodiment Ee43(s2) the set includes the proteasome inhibitor bortezomib.

Embodiment E44 is a method for obtaining a complete response or a high probability of a complete response in a subject with refractory metastatic cancer comprised of administering the drugs BCNU, doxorubicin, and melphalan.

Embodiment Ee44 is a set of drugs comprised of BCNU, doxorubicin and melphalan for use in a regimen to obtain a complete response or a high probability of a complete response in a subject with refractory metastatic cancer wherein said method is comprised of administering the drugs BCNU, doxorubicin, and melphalan.

Embodiment E45 is a method for the effective treatment of metastatic cancer or refractory metastatic cancer in a subject; comprised of administering the drugs BCNU, doxorubicin, and melphalan simultaneously or within a 6 hour time period and optionally administering a proteasome inhibitor within said 6 hour time period or within the following 24 hours; and wherein the melphalan dose is in the range of 20 to 200 mg/m$^2$. In Embodiment E45(s1) the methods includes administration of the proteasome inhibitor is carfilzomib. In Embodiment E45(s2) the methods includes administration of the proteasome inhibitor is bortezomib.

Embodiment Ee45 is a set of drugs method for use in a regimen to treat metastatic cancer or refractory metastatic cancer in a subject; comprised of
BCNU, doxorubicin, and melphalan and optionally a proteasome inhibitor; wherein said method is comprised of the administration of BCNU, doxorubicin, and melphalan within said 6 hour time period and optionally said proteasome inhibitor within said 6 hour time period or within the following 24 hours; and wherein the melphalan dose is in the range of 20 to 200 mg/m$^2$. In Embodiment Ee45(s1) the set includes the proteasome inhibitor carfilzomib. In Embodiment Ee45(s2) the set includes the proteasome inhibitor bortezomib.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), respectively named E42(a), Ee42(a), E42(a,s1), Ee42(a,s1), E42 (a,s2), and Ee42(a,s2) and E43 (a), Ee43(a), E43(a,s1), Ee43(a,s1), E43 (a,s2), and Ee43(a, s2) E44(a), Ee44(a), E44(a,s1), Ee44(a,s1), E44 (a,s2), and Ee44(a,s2) and E45(a), Ee45(a), E45(a,s1), Ee45(a,s1), E45 (a,s2), and Ee45(a,s2) the method or treatment regimen also includes the infusion of bone marrow stem cells to reverse toxicity of said drugs.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is in the range of 50 to 300 mg/m$^2$; the doxorubicin dose is in the range of 10 to 80 mg/m^2; the melphalan dose is in the range of 20 to 200 mg/m$^2$; and the carfilzomib dose is of 0 or 10 to 60 mg/m$^2$; and the bortezomib dose is 0 or 1 to 1.3 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 75 mg/m$^2$; the doxorubicin dose is approximately 20 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 100 mg/m$^2$; the doxorubicin dose is approximately 20 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 150 mg/m^2; the doxorubicin dose is approximately 20 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 200 mg/m$^2$; the doxorubicin dose is approximately 20 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 250 mg/m$^2$; the doxorubicin dose is approximately 20 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 300 mg/m$^2$; the doxorubicin dose is approximately 20 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 75 mg/m^2; the doxorubicin dose is approximately 30 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 100 mg/m^2; the doxorubicin dose is approximately 30 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 150 mg/m^2; the doxorubicin dose is approximately 30 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a, s2) the BCNU dose is approximately 200 mg/m^2; the doxorubicin dose is approximately 30 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a, s1), E42 (a,s2), and Ee42(a,s2) and E43(a), Ee43(a), E43(a, s1), Ee43(a,s1), E43 (a,s2), and Ee43(a,s2) E44(a), Ee44(a), E44(a,s1), Ee44(a,s1), E44 (a,s2), and Ee44(a,s2) and E45

(a), Ee45(a), E45(a,s1), Ee45(a,s1), E45 (a,s2), and Ee45(a,s2) the BCNU dose is approximately 250 mg/m^2; the doxorubicin dose is approximately 30 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 300 mg/m^2; the doxorubicin dose is approximately 30 mg/m^2; and the carfilzomib dose is approximately 20 mg/m^2 and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 75 mg/m^2; the doxorubicin dose is approximately 40 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 100 mg/m^2; the doxorubicin dose is approximately 40 mg/m^2; and the carfilzomib dose is approximately 20 mg/m^2 and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 150 mg/m^2; the doxorubicin dose is approximately 40 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), Ee42(s2), E42(a), Ee42(a), E42(a,s1), Ee42(a,s1), E42 (a,s2), and Ee42(a,s2) the BCNU dose is approximately 200 mg/m^2; the doxorubicin dose is approximately 40 mg/m^2; and the carfilzomib dose is approximately 20 mg/m^2 and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 250 mg/m^2; the doxorubicin dose is approximately 40 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 300 mg/m^2; the doxorubicin dose is approximately 40 mg/m^2; and the carfilzomib dose is approximately 20 mg/m^2 and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 75 mg/m^2; the doxorubicin dose is approximately 50 mg/m^2; and the carfilzomib dose is approximately 20 mg/m^2; and the melphalan dose is approximately 20 mg/m^2, or 30 mg/m^2, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 100 mg/m$^2$; the doxorubicin dose is approximately 50 mg/m$^2$; and the carfilzomib dose is approximately 20 mg/m$^2$ and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 150 mg/m$^2$; the doxorubicin dose is approximately 50 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 200 mg/m$^2$; the doxorubicin dose is approximately 50 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), Ee42(s2), E42(a), Ee42(a), E42(a,s1), Ee42(a,s1), E42 (a,s2), and Ee42(a,s2) the BCNU dose is approximately 250 mg/m$^2$; the doxorubicin dose is approximately 50 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 300 mg/m$^2$; the doxorubicin dose is approximately 50 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), Ee42(s2), E42(a), Ee42(a), E42(a,s1), Ee42(a,s1), E42 (a,s2), and Ee42(a,s2) the BCNU dose is approximately 75 mg/m$^2$; the doxorubicin dose is approximately 60 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 100 mg/m$^2$; the doxorubicin dose is approximately 60 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), Ee42(s2), E42(a), Ee42(a), E42(a,s1), Ee42(a,s1), E42 (a,s2), and Ee42(a,s2) the BCNU dose is approximately 150 mg/m$^2$; the doxorubicin dose is approximately 60 mg/m$^2$; and the carfilzomib dose is approximately 20 mg/m$^2$ and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m$^2$, or 90 mg/m$^2$, or 100 mg/m$^2$, or 120 mg/m$^2$, or 140 mg/m$^2$, or 160 mg/m$^2$, or 180 mg/m$^2$, or 200 mg/m$^2$.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 200 mg/m$^2$; the doxorubicin dose is approximately 60 mg/m$^2$; and the carfilzomib dose is approximately 20 mg/m$^2$; and the melphalan dose is approximately 20 mg/m$^2$, or 30 mg/m$^2$, or 40 mg/m$^2$, or 50 mg/m$^2$, or 60 mg/m$^2$, or 70 mg/m$^2$, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 250 mg/m^2; the doxorubicin dose is approximately 60 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) the BCNU dose is approximately 300 mg/m^2; the doxorubicin dose is approximately 60 mg/m^2; and the carfilzomib dose is approximately 20 mg/m^2; and the melphalan dose is approximately 20 mg/m^2, or 30 mg/m^2, or 40 mg/m^2, or 50 mg/m^2, or 60 mg/m^2, or 70 mg/m^2, or 80 mg/m^2, or 90 mg/m^2, or 100 mg/m^2, or 120 mg/m^2, or 140 mg/m^2, or 160 mg/m^2, or 180 mg/m^2, or 200 mg/m^2.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) and in the related embodiments that specify dose ranges or approximate drug doses, the metastatic cancer is pancreatic cancer, Stage IV breast cancer, platinum-resistant ovarian cancer or melanoma or other cancers given in List A.

In embodiments of E42, Ee42, E42(s1), Ee42(s1), E42 (s2), and Ee42(s2), and E43, Ee43, E43(s1), Ee43(s1), E43 (s2), and Ee43(s2), and E44, Ee44, E44(s1), Ee44(s1), E44 (s2), and Ee44(s2), and E45, Ee45, E45(s1), Ee45(s1), E45 (s2), and Ee45(s2), and E42(a), Ee42(a), E42(a,s1), Ee42(a,s1), E42 (a,s2), and Ee42(a,s2) and E43(a), Ee43(a), E43(a,s1), Ee43(a,s1), E43 (a,s2), and Ee43(a,s2) E44(a), Ee44(a), E44(a,s1), Ee44(a,s1), E44 (a,s2), and Ee44(a,s2) and E45 (a), Ee45(a), E45(a,s1), Ee45(a,s1), E45 (a,s2), and Ee45(a,s2) and in the related embodiments that specify dose ranges or approximate drug doses, the drugs are administered during a window of time that is approximately 30 minutes long. In other embodiments the window of time is approximately 45 minutes. In other embodiments the window of time is approximately 60 minutes. In other embodiments the window of time is approximately 90 minutes. In other embodiments the window of time is approximately 120 minutes. In other embodiments the window of time is approximately 180 minutes. In other embodiments the window of time is approximately 240 minutes. In other embodiments the window of time is approximately 300 minutes. In other embodiments the window of time is approximately 360 minutes.

Timing of Drug Administration

For all embodiments of the present invention including all embodiments of En and EeN for n=1, 2, 3, 4, . . . 45; that involve the administration of more than one drug, said drugs are administered on a time schedule such that the combined pharmacologic effects of the drugs are experienced by the cancer cells. The present method exploits the profound synergy that results from the combination of drugs that together hypersensitize cancer cells to DNA crosslinking agents. The drugs can all be given at essentially the same time. However, as discussed previously, proteasome inhibitors can be given approximately 2-6 hours after the DNA crosslinking agent and repeated in 24 hours. Many dosing times can be used provided that the cells are exposed to the combined pharmacologic effects of the combination of drugs.

In embodiments the drugs are administered essentially at the same time. In other embodiments the drugs are administered within a window of time that is approximately 30 minutes long or 1 hour long, or 1.5 hours log, or 2 hours long, or 3 hours long or 4-6 hours long.

For example the full dose of BCNU can be administered and immediately thereafter doxorubicin and melphalan given at the same time. Alternatively, half the dose of BCNU can be administered, followed immediately by doxorubicin and melphalan, followed immediately be the remaining half dose of BCNU. One skilled in the arts would recognize many such drug timing and administration schedules that would produce essentially the same combined pharmacologic effects at the cellular level, these are within the scope of the present invention.

By contrast, the administration of doxorubicin followed 2 days later by BCNU followed 3 days later by melphalan would be very different from the present methods because the cells do not experience the combined pharmacologic effects and synergy of the drugs.

Drug Doses

Melphalan

In the all embodiments with melphalan unless otherwise specified the dose of melphalan is in the range of approximately 20 mg/m^2 to 200 mg/m^2. In embodiments the melphalan dose is approximately 20, 25, 30, 35, 40, 45, 50, 55, 60, 65, 70, 75, 80, 85, 90, 95, 100, 125, 150, 175, or 200 mg/m^2. Higher doses are used when the intent of the treatment regimen is to give higher log-reductions in cancer cell survival. The drug is given intravenously generally by means of a central venous catheter. However, in certain situations it could be administered intra-arterially. The drug is generally given over a time period of approximately 30 to 60 minutes. The melphalan can be administered in any pharmacologically acceptable formulation. Prodrugs of melphalan that convert to melphalan can also be used and are within the scope of the present methods and would be used at clinically equivalent doses. Techniques for the administration of melphalan and for dose adjustments in specific patient populations and clinical situations (e.g., in the setting of liver disease) are well known to one skilled in the art. Melphalan 200 mg/m^2 is widely used in the treatment of myeloma in conjunction with bone marrow stem cell infusion.

BCNU

In the all embodiments with BCNU unless otherwise specified the dose of BCNU is administered at an intravenous dose of approximately 50-300 mg/m^2. In preferred embodiments the BCNU dose is approximately 50, 75, 100, 125, 150, 175, 200, 225, 250, 275, 300, or 350 mg/m^2. Higher doses are used when the intent of the treatment regimen is to give higher log-reductions in cancer cell survival. Any pharmacologically acceptable formulation of BCNU can be used.

Techniques for the administration of BCNU to patients and dose modification for particular patient conditions (e.g., liver disease) are known to one skilled in the arts. The following reference relates to this matter and is hereby incorporated by reference in its entirety: Carmustine infusion reactions are more common with rapid administration; Janson B, Van Koeverden P, Yip S W, Thakerar A, Mellor J D.; Support Care Cancer. 2012 October; 20(10):2531-5.

Doxorubicin

In embodiments with doxorubicin unless otherwise specified the dose of the IV doxorubicin dose is approximately 10 to 80 mg/m^2. In embodiments the doxorubicin dose is approximately 10, 15, 20, 25, 30, 35, 40, 45, 50, 55, 60, 65, 70, 75, or 80 mg/m^2. Higher doses are used when the intent of the treatment regimen is to give higher log-reductions in cancer cell survival. Any pharmacologically acceptable formulation of doxorubicin, including liposomal doxorubicin (i.e., Doxil™) can be used. Prodrugs of doxorubicin that are converted into doxorubicin can also be used at clinically equivalent doses. The doxorubicin is generally administer over approximately 15 minutes. Techniques for the administration of doxorubicin to patients and dose modification for particular patient conditions are known to one skilled in the arts and provided in the FDA package label.

Carfilzomib

In embodiments with carfilzomib unless otherwise specified the dose of IV carfilzomib is approximately 10 to 60 mg/m^2. In embodiments the dose is approximately 10, 15, 20, 25, 30, 35, 40, 45, 50, 55, or 60 mg/m^2. The drug is typically given over approximately 30 minutes and is given in conjunction with dexamethasone. Techniques for the administration of carfilzomib and dose modification for particular clinical conditions are known to one skilled in the arts and described in the FDA package label. Any pharmacologically acceptable formulation of can be used. The following references relate to this matter: A Phase 1b/2 Study of Prolonged Infusion Carfilzomib in Patients with Relapsed and/or Refractory (R/R) Multiple Myeloma: Updated Efficacy and Tolerability From the Completed 20/56 mg/m2 Expansion Cohort of PX-171-007; Kyriakos P Papadopoulos, et al.; 53rd ASH Meeting 2011, Abstract 2930 Poster; A Phase 1b Study of 30-Minute Infusion Carfilzomib 20/45 and 20/56 Mg/m2 Plus 40 Mg Weekly Dexamethasone in Patients with Relapsed and/or Refractory (R/R) Multiple Myeloma; Ashraf Z. et al.; 54th ASH Meeting, Dec. 10, 2012; Abstract 4036; Phase II results of Study PX-171-007: A phase Ib/II study of carfilzomib (CFZ), a selective proteasome inhibitor, in patients with selected advanced metastatic solid tumors.; Rosen, P J, et al.; J Clin Oncol 27:15s, 2009 (suppl; abstr 3515)

Bortezomib

In the embodiments with bortezomib unless otherwise specified the dose of IV bortezomib is approximately 1 to 1.3 mg/m^2. Any pharmacologically acceptable formulation can be used. Techniques for the administration of bortezomib and dose modification for particular clinical conditions are known to one skilled in the arts and described in the FDA package label.

Epirubicin

In the above embodiments unless otherwise specified the dose of IV epirubicin is approximately 10-100 mg/m^2. Any pharmacologically acceptable formulation can be used. Techniques for the administration of epirubicin and dose modification for particular clinical conditions are known to one skilled in the arts and described in the FDA package label.

Daunorubicin

In the above embodiments unless otherwise specified the dose of IV daunorubicin is approximately 10 to 45 mg/m^2. Any pharmacologically acceptable formulation can be used. Techniques for the administration of daunorubicin and dose modification for particular clinical conditions are known to one skilled in the arts and described in the FDA package label.

Idarubicin

In the above embodiments unless otherwise specified the dose of IV idarubicin dose is approximately 3 to 12 mg/m². Any pharmacologically acceptable formulation can be used. Techniques for the administration of idarubicin and dose modification for particular clinical conditions are known to one skilled in the arts and described in the FDA package label.

Antiemetic Drugs

The drugs combinations employed in the present methods have high potential to cause nausea and emesis. Effective methods to control these side effects are known to one skilled in the arts and would be employed in conjunction with the current methods. Generally patients would be pre-treated with dexamethasone, and a serotonin antagonist. Suitable protocols are known to one skilled in the arts. The following references relate to this matter: Guideline update for MASCC and ESMO in the prevention of chemotherapy- and radiotherapy-induced nausea and vomiting: results of the Perugia consensus conference. Roila F; et al; ESMO/MASCC Guidelines Working Group.; Ann Oncol. 2010 May; 21 Suppl 5:v232-43

The following reference relates to this matter and is hereby incorporated in its entirety by reference: Cancer Management: A Multidisciplinary Approach. Medical, Surgical, and Radiation Oncology—13th edition; by Richard Pazdur et. al.; Publisher: Matthews Medical Books; 2010

Pharmaceutical Compositions and Formulations

The doses or compositions (drugs) of the present invention are each administered individually or in combination. When administered separately from the second agent, the first agent is administered either alone or as a pharmaceutical composition. Likewise, when administered separately from the first agent, the second agent is administered either alone or as a pharmaceutical composition. When the first and second agents are administered in combination, they are administered without any additional components or with additional components in a pharmaceutical composition. In certain embodiments, the pharmaceutical compositions are prepared by admixing at least one active ingredient together with one or more carriers, excipients, buffers, adjuvants, stabilizers, or other materials well known to those skilled in the art and optionally other therapeutic agents. The formulations may conveniently be presented in unit dosage form and may be prepared by any known methods. All formulations and pharmaceutical compositions, as well as any methods of using such pharmaceutical compositions, disclosed herein are contemplated and considered to be within the scope of the disclosure provided herein.

Administration of the agents and pharmaceutical compositions described herein can be effected by any method that enables delivery of the agents to the site of action. The anticancer drugs especially the alkylating agents would generally be given by means of a central veous line. However, other drugs employed in the methods can be administered by a variety of routes that are pharmacologically acceptable for the particular drug and that result in adequate systemic drug levels. The present invention does not involve, teach, or anticipate local injection of the DNA crosslinking agents or drugs that inhibit the potential for cell proliferation; such local use would be expected to cause severe local tissue destruction. These methods include oral routes, intraduodenal routes, parenteral injection (including intravenous, subcutaneous, intraperitoneal, intramuscular, intravascular or infusion), and other suitable methods. Those of ordinary skill in the art are familiar with formulation and administration techniques that can be employed with the agents and methods of the invention, e.g., as discussed in Goodman and Gilman, The Pharmacological Basis of Therapeutics (current edition); Pergamon; and Remington's, Pharmaceutical Sciences (current edition), Mack Publishing Co., Easton, Pa.

The pharmaceutical compositions included herein are for those suitable for oral, parenteral (including subcutaneous, intradermal, intramuscular, intravenous, intraarticular, intramedullary, intracardiac, intrathecal, intraspinal, intracapsular, subcapsular, intraperitoneal, transmucosal, transdermal, rectal and topical (including dermal, buccal, sublingual, intranasal, and vaginal) administration. In certain embodiments, the pharmaceutical compositions described herein are conveniently formulated in unit dosage form and may be prepared by any of the methods well known in the art of pharmacy. All methods include the step of bringing into association an agent ("active ingredient") or combination of agents ("active ingredients") with the carrier which constitutes one or more accessory ingredients. In general, formulations are prepared by uniformly and intimately bringing into association the active ingredient with liquid carriers or finely divided solid carriers or both and then, if necessary, shaping the product into the desired formulation In certain embodiments, formulations suitable for oral administration are presented as discrete units such as capsules, cachets or tablets each containing a predetermined amount of the active ingredient or ingredients; as a powder or granules; as a solution or a suspension in an aqueous liquid or a non-aqueous liquid; or as an oil-in-water liquid emulsion or a water-in-oil liquid emulsion. In other embodiments, the active ingredient or ingredients are presented as a bolus, electuary or paste.

In some embodiments, formulations suitable for oral administration include tablets, push-fit capsules made of gelatin, as well as soft, sealed capsules made of gelatin and a plasticizer, such as glycerol or sorbitol. In certain embodiments, tablets are made by compression or molding, optionally with one or more accessory ingredients. In some embodiments, compressed tablets are prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. In other embodiments, molded tablets are made by molding in a suitable machine a mixture of the powdered active ingredient or ingredients moistened with an inert liquid diluent. The tablets are optionally coated or scored. In certain embodiments, tablets are formulated so as to provide slow or controlled release of the active ingredient therein. Tablets are optionally provided with an enteric coating, to provide release in parts of the gut other than the stomach. All formulations for oral administration should be in dosages suitable for such administration. In other embodiments, the push-fit capsules contain the active ingredient or ingredients in admixture with filler such as lactose, binders such as starches, and/or lubricants such as talc or magnesium stearate and, optionally, stabilizers. In certain embodiments, soft capsules contain the active ingredient or ingredients dissolved or suspended in suitable liquids, such as fatty oils, liquid paraffin, or liquid polyethylene glycols. In addition, stabilizers are optionally added. Dragee cores are provided with suitable coatings. For this purpose, concentrated sugar solutions may be used, which optionally contains gum arabic, talc, polyvinyl pyrrolidone, carbopol gel, polyethylene glycol, and/or titanium dioxide, lacquer solutions, and suitable organic solvents or solvent mixtures. Dye stuffs, pigments or other color agents are optionally to the tablets or Dragee coatings for identification (e.g., as a pharmaceutical composition comprising the first agent, the second agent or a combination of first and second agents) or to characterize different doses.

In other embodiments, pharmaceutical compositions are formulated for parenteral administration by injection, e.g., by bolus injection or continuous infusion. In various embodiments, formulations for injection are presented in unit dosage form, e.g., in ampoules or in multi-dose containers, with an optional preservative. In certain embodiments, formulations take forms including, by way of non-limiting example, suspensions, solutions or emulsions in oily or aqueous vehicles, and optionally contain formulatory agents such as suspending, stabilizing and/or dispersing agents. In some embodiments, the formulations are presented in unit-dose or multi-dose containers, for example sealed ampoules and vials. In some embodiments, the formulations are stored in powder form or in a freeze-dried (lyophilized) condition requiring only the addition of the sterile liquid carrier, for example, saline or sterile pyrogen-free water, immediately prior to use. Extemporaneous injection solutions and suspensions are prepared, by way of non-limiting example, from sterile powders, granules and tablets of the kind previously described.

Formulations for parenteral administration include aqueous and non-aqueous (oily) sterile injection solutions of the active agents which may contain antioxidants, buffers, biocide, bacteriostats and solutes which render the formulation isotonic with the blood of the intended recipient; and aqueous and non-aqueous sterile suspensions which optionally include suspending agents and thickening agents. Examples of suitable isotonic vehicles for use in such formulations include Sodium Chloride Injection, Ringer's Solution, or Lactated Ringer's Injection. Suitable lipophilic solvents or vehicles include fatty oils such as sesame oil, or synthetic fatty acid esters, such as ethyl oleate or triglycerides, or liposomes or other microparticulate systems may be used to target the agent to blood components or one or more organs. The concentration of the active ingredient or ingredients in the solution varies depending on intended usage.

As such, the invention further provides pharmaceutical compositions and methods of making said pharmaceutical composition. In some embodiments, the pharmaceutical compositions comprise an effective amount of the first and second agents. In other embodiments, a first pharmaceutical composition comprises the first agent and a second pharmaceutical composition comprises the second agent. The pharmaceutical composition may comprise admixing at least one active ingredient with one or more carriers, excipients, buffers, adjuvants, stabilizers, or other materials well known to those skilled in the art and optionally other therapeutic agents. The formulations may conveniently be presented in unit dosage form and may be prepared by any known methods.

Non-limiting examples of excipients that are used in conjunction with the present invention include water, saline, dextrose, glycerol or ethanol. The injectable compositions optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Example of pharmaceutically acceptable carriers that are optionally used include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

In some embodiments, pharmaceutical compositions are formulated as a depot preparation. In certain embodiments, such long acting formulations are administered by implantation (for example subcutaneously or intramuscularly) or by intramuscular injection. Thus, in various examples, the agents or combinations described herein are formulated with suitable polymeric or hydrophobic materials (for example as an emulsion in an acceptable oil) or ion exchange resins, or as sparingly soluble derivatives, for example, as a sparingly soluble salt.

In other embodiments, wherein the pharmaceutical compositions described herein are formulated for buccal or sublingual administration, the pharmaceutical compositions described herein takes the form of tablets, lozenges, pastilles, or gels formulated in conventional manner. Such compositions optionally flavored agents such as sucrose and acacia or tragacanth.

In still other embodiments of the present invention, pharmaceutical compositions are formulated in rectal compositions such as suppositories or retention enemas, e.g., containing conventional suppository bases such as cocoa butter, polyethylene glycol, or other glycerides.

In alternative embodiments, the pharmaceutical compositions described herein are delivered systemically, which includes oral, intravenous, intraperitoneal and intramuscular administration.

It should be understood that in addition to the ingredients particularly mentioned above, the agents and compositions described herein may include other agents or components conventional in the art having regard to the type of formulation in question, for example those suitable for oral administration may include flavoring agents.

In certain embodiments, the agents or pharmaceutical compositions described herein are delivered in a vesicle, e.g., a liposome. In various embodiments, the agents and pharmaceutical compositions described herein are delivered in a controlled release system. In one embodiment, a pump is used. In additional embodiments, a controlled release system is placed in proximity of the therapeutic target. In certain aspects of the present invention, the pharmaceutical compositions described are formulated into a formulation suitable for oral use, for example, as tablets, troches, lozenges, aqueous or oily suspensions, dispersible powders or granules, emulsions, hard or soft capsules, or syrups or elixirs. Pharmaceutical compositions intended for oral use are prepared according to any method known to the art for the manufacture of pharmaceutical compositions. In order to provide pharmaceutically elegant and palatable preparations pharmaceutical compositions described herein optionally contain one or more agents selected from the group consisting of sweetening agents, flavoring agents, coloring agents and preserving agents. Tablets contain the active ingredient or ingredients in admixture with one or more non-toxic pharmaceutically acceptable excipient which is suitable for the manufacture of tablets. Excipients include, by way of non-limiting example, inert diluents (e.g., calcium carbonate, sodium carbonate, lactose, calcium phosphate or sodium phosphate), granulating and disintegrating agents (e.g., microcrystalline cellulose, sodium crosscarmellose, corn starch, or alginic acid), binding agents (e.g., starch, gelatin, polyvinyl-pyrrolidone or acacia), and lubricating agents (e.g., magnesium stearate, stearic acid or talc). The tablets are optionally coated or un-coated. Coating of a tablet is accomplished by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. In alternative embodiments, formulations for oral use are in the form of hard gelatin capsules wherein the active ingredient or ingredients are mixed with an inert solid diluent. Suitable inert solid diluents include, by way of non-limiting example, calcium carbonate, calcium phosphate or kaolin. In further embodiments, formulations for oral use are in the form of soft gelatin capsules wherein the active ingredient or ingredients are mixed with water soluble carrier. Water soluble carriers include, by way of non-limiting example, polyethyleneglycol or an oil medium (e.g., peanut oil, liquid paraffin, or olive oil).

Aqueous suspensions contain the active material in admixture with one or more excipient suitable for the manufacture of aqueous suspensions. Suitable excipients include, by way of non-limiting example, suspending agents (e.g., sodium carboxymethylcellulose, methylcellulose, hydroxypropylmethyl-cellulose, sodium alginate, polyvinylpyrrolidone, gum tragacanth and gum acacia), dispersing or wetting agents (e.g., a naturally-occurring phosphatide such as lecithin, condensation products of an alkylene oxide with fatty acids such as polyoxyethylene stearate, condensation products of ethylene oxide with long chain aliphatic alcohols such as heptadecaethylene-oxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides, such as polyethylene sorbitan monooleate). The aqueous suspensions optionally contain one or more preservatives (e.g., ethyl, or n-propyl p-hydroxybenzoate), one or more coloring agents, one or more flavoring agents, and one or more sweetening agents (e.g., sucrose, saccharin or aspartame).

In various embodiments, oily suspensions are formulated by suspending the active ingredient in, by way of non-limiting example, a vegetable oil (e.g., arachis oil, olive oil, sesame oil or coconut oil), or in mineral oil (e.g., liquid paraffin). The oily suspensions optionally contain a thickening agent (e.g., beeswax, hard paraffin or cetyl alcohol).

Sweetening agents such as those set forth above, and flavoring agents are optionally added to provide a palatable oral preparation. Preservatives and/or anti-oxidants (e.g., butylated hydroxyanisol or alpha-tocopherol) are optionally added as well.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional optional excipients include, by way of non-limiting example, sweetening, flavoring, coloring agents and anti-oxidants. Anti-oxidants include ascorbic acid.

In certain embodiments, pharmaceutical compositions are formulated as oil-in-water emulsions. The oily phase is selected from, by way of non-limiting example, vegetable oil (e.g., olive oil or arachis oil), a mineral oil (e.g., liquid paraffin) or mixtures thereof. Suitable emulsifying agents include naturally-occurring phosphatides (e.g., soy bean lecithin), esters or partial esters derived from fatty acids and hexitol anhydrides (e.g., sorbitan monooleate), and condensation products of the said partial esters with ethylene oxide (e.g., polyoxyethylene sorbitan monooleate). The emulsions optionally contain sweetening agents, flavoring agents, preservatives and antioxidants.

Syrups and elixirs are optionally formulated with sweetening agents (e.g., glycerol, propylene glycol, sorbitol or sucrose). Such formulations also optionally contain one or more demulcent, one or more preservative, one or more flavoring agent, one or more coloring agent and/or one or more antioxidant.

In another embodiment, pharmaceutical compositions are in the form of a sterile injectable aqueous solution. Acceptable vehicles and solvents that are employed are, by way of non-limiting example, water, Ringer's solution and isotonic sodium chloride solution. In some embodiments, the sterile injectable preparation is a sterile injectable oil-in-water microemulsion where the active ingredient is dissolved in the oily phase. In an example, the active ingredient is dissolved in a mixture of soybean oil and lecithin. The oil solution is then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant active ingredient or ingredients. In order to maintain such a constant concentration, a continuous intravenous delivery device is utilized in some embodiments. An example of such a device is the Deltec CADD-PLUS™ model 5400 intravenous pump. In other embodiments of the present invention, the pharmaceutical compositions is in the form of a sterile injectable aqueous or oleagenous suspension for intramuscular and subcutaneous administration. This suspension is formulated according to the known art using suitable dispersing, wetting agents and/or suspending agents, all of which are discussed herein. In still other embodiments, the sterile injectable preparation is a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In other embodiments of the present invention, pharmaceutical compositions are administered in the form of suppositories for rectal administration of the drug. In some embodiments, these pharmaceutical compositions are prepared by mixing the active ingredient or ingredients with a suitable non-irritating excipient which is solid at ordinary temperatures but liquid at the rectal temperature and will therefore melt in the rectum to release the drug. Such materials include, by way of non-limiting example, cocoa butter, glycerinated gelatin, hydrogenated vegetable oils, mixtures of polyethylene glycols of various molecular weights and fatty acid esters of polyethylene glycol.

In yet other embodiments, pharmaceutical compositions are administered via transdermal routes, using those forms of transdermal skin patches well known to those of ordinary skill in the art. Transdermal delivery system, include continuous administration of the active ingredient or ingredients.

Dosage Forms

In certain embodiments, the pharmaceutical compositions described herein are formulated as a form suitable for oral administration, as a tablet, as a capsule, as a cachet, as a pill, as a lozenge, as a powder or as a granule. In some embodiments of the present invention, the pharmaceutical compositions are formulated as sustained release formulations, solutions, liquids, suspensions, for parenteral injection as a sterile solution, suspension or emulsion, for topical administration as an ointment, cream, lotions, sprays, foams, gel or paste, or for rectal or vaginal administration as a suppository or pessary. In certain embodiments, the pharmaceutical compositions are formulated in unit dosage forms suitable for single administration of precise dosages. In certain aspects, the pharmaceutical composition includes a conventional pharmaceutical carrier or excipient and an agent as described herein as an active ingredient. In addition, other medicinal or pharmaceutical agents, carriers, adjuvants, etc. are included.

Exemplary parenteral administration forms include solutions or suspensions of active agents in sterile aqueous solutions, for example, aqueous propylene glycol or dextrose solutions. Such dosage forms are optionally buffered.

Suitable pharmaceutical carriers include inert diluents or fillers, water and various organic solvents. The pharmaceutical compositions optionally contain additional ingredients such as flavorings, binders, excipients and the like. For example, in a specific embodiment, tablets containing various excipients, such as citric acid are employed together with various disintegrants. Disintegrants include, by way of non-limiting example, starch or other cellulosic material, alginic acid and certain complex silicates and with binding agents such as sucrose, gelatin and acacia. Additionally, lubricating agents such as magnesium stearate, sodium lauryl sulfate and talc are optionally used. Other reagents such as an inhibitor, surfactant or solubilizer, plasticizer, stabilizer, viscosity increasing agent, or film forming agent are also optionally added. In certain embodiments, solid compositions of a similar type are employed in soft and hard filled gelatin capsules. In certain embodiments, the pharmaceutical compositions and/or formulations described herein include lactose or milk sugar and high molecular weight polyethylene glycols. When aqueous suspensions or elixirs are desired for oral administration the active ingredient or ingredients are optionally combined with various sweetening or flavoring agents, coloring agents or dyes and, emulsifying agents or suspending agents, together with diluents such as water, ethanol, propylene glycol, glycerin, or combinations thereof.

Additional Therapeutic Agents

The methods and compositions described herein can also further include additional therapeutic agents and drugs for treating the cancer or for alleviating symptoms.

Antiemetic Drugs

The drugs combinations employed in the present methods have high potential to cause nausea and emesis. Effective methods to control these side effects are known to one skilled in the arts and would be employed in conjunction with the current methods. Generally patients would be pre-treated with dexamethasone, and a serotonin antagonist. Suitable protocols are known to one skilled in the arts. The following references relate to this matter: Guideline update for MASCC and ESMO in the prevention of chemotherapy- and radiotherapy-induced nausea and vomiting: results of the Perugia consensus conference. Roila F; et al; ESMO/MASCC Guidelines Working Group.; Ann Oncol. 2010 May; 21 Suppl 5:v232-43.

EXAMPLES

Example 1

A patient with metastatic melanoma would be treated with the following protocol:
1. Treatment with Neupogen followed by the collection of hematopoietic stem cells from peripheral blood
   a. Sufficient CD34+ cells would be collected for 3 stem cell infusions and one reserve (i.e., greater than ~2×10^6 cells/kg/infusion)
   b. The CD34+ stem cells would be purified using CliniMacs™ technology
   c. If needed Plerixafor could be used to increase stem cell mobilization and yield. Techniques for using this drug are described in the Plerixafor FDA approved package label.
2. The Hyper-Melphalan regimen:
   a. IV Hydration and antiemetic premedication prior to chemotherapy (e.g., dexamethasone and Palonosetron (Aloxi) day −2)
   b. BCNU 100 mg/m$^2$ IV over 30 minutes: day −2, at t=0 minutes
   c. Adriamycin 40 mg/m$^2$ IV over 15 min: day −2 at t=40 minutes
   d. Melphalan 70 mg/m$^2$ IV over 30 minutes, day −2 at t=60 minutes
   e. Kyprolis (carfilzomib) 20 mg/m$^2$ IV on days −2 at t=5 hours, repeated in 24 h
   f. The drugs would be given by a central venous line
3. Stem cell infusion day 0 (48 hours after the alkylating agent)
4. Pegfilgrastim 6 mg subcutaneously, day +2
5. Repeat steps 2-4 in approx. 6 weeks for a total of 2-3 courses of therapy
6. Conventional supportive therapy post chemotherapy and post stem cell transplantation including anti-emetics, platelet transfusion, RBC transfusion and prophylactic antibiotics (e.g., Cipro), and other supportive therapy as needed.

The same method could be used for patients with a wide range of metastatic cancers including but not limited to pancreatic cancer, Stage IV breast cancer, platinum-resistant ovarian cancer, and the other types of cancers given in List A. (See Guideline update for MASCC and ESMO in the prevention of chemotherapy- and radiotherapy-induced nausea and vomiting: results of the Perugia consensus conference. Roila F; et al; ESMO/MASCC Guidelines Working Group.; Ann Oncol. 2010 May; 21 Suppl 5:v232-43).

Example 2

In example 1, the Kyprolis is replaced with Velcade 1.3 mg/m2.

Example 3

A patient with refractory myeloma would be treated as in Example 1 except step 2 would be as follows:
2. The Bizelesin/Cefoperazone regimen:
   a. IV Hydration and antiemetic premedication prior to chemotherapy (e.g., dexamethasone and Palonosetron (Aloxi) day −2)
   b. Bizelesin 3 microgram/m$^2$ IV bolus injection: day −2 at T=0
   c. Cefoperazone 4 gm IV over 30 minutes: day −2, at immediately after the bizelesin The same method could be used for patients with a wide range of metastatic cancers including but not limited to pancreatic cancer, Stage IV breast cancer, platinum-resistant ovarian cancer, and the other types of cancers given in List A.

Example 4

A patient with refractory non-Hodgkins lymphoma would be treated as in Example 1 except step 2 would be as follows:
1. The Bizelesin/Cyclosporine Regimen:
   d. IV Hydration and antiemetic premedication prior to chemotherapy (e.g., dexamethasone and Palonosetron (Aloxi) day −2)
   e. Cyclosporine 6 mg/kg IV over 2 hours: day −2, at t=0 minutes
   f. Bizelesin 3 microgram/m$^2$ IV bolus injection: day −2 immediately after the cyclosporine The same method could be used for patients with a wide range of metastatic cancers including but not limited to pancreatic cancer, Stage IV breast cancer, platinum-resistant ovarian cancer, and the other types of cancers given in List A.

Example 5

A patient with BRCA2-associated pancreatic cancer, status post Whipple surgery with micrometastatic disease would be treated as in Example 1 except that Step 2 would be as follows:
Step 2:
   a) IV Hydration and antiemetic premedication prior to chemotherapy (e.g., dexamethasone and Palonosetron (Aloxi) day −2)
   b) Melphalan 70 mg/m$^2$ IV over 30 minutes, day −2 at t=60 minutes.

EQUIVALENTS

Those skilled in the arts can recognize or be able to ascertain, using no more then routine experimentation, many equivalents to the inventions, materials, methods, and components described herein. Such equivalents are intended to be within the scope of the claims of this patent. While this invention has been particularly shown and described with references to preferred embodiments thereof, it will be understood by those skilled in the art that various changes in form and details may be made therein without departing from the scope of the present invention.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated. The term and/or includes the both (including) or in the alternative.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

While this invention has been particularly shown and described with references to preferred embodiments thereof, it will be understood by those skilled in the art that various changes in form and details may be made therein without departing from the scope of the invention encompassed by the appended claims.

What is claimed is:

1. A combination for therapy for treating metastatic cancer or refractory metastatic cancer in a subject, comprising:
    a therapeutically effective dose of bizelesin or a pharmaceutically acceptable salt thereof, wherein the therapeutically effective dose of bizelesin is approximately 1 μg/m$^2$ to approximately 20 μg/m$^2$,
    bone marrow stem cells, and
    an MDR-1 pgp pump inhibitor or a pharmaceutically acceptable salt thereof in a range of a milligram to gram dose that inhibits efflux of bizelesin by the MDR-1 pgp pump.

2. The combination of claim 1, wherein the MDR-1 pgp pump inhibitor is selected from cyclosporine, valspodar, tariquidar, cefoperazone, doxorubicin, thaliblastin, zosuquidar, ontogen, disulfiram, erythromycin, 1,3-bis(2-chloroethyl)-1-nitrosourea, thiol-reactive compounds, ritonavir, fluoxetine, toremifene, chloroquine, or a pharmaceutically acceptable salt of any of the foregoing.

3. The combination of claim 2, wherein the MDR-1 pgp pump inhibitor is cefoperazone in an amount of approximately 2 grams IV to approximately 4 grams IV.

4. The combination of claim 2, wherein the MDR-1 pgp pump inhibitor is fluoxetine in an amount of approximately 20 mg/day to approximately 80 mg/day.

5. The combination of claim 1, further comprising melphalan or a pharmaceutically acceptable salt thereof.

6. The combination of claim 1, wherein the bone marrow stems cells are purified to decrease the number of circulating tumor cells.

7. The combination of claim 1, wherein the cancer is solid metastatic cancer.

8. The combination of claim 1, wherein the cancer is leukemia, lymphoma or myeloma.

9. A method of treating metastatic cancer or refractory metastatic cancer in a subject in need thereof, comprising:
    delivering a approximately 1 μg/m$^2$ to approximately 20 μg/m$^2$ dose of bizelesin or a pharmaceutically acceptable salt thereof to a treatment site of the subject, in combination with bone marrow stem cells, and an MDR-1 pgp inhibitor or a pharmaceutically acceptable salt thereof in a range of a milligram to gram dose that inhibits efflux of bizelesin from the MDR-1 pgp pump.

10. The method of claim 9, wherein the MDR-1 pgp pump inhibitor is selected from cyclosporine, valspodar, tariquidar, cefoperazone, doxorubicin, thaliblastin, zosuquidar, ontogen, disulfiram, erythromycin, 1,3-bis(2-chloroethyl)-1-nitrosourea, thiol-reactive compounds, ritonavir, fluoxetine, toremifene, chloroquine, or a pharmaceutically acceptable salt of any of the foregoing.

11. The method of claim 9, wherein the MDR-1 pgp pump inhibitor is delivered prior to, concurrently with, or after the bizelesin.

12. The method of claim 9, further comprising delivering melphalan or a pharmaceutically acceptable salt thereof.

13. The method of claim 9, wherein the bone marrow stems cells are purified to decrease the number of circulating tumor cells.

14. The method of claim 10, wherein the MDR-1 pgp pump inhibitor is cefoperazone in an amount of approximately 2 grams IV to approximately 4 grams IV.

15. The method of claim 10, wherein the MDR-1 pgp pump inhibitor is fluoxetine in an amount of approximately 20 mg/day to approximately 80 mg/day.

16. The method of claim 9, wherein the cancer is solid metastatic cancer.

17. The method of claim 9, wherein the cancer is leukemia, lymphoma or myeloma.

18. A combination for therapy for treating metastatic cancer or refractory metastatic cancer in a subject, comprising:
- a therapeutically effective dose of bizelesin or a pharmaceutically acceptable salt thereof, wherein the therapeutically effective dose of bizelesin is approximately 1 μg/m$^2$ to approximately 20 μg/m$^2$,
- bone marrow stem cells, and
- tariquidar or a pharmaceutically acceptable salt thereof in a range of a milligram to gram dose that inhibits efflux of bizelesin by the MDR-1 pgp pump.

* * * * *